(12) United States Patent
Shirley et al.

(10) Patent No.: US 8,338,661 B2
(45) Date of Patent: Dec. 25, 2012

(54) TRANSGENIC PLANTS WITH INCREASED STRESS TOLERANCE AND YIELD

(75) Inventors: Amber Shirley, Durham, NC (US); Rodrigo Sarria-Millan, West Lafayette, IN (US)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 12/668,665

(22) PCT Filed: Jul. 11, 2008

(86) PCT No.: PCT/EP2008/059070
§ 371 (c)(1),
(2), (4) Date: Jan. 12, 2010

(87) PCT Pub. No.: WO2009/010460
PCT Pub. Date: Jan. 22, 2009

(65) Prior Publication Data
US 2010/0170003 A1    Jul. 1, 2010

Related U.S. Application Data

(60) Provisional application No. 60/959,346, filed on Jul. 13, 2007.

(51) Int. Cl.
*A01H 5/00* (2006.01)
*C12N 15/29* (2006.01)
*C12N 15/82* (2006.01)

(52) U.S. Cl. ....... 800/278; 800/298; 435/91.1; 536/23.1

(58) Field of Classification Search .................. None
See application file for complete search history.

(56) References Cited

U.S. PATENT DOCUMENTS

| 2002/0152502 A1* | 10/2002 | da Costa e Silva et al. ... 800/298 |
| 2004/0216190 A1* | 10/2004 | Kovalic ........................ 800/289 |

FOREIGN PATENT DOCUMENTS

| WO | WO 99/64612 | 12/1999 |
| WO | WO 00/67558 | 11/2000 |
| WO | WO 02/48442 | 6/2002 |
| WO | WO 03/012116 | 2/2003 |
| WO | WO 03/020914 | 3/2003 |
| WO | WO 2004/099415 | 11/2004 |
| WO | WO 2006/069201 | 6/2006 |
| WO | WO 2006/083399 | 8/2006 |
| WO | WO 2006/134162 | 12/2006 |

OTHER PUBLICATIONS

Database EMBE [Online], Nov. 28, 2001, "*Arabidopsis thaliana* unknown protein (At2g20725) mRNA, complete cds." XP002502724 retrieved from EBI accession No. EMBL:AY063007 Database accession No. AY063007 abstract.*
Database EMBL [Online] May 1, 2001, ;*Arabidopsis thaliana* unknown protein (At2920725) mRNA, complete cds. XP002502725 retrieved from EBI accession No. EMBL:AF370273 Database accession No. AF370273 abstract.*
Davletona et al (Plant Physiology, Oct. 2005, vol. 139, pp. 847-856).*
Database EMBL "*Arabidopsis thaliana* unknown protein (At2g20725) mRNA, complete cds." XP002502724, Published 2001.
Database EMBL "*Arabidopsis thaliana* unknown protein (At2g20725) mRNA, complete cds." XP002502725, Published 2001.
& Database UniProt SubName: Full=Putative uncharacterized protein At2g20725 Database accession No. Q94K61 abstract, Published 2001.
Bracha Keren et al: "The Arabidopsis AtSTE24 is a CAAX protease with broad substrate specificity" Journal of Biological Chemistry, vol. 277, No. 33, Aug. 16, 2008 pp. 29856-29864, Published 2002.
Cadinanos Juan et al: "AtFACE-2, a funchtional prenylated protein protease from *Arabidopsis thaliana* related to mammalian Ras-converting enzymes." Journal of Biological Chemistry vol. 278, No. 43, Oct. 24, 2003, pp. 42091-42097, Published 2003.
Bracha-Drori Keren et al: "Functional analysis of Arabidopsis postprenylation CaaX processing enzymes and their function in subcellular protein targeting." Plant Physiology Sep. 2008, vol, 148, No. 1, pp. 119-131, XP002502723, Published 2008.
Lixia Liu, "Over-expression of a *Zea mays* L. Protein phosphatase 2C gene (ZmPP2C) in *Arabidopsis thaliana* decreases tolerance to salt and drought," Journal of Plant Physiology, vol. 166 (2009) pp. 531-542.
Alois Schweighofer, "Plant PP2C phosphatases: emerging functions in stress signaling," Trends in Plant Science, vol. 9, No. 5 May 2004.
S. Tahtiharju, "Antisense inhibition of protein phosphatase 2C accelerates cold acclimation in *Arabidopsis thaliana*" The Plant Journal, 2001 Oxford GB vol. 26, # 4, pp. 461-470.
S. Miyazaki, "Tissue-and environmental response-specific expression of 10 PP2C transcripts in Mesembryanthemum crystallinum", Molecular and General Genetics, Springer Verlag, Berlin, DE, vol. 261, No. 2, Mar. 1, 1999.
Girish Mishra, "A Bifurcating Pathway Directs Abscisic Acid Effects on Stomatal Closure and Opening in Arabidopsis" Science, Washington, DC, vol. 312, No. 5771, pp. 264-255, Apr. 14, 2006.
Xuebo Hu, "Molecular characterization and expression analysis of a rice protein phosphatase 2C gene, OsBIPP2C1, and overexpression in transgenic tobacco conferred enhanced disease resistance and abiotic tolerance", Physiologia Plantarum 2006, vol. 127, pp. 225-236.
Database EMBL, Aug. 29, 2002, "gd49d03.y1 MOss EST library PPAS Physcomilrella patents cDNA clone PEP Source ID: PPAS020706 5 similar to TR: . . . 082479 082479 Protein Phosphatase-2c mRNA Sequence.", XP002663919.
David Reyes, "Overexpression of a Protein Phosphatase 2C from Beech Seeds in Arabidopsis Shows Phenotypes Related to Abscisic Acid Responses and Gibberellin Biosynthesis", Plant Physiology, Aug. 2006, vol. 141, pp. 1414-1424.

* cited by examiner

*Primary Examiner* — Brent T Page
*Assistant Examiner* — Lee A Visone
(74) *Attorney, Agent, or Firm* — Patricia A. McDaniels

(57) ABSTRACT

Polynucleotides are disclosed which are capable of enhancing a growth, yield under water-limited conditions, and/or increased tolerance to an environmental stress of a plant transformed to contain such polynucleotides. Also provided are methods of using such polynucleotides and transgenic plants and agricultural products, including seeds, containing such polynucleotides as transgenes.

3 Claims, 6 Drawing Sheets

Figure 1

```
SEQ ID NO:6   (1)   ------MATDGESISMSLAVATCVAMALFYVLILYVPTVILRLPSASSYTEFMIRRFICAAICT
SEQ ID NO:10  (1)   ---------------------MGRAPTEGFYVAVLYAPTVILRVPPPSSLRTFLHRRFACAAVAS
SEQ ID NO:8   (1)   MATPAGLLLASPPVISGVAAMACAAMAVFYVAVLYAPTVILRFPPPTSLRTFLHRRFACAAVAS

SEQ ID NO:6   (59)  VASLVFTAFILPIKSW-EASYILGVYGIRKDHLWQGVVYPLLLTSLVYAGSLVLKLFTLLESWKE
SEQ ID NO:10  (45)  AASVLATASLLRIWSLSDFADMFAVFGIRKDHLIQAVAIPLLLTSLVYAGSFVARVWLLVSSWG-
SEQ ID NO:8   (66)  AASVLATASLLRVWSLSDFADMFAVFGIRKDHLIQAVAIPLLLTSLVYAGSFVARVWLLVSSWG-

SEQ ID NO:6   (123) NGGGCSSFNYIRSFFQTIPASVLTSASNVSVWRNFIVAPVTEELVFRSCMIPLLLCAGFRINTAI
SEQ ID NO:10  (109) -----GGDEVEIGCAQRLAQWIQAAVADVMVWRNYVVAPFTEELVFRACMIPLLLCGGFKMSTII
SEQ ID NO:8   (130) -----GGDEVEIGCAQRLAQWIQAAVADVMVWRNYVVAPFTEELVFRACMIPLLLCGGFKMSTII

SEQ ID NO:6   (188) FLCPVLFSLAHLNHFREMYIRHNRSYLRASLIVGLQLGYTVIFGAYASFLFIRTGHLAAPLFAHI
SEQ ID NO:10  (169) FLSPIFFS--------------LGVQLGYTVIFGWYATFLLIRTGNLLCPITAHV
SEQ ID NO:8   (190) FLSPIFFSLAHLNHFFELHQQG-CNFMRALLIVGVQLGYTVIFGWYATFLLIRTGNLLCPIIAHV

SEQ ID NO:6   (253) FCNYMGLPVLYA-NGKGLVSAAFLGGVVGFVLLFPLTKPLMYNDSTNDCPCWLGYCLWN-
SEQ ID NO:10  (210) FCNMMGLPVFSSPRTKGAALVAFLAGSIAFFWLLFPATSPELYNSSFDRCSCWHGFCNWK-
SEQ ID NO:8   (254) FCNMMGLPVFSSPRTKGAALVAFLAGSIAFFWLLFPATSPELYNSSFDRCSCWHGFCNWK-
```

Figure 2

```
SEQ ID NO:16   (1)  ----------------------------------------------------------------
SEQ ID NO:18   (1)  ----------------VLRALARPLERCLGSRASGDGLLWQSELKPHAGGDYSIAVVQANSSLED
SEQ ID NO:20   (1)  ----------------------------------------------------MAVVQANNLLED
SEQ ID NO:24   (1)  -MLVKLMNLLRACWRFSSNRHARTGSDVTGRC---DGLLWYKDAGQHVNGEFSMAVVQANNLLED
SEQ ID NO:34   (1)  ----------------------------------------------------------------
SEQ ID NO:26   (1)  MLSALMDYLKSCWGPASPAGRPRKGSDATGRC---DGLLWYKDGGQVVDGFFSMAVVQANNLLED
SEQ ID NO:28   (1)  MLAAVMDYFSTCWGPRSRAGHRGKGSDAAGRQ---DGLLWYKDAGQLVTGGFSMAVVQANQLLED
SEQ ID NO:32   (1)  MLAAVMDYFSTCWGPRSAGHRGKGSDAAGRQ---DGLLWYKDAGQLVTGGFSMAVVQANQLLED
SEQ ID NO:30   (1)  MLAAVMDYFSSCWGPRSGAGHRGKGSDAAGRQ---DGLLWYKDAGQLVTGGFSMAVVQANQLLED
SEQ ID NO:22   (1)  MLQALMNLFSLCWKPFCRDAADRIDSIGVTGRECKDGLLWFRDGGKYGSCDFSMAVVQANQVLED

SEQ ID NO:16   (1)  --------------------------------------------------MSCDVLCQSFK
SEQ ID NO:18  (50)  QSQVFTS--------SSATYVGVYDGEGGPEASRFVNRIILFPYIQKFAKEDG-GLSADVKKAFK
SEQ ID NO:20  (13)  QSQIESGPLSLLDTGPYGTFVGVYDGEGGPETSRYVCDHLFQHLKRFASEQK-SMSMEVIRKAYQ
SEQ ID NO:24  (62)  QCQTESGPLSFLDSGPYGTFVGVYDGEGGPETACYTNDHLFQNLKRFASEQN-AMSADVLKKAYE
SEQ ID NO:34   (1)  --------------------------------------------------MSADVLKKAYE
SEQ ID NO:26  (63)  ESQVESGPLSTSEPGLQGTFVGVYDGEGGPETARYINDHLFNHLRRFASEHK-CMSADVIRKAFR
SEQ ID NO:28  (63)  QSQVESGSLSLADYGPQGTFVGVYDGEGGPETSRFINDHLFNHLRRFATEHK-SMSADVIRKAFQ
SEQ ID NO:32  (63)  QSQVESGSLSLADYGPQGTFVGVYDGEGGPETSRFINDHLFNHLRRFATEHK-SMSADVIRKAFQ
SEQ ID NO:30  (63)  QSQVESGSLSLADPGPQGTFVGVYDGFGGPETSRFINDHLFNHLRRFATEHK-FMSADVIRKAFQ
SEQ ID NO:22  (66)  QSQIESG--------PLGTFVGIYDGEGGPDASRYVCDHLFRHFQAISAESRGVVTTETIERAFR

SEQ ID NO:16  (12)  EVEGKFLEIVERAWAVKPQIAAVGSCCLVGAVWDSKLYIASLGDSRAVLGSCSRDTGL------P
SEQ ID NO:18 (106)  ETEEDFCCMVKRSLPMKPQMATVCSCCLFCAISNGTLYVANLCDSRAVLCSVVAGDDSNSSNKCA
SEQ ID NO:20  (77)  ATEEGFLSVVTKQWPMNPQIAAVGSCCLVGVICGGILYIANLGDSRAVLGRVVRATGE------V
SEQ ID NO:24 (126)  ATEDGFFSIVTKQWPVKPQIAAVGSCCLVGVICGGMLYVANVGDSRVVLGKEVKATGE------V
SEQ ID NO:34  (12)  ATEDGFFSIVTKQWPVKPQIAAVGSCCLVGVICGGMLYVANVGDSRVVLGKIVKATGE------V
SEQ ID NO:26 (127)  ATEEGFISVVSNQWSLRPQLAAVGSCCLVGVVCSGTLYVANLGDSRAVLGRLVKGTGE------V
SEQ ID NO:28 (127)  ETEEGFISLVIKEWSFKPQIASVGSCCLVGVICAGTLYVANLCDSRAVLGRLVKATGE------V
SEQ ID NO:32 (127)  ETEEGFLSLVIKEWSFKPQIASVGSCCLVGVICAGTLYVANLGDSRAVLGRLVKATGE------V
SEQ ID NO:30 (127)  ATEEGFLSLVSKEWSLKPQIASVGSCCLVGVICAGTLYVANVGDSRAVLGRLVKATGE------V
SEQ ID NO:22 (123)  QTEEGYMALVSGSWNARPHIASAGECCLVGVIFQQTLFVANAGDSRVVLGKKVGNTGG------M

SEQ ID NO:16  (71)  VAKQISTEENASIESIRNELFAKHSDDPQIVVLKEGVWRVKGIIQISRSICDFYLKKAEFNQPPL
SEQ ID NO:18 (171)  AAERLSTDENVAVEEVRKEVKELNPDDSQIVMYLRGVWRIKGLIQVSRSIGDVYLKKPEFYRDPI
SEQ ID NO:20 (136)  LAIQLSSEENVAIESVRQEMHSLEPDDSKIVVLKENVWRVKGLIQISRSIGDVYLKKAEFNKEPL
SEQ ID NO:24 (185)  LAVQLSAEENVSIASVRKELQSMEPEDRIIVVLKENVWRVKGLIQVCRSIGDAYLKKQEFNREPL
SEQ ID NO:34  (71)  LAVQLSAEENVSIASVRKELQSMEPEDRHIVVLKENVWRVKGLIQVCRSIGDAYLKKQEFNREPL
SEQ ID NO:26 (186)  LAMQLSAFFNASYEEVRREIQASEPDDPHIVVLKENVWRVKCIQTTRSTCDVYLKKPEFNREPL
SEQ ID NO:28 (186)  LATQLSAEENACYEEVRQELQSSEPDDPRIVVLKENVWRVKGLIQISRSIGDVYLKKPEYNREPL
SEQ ID NO:32 (186)  LATQLSAEENACYEEVRQELQSSEPDDPRIVVLKENVWRVKGLIQISRSIGDVYLKKPEYNREPL
SEQ ID NO:30 (186)  VAMQLSSEENACYEEVRQELQSSEPDDPHIVVLKENVWRVKGLIQISRSIGDVYLKKPEYNREPL
SEQ ID NO:22 (182)  AAIQLSTEENANLEAVRQELKELEPEDPQIVVLKEGVWRVKGIIQVSRSIGDVYLKHAQFNREPL

SEQ ID NO:16 (136)  IARFRLPDPLKRPVISSEPECNVTLGPDDEEVLFASDGLWEHLSSKEAVDLVYSHPRAGIARRL
SEQ ID NO:18 (236)  FQQHGNHIPLRRPAMTAEPSIIVRKLKPQDLIIIFASDGLWEDLSDEAAVEIVLKIIPRTGIARKL
SEQ ID NO:20 (201)  YAKFRVREGFKRPILSSDPSISVHELQQHDQFLIFASDGLWEHLSNQDAVDIVQNNPHNGIARRL
SEQ ID NO:24 (250)  YAKFRLREPFHKPILSSEPSISVQPLQPHDQFLIFASDGLWEQLTNQEAVDIVRSSPRSGCARRL
SEQ ID NO:34 (136)  YAKFRLREPFHKPILSSEPSISVQPLQPHDQFLIFASDGLWEQLTNQEAVDIVRSSPRSGCARRL
SEQ ID NO:26 (251)  ESKFRLQEIFRRPLLSSDPAITVHQLQPTDKFIIFASDGLWEHLSNQEVVDMVQSSPRNGIARKL
SEQ ID NO:28 (251)  ESKFRLREIFQKPIILSSEPQITEERLQPNDQFVIFASDGLWEDLSNQEAVDLVQSSPRNGIARRL
SEQ ID NO:32 (251)  ESKFRLREIFQKPIILSSEPQITEERLQPNDQFVIFASDGLWEDLSNQEAVDLVQSSPRNGIARRL
SEQ ID NO:30 (251)  ESKFRLREIFQRPTISSEPQITEERLQPNDQFVIFASDGLWEHLSNKEAVDLVQSSPRNGIARRL
SEQ ID NO:22 (247)  NAKFRLPEPMNMPILSANPTILSHALQPNDSELLFASDGLWEHLSNEKAVDLVNSNPHAGSAKRL

SEQ ID NO:16 (201)  IKAALQKAATKREMRYSDLKGIERGIRRIIFIIDDIVVVLYLDIKLLNRGGSISNIIISSKCPIDMP
SEQ ID NO:18 (301)  VRAALEEAARKREMRYGDIKKIAKGVRRHFHDDSVVVVYIDQQKTTSSSNDRLIQKGGITAPPD
SEQ ID NO:20 (266)  IKAALQEAAKKREMRYSDLKKIDRGVRRHFHDDTIVVVFIDSNLVSRASSVRGPPLSVRGGGVP
SEQ ID NO:24 (315)  IRAALQEAAKKREMRYSDLKKIDRGVRRHFHDDIVIVVFIDSGLVSQASIERGPTLSLRGGGGGS
SEQ ID NO:34 (201)  IRAALQEAAKKREMRYSDLKKIDRGVRRHFHDDIVIVVFIDSGLVSQASIERGPTLSLRGGGGGS
SEQ ID NO:26 (316)  VKSAVQEAAKKREMRYSDLKKVDRGVRRHFHDDIVIVVFFDSNAMTTAAWSR-PSVSLRGGGFP
SEQ ID NO:28 (316)  VKAAMEEAAKKREMRYSDLKKIDRGVRRHFHDDIVVVVFIDSDAMSKASWSKSPSFSLRGGGVT
SEQ ID NO:32 (316)  VKAAMQEAAKKREMRYSDLKKIDRGVRRHFHDDIVVVVFIDSDAMSKASWSKSPSVSLRGGGVT
SEQ ID NO:30 (316)  VKAAMQEAAKKREMRYSDLKKIDRGVRRHFHDDIVVVVFIDSDAMSKASWSKSPSVSLRGGGVA
SEQ ID NO:22 (312)  IKAALIEAARKREMRYSDLRKIDKKVRRIIFIIDDISVIVLFLNHDLISRGTVLD-PTLSIRSALDII

SEQ ID NO:16 (266)  KGDNPPSLVSSNMNIAFNK-
SEQ ID NO:18 (366)  IYSLRSDFAEQRRLLNVLY-
SEQ ID NO:20 (331)  LPSRTLAPCAAPMET-----
SEQ ID NO:24 (380)  AGLRSNTLAPT---------
SEQ ID NO:34 (266)  AGLRSNTLAPT---------
SEQ ID NO:26 (380)  THSNTLAPFSVPTEINNSY-
SEQ ID NO:28 (381)  LPAKSLAPFSAPAQLNGTH-
SEQ ID NO:32 (381)  LPAKSLAPFSAPAQLNGTH-
SEQ ID NO:30 (381)  LPAKSLAPFSAPARLNSTY-
SEQ ID NO:22 (376)  --------------------
```

Figure 3

```
SEQ ID NO:36    (1)   ----------------MGSSKAEENLALRLGLTAASAMASESVTFPIDITKTRLQLQGEM----
SEQ ID NO:40    (1)   --------------------MQLQG----------ESASIQTNLRPALAFQTSSAVHAPS----
SEQ ID NO:38    (1)   ----------------MGVKSFVEG--------GIAPVVAGCSTHPLDLIKVRLQLHGEASAVT
SEQ ID NO:42    (1)   ------------MAEEKKVAPIGIWTAVKPFVNGGASGMLATCVIQPIDMIKVRIQLGQGS----
SEQ ID NO:44    (1)   ------------MAEEKKVAPIGVWNTVKPFVNGGASGMLATCVIQPIDMIKVRIQLGQGS----
SEQ ID NO:48    (1)   MADAKQQQQQQQQPQQAAAAATGVWKTVKPFVNGEASGMLATCVIQPIDMVKVRIQLGEGS----
SEQ ID NO:46    (1)   ----------MQPRYGEARQPLPGRYALYHFGTSGAAVAAATAVTHPFDVIKVRLQMQLAG----

SEQ ID NO:36   (45)   ----------------GATAGAPKRGAISMAISIGKEEGIAGLYRGLSPA---LLRHVFYTSIRI
SEQ ID NO:40   (31)   --------------------PPPRVGIITIGSRIIRQEGTCTLFSGISATSATVLRQTLYSTTRM
SEQ ID NO:38  (41)   LLRPALAFHNSPPAFLETTHSVPKVGPISLGINLVKTEGAAALFSGVSAT---LLRQTLYSTTRM
SEQ ID NO:42   (50)   -------------------------AASVTTTMLKNEGIGAFYKGLSAG---LLRQATYTTARL
SEQ ID NO:44   (50)   -------------------------AVSVTKNMLKNDGIGAFYKGLSAG---LLRQATYTTARL
SEQ ID NO:48   (62)   -------------------------AGQVTRNMLANEGVRSFYKGLSAG---LLRQATYTTARL
SEQ ID NO:46   (52)   -------------------QRGNLVGMGTIFTQMVEREGTRSLYLGLAPA---LARAVVYGGLRF

SEQ ID NO:36   (91)  VAYENLRTALSHGEHPENLSVAKKAFIGGTSGIIGQVIASPADLVKVRMQADGRLVKLGQQPRYT
SEQ ID NO:40   (76)  GLYDILKTKWTDPETKT-IPLTRKLAAGFIAGGIGAAVGNPADVAMVRMQADGRLPVVDRR-NYK
SEQ ID NO:38  (103)  GLYEVLKNKWTDPESGK-LSLTRKIAAGLVGGGIGAAVGNPADVAMVRMQADGRLPVAERR-NYA
SEQ ID NO:42   (86)  GSFKMLTAKASEANDGKPLPLYQKALCGLTAGAIGACVGSPADLALIRMQADNTLPLAQRR-NYT
SEQ ID NO:44   (86)  GSFKMLTAKAIEANDGKPLPLYQKALCGLTAGAIGACVGSPADLALIRMQADNTLPLAQRR-NYT
SEQ ID NO:48   (98)  GSFRVLTNKAVEKNEGKPLPLFQKAFIGLTAGAIGACVGSPADLALIRMQADSTLPVAQRR-NYK
SEQ ID NO:46   (95)  GLYEPCKHVCSYAFGST--NFAFKFASGVIAGGLATALTNPMEVLKVRLQMS---K------SST

SEQ ID NO:36  (156)  GVADAFTKIARAEGVTGLWRGVGPNAQRAFLVNMGELACYDQSKQWIIGRGIAADNIGAHTLASV
SEQ ID NO:40  (139)  SVLDAIAQMVRGEGVTSLWRGSSMTINRAMLVTASQLATYDSVKETILEKGLMRDGLGTHVTSSF
SEQ ID NO:38  (166)  GVGDAIKRMAKQEGVVSLWRGSALTINRAMIVTAAQLASYDQFKEGMVESGGMKDGLGTHVVASF
SEQ ID NO:42  (150)  NAFHALYRISADEGVLALWKGCGPTVVRAMALNMGMLASYDQSAEYMRDN-LGLGETSTVVGASA
SEQ ID NO:44  (150)  NAFHALYRISADEGVLALWKGCGPTVVRAMALNMGMLASYDQSAEYMRDN-LGLGETSTVVGASA
SEQ ID NO:48  (162)  NAFHALYRISGDEGVLALWKGAGPTVVRAMALNMGMLASYDQSVELFRDK-FGAGEISTVVGASA
SEQ ID NO:46  (149)  STIREMRKVIAHEGFKALWKGVGPAMTRAGCLTASQMATYDEAKQALMKWTPLEEGFQLHLISSF

SEQ ID NO:36  (221)  MSGLSATILSCPADVVKTRMMNQGAAG----AVYRNSLDCLTKTVKAEGVMALWKGFFPTWTRLG
SEQ ID NO:40  (204)  AAGFVASVASNPVDVIKTRVMNMKVEAG-KTAPYKGAVDCALKTVRAEGIMALYKGFLPTVSRQA
SEQ ID NO:38  (231)  AAGIVAAVASNPVDVIKTRVMNMKVDARGGEAQYKGAWDCAVKTVRAEGPMALYKGFVPTVCRQG
SEQ ID NO:42  (214)  VLGFCAAACSLPFDFVKTQIQKMQPDAQG-KYPYTGSQDCAMQNRRTFEILHRLSGILRQDRPSR
SEQ ID NO:44  (214)  VSGFCAAACSLPFDFVKTQIQKMQPDAQG-KYPYTGSLDCAMQTLKSGGPLKFYTGFPVYCVRIA
SEQ ID NO:48  (226)  VSGFFASACSLPFDYVKTQIQKMQPDANG-KYPYTGSLDCAVKTFKSGGPFKFYTGFPVYCVRIA
SEQ ID NO:46  (214)  IAGTAGTLVTSPVDMIKTRLMLQQESKG--ARVYRNGFHCASQVVVTEGVKSLYKGGFATFARVG

SEQ ID NO:36  (282)  PWQFVFWVSYEQLRRISGLSSF-----
SEQ ID NO:40  (268)  PFTVIMFVTLEQVKKVFKDFDF-----
SEQ ID NO:38  (296)  PFTVVLFVTLEQVKKLLRDF------
SEQ ID NO:42  (278)  HGDMDLPEPDYKVPKEHWDVIFKQTL-
SEQ ID NO:44  (278)  PHVMMTWIFLNQITKFQKTIGL-----
SEQ ID NO:48  (290)  PHVMMTWIFLNQIQKFEKKIGI-----
SEQ ID NO:46  (277)  PQTTITFIVCEKLRELAGMTAI-----
```

Figure 4

```
SEQ ID NO:50    (1)  ----------------MVRADLVNLADLDTALNRVHNKLPNSIETASAEPPAPP----------
SEQ ID NO:54    (1)  ---MSVDNSSVGSNESRTVILKHPGLRDAPTASYSVGNSVFRPNRVAAHTLNEDALARVLMDPNH
SEQ ID NO:52    (1)  -MNSKVKGNGSVSRKDMIFRADRIDLKILDVQLEKHLSRVWSRNTTDNAKPK-------------
SEQ ID NO:58    (1)  ------MKEEGGGGDAGFVRADQIDLKSLDEQLERHLTRAWTMEKRKEEASAGAGAGARQHQQSR
SEQ ID NO:60    (1)  -----MRQPTSAGGDAGFLRADQIDLKSLDEQLERHLGHPAERVVGPVSGTGSRRGETAKLGPEE
SEQ ID NO:56    (1)  MTSTAAGASSSAAKSESYLRADKIDLESLDIQLEKQLAKTWEKHKGSYNQGP--R----------

SEQ ID NO:50   (39)  --------EEWEINPREITLKHMIARGTFGTVHKGVYKGQDVAVKLLEWGEENTMKKTEVQYYRN
SEQ ID NO:54   (63)  PTEILSKYQQWAIDLGRLDMGVPFAQGAFGKLYRGTYIGEDVAIKLLEKPDN---DIERAQSLEQ
SEQ ID NO:52   (52)  --------EEWEIDLSKLDIKTQIARGTYGTVYKGTYDNQDVAVKVLDWGEDGMTTVSEAASLRA
SEQ ID NO:58   (60)  ----RPRREDWEIDPAKLVVKGVIARGTFGTVHRGIYDAHDVAVKLLDWGEDGHRSEQDIAALRA
SEQ ID NO:60   (61)  LTPLQRCREDWEIDPTKLIIKGVIARGTFGTVHRGVYDGQDVAVKLLDWGEDGHRSEQEIGALRA
SEQ ID NO:56   (54)  --------EDWEIDLAKLEIRYVIAQGTYGTVYRGTYDGQDVAVKLLDWGEDGFASETETATLRA

SEQ ID NO:50   (96)  QFRQEVAVWHKLDHPNVTKFIGASMGNSDLRIPSAVDGDDGFHHVPNNACCVVVEYLAGGTLKDH
SEQ ID NO:54  (125)  QFVQEVMMLSTLRHPNIVRFIGACR-------------------KSIVWCIITEYAKGGSVRQF
SEQ ID NO:52  (109)  SFRQEVAVWHKLDHPNVTKFVGASMGTSNLKVS----NNKSDGQHTARACCVVVEYQPGGTLKQY
SEQ ID NO:58  (121)  AFSQEVSVWHKLDHPNVTKFIGAIMGARDLN----IQTENGHIGMPTNICCVVVEYLPGGALKSF
SEQ ID NO:60  (126)  AFAQEVAVWHKLEHPNVTKFIGAIMGARDLN----IQTEHGQLGMPSNICCVVVEYLAGGALKNF
SEQ ID NO:56  (111)  SFKQEVAVWHELNHPNVTKFVGASMGTTDLKIPANSSNSGGRTELPPKACCVVVEYLAGGSLKQY

SEQ ID NO:50  (161)  LIRSRRKKLSYKVVVQLALDVSRGLAYLHSQKIAHRDVKTENMLLDKQMRVKIADFGVARVEASN
SEQ ID NO:54  (170)  LAKRQNKSVPLRLAVKQALDVARGMAYVHALGFIHRDLKSDNLLIAADRSIKIADFGVARIEVKT
SEQ ID NO:52  (170)  LIRNRRKKLPYKVVIQLALDLSRGLSYLHSKKIVHRDVKSENMLLDNHRNLRIADFGVARVEAQN
SEQ ID NO:58  (182)  LIKNRRKKLAFKVVVQIALDLARGLSYLHSKKIVHRDVKTENMLLDKTRTVKIADFGVARLEASN
SEQ ID NO:60  (187)  LIKNRRRKLAFKVVVQIALDLARGLCYLHSKKIVHRDVKTENMLLDKTRTVKIADFGVARVEASN
SEQ ID NO:56  (176)  LIKNRRRKLAYKVVVQIALDLARGLNYLHSRKIVHRDVKTENMLLDTQRNLKIADFGVARVEAQN

SEQ ID NO:50  (226)  PKDMTGDTGTPGYMAPEILDGKPYNKKCDVYSFGICLWEVYCCDMPYLDLSFADMTSAVVHQNLR
SEQ ID NO:54  (235)  EG-MTPETGTYRWMAPEMIQHRPYDHKVDVYSFGIVLWELITGMLPFTNMTAVQAAFAVVNKGAR
SEQ ID NO:52  (235)  PSDMTGETGTLGYMAPEVLDGKPYNRRCDVYSFGICLWEIYCCDMPYPDLSFADVTSAVVRQNLR
SEQ ID NO:58  (247)  PSDMTGETGTLGYMTPEVLNGNPYNRKCDVYSFGICLWEIYCCDMPYPDLSFSEVTSAVVRQNLR
SEQ ID NO:60  (252)  PSDMTGETGTLGYMAPEVLNGHAYNRKCDVYSFGICLWEIYCCDMPYPDLSFSEVTSAVVRQNLR
SEQ ID NO:56  (241)  PKDMTGATGTLGYMAPEVLEGKPYNRKCDVYSFGICLWEIYCCDMPYPDLSFADVSSAVVHQNLR

SEQ ID NO:50  (291)  PEVPKCCPQGLADIMRQCWDANPEKRPAMADVVQMLEALDTSKGGGMIPTDAQPHGCLCFGRFKG
SEQ ID NO:54  (299)  PAIPHDCLPSLTHIMTRCWDANPEVRPPFTEIVCMLENAEMEVVSHVRK--ARFRCCVAEPMTTD
SEQ ID NO:52  (300)  PEIPRCCPSSLGSIMKKCWDAQSENRPEMAEVVKMLEAIDTSKGGGMIPEDQNPG-CFCFAPTRG
SEQ ID NO:58  (312)  PEIPRCCPSSLSNVMKRCWDANPDKRPEMAEAVSMLEAIDTSKGGGMIPVDQRPGCLACFRQYRG
SEQ ID NO:60  (317)  PEIPRCCPSSLANVMKRCWDANPDKRPEMAEVVSMLEAIDTSKGGGMIPKDQTQGCLSCFRQYRG
SEQ ID NO:56  (306)  PDIPRCCPSPMANIMRKCWDANPDKRPDMDDVVRFLEALDTSKGGGMIP-EGQAGGCLCFFRARG

SEQ ID NO:50  (356)  P-
SEQ ID NO:54  (362)  --
SEQ ID NO:52  (364)  P-
SEQ ID NO:58  (377)  P-
SEQ ID NO:60  (382)  P-
SEQ ID NO:56  (370)  P-
```

Figure 5

```
SEQ ID NO:74    (1)   -MPSHGDLDRQIAQLRDCKYLPEAEVKALCEQAKAILMEEWNVQPVRCPVTVCGDIHGQFYDLIE
SEQ ID NO:90    (1)   -MPSHGDLDRQIAQLRDCKYLPEAEVKALCEQAKAILMEEWNVQPVRCPVTVCGDIHGQFYDLIE
SEQ ID NO:88    (1)   -MPSHGDLDRQIAQLRDCKYLPEAEVKVLCEQAKAILMEEWNVQPVRCPVTVCGDIHGQFYDLIE
SEQ ID NO:84    (1)   MPSSHGDLDRQIAQLRECKHLAEGEVRALCEQAKAILMEEWNVQPVRCPVTVCGDIHGQFYDLIE
SEQ ID NO:76    (1)   -MPPNGDLDRQISQLMECKPLSEADVKTLCDQARAILVEEWNVQPVKCPVTVCGDIHGQFYDLIE
SEQ ID NO:78    (1)   -MPPNGDLDRQIEHLMECKPLSEEDVRTLCDQAKAILVEEWNVQPVKCPVTVCGDIHGQFYDLIE
SEQ ID NO:80    (1)   -MPSQSDLDRQIEHLMDCKPLPEAEVRTLCDQARTILVEEWNVQPVKCPVTVCGDIHGQFHDLLE
SEQ ID NO:82    (1)   -MPSHADLDRQIEHLMQCKPLSEAEVKALCEQARAVLVEEWNVQPVKCPVTVCGDIHGQFHDLVE
SEQ ID NO:86    (1)   -MPSHADLERQIEQLMECKPLSESEVKALCDQARAILVEEWNVQPVKCPVTVCGDIHGQFYDLIE

SEQ ID NO:74   (65)   LFRIGGDAPDTNYLFMGDYVDRGYYSVETVSLLVALKVRYRDRITILRGNHESRQITQVYGFYDE
SEQ ID NO:90   (65)   LFRIGGDAPDTNYLFMGDYVDRGYYSVETVSLLVALKVRYRDRITILRGNHESRQITQVYGFYDE
SEQ ID NO:88   (65)   LFRIGGDSPDTNYLFMGDYVDRGYYSVETVSLLVALKVRYRDRITILRGNHESRQITQVYGFYDE
SEQ ID NO:84   (66)   LFRIGGEAPDTNYLFMGDYVDRGYYSVETVSLLVALKVRYRDRITILRGNHESRQITQVYGFYDE
SEQ ID NO:76   (65)   LFRIGGNPPDTNYLFMGDYVDRGYYSVETVSLLVALKVRYRDRITILRGNHESRQITQVYGFYDE
SEQ ID NO:78   (65)   LFRIGGNAPDTNYLFMGDYVDRGYYSVETVSLLVALKVRYRDRITILRGNHESRQITQVYGFYDE
SEQ ID NO:80   (65)   LFRIGGSAPDTNYLFMGDYVDRGYYSVETVTLLVALKVRYRDRITILRGNHESRQITQVYGFYDE
SEQ ID NO:82   (65)   LFRIGGNAPDTNYLFMGDYVDRGYYSVETVTLLVALKVRYRDRITILRGNHESRQITQVYGFYDE
SEQ ID NO:86   (65)   LFRIGGNAPDTNYLFMGDYVDRGYYSVETVTLLVALKVRYRDRITILRGNHESRQITQVYGFYDE

SEQ ID NO:74  (130)   CLRKYGNANVWKYFTDLFDFLPLTALIENQVFCLHGGLSPSLDTLDNIRSLDRVQEVPHEGPMCD
SEQ ID NO:90  (130)   CLRKYGNANVWKYFTDLFDFLPLTALIENQVFCLHGGLSPSLDTLDNIRSLDRVQEVPHEGPMCD
SEQ ID NO:88  (130)   CLRKYGNANVWKYFTDLFDYLPLTALIENQVFCLHGGLSPSLDTLDNIRSLDRIQEVPHEGPMCD
SEQ ID NO:84  (131)   CLRKYGNANVWKYFTDLFDYLPLTALIENQVFCLHGGLSPSLDTLDNIRALDRIQEVPHEGPMCD
SEQ ID NO:76  (130)   CLRKYGNANVWKFFTDLFDYLPLTALIESQVFCLHGGLSPSLDTLDNIRSLDRIQEVPHEGPMCD
SEQ ID NO:78  (130)   CLRKYGNANVWKYFTDLFDYLPLTALIESQVFCLHGGLSPSLDTLDNIRSLDRIQEVPHEGPMCD
SEQ ID NO:80  (130)   CLRKYGNANVWKHFTDLFDYLPLTALIESQIFCLHGGLSPSLDTLDNIRALDRIQEVPHEGPMCD
SEQ ID NO:82  (130)   CLRKYGNANVWKHFTDLFDYLPLTALIESQVFCLHGGLSPSLDTLDNIRSLDRIQEVPHEGPMCD
SEQ ID NO:86  (130)   CLRKYGNANVWKYFTDLFDYLPLTALIESQIFCLHGGLSPSLDTLDNIRALDRIQEVPHEGPMCD

SEQ ID NO:74  (195)   LLWSDPDDRCGWGISPRGAGYTFGQDIAQQFNHTNGLSLISRAHQLVMEGFNWCQDKNVVTVFSA
SEQ ID NO:90  (195)   LLWSDPDDRCGWGISPRGAGYTFGQDIAQQFNHTNGLSLISRAHQLVMEGFNWCQDKNVVTVFSA
SEQ ID NO:88  (195)   LLWSDPDDRCGWGISPRGAGYTFGQDIAQQFNHTNGLSLISRAHQLVMEGFNWCQDKNVVTVFSA
SEQ ID NO:84  (196)   LLWSDPDDRCGWGISPRGAGYTFGQDIAQQFNHTNGLSLISRAHQLVMEGFNWCQDKNVVTVFSA
SEQ ID NO:76  (195)   LLWSDPDDRCGWGISPRGAGYTFGQDIATQFNHNNGLSLISRAHQLVMEGFNWCQDKNVVTVFSA
SEQ ID NO:78  (195)   LLWSDPDDRCGWGISPRGAGYTFGQDIATQFNHNNGLSLISRAHQLVMEGFNWCQDKNVVTVFSA
SEQ ID NO:80  (195)   LLWSDPDDRCGWGISPRGAGYTFGQDIAAQFNHTNGLSLISRAHQLVMEGYNWSQENNVVTIFSA
SEQ ID NO:82  (195)   LLWSDPDDRCGWGISPRGAGYTFGQDISQQFNHTNGLSLISRAHQLVMEGYNWAQDKNVVTVFSA
SEQ ID NO:86  (195)   LLWSDPDDRCGWGISPRGAGYTFGQDIAQQFNHTNGLSLISRAHQLVMEGFNWCQDKNVVTVFSA

SEQ ID NO:74  (260)   PNYCYRCGNMAAILEIGENMDQNFLQFDPAPRQIEPDTTRKTPDYFL-
SEQ ID NO:90  (260)   PNYCYRCGNMAAILEIGKNMDQNFLQFDPAPRQIEPDTTRKTPDYFL-
SEQ ID NO:88  (260)   PNYCYRCGNMAAILEIGENMDQNFLQFNPAPRQIEPDTTRKTPDYFL-
SEQ ID NO:84  (261)   PNYCYRCGNMAAILEIGENMDQNFLQFDPAPRQIEPDTTRKTPDYFL-
SEQ ID NO:76  (260)   PNYCYRCGNMAAILEIGENMDQNFLQFDPAPRQVEPDTTRKTPDYFL-
SEQ ID NO:78  (260)   PNYCYRCGNMAAILEISENMEQNFLQFDPAPRQVEPDTTRKTPDYFL-
SEQ ID NO:80  (260)   PNYCYRCGNMAAILEVGENMDQNFLQFDPAPRQVEPDVARRTPDYFL-
SEQ ID NO:82  (260)   PNYCYRCGNMAAILEIGENMEQNFLQFDPAPRQIEPETTRRTPDYFL-
SEQ ID NO:86  (260)   PNYCYRCGNMAAILEIGENMDQNFLQFDPAPRQIEPDTTRKTPDYFL-
```

Figure 6

```
SEQ ID NO:92   (1)   MKGKKPVKELKLTVPAQETPVDKFLTASGTFKDGELRLNQSGLRLISEENGDEDESTKLKVEDVQ
SEQ ID NO:96   (1)   ---MKPIQPPPGVIGPVKNRPRRRPDLSLPLPHRDVSLAVP-LPLPPTSGGGS-------TTSEP
SEQ ID NO:94   (1)   -MKRGSLSLNPISLPPPEQSISKFLTQSGTFKDGDLQVNKDGIQTVSHSEPGAP--PPIDPLDNQ
SEQ ID NO:100  (1)   --MATPRKPIKLTLPSHETTIGKFLTHSGTFTDGDLRVNKDGLRIVSRREGGE--APPIEPLDSQ

SEQ ID NO:92   (66)  LSMDDLEMIQVIGKGSGGVVQLVRHKWVGTLFALKGIQMNIQESVRKQIVQELKINQATQSPHIV
SEQ ID NO:96   (55)  KSYSDLVRGNRIGSGAGGTVYRVVHRPTSRVYALKIINGNHDDTVRGQICREIKILRDVNHPNVV
SEQ ID NO:94   (63)  LSLADLEVIKVIGKGSSGSVQLVKHKLTQQFFATKVIQLNTEESTCRAISQELRINLASQCPYLV
SEQ ID NO:100  (62)  LSLDDLDVIKVIGKGSSGNVQLVRHKFTGQFFALKVIQLNIDESIRKQIAKELKINLSTQCQYVV

SEQ ID NO:92   (131) MCHQSFYHNGVIYLVLEYMDRGSLADIVKQVKTILEPYLAVLCKQVLEGLLYLHHQRHVIHRDIK
SEQ ID NO:96   (120) KCHEMFDQNGEIQVLLELMDQGSLEGAHIS----NEQQLSDLSRQILNGLAYLHG-RHIVHRDIK
SEQ ID NO:94   (128) SCYQSFYHNGLVSIVMEFMDGGSLLDLLKKVQRVPENMLAAISKRVLRGLCYIHDERRIIHRDLK
SEQ ID NO:100  (127) VFYQCFYFNGAISIVLEYMDGGSLADFLKTVKTIPEAYLAAICTQMLKGLIYLHNEKRVIHRDLK

SEQ ID NO:92   (196) PSNLLVNRKGEVKITDFGVSAVLASSIGQRDTFVGTYNYMAPERI-----SGSTYDYKSDIWSLG
SEQ ID NO:96   (180) PSNLLINSDNNVKIADFGVSRVLAQTLSPCKSSVGTIAYMSPERINTDLNQGMYDGCAGDIWSFG
SEQ ID NO:94   (193) PSNLLINHRGEVKIADFGVSKILSSTSSLAHTFVGTDFYMSPERI-----SGKAYGNKCDIWSLG
SEQ ID NO:100  (192) PSNILINHRGEVKISDFGVSAIISSSSSQRDTFIGTRNYMAPERI-----DGKKHGSMSDIWSLG

SEQ ID NO:92   (256) LVILECAIGRFPYIPSEGEG-WLSFYELLEAIVDQPPPSAPADQFSPEFCSFISSCIQKDPAQRM
SEQ ID NO:96   (245) VSVLEFFLGRFPFNVNRLG----DWASLMCAICMSKPPEAPAT-ASPEFRHFVSCCLQREPGRRQ
SEQ ID NO:94   (253) VVLLECATGKFPYTPPENMKGWTSMYELVDAIVENPPPRAPSHLFSPEFCSFISQCVQKDPRDRK
SEQ ID NO:100  (252) LVILECATGIFPFPPCES------FYELLAVVDQPPPSAPPDQFSPEFCGFISACLQKDANDRS

SEQ ID NO:92   (320) SASELLNHPFLKKFEDKDLNLGILVENLEPPMNIPE-----
SEQ ID NO:96   (305) TAVQLLQHPFVRRGAIQSQNRSP--QNLHQLLPPPH-----
SEQ ID NO:94   (318) SAMELLDHRFVNMFEDVDVDLSSYFTAAGSLIPPLANS---
SEQ ID NO:100  (311) SAQALLDHPFLSMYDDLHVDLASYFTTAGSPLATFNSRQL-
```

TRANSGENIC PLANTS WITH INCREASED STRESS TOLERANCE AND YIELD

This application is a national stage application under 35 U.S.C. §371 of PCT/EP2008/059070, filed Jul. 11, 2008, which claims benefit of U.S. provisional application No. 60/959,346, filed Jul. 13, 2007. The entire contents of the above-identified applications are incorporated herein by reference.

FIELD OF THE INVENTION

This invention relates generally to transgenic plants which overexpress nucleic acid sequences encoding polypeptides capable of conferring increased stress tolerance and consequently, increased plant growth and crop yield, under normal or abiotic stress conditions. Additionally, the invention relates to novel isolated nucleic acid sequences encoding polypeptides that confer upon a plant increased tolerance under abiotic stress conditions, and/or increased plant growth and/or increased yield under normal or abiotic stress conditions.

BACKGROUND OF THE INVENTION

Abiotic environmental stresses, such as drought, salinity, heat, and cold, are major limiting factors of plant growth and crop yield. Crop yield is defined herein as the number of bushels of relevant agricultural product (such as grain, forage, or seed) harvested per acre. Crop losses and crop yield losses of major crops such as soybean, rice, maize (corn), cotton, and wheat caused by these stresses represent a significant economic and political factor and contribute to food shortages in many underdeveloped countries.

Water availability is an important aspect of the abiotic stresses and their effects on plant growth. Continuous exposure to drought conditions causes major alterations in the plant metabolism which ultimately lead to cell death and consequently to yield losses. Because high salt content in some soils results in less water being available for cell intake, high salt concentration has an effect on plants similar to the effect of drought on plants. Additionally, under freezing temperatures, plant cells lose water as a result of ice formation within the plant. Accordingly, crop damage from drought, heat, salinity, and cold stress, is predominantly due to dehydration.

Because plants are typically exposed to conditions of reduced water availability during their life cycle, most plants have evolved protective mechanisms against desiccation caused by abiotic stresses. However, if the severity and duration of desiccation conditions are too great, the effects on development, growth, plant size, and yield of most crop plants are profound. Developing plants efficient in water use is therefore a strategy that has the potential to significantly improve human life on a worldwide scale.

Traditional plant breeding strategies are relatively slow and require abiotic stress-tolerant founder lines for crossing with other germplasm to develop new abiotic stress-resistant lines. Limited germplasm resources for such founder lines and incompatibility in crosses between distantly related plant species represent significant problems encountered in conventional breeding. Breeding for tolerance has been largely unsuccessful.

Many agricultural biotechnology companies have attempted to identify genes that could confer tolerance to abiotic stress responses, in an effort to develop transgenic abiotic stress-tolerant crop plants. Although some genes that are involved in stress responses or water use efficiency in plants have been characterized, the characterization and cloning of plant genes that confer stress tolerance and/or water use efficiency remains largely incomplete and fragmented. To date, success at developing transgenic abiotic stress-tolerant crop plants has been limited, and no such plants have been commercialized.

In order to develop transgenic abiotic stress-tolerant crop plants, it is necessary to assay a number of parameters in model plant systems, greenhouse studies of crop plants, and in field trials. For example, water use efficiency (WUE), is a parameter often correlated with drought tolerance. Studies of a plant's response to desiccation, osmotic shock, and temperature extremes are also employed to determine the plant's tolerance or resistance to abiotic stresses. When testing for the impact of the presence of a transgene on a plant's stress tolerance, the ability to standardize soil properties, temperature, water and nutrient availability and light intensity is an intrinsic advantage of greenhouse or plant growth chamber environments compared to the field.

WUE has been defined and measured in multiple ways. One approach is to calculate the ratio of whole plant dry weight, to the weight of water consumed by the plant throughout its life. Another variation is to use a shorter time interval when biomass accumulation and water use are measured. Yet another approach is to use measurements from restricted parts of the plant, for example, measuring only aerial growth and water use. WUE also has been defined as the ratio of $CO_2$ uptake to water vapor loss from a leaf or portion of a leaf, often measured over a very short time period (e.g. seconds/minutes). The ratio of $^{13}C/^{12}C$ fixed in plant tissue, and measured with an isotope ratio mass-spectrometer, also has been used to estimate WUE in plants using $C_3$ photosynthesis.

An increase in WUE is informative about the relatively improved efficiency of growth and water consumption, but this information taken alone does not indicate whether one of these two processes has changed or both have changed. In selecting traits for improving crops, an increase in WUE due to a decrease in water use, without a change in growth would have particular merit in an irrigated agricultural system where the water input costs were high. An increase in WUE driven mainly by an increase in growth without a corresponding jump in water use would have applicability to all agricultural systems. In many agricultural systems where water supply is not limiting, an increase in growth, even if it came at the expense of an increase in water use (i.e. no change in WUE), could also increase yield. Therefore, new methods to increase both WUE and biomass accumulation are required to improve agricultural productivity.

Concomitant with measurements of parameters that correlate with abiotic stress tolerance are measurements of parameters that indicate the potential impact of a transgene on crop yield. For forage crops like alfalfa, silage corn, and hay, the plant biomass correlates with the total yield. For grain crops, however, other parameters have been used to estimate yield, such as plant size, as measured by total plant dry weight, above-ground dry weight, above-ground fresh weight, leaf area, stem volume, plant height, rosette diameter, leaf length, root length, root mass, tiller number, and leaf number. Plant size at an early developmental stage will typically correlate with plant size later in development. A larger plant with a greater leaf area can typically absorb more light and carbon dioxide than a smaller plant and therefore will likely gain a greater weight during the same period. This is in addition to the potential continuation of the micro-environmental or genetic advantage that the plant had to achieve the larger size initially. There is a strong genetic component to plant size and growth rate, and so for a range of diverse genotypes plant size under one environmental condition is likely to correlate with size under another. In this way a standard environment is used to approximate the diverse and dynamic environments encountered at different locations and times by crops in the field.

Harvest index, the ratio of seed yield to above-ground dry weight, is relatively stable under many environmental conditions and so a robust correlation between plant size and grain yield is possible. Plant size and grain yield are intrinsically linked, because the majority of grain biomass is dependent on current or stored photosynthetic productivity by the leaves and stem of the plant. Therefore, selecting for plant size, even at early stages of development, has been used as to screen for plants that may demonstrate increased yield when exposed to field testing. As with abiotic stress tolerance, measurements of plant size in early development, under standardized conditions in a growth chamber or greenhouse, are standard practices to measure potential yield advantages conferred by the presence of a transgene.

There is a need, therefore, to identify additional genes expressed in stress tolerant plants and/or plants that are efficient in water use that have the capacity to confer stress tolerance and/or increased water use efficiency to the host plant and to other plant species. Newly generated stress tolerant plants and/or plants with increased water use efficiency will have many advantages, such as an increased range in which the crop plants can be cultivated, by for example, decreasing the water requirements of a plant species. Other desirable advantages include increased resistance to lodging, the bending of shoots or stems in response to wind, rain, pests, or disease.

SUMMARY OF THE INVENTION

The present inventors have discovered that transforming a plant with certain polynucleotides results in enhancement of the plant's growth and response to environmental stress, and accordingly the yield of the agricultural products of the plant is increased, when the polynucleotides are present in the plant as transgenes. The polynucleotides capable of mediating such enhancements have been isolated from *Arabidopsis thaliana*, *Capsicum annuum*, *Escherichia coli*, *Physcomitrella patens*, *Saccharomyces cerevisiae*, *Triticum aestivum*, *Zea mays*, *Glycine max*, *Linum usitatissimum*, *Triticum aestivum*, *Oryza sativa*, *Helianthus annuus*, and *Brassica napus* and the sequences thereof are set forth in the Sequence Listing as indicated in Table 1.

TABLE 1

| Gene Name | Organism | Polynucleotide SEQ ID NO | Amino acid SEQ ID NO |
|---|---|---|---|
| At2g20725 | A. thaliana | 1 | 2 |
| At3g26085 | A. thaliana | 3 | 4 |
| AtFACE-2 | A. thaliana | 5 | 6 |
| ZM57353913 | Z. mays | 7 | 8 |
| ZM59252659 | Z. mays | 9 | 10 |
| CASAR82A | C. annuum | 11 | 12 |
| b3358 | E. coli | 13 | 14 |
| EST564 | P. patens | 15 | 16 |
| BN49502266 | B. napus | 17 | 18 |
| GM49788080 | G. max | 19 | 20 |
| GM53049821 | G. max | 21 | 22 |
| ZM58462719 | Z. mays | 23 | 24 |
| ZM61092633 | Z. mays | 25 | 26 |
| ZM62016485 | Z. mays | 27 | 28 |
| ZM62051019 | Z. mays | 29 | 30 |
| ZM65086957 | Z. mays | 31 | 32 |
| ZM68587657 | Z. mays | 33 | 34 |

TABLE 1-continued

| Gene Name | Organism | Polynucleotide SEQ ID NO | Amino acid SEQ ID NO |
|---|---|---|---|
| EST390 | P. patens | 35 | 36 |
| BN51363030 | B. napus | 37 | 38 |
| BN42986056 | B. napus | 39 | 40 |
| BN49389066 | B. napus | 41 | 42 |
| BN51339479 | B. napus | 43 | 44 |
| ZM57651070 | Z. mays | 45 | 46 |
| ZM62073276 | Z. mays | 47 | 48 |
| EST257 | P. patens | 49 | 50 |
| LU61665952 | L. usitatissimum | 51 | 52 |
| TA56863186 | T. aestivum | 53 | 54 |
| ZM62026837 | Z. mays | 55 | 56 |
| ZM65457595 | Z. mays | 57 | 58 |
| ZM67230154 | Z. mays | 59 | 60 |
| EST465 | P. patens | 61 | 62 |
| YBL109w | S. cerevisiae | 63 | 64 |
| YBL100c | S. cerevisiae | 65 | 66 |
| YKL184w | S. cerevisiae | 67 | 68 |
| YPL091w | S. cerevisiae | 69 | 70 |
| TA54587433 | T. aestivum | 71 | 72 |
| ZM68532504 | Z. mays | 73 | 74 |
| BN42856089 | B. napus | 75 | 76 |
| BN43206527 | B. napus | 77 | 78 |
| HA66872964 | H. annuus | 79 | 80 |
| LU61662612 | L. usitatissimum | 81 | 82 |
| OS32806943 | O. sativa | 83 | 84 |
| OS34738749 | O. sativa | 85 | 86 |
| ZM59400933 | Z. mays | 87 | 88 |
| ZM62132060 | Z. mays | 89 | 90 |
| ZM59202533 | Z. mays | 91 | 92 |
| BN41901422 | B. napus | 93 | 94 |
| BN47868329 | B. napus | 95 | 96 |
| BN42671700 | B. napus | 97 | 98 |
| ZM68416988 | Z. mays | 99 | 100 |

In one embodiment, the invention provides a transgenic plant transformed with an expression cassette comprising an isolated polynucleotide encoding a CAAX amino terminal protease family protein.

In another embodiment, the invention provides a transgenic plant transformed with an expression cassette comprising an isolated polynucleotide encoding a prenyl-dependent CAAX protease.

In another embodiment, the invention provides a transgenic plant transformed with an expression cassette comprising an isolated polynucleotide encoding a SAR8.2 protein precursor.

In another embodiment, the invention provides a transgenic plant transformed with an expression cassette comprising an isolated polynucleotide encoding a putative membrane protein.

In another embodiment, the invention provides a transgenic plant transformed with an expression cassette comprising an isolated polynucleotide encoding a protein phosphatase 2C protein.

In another embodiment, the invention provides a transgenic plant transformed with an expression cassette comprising an isolated polynucleotide encoding a mitochondrial carrier protein.

In another embodiment, the invention provides a transgenic plant transformed with an expression cassette comprising an isolated polynucleotide encoding a protein kinase.

In another embodiment, the invention provides a transgenic plant transformed with an expression cassette comprising an isolated polynucleotide encoding a peptidyl prolyl isomerase.

In another embodiment, the invention provides a transgenic plant transformed with an expression cassette comprising an isolated polynucleotide encoding a unknown protein 1.

In another embodiment, the invention provides a transgenic plant transformed with an expression cassette comprising an isolated polynucleotide encoding a unknown protein 2.

In another embodiment, the invention provides a transgenic plant transformed with an expression cassette comprising an isolated polynucleotide encoding a ornithine decarboxylase.

In another embodiment, the invention provides a transgenic plant transformed with an expression cassette comprising an isolated polynucleotide encoding a glutathione reductase.

In another embodiment, the invention provides a transgenic plant transformed with an expression cassette comprising an isolated polynucleotide encoding a unknown protein 3.

In another embodiment, the invention provides a transgenic plant transformed with an expression cassette comprising an isolated polynucleotide encoding a protein phosphatase 2A protein.

In another embodiment, the invention provides a transgenic plant transformed with an expression cassette comprising an isolated polynucleotide encoding a MEK1 protein kinase.

In another embodiment, the invention provides a transgenic plant transformed with an expression cassette comprising an isolated polynucleotide encoding a AP2 domain containing transcription factor.

In a further embodiment, the invention concerns a seed produced by the transgenic plant of the invention, wherein the seed is true breeding for a transgene comprising the polynucleotide described above. Plants derived from the seed of the invention demonstrate increased tolerance to an environmental stress, and/or increased plant growth, and/or increased yield, under normal or stress conditions as compared to a wild type variety of the plant.

In a still another aspect, the invention concerns products produced by or from the transgenic plants of the invention, their plant parts, or their seeds, such as a foodstuff, feedstuff, food supplement, feed supplement, cosmetic or pharmaceutical.

The invention further provides certain isolated polynucleotides identified in Table 1, and certain isolated polypeptides identified in Table 1. The invention is also embodied in recombinant vector comprising an isolated polynucleotide of the invention.

In yet another embodiment, the invention concerns a method of producing the aforesaid transgenic plant, wherein the method comprises transforming a plant cell with an expression vector comprising an isolated polynucleotide of the invention, and generating from the plant cell a transgenic plant that expresses the polypeptide encoded by the polynucleotide. Expression of the polypeptide in the plant results in increased tolerance to an environmental stress, and/or growth, and/or yield under normal and/or stress conditions as compared to a wild type variety of the plant.

In still another embodiment, the invention provides a method of increasing a plant's tolerance to an environmental stress, and/or growth, and/or yield. The method comprises the steps of transforming a plant cell with an expression cassette comprising an isolated polynucleotide of the invention, and generating a transgenic plant from the plant cell, wherein the transgenic plant comprises the polynucleotide.

BRIEF DESCRIPTION OF THE DRAWINGS

FIG. 1 shows an alignment of the disclosed amino acid sequences AtFACE-2 (SEQ ID NO:6), ZM57353913 (SEQ ID NO:8), and ZM59252659 (SEQ ID NO:10). The alignment was generated using Align X of Vector NTI.

FIG. 2 shows an alignment of the disclosed amino acid sequences EST564 (SEQ ID NO:16), BN49502266 (SEQ ID NO:18), GM49788080 (SEQ ID NO:20), GM53049821 (SEQ ID NO:22), ZM58462719 (SEQ ID NO:24), ZM61092633 (SEQ ID NO:26), ZM62016485 (SEQ ID NO:28), ZM62051019 (SEQ ID NO:30), ZM65086957 (SEQ ID NO:32), and ZM68587657 (SEQ ID NO:34). The alignment was generated using Align X of Vector NTI.

FIG. 3 shows an alignment of the disclosed amino acid sequences EST390 (SEQ ID NO:36), BN51363030 (SEQ ID NO:38), BN42986056 (SEQ ID NO:40), BN49389066 (SEQ ID NO:42), BN51339479 (SEQ ID NO:44), ZM57651070 (SEQ ID NO:46), and ZM62073276 (SEQ ID NO:48). The alignment was generated using Align X of Vector NTI.

FIG. 4 shows an alignment of the disclosed amino acid sequences EST257 (SEQ ID NO:50), LU61665952 (SEQ ID NO:52), TA56863186 (SEQ ID NO:54), ZM62026837 (SEQ ID NO:56), ZM65457595 (SEQ ID NO:58), ZM67230154 (SEQ ID NO:60). The alignment was generated using Align X of Vector NTI.

FIG. 5 shows an alignment of the disclosed amino acid sequences ZM68532504 (SEQ ID NO:74), BN42856089 (SEQ ID NO:76), BN43206527 (SEQ ID NO:78), HA66872964 (SEQ ID NO:80), LU61662612 (SEQ ID NO:82), OS32806943 (SEQ ID NO:84), OS34738749 (SEQ ID NO:86), ZM59400933 (SEQ ID NO:88), and ZM62132060 (SEQ ID NO:90). The alignment was generated using Align X of Vector NTI.

FIG. 6 shows an alignment of the disclosed amino acid sequences ZM59202533 (SEQ ID NO:92), BN41901422 (SEQ ID NO:94), BN47868329 (SEQ ID NO:96), and ZM68416988 (SEQ ID NO:100). The alignment was generated using Align X of Vector NTI.

DETAILED DESCRIPTION OF THE PREFERRED EMBODIMENTS

Throughout this application, various publications are referenced. The disclosures of all of these publications and those references cited within those publications in their entireties are hereby incorporated by reference into this application in order to more fully describe the state of the art to which this invention pertains. The terminology used herein is for the purpose of describing specific embodiments only and is not intended to be limiting. As used herein, "a" or "an" can mean one or more, depending upon the context in which it is used. Thus, for example, reference to "a cell" can mean that at least one cell can be used.

In one embodiment, the invention provides a transgenic plant that overexpresses an isolated polynucleotide identified in Table 1, or a homolog thereof. The transgenic plant of the invention demonstrates an increased tolerance to an environmental stress as compared to a wild type variety of the plant. The overexpression of such isolated nucleic acids in the plant may optionally result in an increase in plant growth or in yield of associated agricultural products, under normal or stress conditions, as compared to a wild type variety of the plant.

As defined herein, a "transgenic plant" is a plant that has been altered using recombinant DNA technology to contain an isolated nucleic acid which would otherwise not be present in the plant. As used herein, the term "plant" includes a whole plant, plant cells, and plant parts. Plant parts include, but are not limited to, stems, roots, ovules, stamens, leaves, embryos, meristematic regions, callus tissue, gametophytes, sporophytes, pollen, microspores, and the like. The transgenic plant of the invention may be male sterile or male fertile, and may further include transgenes other than those that comprise the isolated polynucleotides described herein.

As used herein, the term "variety" refers to a group of plants within a species that share constant characteristics that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more isolated polynucleotides introduced into a plant variety. As also used herein, the term "wild type variety" refers to a group of plants that are analyzed for comparative purposes as a control plant, wherein the wild type variety plant is identical to the transgenic plant (plant transformed with an isolated polynucleotide in accordance with the invention) with the exception that the wild type variety plant has not been transformed with an isolated polynucleotide of the invention.

As defined herein, the term "nucleic acid" and "polynucleotide" are interchangeable and refer to RNA or DNA that is linear or branched, single or double stranded, or a hybrid thereof. The term also encompasses RNA/DNA hybrids. An "isolated" nucleic acid molecule is one that is substantially separated from other nucleic acid molecules which are present in the natural source of the nucleic acid (i.e., sequences encoding other polypeptides). For example, a cloned nucleic acid is considered isolated. A nucleic acid is also considered isolated if it has been altered by human intervention, or placed in a locus or location that is not its natural site, or if it is introduced into a cell by transformation. Moreover, an isolated nucleic acid molecule, such as a cDNA molecule, can be free from some of the other cellular material with which it is naturally associated, or culture medium when produced by recombinant techniques, or chemical precursors or other chemicals when chemically synthesized. While it may optionally encompass untranslated sequence located at both the 3' and 5' ends of the coding region of a gene, it may be preferable to remove the sequences which naturally flank the coding region in its naturally occurring replicon.

As used herein, the term "environmental stress" refers to a sub-optimal condition associated with salinity, drought, nitrogen, temperature, metal, chemical, pathogenic, or oxidative stresses, or any combination thereof. The terms "water use efficiency" and "WUE" refer to the amount of organic matter produced by a plant divided by the amount of water used by the plant in producing it, i.e., the dry weight of a plant in relation to the plant's water use. As used herein, the term "dry weight" refers to everything in the plant other than water, and includes, for example, carbohydrates, proteins, oils, and mineral nutrients.

Any plant species may be transformed to create a transgenic plant in accordance with the invention. The transgenic plant of the invention may be a dicotyledonous plant or a monocotyledonous plant. For example and without limitation, transgenic plants of the invention may be derived from any of the following diclotyledonous plant families: Leguminosae, including plants such as pea, alfalfa and soybean; Umbelliferae, including plants such as carrot and celery; Solanaceae, including the plants such as tomato, potato, aubergine, tobacco, and pepper; Cruciferae, particularly the genus *Brassica*, which includes plant such as oilseed rape, beet, cabbage, cauliflower and broccoli); and *A. thaliana*; Compositae, which includes plants such as lettuce; Malvaceae, which includes cotton; Fabaceae, which includes plants such as peanut, and the like. Transgenic plants of the invention may be derived from monocotyledonous plants, such as, for example, wheat, barley, sorghum, millet, rye, triticale, maize, rice, oats and sugarcane. Transgenic plants of the invention are also embodied as trees such as apple, pear, quince, plum, cherry, peach, nectarine, apricot, papaya, mango, and other woody species including coniferous and deciduous trees such as poplar, pine, sequoia, cedar, oak, and the like. Especially preferred are *Arabidopsis thaliana, Nicotiana tabacum*, oilseed rape, soybean, corn (maize), wheat, linseed, potato and tagetes.

As shown in Table 1, one embodiment of the invention is a transgenic plant transformed with an expression cassette comprising an isolated polynucleotide encoding a CAAX amino terminal protease family protein. The transgenic plant of this embodiment may comprise any polynucleotide encoding a CAAX amino terminal protease family protein. The transgenic plant of this embodiment comprises a polynucleotide encoding a CAAX amino terminal protease family protein having a sequence comprising amino acids 1 to 301 of SEQ ID NO:2; and a protein having a sequence comprising amino acids 1 to 293 of SEQ ID NO:4.

In another embodiment, the invention provides a transgenic plant transformed with an expression cassette comprising an isolated polynucleotide encoding a prenyl-dependent CAAX protease. The transgenic plant of this embodiment may comprise any polynucleotide encoding a prenyl-dependent CAAX protease. The transgenic plant of this embodiment comprises a polynucleotide encoding a prenyl-dependent CAAX protease having a sequence comprising amino acids 1 to 311 of SEQ ID NO:6; a protein having a sequence comprising amino acids 1 to 313 of SEQ ID NO:8; a protein having a sequence comprising amino acids 1 to 269 of SEQ ID NO:10.

In another embodiment, the invention provides a transgenic plant transformed with an expression cassette comprising an isolated polynucleotide encoding a SAR8.2 protein precursor. The transgenic plant of this embodiment may comprise any polynucleotide encoding a SAR8.2 protein precursor. The transgenic plant of this embodiment comprises a polynucleotide encoding a SAR8.2 protein precursor having a sequence comprising amino acids 1 to 86 of SEQ ID NO:12.

In another embodiment, the invention provides a transgenic plant transformed with an expression cassette comprising an isolated polynucleotide encoding a putative membrane protein. The transgenic plant of this embodiment may comprise any polynucleotide encoding a putative membrane protein. The transgenic plant of this embodiment comprises a polynucleotide encoding a putative membrane protein having a sequence comprising amino acids 1 to 696 of SEQ ID NO:14.

In another embodiment, the invention provides a transgenic plant transformed with an expression cassette comprising an isolated polynucleotide encoding a protein phosphatase 2C protein. The transgenic plant of this embodiment may comprise any polynucleotide encoding a protein phosphatase 2C protein. The transgenic plant of this embodiment comprises a polynucleotide encoding a protein phosphatase 2C protein having a sequence comprising amino acids 1 to 284 of SEQ ID NO:16; a protein having a sequence comprising amino acids 1 to 384 of SEQ ID NO:18; a protein having a sequence comprising amino acids 1 to 346 of SEQ ID NO:20; a protein having a sequence comprising amino acids 1 to 375 of SEQ ID NO:22; a protein having a sequence comprising amino acids 1 to 390 of SEQ ID NO:24; a protein having a sequence comprising amino acids 1 to 398 of SEQ ID NO:26; a protein having a sequence comprising amino acids 1 to 399 of SEQ ID NO:28; a protein having a sequence comprising amino acids 1 to 399 of SEQ ID NO:30; a protein having a sequence comprising amino acids 1 to 399 of SEQ ID NO:32; a protein having a sequence comprising amino acids 1 to 276 of SEQ ID NO:34.

In another embodiment, the invention provides a transgenic plant transformed with an expression cassette comprising an isolated polynucleotide encoding a mitochondrial carrier protein. The transgenic plant of this embodiment may comprise any polynucleotide encoding a mitochondrial carrier protein. The transgenic plant of this embodiment comprises a polynucleotide encoding a mitochondrial carrier protein having a sequence comprising amino acids 1 to 303 of SEQ ID NO:36; a protein having a sequence comprising amino acids 1 to 315 of SEQ ID NO:38; a protein having a sequence comprising amino acids 1 to 289 of SEQ ID NO:40; a protein having a sequence comprising amino acids 1 to 303 of SEQ ID NO:42; a protein having a sequence comprising amino acids 1 to 299 of SEQ ID NO:44; a protein having a sequence comprising amino acids 1 to 299 of SEQ ID NO:46; a protein having a sequence comprising amino acids 1 to 311 of SEQ ID NO:48.

In another embodiment, the invention provides a transgenic plant transformed with an expression cassette comprising an isolated polynucleotide encoding a protein kinase. The transgenic plant of this embodiment may comprise any polynucleotide encoding a protein kinase. The transgenic plant of this embodiment comprises a polynucleotide encoding a protein kinase having a sequence comprising amino acids 1 to 356 of SEQ ID NO:50; a protein having a sequence comprising amino acids 1 to 364 of SEQ ID NO:52; a protein having a sequence comprising amino acids 1 to 361 of SEQ ID NO:54; a protein having a sequence comprising amino acids 1 to 370 of SEQ ID NO:56; a protein having a sequence comprising amino acids 1 to 377 of SEQ ID NO:58; a protein having a sequence comprising amino acids 1 to 382 of SEQ ID NO:60.

In another embodiment, the invention provides a transgenic plant transformed with an expression cassette comprising an isolated polynucleotide encoding a peptidyl prolyl isomerase. The transgenic plant of this embodiment may comprise any polynucleotide encoding a peptidyl prolyl isomerase. The transgenic plant of this embodiment comprises a polynucleotide encoding a peptidyl prolyl isomerase having a sequence comprising amino acids 1 to 523 of SEQ ID NO:62.

In another embodiment, the invention provides a transgenic plant transformed with an expression cassette comprising an isolated polynucleotide encoding an unknown protein 1. The transgenic plant of this embodiment may comprise any polynucleotide encoding an unknown protein 1. The transgenic plant of this embodiment comprises a polynucleotide encoding a unknown protein 1 having a sequence comprising amino acids 1 to 111 of SEQ ID NO:64.

In another embodiment, the invention provides a transgenic plant transformed with an expression cassette comprising an isolated polynucleotide encoding an unknown protein 2. The transgenic plant of this embodiment may comprise any polynucleotide encoding an unknown protein 2. The transgenic plant of this embodiment comprises a polynucleotide encoding a unknown protein 2 having a sequence comprising amino acids 1 to 104 of SEQ ID NO:66.

In another embodiment, the invention provides a transgenic plant transformed with an expression cassette comprising an isolated polynucleotide encoding a ornithine decarboxylase. The transgenic plant of this embodiment may comprise any polynucleotide encoding a ornithine decarboxylase. The transgenic plant of this embodiment comprises a polynucleotide encoding a ornithine decarboxylase having a sequence comprising amino acids 1 to 466 of SEQ ID NO:68.

In another embodiment, the invention provides a transgenic plant transformed with an expression cassette comprising an isolated polynucleotide encoding a glutathione reductase. The transgenic plant of this embodiment may comprise any polynucleotide encoding a glutathione reductase. The transgenic plant of this embodiment comprises a polynucleotide encoding a glutathione reductase having a sequence comprising amino acids 1 to 483 of SEQ ID NO:70.

In another embodiment, the invention provides a transgenic plant transformed with an expression cassette comprising an isolated polynucleotide encoding an unknown protein 3. The transgenic plant of this embodiment may comprise any polynucleotide encoding a unknown protein 3. The transgenic plant of this embodiment comprises a polynucleotide encoding a unknown protein 3 having a sequence comprising amino acids 1 to 129 of SEQ ID NO:72.

In another embodiment, the invention provides a transgenic plant transformed with an expression cassette comprising an isolated polynucleotide encoding a protein phosphatase 2A protein. The transgenic plant of this embodiment may comprise any polynucleotide encoding a protein phosphatase 2A protein. The transgenic plant of this embodiment comprises a polynucleotide encoding a protein phosphatase 2A protein having a sequence comprising amino acids 1 to 306 of SEQ ID NO:74; a protein having a sequence comprising amino acids 1 to 306 of SEQ ID NO:76; a protein having a sequence comprising amino acids 1 to 306 of SEQ ID NO:78; a protein having a sequence comprising amino acids 1 to 306 of SEQ ID NO:80; a protein having a sequence comprising amino acids 1 to 306 of SEQ ID NO:82; a protein having a sequence comprising amino acids 1 to 307 of SEQ ID NO:84; a protein having a sequence comprising amino acids 1 to 306 of SEQ ID NO:86; a protein having a sequence comprising amino acids 1 to 306 of SEQ ID NO:88; a protein having a sequence comprising amino acids 1 to 306 of SEQ ID NO:90.

In another embodiment, the invention provides a transgenic plant transformed with an expression cassette comprising an isolated polynucleotide encoding a MEK1 protein kinase. The transgenic plant of this embodiment may comprise any polynucleotide encoding a MEK1 protein kinase. The transgenic plant of this embodiment comprises a polynucleotide encoding a MEK1 protein kinase having a sequence comprising amino acids 1 to 355 of SEQ ID NO:92; a protein having a sequence comprising amino acids 1 to 355 of SEQ ID NO:94; a protein having a sequence comprising amino acids 1 to 338 of SEQ ID NO:96; a protein having a sequence comprising amino acids 1 to 350 of SEQ ID NO:100.

In another embodiment, the invention provides a transgenic plant transformed with an expression cassette comprising an isolated polynucleotide encoding an AP2 domain containing transcription factor. The transgenic plant of this embodiment may comprise any polynucleotide encoding a AP2 domain containing transcription factor. The transgenic plant of this embodiment comprises a polynucleotide encoding a AP2 domain containing transcription factor having a sequence comprising amino acids 1 to 197 of SEQ ID NO:98.

The invention further provides a seed produced by a transgenic plant expressing polynucleotide listed in Table 1, wherein the seed contains the polynucleotide, and wherein the plant is true breeding for increased growth and/or yield under normal or stress conditions and/or increased tolerance to an environmental stress as compared to a wild type variety of the plant. The invention also provides a product produced by or from the transgenic plants expressing the polynucleotide, their plant parts, or their seeds. The product can be obtained using various methods well known in the art. As used herein, the word "product" includes, but not limited to, a foodstuff, feedstuff, a food supplement, feed supplement, cosmetic or pharmaceutical. Foodstuffs are regarded as compositions used for nutrition or for supplementing nutrition. Animal feedstuffs and animal feed supplements, in particular, are regarded as foodstuffs. The invention further provides an agricultural product produced by any of the transgenic plants, plant parts, and plant seeds. Agricultural products include, but are not limited to, plant extracts, proteins, amino acids, carbohydrates, fats, oils, polymers, vitamins, and the like.

In a preferred embodiment, an isolated polynucleotide of the invention comprises a polynucleotide having a sequence selected from the group consisting of the polynucleotide sequences listed in Table 1. These polynucleotides may comprise sequences of the coding region, as well as 5' untranslated sequences and 3' untranslated sequences.

A polynucleotide of the invention can be isolated using standard molecular biology techniques and the sequence information provided herein, for example, using an automated DNA synthesizer.

"Homologs" are defined herein as two nucleic acids or polypeptides that have similar, or substantially identical, nucleotide or amino acid sequences, respectively. Homologs include allelic variants, analogs, and orthologs, as defined below. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. The term homolog further encompasses nucleic acid molecules that differ from one of the nucleotide sequences shown in Table 1 due to degeneracy of the genetic code and thus encode the same polypeptide. As used herein, a "naturally occurring" nucleic acid molecule refers to an RNA or DNA molecule having a nucleotide sequence that occurs in nature (e.g., encodes a natural polypeptide).

To determine the percent sequence identity of two amino acid sequences (e.g., one of the polypeptide sequences of Table 1 and a homolog thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence then the molecules are identical at that position. The same type of comparison can be made between two nucleic acid sequences.

Preferably, the isolated amino acid homologs, analogs, and orthologs of the polypeptides of the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence identified in Table 1. In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence shown in Table 1.

For the purposes of the invention, the percent sequence identity between two nucleic acid or polypeptide sequences is determined using the Vector NTI 9.0 (PC) software package (Invitrogen, 1600 Faraday Ave., Carlsbad, Calif. 92008). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

Nucleic acid molecules corresponding to homologs, analogs, and orthologs of the polypeptides listed in Table 1 can be isolated based on their identity to said polypeptides, using the polynucleotides encoding the respective polypeptides or primers based thereon, as hybridization probes according to standard hybridization techniques under stringent hybridization conditions. As used herein with regard to hybridization for DNA to a DNA blot, the term "stringent conditions" refers to hybridization overnight at 60° C. in 10×Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in a preferred embodiment, the phrase "stringent conditions" refers to hybridization in a 6×SSC solution at 65° C. In another embodiment, "highly stringent conditions" refers to hybridization overnight at 65° C. in 10×Denhart's solution, 6×SSC, 0.5% SDS and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for performing nucleic acid hybridizations are well known in the art. Preferably, an isolated nucleic acid molecule of the invention that hybridizes under stringent or highly stringent conditions to a nucleotide sequence listed in Table 1 corresponds to a naturally occurring nucleic acid molecule.

There are a variety of methods that can be used to produce libraries of potential homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential sequences. Methods for synthesizing degenerate oligonucleotides are known in the art.

Additionally, optimized nucleic acids can be created. Preferably, an optimized nucleic acid encodes a polypeptide that has a function similar to those of the polypeptides listed in Table 1 and/or modulates a plant's growth and/or yield under normal and/or water-limited conditions and/or tolerance to an environmental stress, and more preferably increases a plant's growth and/or yield under normal and/or water-limited conditions and/or tolerance to an environmental stress upon its overexpression in the plant. As used herein, "optimized" refers to a nucleic acid that is genetically engineered to increase its expression in a given plant or animal. To provide plant optimized nucleic acids, the DNA sequence of the gene can be modified to: 1) comprise codons preferred by highly expressed plant genes; 2) comprise an A+T content in nucleotide base composition to that substantially found in plants; 3) form a plant initiation sequence; 4) to eliminate sequences that cause destabilization, inappropriate polyadenylation, degradation and termination of RNA, or that form secondary structure hairpins or RNA splice sites; or 5) elimination of antisense open reading frames. Increased expression of nucleic acids in plants can be achieved by utilizing the distribution frequency of codon usage in plants in general or in a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, Proc. Natl. Acad. Sci. USA 88:3324-3328; and Murray et al., 1989, Nucleic Acids Res. 17:477-498.

An isolated polynucleotide of the invention can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots, whereas the XTA codon is avoided in both monocots and dicots. Optimized nucleic acids of this invention also preferably have CG and TA doublet avoidance indices closely approximating those of the chosen host plant. More preferably, these indices deviate from that of the host by no more than about 10-15%.

The invention further provides an isolated recombinant expression vector comprising a polynucleotide as described above, wherein expression of the vector in a host cell results in the plant's increased growth and/or yield under normal or water-limited conditions and/or increased tolerance to environmental stress as compared to a wild type variety of the host cell. The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in a bacterial or plant host cell when the vector is introduced into the host cell). The term "regulatory sequence" is intended to include promoters, enhancers, and other expression control elements (e.g., polyadenylation signals). Such regulatory sequences are well known in the art. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides encoded by nucleic acids as described herein.

Plant gene expression should be operatively linked to an appropriate promoter conferring gene expression in a timely, cell specific, or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35S promoters, the sX CaMV 35S promoter, the Sep1 promoter, the rice actin promoter, the *Arabidopsis* actin promoter, the ubiquitan promoter, pEmu, the figwort mosaic virus 35S promoter, the Smas promoter, the super promoter (U.S. Pat. No. 5,955,646), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssu-RUBISCO) promoter, and the like.

Inducible promoters are preferentially active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoters from tobacco, *Arabidopsis*, and maize are inducible by infection with a pathogen; and the Adh1 promoter is induced by hypoxia and cold stress. Plant gene expression can also be facilitated via an inducible promoter (For a review, see Gatz, 1997, Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2: 397-404), and an ethanol inducible promoter (PCT Application No. WO 93/21334).

In one preferred embodiment of the present invention, the inducible promoter is a stress-inducible promoter. For the purposes of the invention, stress-inducible promoters are preferentially active under one or more of the following stresses: sub-optimal conditions associated with salinity, drought, nitrogen, temperature, metal, chemical, pathogenic, and oxidative stresses. Stress inducible promoters include, but are not limited to, Cor78 (Chak et al., 2000, Planta 210: 875-883; Hovath et al., 1993, Plant Physiol. 103:1047-1053), Cor15a (Artus et al., 1996, PNAS 93(23):13404-09), Rci2A (Medina et al., 2001, Plant Physiol. 125:1655-66; Nylander et al., 2001, Plant Mol. Biol. 45:341-52; Navarre and Goffeau, 2000, EMBO J. 19:2515-24; Capel et al., 1997, Plant Physiol. 115:569-76), Rd22 (Xiong et al., 2001, Plant Cell 13:2063-83; Abe et al., 1997, Plant Cell 9:1859-68; Iwasaki et al., 1995, Mol. Gen. Genet. 247:391-8), cDet6 (Lang and Palve, 1992, Plant Mol. Biol. 20:951-62), ADH1 (Hoeren et al., 1998, Genetics 149:479-90), KAT1 (Nakamura et al., 1995, Plant Physiol. 109:371-4), KST1 (Müller-Röber et al., 1995, EMBO 14:2409-16), Rha1 (Terryn et al., 1993, Plant Cell 5:1761-9; Terryn et al., 1992, FEBS Lett. 299(3):287-90), ARSK1 (Atkinson et al., 1997, GenBank Accession #L22302, and PCT Application No. WO 97/20057), PtxA (Plesch et al., GenBank Accession #X67427), SbHRGP3 (Ahn et al., 1996, Plant Cell 8:1477-90), GH3 (Liu et al., 1994, Plant Cell 6:645-57), the pathogen inducible PRP1-gene promoter (Ward et al., 1993, Plant. Mol. Biol. 22:361-366), the heat inducible hsp80-promoter from tomato (U.S. Pat. No. 5,187,267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331-340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue-preferred and organ-preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, petal-preferred, sepal-preferred, pedicel-preferred, silique-preferred, stem-preferred, root-preferred promoters, and the like. Seed-preferred promoters are preferentially expressed during seed development and/or germination. For example, seed-preferred promoters can be embryo-preferred, endosperm-preferred, and seed coat-preferred (See Thompson et al., 1989, BioEssays 10:108). Examples of seed-preferred promoters include, but are not limited to, cellulose synthase (celA), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol. Gen. Genet. 225(3): 459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, *Sorghum* kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43:729-736).

In a preferred embodiment of the present invention, the polynucleotides listed in Table 1 are expressed in plant cells from higher plants (e.g., the spermatophytes, such as crop plants). A polynucleotide may be "introduced" into a plant cell by any means, including transfection, transformation or transduction, electroporation, particle bombardment, agroinfection, and the like. Suitable methods for transforming or transfecting plant cells are disclosed, for example, using particle bombardment as set forth in U.S. Pat. Nos. 4,945,050; 5,036,006; 5,100,792; 5,302,523; 5,464,765; 5,120,657; 6,084,154; and the like. More preferably, the transgenic corn seed of the invention may be made using *Agrobacterium* transformation, as described in U.S. Pat. Nos. 5,591,616; 5,731,179; 5,981,840; 5,990,387; 6,162,965; 6,420,630, U.S. patent application publication number 2002/0104132, and the like. Transformation of soybean can be performed using for example a technique described in European Patent No. EP 0424047, U.S. Pat. No. 5,322,783, European Patent No. EP 0397 687, U.S. Pat. No. 5,376,543, or U.S. Pat. No. 5,169,770. A specific example of wheat transformation can be found in PCT Application No. WO 93/07256. Cotton may be transformed using methods disclosed in U.S. Pat. Nos. 5,004,863; 5,159,135; 5,846,797, and the like. Rice may be transformed using methods disclosed in U.S. Pat. Nos. 4,666,844; 5,350,688; 6,153,813; 6,333,449; 6,288,312; 6,365,807; 6,329,571, and the like. Other plant transformation methods are disclosed, for example, in U.S. Pat. Nos. 5,932,782; 6,153,811; 6,140,553; 5,969,213; 6,020,539, and the like. Any plant transformation method suitable for inserting a transgene into a particular plant may be used in accordance with the invention.

According to the present invention, the introduced polynucleotide may be maintained in the plant cell stably if it is incorporated into a non-chromosomal autonomous replicon or integrated into the plant chromosomes. Alternatively, the introduced polynucleotide may be present on an extra-chromosomal non-replicating vector and may be transiently expressed or transiently active.

Another aspect of the invention pertains to an isolated polypeptide having a sequence selected from the group consisting of the polypeptide sequences listed in Table 1. An "isolated" or "purified" polypeptide is free of some of the cellular material when produced by recombinant DNA techniques, or chemical precursors or other chemicals when chemically synthesized. The language "substantially free of cellular material" includes preparations of a polypeptide in which the polypeptide is separated from some of the cellular components of the cells in which it is naturally or recombinantly produced. In one embodiment, the language "substantially free of cellular material" includes preparations of a polypeptide of the invention having less than about 30% (by dry weight) of contaminating polypeptides, more preferably less than about 20% of contaminating polypeptides, still more preferably less than about 10% of contaminating polypeptides, and most preferably less than about 5% contaminating polypeptides.

The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities are abundant and well known to one skilled in the art.

The invention is also embodied in a method of producing a transgenic plant comprising at least one polynucleotide listed in Table 1, wherein expression of the polynucleotide in the plant results in the plant's increased growth and/or yield under normal or water-limited conditions and/or increased tolerance to an environmental stress as compared to a wild type variety of the plant comprising the steps of: (a) introducing into a plant cell an expression vector comprising at least one polynucleotide listed in Table 1, and (b) generating from the plant cell a transgenic plant that expresses the polynucleotide, wherein expression of the polynucleotide in the transgenic plant results in the plant's increased growth and/or yield under normal or water-limited conditions and/or increased tolerance to environmental stress as compared to a wild type variety of the plant. The plant cell may be, but is not limited to, a protoplast, gamete producing cell, and a cell that regenerates into a whole plant. As used herein, the term "transgenic" refers to any plant, plant cell, callus, plant tissue, or plant part, that contains at least one recombinant polynucleotide listed in Table 1. In many cases, the recombinant polynucleotide is stably integrated into a chromosome or stable extra-chromosomal element, so that it is passed on to successive generations.

The present invention also provides a method of increasing a plant's growth and/or yield under normal or water-limited conditions and/or increasing a plant's tolerance to an environmental stress comprising the steps of increasing the expression of at least one polynucleotide listed in Table 1 in the plant. Expression of a protein can be increased by any method known to those of skill in the art.

The effect of the genetic modification on plant growth and/or yield and/or stress tolerance can be assessed by growing the modified plant under normal and or less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, metabolite composition, etc., using methods known to those of skill in biotechnology.

The invention is further illustrated by the following examples, which are not to be construed in any way as imposing limitations upon the scope thereof.

EXAMPLE 1

Cloning of cDNAs cDNAs were isolated from proprietary libraries of the respective plant species using known methods. Sequences were processed and annotated using bioinformatics analyses. The degrees of amino acid identity and similarity of the isolated sequences to the respective closest known public sequences are indicated in Tables 2 through 18 (Pairwise Comparison was used: gap penalty: 10; gap extension penalty: 0.1; score matrix: blosum62).

TABLE 2

Comparison of At2g20725 (SEQ ID NO: 2) to known CAAX amino terminal protease proteins

| Public Database Accession # | Species | Sequence Identity (%) |
|---|---|---|
| NP_565483 | A. thaliana | 99.70% |
| ABE87113 | Medicago truncatula | 27.00% |
| NP_563943 | A. thaliana | 25.60% |
| AAU90306 | Solanum tuberosum | 25.20% |
| AAM65055 | A. thaliana | 25.00% |

TABLE 3

Comparison of At3g26085 (SEQ ID NO: 4) to known CAAX amino terminal protease proteins

| Public Database Accession # | Species | Sequence Identity (%) |
|---|---|---|
| NP_566788 | A. thaliana | 100.00% |
| BAC43478 | A. thaliana | 99.70% |
| AAM63917 | A. thaliana | 99.30% |
| NP_001078210 | A. thaliana | 91.00% |
| BAB01072 | A. thaliana | 65.30% |

TABLE 4

Comparison of AtFACE-2 (SEQ ID NO: 6) to known prenyl-dependent CAAX proteases

| Public Database Accession # | Species | Sequence Identity (%) |
|---|---|---|
| NP_850262 | A. thaliana | 100.00% |
| BAC43705 | A. thaliana | 99.70% |
| CAN61196 | Vitis vinifera | 36.70% |
| XP_695285 | Danio rerio | 32.70% |
| XP_001342272 | D. rerio | 32.70% |

TABLE 5

Comparison of CASAR82A (SEQ ID NO: 12) to known SAR8.2 protein precursors

| Public Database Accession # | Species | Sequence Identity (%) |
|---|---|---|
| AAF18935 | C. annuum | 100.00% |
| AAL56986 | C. annuum | 97.70% |
| AAL16783 | C. annuum | 93.00% |
| AAL16782 | C. annuum | 91.90% |
| AAR97871 | C. annuum | 52.30% |

TABLE 6

Comparison of b3358 (SEQ ID NO: 14) to known putative membrane proteins

| Public Database Accession # | Species | Sequence Identity (%) |
|---|---|---|
| YP_312284 | Shigella sonnei | 99.90% |
| ZP_00715046 | E. coli | 99.90% |
| ZP_00725390 | E. coli | 99.60% |
| AP_004431 | E. coli | 99.40% |
| YP_858957 | E. coli | 99.40% |

TABLE 7

Comparison of EST564 (SEQ ID NO: 16) to known protein phosphatase 2C proteins

| Public Database Accession # | Species | Sequence Identity (%) |
|---|---|---|
| ABF93864 | O. sativa | 56.40% |
| NP_974411 | A. thaliana | 51.60% |
| AAC35951 | Mesembryanthemum crystallinum | 51.10% |
| EAZ25504 | O. sativa | 45.70% |
| EAZ02383 | O. sativa | 43.40% |

TABLE 8

Comparison of EST390 (SEQ ID NO: 36) to known mitochondrial carrier proteins

| Public Database Accession # | Species | Sequence Identity (%) |
|---|---|---|
| NP_172866 | A. thaliana | 63.50% |
| AAT66766 | Solanum demissum | 60.80% |
| CAH67091 | O. sativa | 60.00% |
| CAE01569 | O. sativa | 59.70% |
| CAN75338 | V. vinifera | 59.50% |

TABLE 9

Comparison of EST257 (SEQ ID NO: 50) to known protein kinases

| Public Database Accession # | Species | Sequence Identity (%) |
|---|---|---|
| NP_001043682 | O. sativa | 62.20% |
| CAN82019 | V. vinifera | 62.10% |
| AAR01726 | O. sativa | 61.10% |
| NP_001056408 | O. sativa | 61.10% |
| CAN64754 | V. vinifera | 60.90% |

TABLE 10

Comparison of EST465 (SEQ ID NO: 62) to known peptidyl prolyl isomerases

| Public Database Accession # | Species | Sequence Identity (%) |
|---|---|---|
| AAC39445 | A. thaliana | 54.30% |
| ABE85899 | M. truncatula | 54.20% |
| CAB88363 | A. thaliana | 54.10% |
| NP_566993 | A. thaliana | 53.80% |
| NP_001050182 | O. sativa | 53.00% |

TABLE 11

Comparison of YBL109w (SEQ ID NO: 64) to unknown protein 1

| Public Database Accession # | Species | Sequence Identity (%) |
|---|---|---|
| CAA84936 | S. cerevisiae | 49.50% |
| P38898 | S. cerevisiae | 43.10% |

TABLE 12

Comparison of YBL100c (SEQ ID NO: 66) to unknown protein 2

| Public Database Accession # | Species | Sequence Identity (%) |
|---|---|---|
| P38168 | S. cerevisiae | 100.00% |

TABLE 13

Comparison of YKL184w (SEQ ID NO: 68) to known ornithine decarboxylases

| Public Database Accession # | Species | Sequence Identity (%) |
|---|---|---|
| NP_012737 | S. cerevisiae | 100.00% |
| XP_445434 | Candida glabrata | 70.90% |

TABLE 13-continued

Comparison of YKL184w (SEQ ID NO: 68) to known ornithine decarboxylases

| Public Database Accession # | Species | Sequence Identity (%) |
|---|---|---|
| XP_451651 | Kluyveromyces lactis | 60.30% |
| NP_984947 | Ashbya gossypii | 57.40% |
| XP_001385782 | P. stipitis | 49.80% |

TABLE 14

Comparison of YPL091w (SEQ ID NO: 70) to known glutathione reductases

| Public Database Accession # | Species | Sequence Identity (%) |
|---|---|---|
| NP_015234 | S. cerevisiae | 100.00% |
| AAA92575 | S. cerevisiae | 96.70% |
| BAA07109 | S. cerevisiae | 95.70% |
| XP_447042 | C. glabrata | 79.90% |
| XP_455036 | K. lactis | 73.30% |

TABLE 15

Comparison of TA54587433 (SEQ ID NO: 72) to unknown protein 3

| Public Database Accession # | Species | Sequence Identity (%) |
|---|---|---|
| EAY88696 | O. sativa | 22.80% |
| EAZ25723 | O. sativa | 21.90% |
| NP_001049087 | O. sativa | 21.20% |

TABLE 16

Comparison of ZM68532504 (SEQ ID NO: 74) to known protein phosphatase 2A proteins

| Public Database Accession # | Species | Sequence Identity (%) |
|---|---|---|
| AAC72838 | O. sativa | 95.40% |
| AAA91806 | O. sativa | 94.10% |
| BAA92697 | Vicia faba | 93.10% |
| AAQ67226 | Lycopersicon esculentum | 92.80% |
| BAD17175 | O. sativa | 92.80% |

TABLE 17

Comparison of ZM59202533 (SEQ ID NO: 92) to known MEK1 protein kinases

| Public Database Accession # | Species | Sequence Identity (%) |
|---|---|---|
| AAC83393 | Z. mays | 100.00% |
| ABG45894 | O. sativa | 92.70% |
| NP_001043164 | O. sativa | 85.90% |
| BAB32405 | Nicotiana tabacum | 77.80% |
| CAC24705 | N. tabacum | 77.20% |

TABLE 18

Comparison of BN42671700 (SEQ ID NO: 98) to known AP2 domain containing transcription factors

| Public Database Accession # | Species | Sequence Identity (%) |
|---|---|---|
| NP_177631 | A. thaliana | 58.60% |
| NP_173355 | A. thaliana | 56.70% |
| AAF82238 | A. thaliana | 54.80% |

The full-length DNA sequence of the AtFACE-2 (SEQ ID NO: 5) was blasted against proprietary databases of canola, soybean, rice, maize, linseed, sunflower, and wheat cDNAs at an e value of $e^{-10}$ (Altschul et al., 1997, Nucleic Acids Res. 25: 3389-3402). All the contig hits were analyzed for the putative full length sequences, and the longest clones representing the putative full length contigs were fully sequenced. Two homologs from maize were identified. The degree of amino acid identity of these sequences to the closest known public sequences is indicated in Tables 19 and 20 (Pairwise Comparison was used: gap penalty: 10; gap extension penalty: 0.1; score matrix: blosum62).

TABLE 19

Comparison of ZM57353913 (SEQ ID NO: 8) to known prenyl-dependent CAAX proteases

| Public Database Accession # | Species | Sequence Identity (%) |
|---|---|---|
| NP_850262 | A. thaliana | 52.20% |
| BAC43705 | A. thaliana | 52.20% |
| NP_001055298 | O. sativa | 42.10% |
| EAZ33973 | O. sativa | 36.60% |
| XP_001353747 | Drosophila pseudoobscura | 33.50% |

TABLE 20

Comparison of ZM59252659 (SEQ ID NO: 10) to known prenyl-dependent CAAX proteases

| Public Database Accession # | Species | Sequence Identity (%) |
|---|---|---|
| NP_850262 | A. thaliana | 47.00% |
| BAC43705 | A. thaliana | 47.00% |
| EAZ33973 | O. sativa | 41.10% |
| NP_001055298 | O. sativa | 38.30% |
| CAN61196 | V. vinifera | 31.90% |

The full-length DNA sequence of EST564 (SEQ ID NO: 15) was blasted against proprietary databases of canola, soybean, rice, maize, linseed, sunflower, and wheat cDNAs at an e value of $e^{-10}$ (Altschul et al., 1997, Nucleic Acids Res. 25: 3389-3402). All the contig hits were analyzed for the putative full length sequences, and the longest clones representing the putative full length contigs were fully sequenced. Six homologs from maize, two homologs from soybean, and one homolog from canola were identified. The degree of amino acid identity of these sequences to the closest known public sequences is indicated in Tables 21-29 (Pairwise Comparison was used: gap penalty: 10; gap extension penalty: 0.1; score matrix: blosum62).

TABLE 21

Comparison of BN49502266 (SEQ ID NO: 18) to known protein phosphatase 2C proteins

| Public Database Accession # | Species | Sequence Identity (%) |
|---|---|---|
| NP_195118 | A. thaliana | 91.10% |
| NP_001067133 | O. sativa | 63.20% |
| EAY83661 | O. sativa | 60.80% |
| EAZ21008 | O. sativa | 60.50% |
| CAN76780 | V. vinifera | 57.60% |

TABLE 22

Comparison of GM49788080 (SEQ ID NO: 20) to known protein phosphatase 2C proteins

| Public Database Accession # | Species | Sequence Identity (%) |
|---|---|---|
| EAZ02383 | O. sativa | 75.60% |
| EAZ38299 | O. sativa | 75.30% |
| CAB90634 | Fagus sylvatica | 73.80% |
| EAZ25504 | O. sativa | 73.00% |
| AAC35951 | M. crystallinum | 72.80% |

TABLE 23

Comparison of GM53049821 (SEQ ID NO: 22) to known protein phosphatase 2C proteins

| Public Database Accession # | Species | Sequence Identity (%) |
|---|---|---|
| CAN72598 | V. vinifera | 82.40% |
| NP_566566 | A. thaliana | 73.50% |
| AAM61747 | A. thaliana | 73.50% |
| BAA94987 | A. thaliana | 73.00% |
| NP_001051801 | O. sativa | 60.20% |

TABLE 24

Comparison of ZM58462719 (SEQ ID NO: 24) to known protein phosphatase 2C proteins

| Public Database Accession # | Species | Sequence Identity (%) |
|---|---|---|
| NP_001058597 | O. sativa | 91.10% |
| EAZ02383 | O. sativa | 81.20% |
| EAZ38299 | O. sativa | 81.00% |
| AAD11430 | M. crystallinum | 75.70% |
| CAB90634 | F. sylvatica | 74.20% |

TABLE 25

Comparison of ZM61092633 (SEQ ID NO: 26) to known protein phosphatase 2C proteins

| Public Database Accession # | Species | Sequence Identity (%) |
|---|---|---|
| NP_001065203 | O. sativa | 87.00% |
| AAK20060 | O. sativa | 86.00% |
| NP_001048899 | O. sativa | 80.70% |
| EAY88457 | O. sativa | 79.90% |
| ABE77197 | Sorghum bicolor | 77.20% |

TABLE 26

Comparison of ZM62016485 (SEQ ID NO: 28)
to known protein phosphatase 2C proteins

| Public Database Accession # | Species | Sequence Identity (%) |
|---|---|---|
| ABE77197 | S. bicolor | 90.70% |
| NP_001048899 | O. sativa | 86.20% |
| EAY88457 | O. sativa | 85.20% |
| NP_001065203 | O. sativa | 78.50% |
| AAK20060 | O. sativa | 77.80% |

TABLE 27

Comparison of ZM62051019 (SEQ ID NO: 30)
to known protein phosphatase 2C proteins

| Public Database Accession # | Species | Sequence Identity (%) |
|---|---|---|
| ABE77197 | S. bicolor | 92.50% |
| NP_001048899 | O. sativa | 88.00% |
| EAY88457 | O. sativa | 87.00% |
| NP_001065203 | O. sativa | 79.50% |
| AAK20060 | O. sativa | 78.80% |

TABLE 28

Comparison of ZM65086957 (SEQ ID NO: 32)
to known protein phosphatase 2C proteins

| Public Database Accession # | Species | Sequence Identity (%) |
|---|---|---|
| ABE77197 | S. bicolor | 91.00% |
| NP_001048899 | O. sativa | 86.50% |
| EAY88457 | O. sativa | 85.50% |
| NP_001065203 | O. sativa | 78.80% |
| AAK20060 | O. sativa | 78.00% |

TABLE 29

Comparison of ZM68587657 (SEQ ID NO: 34)
to known protein phosphatase 2C proteins

| Public Database Accession # | Species | Sequence Identity (%) |
|---|---|---|
| EAZ02383 | O. sativa | 70.60% |
| EAZ38299 | O. sativa | 70.60% |
| AAC35951 | M. crystallinum | 69.80% |
| ABF93864 | O. sativa | 68.50% |
| NP_974411 | A. thaliana | 65.00% |

The full-length DNA sequence of the EST390 (SEQ ID NO: 35) was blasted against proprietary databases of canola, soybean, rice, maize, linseed, sunflower, and wheat cDNAs at an e value of $e^{-10}$ (Altschul et al., 1997, Nucleic Acids Res. 25: 3389-3402). All the contig hits were analyzed for the putative full length sequences, and the longest clones representing the putative full length contigs were fully sequenced. Four homologs from canola and two homologs from maize were identified. The degree of amino acid identity of these sequences to the closest known public sequences is indicated in Tables 30-35 (Pairwise Comparison was used: gap penalty: 10; gap extension penalty: 0.1; score matrix: blosum62).

TABLE 30

Comparison of BN51363030 (SEQ ID NO: 38)
to known mitochondrial carrier proteins

| Public Database Accession # | Species | Sequence Identity (%) |
|---|---|---|
| CAN77545 | V. vinifera | 71.90% |
| BAE71294 | Trifolium pratense | 71.90% |
| NP_194188 | A. thaliana | 70.70% |
| AAU11466 | Saccharum officinarum | 70.60% |
| AAU11465 | S. officinarum | 69.90% |

TABLE 31

Comparison of BN42986056 (SEQ ID NO: 40)
to known mitochondrial carrier proteins

| Public Database Accession # | Species | Sequence Identity (%) |
|---|---|---|
| NP_179836 | A. thaliana | 74.80% |
| AAK44155 | A. thaliana | 74.50% |
| AAM63236 | A. thaliana | 74.20% |
| CAN77545 | V. vinifera | 67.70% |
| BAE71294 | Trifolium pratense | 65.50% |

TABLE 32

Comparison of BN49389066 (SEQ ID NO: 42)
to known mitochondrial carrier proteins

| Public Database Accession # | Species | Sequence Identity (%) |
|---|---|---|
| AAY97866 | L. esculentum | 73.50% |
| CAA68164 | Solanum tuberosum | 73.50% |
| CAC84547 | N. tabacum | 73.30% |
| AAR06239 | Citrus junos | 73.00% |
| CAC84545 | N. tabacum | 73.00% |

TABLE 33

Comparison of BN51339479 (SEQ ID NO: 44)
to known mitochondrial carrier proteins

| Public Database Accession # | Species | Sequence Identity (%) |
|---|---|---|
| CAC84545 | N. tabacum | 85.60% |
| CAC84547 | N. tabacum | 85.30% |
| AAR06239 | C. junos | 85.30% |
| CAA68164 | S. tuberosum | 85.30% |
| CAC12820 | N. tabacum | 85.30% |

TABLE 34

Comparison of ZM57651070 (SEQ ID NO: 46)
to known mitochondrial carrier proteins

| Public Database Accession # | Species | Sequence Identity (%) |
|---|---|---|
| NP_001066927 | O. sativa | 57.00% |
| NP_680566 | A. thaliana | 53.80% |
| BAF00711 | A. thaliana | 51.70% |
| CAN71674 | V. vinifera | 43.20% |
| CAN71674 | V. vinifera | 43.20% |

TABLE 35

Comparison of ZM62073276 (SEQ ID NO: 48)
to known mitochondrial carrier proteins

| Public Database Accession # | Species | Sequence Identity (%) |
|---|---|---|
| AAU11471 | S. officinarum | 94.90% |
| NP_001054904 | O. sativa | 92.30% |
| BAA08105 | Panicum miliaceum | 86.20% |
| BAA08103 | P. miliaceum | 85.50% |
| EAY80779 | O. sativa | 82.90% |

The full-length DNA sequence of the EST257 (SEQ ID NO: 49) was blasted against proprietary databases of canola, soybean, rice, maize, linseed, sunflower, and wheat cDNAs at an e value of $e^{-10}$ (Altschul et al., 1997, Nucleic Acids Res. 25: 3389-3402). All the contig hits were analyzed for the putative full length sequences, and the longest clones representing the putative full length contigs were fully sequenced. Three homologs from maize, one homolog from linseed, and one sequence from wheat were identified. The degree of amino acid identity of these sequences to the closest known public sequences is indicated in Tables 36-40 (Pairwise Comparison was used: gap penalty: 10; gap extension penalty: 0.1; score matrix: blosum62).

TABLE 36

Comparison of LU61665952 (SEQ ID NO: 52) to known protein kinases

| Public Database Accession # | Species | Sequence Identity (%) |
|---|---|---|
| NP_566716 | A. thaliana | 75.10% |
| CAN82019 | V. vinifera | 74.50% |
| NP_193214 | A. thaliana | 74.50% |
| ABK06452 | synthetic construct | 73.00% |
| ABK06453 | synthetic construct | 72.30% |

TABLE 37

Comparison of TA56863186 (SEQ ID NO: 54) to known protein kinases

| Public Database Accession # | Species | Sequence Identity (%) |
|---|---|---|
| AAO72550 | O. sativa | 87.30% |
| NP_001046047 | O. sativa | 79.80% |
| EAZ01979 | O. sativa | 73.80% |
| NP_001058291 | O. sativa | 73.60% |
| AAO48744 | O. sativa | 73.40% |

TABLE 38

Comparison of ZM62026837 (SEQ ID NO: 56) to known protein kinases

| Public Database Accession # | Species | Sequence Identity (%) |
|---|---|---|
| AAR01726 | O. sativa | 83.40% |
| NP_001050732 | O. sativa | 77.00% |
| EAY91142 | O. sativa | 76.30% |
| EAZ27891 | O. sativa | 76.00% |
| CAN82019 | V. vinifera | 73.30% |

TABLE 39

Comparison of ZM65457595 (SEQ ID NO: 58) to known protein kinases

| Public Database Accession # | Species | Sequence Identity (%) |
|---|---|---|
| NP_001056408 | O. sativa | 89.60% |
| AAO72572 | O. sativa | 87.20% |
| NP_001043682 | O. sativa | 81.50% |
| CAN64754 | V. vinifera | 79.80% |
| NP_199811 | A. thaliana | 77.20% |

TABLE 40

Comparison of ZM67230154 (SEQ ID NO: 60) to known protein kinases

| Public Database Accession # | Species | Sequence Identity (%) |
|---|---|---|
| NP_001043682 | O. sativa | 87.10% |
| NP_001056408 | O. sativa | 82.80% |
| AAO72572 | O. sativa | 80.80% |
| EAZ12861 | O. sativa | 79.20% |
| CAN64754 | V. vinifera | 77.50% |

The full-length DNA sequence of the ZM68532504 (SEQ ID NO: 73) was blasted against proprietary databases of canola, soybean, rice, maize, linseed, sunflower, and wheat cDNAs at an e value of $e^{-10}$ (Altschul et al., 1997, Nucleic Acids Res. 25: 3389-3402). All the contig hits were analyzed for the putative full length sequences, and the longest clones representing the putative full length contigs were fully sequenced. Two homologs from canola, two homologs from maize, one homolog from linseed, two sequences from rice and one sequence from sunflower were identified. The degree of amino acid identity of these sequences to the closest known public sequences is indicated in Tables 41-48 (Pairwise Comparison was used: gap penalty: 10; gap extension penalty: 0.1; score matrix: blosum62).

TABLE 41

Comparison of BN42856089 (SEQ ID NO: 76) to known protein phosphatase 2A proteins

| Public Database Accession # | Species | Sequence Identity (%) |
|---|---|---|
| NP_172514 | A. thaliana | 97.10% |
| AAM65099 | A. thaliana | 95.80% |
| AAQ67226 | L. esculentum | 95.40% |
| BAA92697 | Vicia faba | 95.10% |
| CAC11129 | Fagus sylvatica | 94.40% |

TABLE 42

Comparison of BN43206527 (SEQ ID NO: 78) to known protein phosphatase 2A proteins

| Public Database Accession # | Species | Sequence Identity (%) |
|---|---|---|
| NP_172514 | A. thaliana | 97.40% |
| AAM65099 | A. thaliana | 96.10% |
| AAQ67226 | L. esculentum | 95.10% |
| BAA92697 | V. faba | 94.10% |
| AAQ67225 | L. esculentum | 94.10% |

TABLE 43

Comparison of HA66872964 (SEQ ID NO: 80)
to known protein phosphatase 2A proteins

| Public Database Accession # | Species | Sequence Identity (%) |
|---|---|---|
| P48579 | H. annuus | 99.30% |
| BAA92697 | V. faba | 93.50% |
| CAC11129 | F. sylvatica | 93.10% |
| BAA92698 | V. faba | 92.80% |
| Q9ZSE4 | Hevea brasiliensis | 92.80% |

TABLE 44

Comparison of LU61662612 (SEQ ID NO: 82)
to known protein phosphatase 2A proteins

| Public Database Accession # | Species | Sequence Identity (%) |
|---|---|---|
| AAQ67226 | L. esculentum | 94.10% |
| BAA92697 | V. faba | 94.10% |
| BAA92698 | V. faba | 94.10% |
| CAN74947 | V. vinifera | 93.50% |
| CAC11129 | F. sylvatica | 93.10% |

TABLE 45

Comparison of OS32806943 (SEQ ID NO: 84)
to known protein phosphatase 2A proteins

| Public Database Accession # | Species | Sequence Identity (%) |
|---|---|---|
| AAC72838 | O. sativa | 96.10% |
| BAD17175 | O. sativa | 95.80% |
| AAA91806 | O. sativa | 94.80% |
| AAQ67226 | L. esculentum | 93.20% |
| BAA92697 | V. faba | 93.20% |

TABLE 46

Comparison of OS34738749 (SEQ ID NO: 86)
to known protein phosphatase 2A proteins

| Public Database Accession # | Species | Sequence Identity (%) |
|---|---|---|
| AAQ67226 | L. esculentum | 97.70% |
| BAA92697 | V. faba | 97.10% |
| CAC11129 | F. sylvatica | 96.70% |
| BAA92698 | V. faba | 96.10% |
| AAQ67225 | L. esculentum | 96.10% |

TABLE 47

Comparison of ZM59400933 (SEQ ID NO: 88)
to known protein phosphatase 2A proteins

| Public Database Accession # | Species | Sequence Identity (%) |
|---|---|---|
| AAC72838 | O. sativa | 95.80% |
| AAA91806 | O. sativa | 94.40% |
| BAA92697 | V. faba | 92.80% |
| AAQ67226 | L. esculentum | 92.80% |
| AAQ67225 | L. esculentum | 92.80% |

TABLE 48

Comparison of ZM62132060 (SEQ ID NO: 90)
to known protein phosphatase 2A proteins

| Public Database Accession # | Species | Sequence Identity (%) |
|---|---|---|
| AAC72838 | O. sativa | 95.10% |
| AAA91806 | O. sativa | 93.80% |
| BAA92697 | V. faba | 92.80% |
| AAQ67226 | L. esculentum | 92.50% |
| BAD17175 | O. sativa | 92.50% |

The full-length DNA sequence of the ZM59202533 (SEQ ID NO: 91) was blasted against proprietary databases of canola, soybean, rice, maize, linseed, sunflower, and wheat cDNAs at an e value of $e^{-10}$ (Altschul et al., 1997, Nucleic Acids Res. 25: 3389-3402). All the contig hits were analyzed for the putative full length sequences, and the longest clones representing the putative full length contigs were fully sequenced. Two homologs from canola and one homolog from maize were identified. The degree of amino acid identity of these sequences to the closest known public sequences is indicated in Tables 49-51 (Pairwise Comparison was used: gap penalty: 10; gap extension penalty: 0.1; score matrix: blosum62).

TABLE 49

Comparison of BN41901422 (SEQ ID NO: 94) to known MEK1 protein kinases

| Public Database Accession # | Species | Sequence Identity (%) |
|---|---|---|
| ABF55661 | synthetic construct | 79.80% |
| NP_849446 | A. thaliana | 76.30% |
| AAQ96337 | Vitis aestivalis | 66.00% |
| AAL62336 | G. max | 64.10% |
| AAS21304 | Petroselinum crispum | 63.60% |

TABLE 50

Comparison of BN47868329 (SEQ ID NO: 96) to known MEK1 protein kinases

| Public Database Accession # | Species | Sequence Identity (%) |
|---|---|---|
| NP_188759 | A. thaliana | 72.30% |
| CAA68958 | A. thaliana | 72.00% |
| ABF55664 | synthetic construct | 70.90% |
| AAL91161 | A. thaliana | 70.10% |
| AAU04434 | L. esculentum | 66.40% |

TABLE 51

Comparison of ZM68416988 (SEQ ID NO: 100) to known MEK1 protein kinases

| Public Database Accession # | Species | Sequence Identity (%) |
|---|---|---|
| ABI93775 | Oryza minuta | 80.00% |
| NP_001056806 | O. sativa | 79.70% |
| ABP88102 | O. sativa | 78.90% |
| CAD45180 | O. sativa | 75.20% |
| ABI93776 | O. minuta | 72.40% |

EXAMPLE 2

Well-Watered *Arabidopsis* Plants

The polynucleotides of Table 1 are ligated into a binary vector containing a selectable marker. The resulting recombinant vector contains the corresponding gene in the sense orientation under a constitutive promoter. The recombinant vectors are transformed into an *Agrobacterium tumefaciens* strain according to standard conditions. *A. thaliana* ecotype Col-0 or C24 are grown and transformed according to standard conditions. T1 and T2 plants are screened for resistance to the selection agent conferred by the selectable marker gene. T3 seeds are used in greenhouse or growth chamber experiments.

Approximately 3-5 days prior to planting, seeds are refrigerated for stratification. Seeds are then planted, fertilizer is applied and humidity is maintained using transparent domes. Plants are grown in a greenhouse at 22° C. with photoperiod of 16 hours light/8 hours dark. Plants are watered twice a week.

At 19 and 22 days, plant area, leaf area, biomass, color distribution, color intensity, and growth rate for each plant are measured using a commercially available imaging system. Biomass is calculated as the total plant leaf area at the last measuring time point. Growth rate is calculated as the plant leaf area at the last measuring time point minus the plant leaf area at the first measuring time point divided by the plant leaf area at the first measuring time point. Health index is calculated as the dark green leaf area divided by the total plant leaf area.

EXAMPLE 3

Nitrogen Stress Tolerant *Arabidopsis* Plants

The polynucleotides of Table 1 are ligated into a binary vector containing a selectable marker. The resulting recombinant vector contains the corresponding gene in the sense orientation under a constitutive promoter. The recombinant vectors are transformed into an *A. tumefaciens* strain according to standard conditions. *A. thaliana* ecotype Col-0 or C24 are grown and transformed according to standard conditions. T1 and T2 plants are screened for resistance to the selection agent conferred by the selectable marker gene.

Plants are grown in flats using a substrate that contains no organic components. Each flat is wet with water before seedlings resistant to the selection agent are transplanted onto substrate. Plants are grown in a growth chamber set to 22° C. with a 55% relative humidity with photoperiod set at 16 h light/8 h dark. A controlled low or high nitrogen nutrient solution is added to waterings on Days 12, 15, 22 and 29. Watering without nutrient solution occurs on Days 18, 25, and 32. Images of all plants in a tray are taken on days 26, 30, and 33 using a commercially available imaging system. At each imaging time point, biomass and plant phenotypes for each plant are measured including plant area, leaf area, biomass, color distribution, color intensity, and growth rate.

EXAMPLE 4

Stress-Tolerant Rapeseed/Canola Plants

Canola cotyledonary petioles of 4 day-old young seedlings are used as explants for tissue culture and transformed according to EP1566443. The commercial cultivar Westar (Agriculture Canada) is the standard variety used for transformation, but other varieties can be used. *A. tumefaciens* GV3101:pMP90RK containing a binary vector is used for canola transformation. The standard binary vector used for transformation is pSUN (WO02/00900), but many different binary vector systems have been described for plant transformation (e.g. An, G. in *Agrobacterium* Protocols, Methods in Molecular Biology vol 44, pp 47-62, Gartland K M A and M R Davey eds. Humana Press, Totowa, N.J.). A plant gene expression cassette comprising a selection marker gene, a plant promoter, and a polynucleotide of Table 1 is employed. Various selection marker genes can be used including the mutated acetohydroxy acid synthase (AHAS) gene disclosed in U.S. Pat. Nos. 5,767,366 and 6,225,105. A suitable promoter is used to regulate the trait gene to provide constitutive, developmental, tissue or environmental regulation of gene transcription.

Canola seeds are surface-sterilized in 70% ethanol for 2 min, incubated for 15 min in 55° C. warm tap water and then in 1.5% sodium hypochlorite for 10 minutes, followed by three rinses with sterilized distilled water. Seeds are then placed on MS medium without hormones, containing Gamborg B5 vitamins, 3% sucrose, and 0.8% Oxoidagar. Seeds are germinated at 24° C. for 4 days in low light (<50 µMol/$m^2$s, 16 hours light). The cotyledon petiole explants with the cotyledon attached are excised from the in vitro seedlings, and inoculated with *Agrobacterium* by dipping the cut end of the petiole explant into the bacterial suspension. The explants are then cultured for 3 days on MS medium including vitamins containing 3.75 mg/l BAP, 3% sucrose, 0.5 g/l MES, pH 5.2, 0.5 mg/l GA3, 0.8% Oxoidagar at 24° C., 16 hours of light. After three days of co-cultivation with *Agrobacterium*, the petiole explants are transferred to regeneration medium containing 3.75 mg/l BAP, 0.5 mg/l GA3, 0.5 g/l MES, pH 5.2, 300 mg/l timentin and selection agent until shoot regeneration. As soon as explants start to develop shoots, they are transferred to shoot elongation medium (A6, containing full strength MS medium including vitamins, 2% sucrose, 0.5% Oxoidagar, 100 mg/l myo-inositol, 40 mg/l adenine sulfate, 0.5 g/l MES, pH 5.8, 0.0025 mg/l BAP, 0.1 mg/l IBA, 300 mg/l timentin and selection agent).

Samples from both in vitro and greenhouse material of the primary transgenic plants (T0) are analyzed by qPCR using TaqMan probes to confirm the presence of T-DNA and to determine the number of T-DNA integrations.

Seed is produced from the primary transgenic plants by self-pollination. The second-generation plants are grown in greenhouse conditions and self-pollinated. The plants are analyzed by qPCR using TaqMan probes to confirm the presence of T-DNA and to determine the number of T-DNA integrations. Homozygous transgenic, heterozygous transgenic and azygous (null transgenic) plants are compared for their stress tolerance, for example, in the assays described in Examples 2 and 3, and for yield, both in the greenhouse and in field studies.

EXAMPLE 5

Screening for Stress-Tolerant Rice Plants

Transgenic rice plants comprising a polynucleotide of Table 1 are generated using known methods. Approximately 15 to 20 independent transformants (T0) are generated. The primary transformants are transferred from tissue culture chambers to a greenhouse for growing and harvest of T1 seeds. Five events of the T1 progeny segregated 3:1 for presence/absence of the transgene are retained. For each of these events, 10 T1 seedlings containing the transgene (hetero- and homozygotes), and 10 T1 seedlings lacking the transgene (nullizygotes) are selected by visual marker screening. The selected T1 plants are transferred to a greenhouse. Each plant receives a unique barcode label to link unambiguously the phenotyping data to the corresponding plant. The selected T1 plants are grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes are grown side-by-side at random positions. From the stage of sowing until the stage of maturity, the plants are passed several times through a digital imaging cabinet. At each time point digital, images (2048×1536 pixels, 16 million colours) of each plant are taken from at least 6 different angles.

The data obtained in the first experiment with T1 plants are confirmed in a second experiment with T2 plants. Lines that have the correct expression pattern are selected for further analysis. Seed batches from the positive plants (both hetero- and homozygotes) in T1 are screened by monitoring marker expression. For each chosen event, the heterozygote seed batches are then retained for T2 evaluation. Within each seed batch, an equal number of positive and negative plants are grown in the greenhouse for evaluation.

Transgenic plants are screened for their improved growth and/or yield and/or stress tolerance, for example, using the assays described in Examples 2 and 3, and for yield, both in the greenhouse and in field studies.

EXAMPLE 6

Stress-Tolerant Soybean Plants

The polynucleotides of Table 1 are transformed into soybean using the methods described in commonly owned copending international application number WO 2005/121345, the contents of which are incorporated herein by reference.

The transgenic plants generated are then screened for their improved growth under water-limited conditions and/or drought, salt, and/or cold tolerance, for example, using the assays described in Examples 2 and 3, and for yield, both in the greenhouse and in field studies.

EXAMPLE 7

Stress-Tolerant Wheat Plants

The polynucleotides of Table 1 are transformed into wheat using the method described by Ishida et al., 1996, Nature Biotech. 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved growth and/or yield under water-limited conditions and/or stress tolerance, for example, is the assays described in Examples 2 and 3, and for yield, both in the greenhouse and in field studies.

EXAMPLE 8

Stress-Tolerant Corn Plants

The polynucleotides of Table 1 are transformed into immature embryos of corn using *Agrobacterium*. After imbibition, embryos are transferred to medium without selection agent. Seven to ten days later, embryos are transferred to medium containing selection agent and grown for 4 weeks (two 2-week transfers) to obtain transformed callus cells. Plant regeneration is initiated by transferring resistant calli to medium supplemented with selection agent and grown under light at 25-27° C. for two to three weeks. Regenerated shoots are then transferred to rooting box with medium containing selection agent. Plantlets with roots are transferred to potting mixture in small pots in the greenhouse and after acclimatization are then transplanted to larger pots and maintained in greenhouse till maturity.

Using assays such as the assay described in Examples 2 and 3, each of these plants is uniquely labeled, sampled and analyzed for transgene copy number. Trans-gene positive and negative plants are marked and paired with similar sizes for transplanting together to large pots. This provides a uniform and competitive environment for the trans-gene positive and negative plants. The large pots are watered to a certain percentage of the field water capacity of the soil depending the severity of water-stress desired. The soil water level is maintained by watering every other day. Plant growth and physiology traits such as height, stem diameter, leaf rolling, plant wilting, leaf extension rate, leaf water status, chlorophyll content and photosynthesis rate are measured during the growth period. After a period of growth, the above ground portion of the plants is harvested, and the fresh weight and dry weight of each plant are taken. A comparison of the drought tolerance phenotype between the transgene positive and negative plants is then made.

Using assays such as the assay described in Example 2 and 3, the pots are covered with caps that permit the seedlings to grow through but minimize water loss. Each pot is weighed periodically and water added to maintain the initial water content. At the end of the experiment, the fresh and dry weight of each plant is measured, the water consumed by each plant is calculated and WUE of each plant is computed. Plant growth and physiology traits such as WUE, height, stem diameter, leaf rolling, plant wilting, leaf extension rate, leaf water status, chlorophyll content and photosynthesis rate are measured during the experiment. A comparison of WUE phenotype between the transgene positive and negative plants is then made.

Using assays such as the assay described in Example 2 and 3, these pots are kept in an area in the greenhouse that has uniform environmental conditions, and cultivated optimally. Each of these plants is uniquely labeled, sampled and analyzed for trans-gene copy number. The plants are allowed to grow under theses conditions until they reach a predefined growth stage. Water is then withheld. Plant growth and physiology traits such as height, stem diameter, leaf rolling, plant wilting, leaf extension rate, leaf water status, chlorophyll content and photosynthesis rate are measured as stress intensity increases. A comparison of the dessication tolerance phenotype between transgene positive and negative plants is then made.

Segregating transgenic corn seeds for a transformation event are planted in small pots for testing in a cycling drought assay. These pots are kept in an area in the greenhouse that has uniform environmental conditions, and cultivated optimally. Each of these plants is uniquely labeled, sampled and analyzed for transgene copy number. The plants are allowed to grow under theses conditions until they reach a predefined growth stage. Plants are then repeatedly watered to saturation at a fixed interval of time. This water/drought cycle is repeated for the duration of the experiment. Plant growth and physiology traits such as height, stem diameter, leaf rolling, leaf extension rate, leaf water status, chlorophyll content and photosynthesis rate are measured during the growth period. At the end of the experiment, the plants are harvested for above-ground fresh and dry weight. A comparison of the cycling drought tolerance phenotype between transgene positive and negative plants is then made.

In order to test segregating transgenic corn for drought tolerance under rain-free conditions, managed-drought stress at a single location or multiple locations is used. Crop water availability is controlled by drip tape or overhead irrigation at a location which has less than 10 cm rainfall and minimum temperatures greater than 5° C. expected during an average 5 month season, or a location with expected in-season precipitation intercepted by an automated "rain-out shelter" which retracts to provide open field conditions when not required. Standard agronomic practices in the area are followed for soil preparation, planting, fertilization and pest control. Each plot is sown with seed segregating for the presence of a single transgenic insertion event. A Taqman transgene copy number assay is used on leaf samples to differentiate the transgenics from null-segregant control plants. Plants that have been genotyped in this manner are also scored for a range of phenotypes related to drought-tolerance, growth and yield. These phenotypes include plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plants are used as the replicate unit per event.

In order to test non-segregating transgenic corn for drought tolerance under rain-free conditions, managed-drought stress at a single location or multiple locations is used. Crop water availability is controlled by drip tape or overhead irrigation at a location which has less than 10 cm rainfall and minimum temperatures greater than 5° C. expected during an average 5 month season, or a location with expected in-season precipitation intercepted by an automated "rain-out shelter" which retracts to provide open field conditions when not required. Standard agronomic practices in the area are followed for soil preparation, planting, fertilization and pest control. Trial layout is designed to pair a plot containing a non-segregating transgenic event with an adjacent plot of null-segregant controls. A null segregant is progeny (or lines derived from the progeny) of a transgenic plant that does not contain the transgene due to Mendelian segregation. Additional replicated paired plots for a particular event are distributed around the trial. A range of phenotypes related to drought-tolerance, growth and yield are scored in the paired plots and estimated at the plot level. When the measurement technique could only be applied to individual plants, these are selected at random each time from within the plot. These phenotypes include plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

To perform multi-location testing of transgenic corn for drought tolerance and yield, five to twenty locations encompassing major corn growing regions are selected. These are widely distributed to provide a range of expected crop water availabilities based on average temperature, humidity, precipitation and soil type. Crop water availability is not modified beyond standard agronomic practices. Trial layout is designed to pair a plot containing a non-segregating transgenic event with an adjacent plot of null-segregant controls. A range of phenotypes related to drought-tolerance, growth and yield are scored in the paired plots and estimated at the plot level. When the measurement technique could only be applied to individual plants, these are selected at random each time from within the plot. These phenotypes included plant height, grain weight per plant, grain number per plant, ear number per plant, above ground dry-weight, leaf conductance to water vapor, leaf $CO_2$ uptake, leaf chlorophyll content, photosynthesis-related chlorophyll fluorescence parameters, water use efficiency, leaf water potential, leaf relative water content, stem sap flow rate, stem hydraulic conductivity, leaf temperature, leaf reflectance, leaf light absorptance, leaf area, days to flowering, anthesis-silking interval, duration of grain fill, osmotic potential, osmotic adjustment, root size, leaf extension rate, leaf angle, leaf rolling and survival. All measurements are made with commercially available instrumentation for field physiology, using the standard protocols provided by the manufacturers. Individual plots are used as the replicate unit per event.

APPENDIX cDNA sequence of At2g20725 from *Arabidopsis* (SEQ ID NO:1):

```
ATGATTCTAGGCCGATGGGTTTCCTTCAGTTGCGGAAACACGCCGGTGAC

TAATTGTTCCGAACGACGACGACATACGGAGTTTCGTCGTCTCTCCTCTG

CTAGTACTTGTCGACCTTCTCTGATATGCTCTTGTCTCAAAAGCAAATCC

TCCCAAGAAACTACTCAGATTGAACAGTTGGGGAATGGAGAAGGGTTCTC

AGTTTTGGCATCAGAGATTCCATGGGAGGATGATAACATATGGAGCACAT

TTGCTCTTTACATGTTCTCTCTGCATATTCCTCTCAGTTTTGGGGGTTTA

TCCATTGTTGCCAACATACTCCACCGGCAGGTTCTTGATCCTCAGACCCA

AGTGCTATCACTTGTGGTTCTCCAAATGGTAGAACTTGCAGGGACAGTCT

TGCTGCTGAGGACCACAGCGAAGCCTCAGTGCAAATCAATCAACTTTCTA

AAGGGTAATAACGAAACAAGGGAAGGAAGAAACTGTGTGGTTGGCTCAGC

ATTGGGTTTGGGATGTCTTGTGGGCTTTATCTTCGTCACGTCGCTTGTAG

CTGATCAACTCTTTGGCCCTAAGGCTGTACATGAATCAGAATTGGAGAAG

ATAATGGTGAGGCGGGAAGTGGCGAGAAGCGGATGTTTTGCTCTCTACTG

CGTAGTAGCTCCCATCCTTGAGGAGATAGTGTACAGACGCTTTCTCCTGA

CCTCCTTAGCGTCGAGAATGGAATGGTGGAAGGCACTAGTGATCAGCTCA

GGAGTATTTGCTGCAGGTCACTTCTCAGGTGAGGATTTTGTGCAGCTGTT
```

TGGGATAGGTTGCGGTCTCGGGTTATGTTACAGCTGGTCAGGGAACTTAG

CCTCATCAGTGCTCGTCCACTCCTTGTACAATGCATTGACACTTCTCTTC

TCTTAG

The At2g20725 cDNA is translated into the following amino acid sequence (SEQ ID NO:2):

MILGRWVSFSCGNTPVTNCSERRRHTEFRRLSSASTCRPSLICSCLKSKS

SQETTQIEQLGNGEGFSVLASEIPWEDDNIWSTFALYMFSLHIPLSFGGL

SIVANILHRQVLDPQTQVLSLVVLQMVELAGTVLLLRTTAKPQCKSINFL

KGNNETREGRNCVVGSALGLGCLVGFIFVTSLVADQLFGPKAVHESELEK

IMVSGEVARSGCFALYCVVAPILEEIVYRRFLLTSLASRMEWWKALVISS

GVFAAGHESGEDEVQLFGIGCGLGLCYSWSGNLASSVLVHSLYNALTLLF

S cDNA sequence of At3g26085 from *Arabidopsis* (SEQ ID NO:3):

ATGGGTTCCATCGCTCTGCAATCTTGGAGCAGAGGAGCTTCAACTTCTCT

TCATCTCCTTTTTCGTCCAGTTGGCTCGAACCCTAAGCTATATGATGCTC

GAAGAGTACAATTTGATGTAAGAGCCTCTTCAAGTCGTAAATCACTTAAG

AAACTCAAAAGAGAGTCACAACAAGGTAAAGACATAGGCTTAAGAAATGT

TACAGATGAAGAAGTTTCTTCTCCAAGATTTGAGGAAGCTCAAGTTGATT

CTTCAACTTCAAAGGACTCCATTGATGTTTTTGTTGCTGCTCCTCGAGAC

AAAGTGCTTCAGGCTTGCACTGTAACTTCCGGTTTGATGGCTGCACTAGG

TCTGATCATCAGAAAGGCGTCTCATGTTGCTTCGACTGAAGGATTACTGG

TTCCAGACTGCTCTATAGATGTACCATTTGGGTTTGAAACTTGGCATCTC

GGTTTAATTGCTGGAATCGTTGTGTTTATATCGTCAAGTAGGTTCTTGCT

ACTTAAATCTTGGCCAGATTTTGCTGATTCTAGTGAAGCAGCAAACCGAC

AGATTCTCACTTCCCTCGAACCTCTAGATTACCTTGTTGTTGCAATGTTA

CCGGGAATAAGTGAGGAGCTGCTGTTTAGAGGTGCATTAATGCCTTTGTT

CGGAACTAATTGGAATGGTATTGTAGCGGTTGGCCTCATTTTCGGTTTAC

TTCATCTCGGGAGCGGAAGAAAGTATTCTTTTGCAGTTTGGGCTTCGATT

GTCGGTATAGTCTACGGTTATGCAGCTGTTTTGTCGTCGAGTCTTATCGT

TCCAATGGCCTCGCACGCACTCAACAATTTGGTGGGAGGTCTGTTGTGGC

GATATAGTTCCAAGATCAAGTCATTGGAG-TAA

The At3g26085 cDNA is translated into the following amino acid sequence (SEQ ID NO:4):

MGSIALQSWSRGASTSLHLLFRPVGSNPKLYDARRVQFDVRASSSRKSLK

KLKRESQQGKDIGLRNVTDEEVSSPRFEEAQVDSSTSKDSIDVFVAAPRD

KVLQACTVTSGLMAALGLIIRKASHVASTEGLLVPDCSIDVPFGFETWHL

GLIAGIVVFISSSRFLLLKSWPDFADSSEAANRQILTSLEPLDYLVVAML

PGISEELLFRGALMPLFGTNWNGIVAVGLIFGLLHLGSGRKYSFAVVWASI

VGIVYGYAAVLSSSLIVPMASHALNNLVGGLLWRYSSKIKSLE cDNA sequence of AtFACE-2 from *Arabidopsis* (SEQ ID NO:5):

ATGGCCACCGATGGCGAGAGTATCTCGATGTCGTTGGCGGTGGCTACCTG

CGTCGCGATGGCACTATTCTACGTTTTGATCCTTTACGTTCCCACCGTGA

TACTCCGTGTCCCGTCGGCTTCTTCTTACACCGAATTCATGATTCGGCGA

TTCATCTGCGCGGCCATTTGTACTGTAGCATCTCTCGTCTTCACAGCTTT

TATACTTCCGATAAAAAGCTGGGAGGCCTCTTATATACTTGGAGTTTATG

GCATAAGGAAAGATCATCTGTGGCAAGGAGTGGTGTATCCTCTTCTATTG

ACCTCGCTCGTTTATGCTGGGTCTTTGGTGTTGAAGTTGTTTACTCTCCT

GGAATCATGGAAGGAAAATGGCGGAGGATGTAGTTCCTTTAATTACATCA

GAAGCTTTTTCCAAACAATCCCTGCTTCGGTATTGACAAGTGCTTCTAAT

GTTTCCGTTTGGCGCAATTTTATCGTGGCACCAGTAACTGAGGAGCTGGT

TTTCCGATCATGTATGATACCTTTGCTTCTGTGTGCTGGGTTTAGGATTA

ACACTGCCATCTTTCTGTGCCCAGTTCTCTTTAGCTTGGCTCACTTAAAC

CATTTTAGAGAGATGTACATCAGGCATAACCGCAGCTATCTCCGGGCTTC

ACTTATTGTTGGTCTTCAGCTTGGCTACACAGTCATTTTTGGTGCATATG

CATCGTTTCTCTTCATCAGAACCGGACATCTTGCTGCTCCTTTGTTTGCT

CATATATTTTGCAACTACATGGGATTGCCTGTGCTATACGCAAATGGAAA

AGGTTTGGTGAGTGCAGCGTTCTTAGGCGGTGTGGTTGGGTTCGTCTTAC

TTCTCTTTCCTTTAACAAAGCCTCTCATGTACAACGATAGTACCAACGAT

TGTCCGTGTTGGCTTGGCTATTGTTTGTGGAATTGA

The AtFACE-2 cDNA is translated into the following amino acid sequence (SEQ ID NO:6):

MATDGESISMSLAVATCVAMALFYVLILYVPTVILRLPSASSYTEFMIRR

FICAAICTVASLVFTAFILPIKSWEASYILGVYGIRKDHLWQGVVYPLLL

TSLVYAGSLVLKLFTLLESWKENGGGCSSFNYIRSFFQTIPASVLTSASN

VSVWRNFIVAPVTEELVFRSCMIPLLLCAGFRINTAIFLCPVLFSLAHLN

HEREMYIRHNRSYLRASLIVGLQLGYTVIFGAYASFLFIRTGHLAAPLFA

HIFCNYMGLPVLYANGKGLVSAAFLGGVVGFVLLLFPLTKPLMYNDSTND

GPGWLGYGLWN cDNA sequence of ZM57353913 from corn (SEQ ID NO:7):

CGAAGCCACGCGACCGACTGTGTTACGATCCCAAATCTTCACTCCCGACG

AAATCTAGAATCCAATGAGCAATCTCGACTGACGCCTGCTTCACCAGATT

ATGGCGACGCCGGCGGGCCTCCTTCTCGCCTCGCCGCCGGTGATATCAGG

TGTCGCGGCGATGGCGGCGTGCGCCGCAATGGCAGTATTCTACGTCGCTG

TCCTCTATGC

CCCGACGGTCATCCTCCGGTTCCCACCCCCAACCTCACTCCGCACCTTCC

```
TCCACCGTCGCTTCGCCTGTGCCGCCGTCGCATCCGCCGCCTCCGTCCTT
GCCACTGCGTCCCTCCTCCGAGTCTGGAGCCTCAGCGACTTCGCTGATAT
GTTTGCTGTGTTCGGCATTAGGAAGGATCACTTGATTCAGGCCGTGGCTA
TTCCACTTCTCCTGACATCCCTAGTGTATGCTGGGTCATTCGTCGCTAGA
GTGTGGCTCCTAGTGAGCTCGTGGGGCGGTGGCGATGAGGTGGAGATAGG
CTGCGCACAGAGGCTTGCACAATGGATCCAAGCTGCTGTTGCGGATGTTA
TGGTTTGGCGGAACTATGTAGTGGCACCATTTACTGAGGAGCTGGTTTTC
AGGGCATGCATGATACCTCTTCTGCTCTGTGGGGATTCAAAATGTCTAC
AATTATATTTCTGAGTCCAATCTTCTTCAGTCTAGCGCACTTGAACCATT
TTTTCGAACTACACCAGCAGGGATGTAACTTTATGAGAGCGCTATTGATT
GTAGGTGTCCAGTTAGGCTACACTGTCATTTTTGGGTGGTATGCAACATT
CTTGTTAATCCGAACAGGGAATCTGTTATGTCCAATTATTGCTCACGTCT
TCTGTAATATGATGGGTTTACCTGTTTTCTCGTCACCACGAACAAAAGGA
GCGGCATTGGTAGCGTTTCTGGCTGGTTCAATAGCCTTCTTTTGGCTGCT
TTTCCCTGCAACAAGTCCTGAACTGTACAACAGCAGTTTTGATCGCTGCA
GTTGCTGGCATGGCTTTTGCAATTGGAAATAACATAGAACTAGATTGGAA
AGCAATGGGTCCTAACTTGAAGCTACTAACAATTGAAACCTCCAGGCCCT
AGCTGACACTTCTGACGGATTTTCTATTTGCAGAAACTCCATATGAATGT
CTTAAAACGTTTTGTAGAAATGTGTCCCTTGTTTTAGCTTAAGACTCAAG
AGCTTAAACTAGCAAAAGATTGTATTTTGCCACTTGTTAAATACGTGCTG
ATCATGAAATCGCTGTCAATCCCTTCTCAAAGTGGAATTTGACTTTGTTG
AGCTGCTTTTATTTATATTGTGCTTGCTACTGCAGCGCCTAGAGTTTGTA
GATTACACATCATGGACCCGTCTGATATTGTAAACGAGAGACATGTTTCT
AAGTTAATATGCTCCCTCCATTTATTTAAAAAAAAAAAAA
```

The ZM57353913 cDNA is translated into the following amino acid sequence (SEQ ID NO:8):

```
MATPAGLLLASPPVISGVAAMAACAAMAVFYVAVLYAPTVILRFPPPTSL
RTFLHRRFACAAVASAASVLATASLLRVWSLSDFADMFAVFGIRKDHLIQ
AVAIPLLLTSLVYAGSFVARVWLLVSSWGGGDEVEIGCAQRLAQWIQAAV
ADVMVWRNYVVAPFTEELVFRACMIPLLLCGGFKMSTIIFLSPIFFSLAH
LNHFFELHQQGCNFMRALLIVGVQLGYTVIFGWYATELLIRTGNLLCPII
AHVFCNMMGLPVFSSPRTKGAALVAFLAGSIAFFWLLFPATSPELYNSSF
DRCSCWHGFCNWK
``` cDNA sequence of ZM59252659 from corn (SEQ ID NO:9):

```
CCCAAATCTTCATTTCCGACGAAATCGAGAATCCAATGTGCAATCTCGAC
TGACGCCTGCTTCAACAGATTATGGCGACGCGGTGGGTCTCCTTCTCGCC
TCGCCGCCGGAATATCAGGGTCGCGCGATGGGTCGTGCGCCAACGGAAGG
ATTCTACGTCGCTGTCCTCTATGCCCCGACGGTCATCCTCCGGGTCCCAC
CCCCAAGCTCACTCCGCACCTTCCTCCACCGTCGCTTCGCCTGTGCCGCC
GTCGCATCCGCCGCCTCCGTCCTTGCCACTGCGTCCCTCCTCCGAATCTG
GAGCCTCAGCGACTTCGCTGATATGTTTGCTGTGTTCGGCATTAGGAAGG
ATCACTTGATTCAGGCCGTGGCTATTCCACTTCTCCTGACATCCCTAGTG
TATGCTGGGTCATTCGTCGCTAGAGTGTGGCTCCTAGTGAGCTCGTGGGG
CGGTGGCGATGAGGTGGAGATAGGCTGCGCACAGAGGCTTGCACAATGGA
TCCAAGCTGCTGTTGCGGATGTTATGGTTTGGCGGAACTATGTAGTGGCA
CCATTTACTGAGGAGCTGGTTTTCAGGGCATGCATGATACCTCTTCTGCT
CTGTGGGGATTCAAAATGTCTACAATTATATTTCTGAGTCCAATCTTCT
TCAGTCTAGGTGTCCAGTTAGGCTACACTGTCATTTTTGGGTGGTATGCA
ACATTCTTGTTAATCCGAACAGGGAATCTGTTATGTCCAATTACTGCTCA
CGTCTTCTGTAATATGATGGGTTTACCTGTTTTCTCGTCACCACGAACAA
AAGGAGCGGCATTGGTAGCGTTTCTGGCTGGTTCAATAGCCTTCTTTTGG
CTGCTTTTCCCTGCAACAAGTCCTGAACTGTACAACAGCAGTTTTGATCG
CTGCAGTTGCTGGCATGGCTTTTGCAATTGGAAATAACATAGAACTAGAT
TGGAAAGCAATGGGTCCTAACTTGAAGCTACTAACAATTGAAACCTCCAG
GCCCTAGCTGACACTGCTGACGGATTTTCTATTTGCAGAAACTCCATATG
AATGTCTTAAAACGTTTTGTAGAAATGTGTCCCTTGTTTTAGCTTAAGAC
TCGAGCTTAAACTAGCAAAAGATTGTATTTTGCCACTTGTTAAATACGTG
CTGATCATGAAATCGCTGTCAATCCCTTCTCAAAGTGGAATTTGACTTTG
TTGTAAAAAAAAAAA
```

The ZM59252659 cDNA is translated into the following amino acid sequence (SEQ ID NO:10):

```
MGRAPTEGFYVAVLYAPTVILRVPPPSSLRTFLHRRFACAAVASAASVLA
TASLLRIWSLSDFADMFAVFGIRKDHLIQAVAIPLLLTSLVYAGSFVARV
WLLVSSWGGGDEVEIGCAQRLAQWIQAAVADVMVWRNYVVAPFTEELVFR
ACMIPLLLCGGFKMSTIIFLSPIFFSLGVQLGYTVIFGWYATFLLIRTGN
LLCPITAHVFCNMMGLPVFSSPRTKGAALVAFLAGSIAFFWLLFPATSPE
LYNSSFDRCSCWHGFCNWK
``` cDNA sequence of CASAR82A from pepper (SEQ ID NO:11):

```
ATGGTGTCTAAGTCCTCAATCTTCATTTGCCTGAGCCTTATCATCCTCGT
GATCATGTCTACCCAGATCGTGGCTAGAGAGATGACCAGTGAAGCTTCTG
CTTCACTCACACAGGCAATGAACGGGAACAATATCTCTGAGACCAAGAAA
GTGGGTCGTCACTTGGTGAAGGGCTTGGATAAGATCTTCAAGGCTGGAAA
GGTGATCTACTGCAAGACCTGCAAAACCTGCCACGGTCGCTGCGATTACT
GTTGCGCC
```

The CASAR82A cDNA is translated into the following amino acid sequence (SEQ ID NO:12):

MVSKSSIFICLSLIILVIMSTQIVAREMTSEASASLTQAMNGNNISETKK
VGRHLVKGLDKIFKAGKVIYCKTCKTCHGRCDYCCA cDNA sequence of b3358 from *E. coli* (SEQ ID NO:13):

ATGTGGCGCAGACTGATTTATCACCCCGATATCAACTATGCACTTCGACA
AACGCTGGTGCTATGTTTGCCCGTGGCCGTTGGGTTAATGCTTGGCGAAT
TACGATTCGGTCTGCTCTTCTCCCTCGTTCCTGCCTGTTGCAATATTGCG
GGCCTTGATA
CGCCTCATAAACGTTTTTTCAAACGCTTAATCATTGGTGCGTCGCTGTTT
GCCACCTGTAGCTTGCTGACACAGCTACTACTGGCAAAGATGTTCCCCT
GCCCTTTTTGCTGACCGGATTAACGCTGGTACTTGGCGTCACTGCTGAGC
TGGGGCCATTGCACGCAAAATTGCTTCCTGCATCGCTGCTCGCCGCCATT
TTTACCCTCAGTTTGGCGGGATACATGCCGGTCTGGGAACCGTTGCTCAT
CTATGCGTTGGGCACTCTCTGGTACGGATTGTTTAACTGGTTTTGGTTCT
GGATCTGGCGCGAACAACCGCTGCGCGAGTCACTAAGTCTGCTGTACCGT
GAACTGGCAGATTATTGTGAAGCCAAATACAGCCTGCTTACCCAGCACAC
CGACCCTGAAAAGCGCTGCCGCCGCTGCTGGTGCGCCAGCAAAAGCGG
TCGATCTAATTACCCAGTGCTATCAGCAAATGCATATGCTTTCCGCGCAA
AATAATACTGACTACAAGCGGATGCTGCGTATTTTCCAGGAGGCGCTGGA
TTTACAGGAACATATTTCGGTCAGTTTGCATCAGCCGGAAGAGGTGCAAA
AGCTGGTCGAGCGTAGCCATGCGGAAGAAGTTATCCGCTGGAATGCGCAA
ACCGTCGCCGCTCGCCTGCGCGTGCTGGCTGATGACATTCTTTACCATCG
CCTGCCAACGCGTTTTACGATGGAAAAGCAAATTGGCGCACTGGAAAAAA
TCGCCCGCCAGCATCCGGATAATCCGGTTGGGCAATTCTGCTACTGGCAT
TTCAGCCGCATCGCCCGCGTGCTGCGCACCCAAAAACCGCTCTATGCCCG
TGACTTACTGGCCGATAAACAGCGGCGAATGCCATTACTTCCGGCGCTGA
AAAGTTATCTGTCACTAAAGTCTCCGGCGCTACGCAATGCCGGACGACTC
AGTGTGATGTTAAGCGTTGCCAGCCTGATGGGCACCGCGCTGCATCTGCC
GAAGTCGTACTGGATCCTGATGACGGTATTGCTGGTGACACAAAATGGCT
ATGGCGCAACCCGTCTGAGGATTGTGAATCGCTCCGTGGGAACCGTGGTC
GGGTTAATCATTGCGGGCGTGGCGCTGCACTTTAAAATTCCCGAAGGTTA
CACCCTGACGTTGATGCTGATTACCACCCTCGCCAGCTACCTGATATTGC
GCAAAAACTACGGCTGGGCGACGGTCGGTTTTACTATTACCGCAGTGTAT
ACCCTGCAACTATTGTGGTTGAACGGCGAGCAATACATCCTTCCGCGTCT
TATCGATACCATTATTGGTTGTTTAATTGCTTTCGGCGGTACTGTCTGGC
TGTGGCCGCAGTGGCAGAGCGGGTTATTGCGTAAAAACGCCCATGATGCT
TTAGAAGCCTATCAGGAAGCGATTCGCTTGATTCTTAGCGAGGATCCGCA
ACCTACGCCACTGGCCTGGCAGCGAATGCGGGTAAATCAGGCACATAACA
CTCTGTATAACTCATTGAATCAGGCGATGCAGGAACCGGCGTTTAACAGC

CATTATCTGGCAGATATGAAACTGTGGGTAACGCACAGCCAGTTTATTGT
TGAGCATATTAATGCCATGACCACGCTGGCGCGGGAACACCGGGCATTGC
CACCTGAACTGGCACAAGAGTATTTACAGTCTTGTGAAATCGCCATTCAG
CGTTGTCAGCAGCGACTGGAGTATGACGAACCGGGTAGTTCTGGCGATGC
CAATATCATGGATGCGCCGGAGATGCAGCCGCACGAAGGCGCGGCAGGTA
CGCTGGAGCAGCATTTACAGCGGGTTATTGGTCATCTGAACACCATGCAC
ACCATTTCGTCGATGGCATGGCGTCAGCGACCGCATCACGGGATTTGGCT
GAGTCGCAAGTTGCGGGATTCGAAGGCGTAA

The b3358 cDNA is translated into the following amino acid sequence (SEQ ID NO:14):

MWRRLIYHPDINYALRQTLVLCLPVAVGLMLGELRFGLLFSLVPACCNIA
GLDTPHKRFFKRLIIGASLFATCSLLTQLLLAKDVPLPFLLTGLTLVLGV
TAELGPLHAKLLPASLLAAIFTLSLAGYMPVWEPLLIYALGTLWYGLFNW
FWFWIWREQPLRESLSLLYRELADYCEAKYSLLTQHTDPEKALPPLLVRQ
QKAVDLITQCYQQMHMLSAQNNTDYKRMLRIFQEALDLQEHISVSLHQPE
EVQKLVERSHAEEVIRWNAQTVAARLRVLADDILYHRLPTRFTMEKQIGA
LEKIARQHPDNPVGQFCYWHFSRIARVLRTQKPLYARDLLADKQRRMPLL
PALKSYLSLKSPALRNAGRLSVMLSVASLMGTALHLPKSYWILMTVLLVT
QNGYGATRLRIVNRSVGTVVGLIIAGVALHFKIPEGYTLTLMLITTLASY
LILRKNYGWATVGFTITAVYTLQLLWLNGEQYILPRLIDTIIGCLIAFGG
TVWLWPQWQSGLLRKNAHDALEAYQEAIRLILSEDPQPTPLAWQRMRVNQ
AHNTLYNSLNQAMQEPAFNSHYLADMKLWVTHSQFIVEHINAMTTLAREH
RALPPELAQEYLQSCEIAIQRCQQRLEYDEPGSSGDANIMDAPEMQPHEG
AAGTLEQHLQRVIGHLNTMHTISSMAWRQRPHHGIWLSRKLRDSKA cDNA sequence of EST564 from moss (SEQ ID NO:15):

ATGTCATGCGACGTTCTCTGCCAATCTTTCAAGGAGGTAGAGGGCAAGTT
CTTGGAAATCGTCGAAAGGGCTTGGGCCGTCAAGCCGCAAATTGCCGCTG
TTGGATCTTGTTGTTTGGTGGGAGCCGTATGGGATTCCAAACTGTACATC
GCTAGTCTTGGAGATTCTCGAGCTGTTTTAGGTAGTTGCTCTCGTGACAC
TGGCCTTCCAGTTGCTAAGCAAATTTCAACAGAGCACAACGCAAGCATCG
AGTCTATCCGGAATGAGTTGTTCGCAAAGCATAGTGATGATCCGCAGATC
GTGGTTTTGAAGCATGGAGTGTGGCGTGTGAAGGGTATTATTCAGATTTC
ACGCTCAATTGGTGATTTTTACTTGAAGAAAGCCGAATTTAATCAGCCGC
CTCTTATAGCCAGGTTCCGG
CTTCCAGATCCCCTCAAGAGACCTGTCATAAGCTCAGAGCCGGAGTGCAA
CGTCATTACACTCGGCCCGGATGACGAATTCGTCATTTTTGCATCTGATG
GCCTTTGGGAGCACTTGAGCAGCAAAGAGGCCGTAGACATTGTGTATAGT
CATCCCCGGGCTGGGATTGCCAGGCGTCTGATCAAAGCTGCTCTTCAAAA
AGCTGCTACTAAACGTGAAATGCGGTACTCTGATTTGAAAGGGATTGAGC

-continued

```
GCGGGATACGACGGCATTTTCATGATGACATAACTGTTGTGGTTCTTTAT

TTGGACACTAAACTGCTCAACAGAGGTGGTAGTATTTCTAATCATATTTC

TTCGAAATGTCCAATTGACATGCCAAAAGGCGATAACCCTCCGTCGTTAG

TTAGCTCTAACATGAACTTAGCTTTTAACAAATAA
```

The EST564 cDNA is translated into the following amino acid sequence (SEQ ID NO:16):

```
MSCDVLCQSFKEVEGKFLEIVERAWAVKPQIAAVGSCCLVGAVWDSKLYI

ASLGDSRAVLGSCSRDTGLPVAKQISTEHNASIESIRNELFAKHSDDPQI

VVLKHGVWRVKGIIQISRSIGDFYLKKAEFNQPPLIARFRLPDPLKRPVI

SSEPECNVITLGPDDEFVIFASDGLWEHLSSKEAVDIVYSHPRAGIARRL

IKAALQKAATKREMRYSDLKGIERGIRRHFHDDITVVVLYLDTKLLNRGG

SISNHISSKCPIDMPKGDNPPSLVSSNMNLAFNK
``` cDNA sequence of BN49502266 from canola (SEQ ID NO:17):

```
CCAATAATCAAATCAAAACCCTTTCGATCAGTTGTTNCAGGAAAAAAAAA

AACCCTTTCGATCTCATTCCATTTCGAATCAGAAAACCCTAGCAATTGAC

GATGTTGCGAGCTTTAGCGCGGCCTCTCGAACGGTGTTTAGGAAGCAGAG

CGAGCGGCGACGGTTTGCTCTGGCAATCGGAGTTGAAACCACACGCCGGC

GGAGATTACTCGATCGCGGTGGTTCAAGCCAATTCTAGCCTAGAGGATCA

GAGTCAGGTGTTCACGTCTTCCTCCGCTACTTACGTCGGCGTCTACGACG

GCCATGGCGGACCCGAAGCTTCTAGATTCGTTAACAGACATCTCTTTCCT

TATATTCAGAAGTTCGCAAAAGAACATGGAGGACTGTCTGCAGACGTTAT

TAAAAAAGCATTCAAAGAAACTGAAGAGGATTTTTGCGGTATGGTTAAAC

GCTCACTTCCCATGAAGCCACAGATGGCTACTGTAGGATCTTGCTGTCTC

TTTGGTGCCATCTCTAACGGCACGCTCTATGTCGCGAATCTTGGAGACTC

GAGAGCCGTTCTTGGGAGCGTTGTTGCAGGGGATGATAGTAATAGTAGTA

ACAAGGGTGCTGCAGCTGAACGGTTGTCCACTGATCATAACGTTGCTGTT

GAAGAAGTGAGGAAGGAGGTTAAGGAACTTAACCCGGATGATTCGCAGAT

CGTCATGTACATTCGTGGAGTTTGGAGGATTAAAGGCATTATTCAGGTAT

CTAGATCAATTGGGGATGTTTACTTGAAGAAACCGGAGTTTTACAGGGAT

CCGATATTCCAGCAACATGGAAATCACATTCCTTTGAGGAGACCCGCGAT

GACAGCTGAACCGTCCATTATAGTAAGGAAGCTTAAGCCGCAAGACTTGT

TTCTGATATTTGCATCAGATGGTCTCTGGGAGCATCTTAGTGATGAAGCA

GCAGTAGAAATTGTACTCAAACACCCAAGAACTGGGATTGCAAGAAAACT

TGTAAGAGCAGCTCTTGAAGAAGCAGCAAGGAAGAGAGAAATGAGATATG

GAGATATAAAGAAAATAGCCAAAGGGGTTAGAAGACATTTCCATGACGAC

ATAAGCGTCGTTGTAGTTTATCTTGATCAACAAAAAACCACTTCTTCATC

GAATGATAGATTGATCCAGAAAGGAGGAATCACTGCTCCACCGGATATCT

ACTCGTTACGTTCAGATGAAGCTGAGCAACGACGGCTACTCAATGTGTTA

TATTGATACTCTCTGGTTAGAGGGATACAACTTGTTTACATATTTGTTTA

ATCTTTTACAAAGAATGTTTGTTCTTTTTTCTTTCTTTTTTTAATATTTG

GAGTTGGATTTGTATATTCTTTTTACCAGCAAGGAACGAAAACCCTTCTC

TTTTGGGGGCAAAACAGTTTTGGTTTTGACAAACAATATAAAGTGAAACC

GTTTGCAAAAAAAAAAAAAAAAA
```

The BN49502266 cDNA is translated into the following amino acid sequence (SEQ ID NO:18):

```
MLRALARPLERCLGSRASGDGLLWQSELKPHAGGDYSIAVVQANSSLEDQ

SQVFTSSSATYVGVYDGHGGPEASRFVNRHLFPYIQKFAKEHGGLSADVI

KKAFKETEEDFCGMVKRSLPMKPQMATVGSCCLFGAISNGTLYVANLGDS

RAVLGSVVAGDDSNSSNKGAAAERLSTDHNVAVEEVRKEVKELNPDDSQI

VMYIRGVWRIKGIIQVSRSIGDVYLKKPEFYRDPIFQQHGNHIPLRRPAM

TAEPSIIVRKLKPQDLFLIFASDGLWEHLSDEAAVEIVLKHPRTGIARKL

VRAALEEAARKREMRYGDIKKIAKGVRRHFHDDISVVVVYLDQQKTTSSS

NDRLIQKGGITAPPDIYSLRSDEAEQRRLLNVLY
``` cDNA sequence of GM49788080 from soybean (SEQ ID NO:19):

```
TCCCGGGTCGACGATTTCGTGGTTACGGGGCGGAAGGAAGGGCTGCTGTG

GTACAAGGATGCGGGGCAGCACTTGTTTGGTGAATACTCAATGGCTGTTG

TCCAGGCCAACAACCTGCTCGAGGACCAGAGCCAGATTGAGTCTGGTCCT

CTCAGCCTGCTTGACACTGGCCCTTATGGGACCTTTGTTGGTGTATATGA

TGGACACGGTGGGCCCGAGACGTCGCGCTACGTCTGTGATCATCTCTTCC

AACATCTAAAACGATTTGCATCTGAGCAGAAGTCCATGTCTATGGAGGTT

ATTCGGAAGGCATACCAAGCCACAGAAGAAGGTTTTTTGTCAGTGGTTAC

CAAACAGTGGCCCATGAATCCCCAAATTGCTGCTGTGGGATCTTGTTGTT

TGGTTGGTGTGATTTGTGGTGGTATCCTCTATATTGCTAACCTTGGTGAT

TCCCGTGCTGTGCTTGGCCGGGTGGTCAGAGCAACTGGGGAGGTTTTGGC

GATCCAGCTTTCGTCAGAGCATAATGTGGCCATAGAATCTGTGAGACAAG

AGATGCATTCTTTGCATCCGGATGACTCAAAAATTGTGGTTCTAAAGCAC

AATGTATGGCGGGTGAAGGGTCTGATACAGATTTCTAGATCCATTGGCGA

TGTATACCTAAAAAAGGCTGAATTTAACAAGGAACCGTTGTATGCTAAGT

TTCGTGTGCGGGAAGGTTTTAAGAGGCCCATTTTGAGCTCTGACCCATCA

ATTTCTGTCCATGAACTTCAACAGCATGATCAATTTCTCATATTTGCTTC

TGATGGTCTTTGGGAACACCTTAGCAATCAGGATGCCGTTGATATAGTTC

AAAACAACCCACACAATGGAATTGCTCGGAGGCTCATCAAAGCTGCGTTG

CAAGAAGCAGCAAAAAGAGAGAGATGAGGTACTCTGATTTGAAGAAAAT

TGACCGTGGTGTCCGCCGGCATTTCCATGATGACATCACAGTTGTAGTTG

TATTTCTTGACTCCAATCTTGTCAGCAGAGCCAGCTCAGTAAGAGGTCCT

CCTTTATCGGTGAGGAGGTGGTGTTCCCCTACCTTCTAGAACTTTGGC

TCCCTGTGCTGCACCTATGGAAACTTAGTTCAGGTTGATGAAGCTGGCTG
```

```
TATGATCTGTTATGCTTCTATTTAGTGTTGTACCCTTAGCAGACATTGAG

CTCTGGTGATCCACCAGATTGTATATCCAATTTAACAGAGATTGAAAAAA

TGTTCGTTCA

ATTAGTACAATGTTACAAGTGACTTGGGGTATGTAGCTTGCGTGAGTAAA

GCATCATG-GAA
```

The GM49788080 cDNA is translated into the following amino acid sequence (SEQ ID NO:20):

```
MAVVQANNLLEDQSQIESGPLSLLDTGPYGTFVGVYDGHGGPETSRYVCD

HLFQHLKRFASEQKSMSMEVIRKAYQATEEGFLSVVTKQWPMNPQIAAVG

SCCLVGVICGGILYIANLGDSRAVLGRVVRATGEVLAIQLSSEHNVAIES

VRQEMHSLHPDDSKIVVLKHNVWRVKGLIQISRSIGDVYLKKAEFNKEPL

YAKFRVREGFKRPILSSDPSISVHELQQHDQFLIFASDGLWEHLSNQDAV

DIVQNNPHNGIARRLIKAALQEAAKKREMRYSDLKKIDRGVRRHFHDDIT

VVVVFLDSNLVSRASSVRGPPLSVRGGGVPLPSRTLAPCAAPMET
``` cDNA sequence of GM53049821 from soybean (SEQ ID NO:21):

```
TGCTCCTCTACCACCGAACACANCCCCGGCCACCACCGAACGCTAACGTG

CGCCCCTTCCTTACCCTGCGCCTCGGCACTCTCCCTTATTCCCCCTCCTT

CATAAGCTCCGCGTTAACCGTCCTCTCTCTCTCTCTCGGATCGGAG

CGAGACTGGCGGCTCCGGCGTTGGGGGCGTTAGGGTTAGGGTTAGGGTTT

CCAAGAGATG

TGGTATGCTCCAGGCATTGATGAATCTGTTCTCGCTGTGTTGGAAGCCAT

TTGGCCGCGATGCTGCTGATCGAATCGATTCCATCGGAGTTACCGGAAGA

GAAGGCAAAGACGGCTTGCTTTGGTTCCGCGACGGCGGAAAATATGGCTC

TGGCGATTTCTCCATGGCCGTCGTTCAGGCCAACCAGGTTCTCGAAGACC

AGAGCCAGATCGAGTCTGGTCCTCTCGGCACCTTCGTCGGCATCTACGAC

GGTCACGGAGGACCCGACGCCTCAAGATACGTTTGCGATCACTTGTTTCG

CCATTTTCAAGCAATATCAGCTGAGTCACGCGGGGTTGTGACAACTGAGA

CAATCGAAAGAGCATTTCGCCAAACAGAAGAGGGGTACATGGCCCTCGTG

TCAGGCTCGTGGAATGCTCGACCTCATATTGCAAGTGCTGGGACCTGTTG

TCTAGTTGGAGTGATATTTCAGCAGACACTCTTTGTGGCAAACGCTGGAG

ATTCCCGTGTTGTATTGGGTAAGAAAGTTGGCAACACTGGAGGTATGGCT

GCAATTCAGCTGTCTACAGAACACAATGCAAATCTTGAGGCTGTTAGGCA

GGAACTTAAAGAATTACATCCTCATGATCCCCAAATTGTTGTCCTCAAAC

ATGGAGTGTGGAGAGTAAAAGGCATTATTCAGGTTTCTAGATCTATAGGT

GATGTATATTTGAAGCATGCACAGTTTAACCGAGAACCACTTAATGCAAA

ATTCAGACTTCCTGAACCGATGAACATGCCTATCTTGAGTGCTAATCCCA

CTATTCTTTCTCATGCTCTCCAACCAAATGATTCCTTCCTTATATTTGCA

TCTGATGGTTTATGGGAGCATTTGAGTAACGAGAAAGCTGTGGATATTGT

AAACAGCAATCCACATGCGGGTAGTGCCAAGAGACTTATCAAGGCTGCTC
```

```
TCCATGAAGCAGCAAGAAAACGAGAAATGCGATATTCAGACCTCCGTAAG

ATTGACAAGAAAGTTCGACGCCATTTTCATGATGATATATCCGTTATTGT

TTTATTCTTAAATCACGACCTTATTTCCAGAGGCACAGTGCTAGACCCGA

CACTTTCAATTCGAAGCGCTCTCGATCACTGACTTGTATCACTGTAAGCA

GTCTTGTACGAGTTTTTGGCAACTGTACCGATACCTGAAGCATTGGTAGG

TACCTGGCTATAATATGTCATTTCTATGGCACATATGGCTTCTGGTACCG

ACATCATTCT

TGAGGCACGAGAATTTATTAAGTTATAACATATTATTAGAAATTTATTCA

TAAAGAGGAAAAAAATAAATACAAAAATATCTTATTCCCTTTTCTAACCT

TATAGTTTTACCCGAAATACTGGATTTTATTTATTTGTTTGTTTTTTTGG

CTGAACATAGCTAATCGAACAGCATGTTGATTGAATTCAAAGTTATTTTA

CAACAAATTATATGGAAAAAAAAAAAAAAA
```

The GM53049821 cDNA is translated into the following amino acid sequence (SEQ ID NO:22):

```
MLQALMNLFSLCWKPFGRDAADRIDSIGVTGREGKDGLLWFRDGGKYGSG

DFSMAVVQANQVLEDQSQIESGPLGTFVGIYDGHGGPDASRYVCDHLFRH

FQAISAESRGVVTTETIERAFRQTEEGYMALVSGSWNARPHIASAGTCCL

VGVIFQQTLFVANAGDSRVVLGKKVGNTGGMAAIQLSTEHNANLEAVRQE

LKELHPHDPQIVVLKHGVWRVKGIIQVSRSIGDVYLKHAQFNREPLNAKF

RLPEPMNMPILSANPTILSHALQPNDSFLIFASDGLWEHLSNEKAVDIVN

SNPHAGSAKRLIKAALHEAARKREMRYSDLKKIDKKVRRHFHDDISVIVL

FLNHDLISRGTVLDPTLSIRSALDH
``` cDNA sequence of ZM58462719 from corn (SEQ ID NO:23):

```
CGTGGCGACGCCCAAATCGAGCGACCTGATCGAGGCCCCTCGCCCCTACT

CGCTGAATCCCAATCCGAGCCCGCCAATTGGGCGCCCCCCCCCGCCCACG

CAAAGGACAGATAGAAGAAATTATTGGCGCTCTGACAAATCCAACTGAG

GTTTTCTTGGACTACAGATGAAGCGGGCTCGAAGGGCGTATGTGCAAGAG

ATGACTGATGAGGGATGCTAGTGAAATTGATGAACTTGTTACGGGCGTGC

TGGCGACCGTCATCGAACCGGCATGCCCGAACAGGCTCAGATGTTACCGG

TAGGCAGGATGGACTTCTATGGTACAAGGACGCCGGGCAACATGTCAATG

GGGAGTTCTCCATGGCTGTTGTTCAGGCAAATAACTTACTTGAGGACCAG

TGTCAGATCGAGTCGGGCCCACTGAGTTTTCTAGATTCTGGACCATATGG

CACTTTCGTTGGTGTTTACGATGGGCATGGTGGTCCAGAGACGGCCTGCT

ATATCAATGATCATCTTTTCCAGAATCTGAAAAGATTTGCATCTGAACAG

AATGCAATGTCTGCTGATGTACTGAAGAAGGCATATGAAGCTACAGAAGA

TGGATTCTTCTCCATTGTTACCAAACAATGGCCTGTAAAGCCTCAGATAG

CAGCTGTCGGCTCATGCTGCCTGGTCGGTGTAATTTGTGGTGGCATGCTT

TATGTTGCCAATGTTGGGGATTCCCGTGTCGTTTTAGGAAAACATGTTAA
```

```
GGCCACTGGAGAAGTTTTGGCTGTCCAACTGTCAGCAGAACATAATGTTA
GTATTGCGTCCGTGAGAAAAGAACTGCAGTCAATGCACCCAGAAGATAGG
CACATTGTTGTTCTCAAGCACAATGTTTGGCGTGTTAAAGGACTAATTCA
GGTTTGTAGATCAATTGGTGATGCATATCTCAAAAAGCAAGAGTTCAACA
GGGAACCCCTATATGCAAAATTTCGCCTCCGTGAACCTTTTCACAAGCCA
ATACTAAGTTCAGAACCATCAATCAGTGTGCAACCACTACAACCACACGA
CCAGTTTCTCATATTTGCATCTGATGGACTTTGGGAGCAGTTAACCAACC
AAGAGGCAGTTGATATTGTTCGAAGTAGCCCCCGCAGTGGCTGTGCTAGG
AGGCTGATAAGAGCGGCACTGCAAGAGGCAGCCAAGAAAAGAGAGATGAG
GTACTCGGACCTCAAGAAGATTGACCGCGGTGTTCGCCGCCACTTCCACG
ACGACATAACAGTCATAGTAGTGTTCCTTGACTCCGGCCTCGTAAGCCAG
GCGAGCACACACCGAGGTCCAACTCTTTCCTTGCGAGGCGGTGGCGGCAG
CGCTGGCCTGCGCAGCAACACACTTGCACCTACGTGACTATAAAGTGCCT
GGTGGAGTGGAGGCTACTGACTGAAGGTGGTTTTCTTTCCTTGTGTCGAA
TGTGTTATATATGTACTTGTACCAGCCAAGATCATTCATCCCCCCCCCTA
AAATGGTGTAAAGAAGTAGGAGAGGCGCCGAAGTTCCTCACCAGCGTATC
TGAATGCCCTCAATGGTGTCAAGTTGTGGACTCAAGTGGATAGCTTCGCT
GAATCTTCTGATGATGCTCTGTGGAAAGCTCGAATCCTTTCCACCTGAAA
AAGCAAGTAATATGTCTTCCAGTGCTGGAATTAACCCCTAGTGCATATAT
ATATGTATGAAATAATAATAAGGCAAAAGGAGGAGTAACTTATTTAACTA
ATGCTGTGAGGTGTATTTATGTTTTGTATGTGTACTGCTTTTGACTGCTA
CTGCATCTACTGTTGTTAATTGACCACTGGTGAAGTGAAATCACTGGTTT
CGTAAAAAAAAAAAAAAA
```

The ZM58462719 cDNA is translated into the following amino acid sequence (SEQ ID NO:24):

```
MLVKLMNLLRACWRPSSNRHARTGSDVTGRQDGLLWYKDAGQHVNGEFSM
AVVQANNLLEDQCQIESGPLSFLDSGPYGTFVGVYDGHGGPETACYINDH
LFQNLKRFASEQNAMSADVLKKAYEATEDGFFSIVTKQWPVKPQIAAVGS
CCLVGVICGGMLYVANVGDSRVVLGKHVKATGEVLAVQLSAEHNVSIASV
RKELQSMHPEDRHIVVLKHNVWRVKGLIQVCRSIGDAYLKKQEFNREPLY
AKFRLREPFHKPILSSEPSISVQPLQPHDQFLIFASDGLWEQLTNQEAVD
IVRSSPRSGCARRLIRAALQEAAKKREMRYSDLKKIDRGVRRHFHDDITV
IVVFLDSGLVSQASTHRGPTLSLRGGGGSAGLRSNTLAPT
``` cDNA sequence of ZM61092633 from corn (SEQ ID NO:25):

```
AGCTTCCTCCCTCTTCCCTGGTCTGGTCGCTTCTCCTGTAGCTGTAATTT
TTGAGAGTCCCTCTCAAACTTTGCTTGCTTGCGCTCTCCATATATCCTGT
GGATCGGAGAGGATGCTCTGATCTACCTGTCTGTTCTTCGATCGAGTCTG
AGAGATTTGGGAGGAGGAGGGAAACAAAGCGAAAGAGCCCATCTTTTTTG
TCTTTTTGGTTCGGTTTCGTGGTTGCTTCTTTTGGACCCCGCGGAGGAGC
CCACCGTTTCTACAAAAACCCAATCTTTGCTGCCTTCTCAGCGGTCGAGA
TCGATAGGTTTCCAGATCTGAGGCTCCGTGTTCTGGCTGTGAGATCGGAG
GCGCAGCAATCCGAGCACGCAGCTAGTAGGGAAAGTATCCGAGAAAAGTT
GCAGATTTTGCTGGGGGCAACGGAGCGAGAACAAGTTACTGCAGAAGGAA
AGGGCAAAGGTGGGGGAGGCGCCGGAGATGAGGGATGCTATCAGCTCTGA
TGGATTATTTGAAATCTTGCTGGGGTCCGGCATCACCGGCTGGGCGTCCC
CGCAAAGGATCGGATGCCACCGGCCGCCAGGACGGGCTCCTGTGGTACAA
GGACGGCGGGCAGGTCGTCGATGGTGAGTTCTCCATGGCCGTGGTCCAGG
CCAATAACCTATTGGAGGACCATAGCCAGGTTGAATCCGGGCCGCTTAGC
ACATCGGAGCCTGGACTGCAAGGCACCTTCGTCGGGGTCTACGATGGGCA
CGGTGGCCCGGAGACAGCGCGTTACATCAATGACCATCTCTTCAACCACT
TGAGGAGATTCGCATCTGAGCACAAGTGCATGTCAGCGGATGTGATTCGG
AAGGCATTCCGAGCGACTGAGGAGGGTTTCATTTCTGTGGTTAGTAACCA
ATGGTCATTGAGACCTCAATTAGCAGCTGTAGGCTCTTGCTGTCTAGTTG
GTGTGGTTTGCAGCGGAACTCTATATGTTGCAAACCTTGGGGACTCCCGT
GCTGTTCTGGGGAGACTTGTCAAGGGAACTGGGGAGGTTTTGGCAATGCA
GCTCTCAGCAGAACACAATGCATCCTATGAGGAGGTTAGACGAGAGCTGC
AGGCATCACATCCTGATGATCCCCATATTGTGGTCCTAAAACACAATGTT
TGGCGTGTAAAGGGTATTATCCAGATAACAAGGTCAATTGGAGATGTGTA
TCTGAAGAAACCAGAATTTAATAGAGAACCTTTGCACAGCAAGTTTCGTC
TTCAGGAAACTTTTAGGAGACCACTTCTTAGTTCTGATCCAGCAATTACT
GTCCACCAAATACAGCCAACTGATAAGTTCATCATTTTTGCATCTGATGG
ACTCTGGGAACATCTTAGTAATCAGGAAGTGGTTGACATGGTCCAAAGTA
GCCCGCGTAATGGAATCGCACGAAAGTTAGTAAAGTCTGCAGTGCAGGAA
GCAGCGAAGAAGAGGGAGATGCGGTATTCAGACCTCAAGAAAGTTGATCG
GGGGGTGAGGCGGCACTTCCACGACGATATAACTGTCATTGTGGTATTTT
TCGATTCAAACGCCATGACAACTGCTGCCTGGAGCAGACCCTCGGTCTCT
CTCCGAGGGGTGGGTTTCCAATCCATTCAAACACCCTTGCTCCATTCTC
GGTTCCTACAGAGCTAAACAACTCCTACTGAAACCACGCGGTATGTGAAG
GAGCCAGGCAAGAGGATAAAAAAAAAGTAAAGGAAAACGGAGAAGGAAAA
ACAGCTGTTGTGATCAGTTGTAGTGTATTTCACCGTTCATGTTCATTTAA
AACATTTTTTAGATTCTCAAGTCTCAACCTGGTGACCAGTGCACTGATAG
CAAGGTATAAGATTAGATTATTCTTAGCTTTTTTATCCTCTTTTTTTTT
CTCGTCCTTACCCTTTAGATTCACTCATGGGATATCCGATATCAGGTGCT
TGTACATTCTTTGGTTCAACTTGTGATAATAGTTCATCGCCCCCCTCTTT
TCGCAAAAAAAAAAA
```

The ZM61092633 cDNA is translated into the following amino acid sequence (SEQ ID NO:26):

```
MLSALMDYLKSCWGPASPAGRPRKGSDATGRQDGLLWYKDGGQVVDGEFS
MAVVQANNLLEDHSQVESGPLSTSEPGLQGTFVGVYDGHGGPETARYIND
```

HLFNHLRRFASEHKCMSADVIRKAFRATEEGFISVVSNQWSLRPQLAAVG

SCCLVGVVCSGTLYVANLGDSRAVLGRLVKGTGEVLAMQLSAEHNASYEE

VRRELQASHPDDPHIVVLKHNVWRVKGIIQITRSIGDVYLKKPEFNREPL

HSKFRLQETFRRPLLSSDPAITVHQIQPTDKFIIFASDGLWEHLSNQEVV

DMVQSSPRNGIARKLVKSAVQEAAKKREMRYSDLKKVDRGVRRHFHDDIT

VIVVFFDSNAMTTAAWSRPSVSLRGGGFPIHSNTLAPFSVPTELNNSY cDNA sequence of ZM62016485 from corn (SEQ ID NO:27):

TGTCTTGCTGCTGGCGCGCCGGGGGCTCCGATTGCGCTCCAGATCTGAGG

CACCTGCTCGGTGGATTCCAGGAATCCGAGCACCAACTCGACAGGGGAGT

TCTCAGGGTAAAGAGGCTGAGAGCGCGTTGGAGATTTGGACTATAAGAGC

GAGCGAGCGAGCTGGGTGCCTTGCTGCCTTGAGGACGCCGTCAAGAAACC

GCGTGGAGGGGAGGGCGATGAGATGAGGGATGCTGGCCGCGGTGATGGAC

TACTTCAGCACCTGCTGGGGCCCGCGGTCTCGTGCGGGGCACCGGGGCAA

GGGCTCCGACGCCGCCGGCCGGCAGGACGGCCTCCTCTGGTACAAGGACG

CCGGGCAGCTCGTCACCGGGGGGTTCTCCATGGCCGTGGTGCAGGCCAAC

CAGCTGCTTGAGGACCAGAGCCAGGTGGAGTCCGGATCGCTCTCCCTGGC

TGACTACGGCCCGCAGGGCACCTTCGTCGGCGTCTATGATGGCCATGGCG

GCCCGGAGACGTCCCGGTTCATCAATGACCACCTCTTCAACCATCTCAGG

AGATTCGCAACTGAGCACAAGTCCATGTCAGCAGACGTGATCCGAAAGC

TTTCCAAGAAACTGAGGAGGGCTTTCTTTCTCTAGTCATCAAGGAATGGT

CTTTCAAGCCTCAGATTGCATCAGTTGGCTCCTGTTGCCTTGTTGGTGTA

ATCTGTGCTGGGACTCTCTATGTTGCAAACCTGGGCGACTCGCGTGCAGT

TCTTGGAAGGCTTGTGAAAGCAACTGGAGAGGTTCTGGCCACTCAGTTGT

CAGCGGAGCACAATGCATGCTATGAAGAAGTTAGACAAGAGCTGCAGTCA

TCACATCCTGATGATCCACGTATTGTGGTTCTCAACATAACGTTTGGCGA

GTGAAGGGTCTCATCCAGATCTCAAGATCTATCGGAGATGTATATCTAAA

GAAACCGGAGTATAACAGAGAACCTCTTCACAGCAAGTTTCGGCTTCGAG

AAACCTTCCAGAAGCCGATTCTTAGTTCTGAACCTCAAATTACTGAACAC

CGAATACAGCCAAACGATCAGTTTGTTATATTTGCTTCCGATGGTCTATG

GGAGCACCTCAGCAATCAGGAAGCTGTTGACCTTGTCCAAAGTAGTCCCC

GTAATGGAATCGCTCGGAGACTAGTGAAAGCCGCGATGCAAGAAGCTGCC

AAGAAGAGGGAGATGAGATACTCAGACCTCAAGAAGATCGACCGTGGCGT

GAGGAGGCATTTCCACGACGATATAACCGTCGTCGTGGTGTTCCTCGACT

CGGATGCCATGAGCAAAGCTAGCTGGAGCAAGAGCCCCTCGTTTTCTCTC

CGAGGGGCGGCGTCACCCTTCCCGCCAAGTCCCTCGCACCCTTCTCGGC

TCCGGCACAGTTGAACGGCACCCACTGAAGCTGCTACTGCTCTTGAAAAG

AAGGGCACAGTGCAGATCTGCTAGAGATGATGAGAGAAGCAGCAATCAAG

TGTAGCTGTTGCTCGTACACCTGCTGTGCTGTTGCTGTTTGCAAAGCTGC

CGTCTTGACTCCGCCTGGTAATTAGTGTACTGATAGCGAGGTATAGAAAT

TAGGTTATTTGTTAGCGACGCAAATCCTTTCTTTTTTTTTCTTCTCCCTC

TGTTCTTATCTCTTTTCTCTTCATCATGGAGGAAACAGGTGGCTGTAAAT

TTGTCCAGAACATGTTTTCCCTAATAGCCCAACAAAAAAAAAA

The ZM62016485 cDNA is translated into the following amino acid sequence (SEQ ID NO:28):

MLAAVMDYFSTCWGPRSRAGHRGKGSDAAGRQDGLLWYKDAGQLVTGGFS

MAVVQANQLLEDQSQVESGSLSLADYGPQGTFVGVYDGHGGPETSRFIND

HLFNHLRRFATEHKSMSADVIRKAFQETEEGFLSLVIKEWSFKPQIASVG

SCCLVGVICAGTLYVANLGDSRAVLGRLVKATGEVLATQLSAEHNACYEE

VRQELQSSHPDDPRIVVLKHNVWRVKGLIQISRSIGDVYLKKPEYNREPL

HSKFRLRETFQKPILSSEPQITEHRIQPNDQFVIFASDGLWEHLSNQEAV

DLVQSSPRNGIARRLVKAAMQEAAKKREMRYSDLKKIDRGVRRHFHDDIT

VVVVFLDSDAMSKASWSKSPSFSLRGGGVTLPAKSLAPFSAPAQLNGTH cDNA sequence of ZM62051019 from corn (SEQ ID NO:29):

TTTTCTCTTATCCAGCTTCTTAGCATGATTCTCTTTGATCCCGGAGAGCA

GCCACCGGTCCAACTAGTCCTTGCTGTTGGTCTGCCGGAACTTTTGATTG

CTCTCCAGATCTGAGGCACCTGCTGGGTGGATTCCAGGAACCCGAGCACG

AAGTTGACAGGTGAGTTCTCAGGGAAAAAGGGGAGGAAGGAAGAGGCTGA

AAGGGCGGTG

GAGAGAGAAAGACTATAAGGGCGAGCTGAGTCCCTTGAGGATGCCGTCAA

GAAACCGCGTGGAGAGGAGGGCGATGAGATGAGGGATGCTGGCCGCGGTG

ATGGACTACTTCAGCTCCTGCTGGGGCCCGCGATCGGGCGCCGGGCACCG

GGGCAAGGGCTCCGACGCCGCCGGCCGGCAGGACGGTCTCCTCTGGTACA

AGGACGCCGGCCAGCTCGTCACTGGGGAGTTCTCCATGGCCGTGGTGCAG

GCCAACCAGCTCCTCGAGGACCAGAGCCAAGTAGAGTCCGGATCGCTCTC

CCTGGCTGACCCGGGCCCACAGGGCACCTTCGTCGGCGTCTATGATGGCC

ATGGCGGCCCGGAGACGTCCCGGTTCATCAATGACCACCTCTTCAACCAT

CTCAGAAGGTTTGCAACTGAGCACAAGTTTATGTCAGCGGACGTGATCCG

GAAAGCTTTCCAAGCAACTGAGGAGGGCTTTCTTTCTCAGTCAGCAAGG

AATGGTCTTTGAAGCCTCAGATTGCTTCAGTGGGCTCCTGCTGCCTTGTT

GGTGTAATCTGTGCTGGGACTCTCTATGTTGCAAACGTGGGCGACTCACG

TGCAGTTCTTGGAAGGCTTGTTAAGGCAACTGGAGAGGTTGTGGCCATGC

AGTTGTCATCGGAGCACAATGCGTGCTATGAGGAAGTTAGACAAGAACTG

CAGTCATCACATCCTGACGATCCACATATTGTGGTTCTCAAACACAATGT

TTGGCGAGTGAAGGGTCTCATCCAGATCTCAAGATCTATTGGAGATGTAT

ATCTAAAGAAACCAGAGTACAACAGAGAACCACTTCACAGCAAGTTTCGG

CTTCGAGAAACCTTCCAGAGGCCGACCCTTAGTTCTGAACCTCAAATTAC

TGAACATCGAATACAGCCGAACGATCAATTTGTTATATTTGCTTCTGATG

```
GTCTATGGGAGCACCTCAGCAATAAGGAAGCAGTTGACCTTGTCCAAAGT
AGTCCCCGAAATGGAATCGCTCGGAGGCTAGTGAAAGCCGCGATGCAAGA
AGCTGCCAAGAAGAGGGAGATGAGATACTCAGACCTCAAGAAGATCGACC
GTGGTGTGAGAAGGCATTTCCACGACGATATAACTGTCGTCGTGGTATTC
CTCGATTCGGATGCCATGAGCAAAGCTAGCTGGAGCAAAAGCCCCTCGGT
TTCTCTCCGAGGGGCGGTGTCGCCCTCCCTGCGAAGTCCCTCGCACCTT
TCTCAGCTCCGGCACGGCTGAACAGCACCTACTGAAGTTGCTACCACTCT
TGAAAGGAAGAACACAGTGCAGATCTGCAGTGGTGAGAGAGAGAGAGAAA
ACAGCAAGGAAGTGTAGCGTTACAGTTACACCTGCTGTGTTGTTGCTCTT
TGCAAAACTACTGTCTAGACTCCGCCTGGTAATTAGTGTACTGATAGCGA
GGTAAAAAAAGTTAGATTATTTGTTAGCGACACACATCCTTTCACCTTCT
CTTCTCTCCCTCGATTCCTATCCCTTTTCTCTTCATCCTTGAGAGAACAG
GTGGATGTAAATTGTTCAGAACATGTTTTCCCTTATAGTCCATCATATCC
CGCTTTTTTCGTGTTGAAAAAAAAAAAAAA
```

The ZM62051019 cDNA is translated into the following amino acid sequence (SEQ ID NO:30):

```
MLAAVMDYFSSCWGPRSGAGHRGKGSDAAGRQDGLLWYKDAGQLVTGEFS
MAVVQANQLLEDQSQVESGSLSLADPGPQGTFVGVYDGHGGPETSRFIND
HLFNHLRRFATEHKFMSADVIRKAFQATEEGFLSLVSKEWSLKPQIASVG
SCCLVGVICAGTLYVANVGDSRAVLGRLVKATGEVVAMQLSSEHNACYEE
VRQELQSSHPDDPHIVVLKHNVWRVKGLIQISRSIGDVYLKKPEYNREPL
HSKFRLRETFQRPTLSSEPQITEHRIQPNDQFVIFASDGLWEHLSNKEAV
DLVQSSPRNGIARRLVKAAMQEAAKKREMRYSDLKKIDRGVRRHFHDDIT
VVVVFLDSDAMSKASWSKSPSVSLRGGGVALPAKSLAPFSAPARLNSTY
``` cDNA sequence of ZM65086957 from corn (SEQ ID NO:31):

```
CTCTGTCTCCTTGGATTTGCGCTTGTGCTCGTCTGGCCGCATACTAGTAT
CCGCACCAGAGAGGAGACACCTCCGACTCCGACCTGCTCTTGCATATAGA
TTGGACAGAGAGTGAGGGAGAGAGAGAGCGCGCGCGCTGAAGGGGTGCCA
AAGGGAGATTTTTTTTTTTAATCCAGCTTCTTAGCCTGACTGACTCTCT
TTGATCCCGG
AGAGCAGCCGCCAGCCCAACTAATCCTTGCTGCTGGCGCGCCGGGGCTCT
GATTGCGCTCCAGATCTGAGGCACCTGCTCGGTGGATTCCAGGAATCCGA
GCACCAACTCGACAGGGAGAGTTCTCAGGGTAAAGGACGACGCTTGATGC
ACACGGGACGGGACAACGAGTTGGCCGCAAGTTTTGTTTGCACACGCACA
CGACCCACCAGCTCACGCGTTTTTTTTTTTTTTTTGCTTCTTAACTCGC
TTTGATTGCATCTGTTGTTTCGGAAGGAAGAGGCTGAGAGCGCGTTGGAG
ATTTGGACTATAAGAGCGAGCGAGCGAGCGAGCTGGGTGCCTTGAGGACG
CCGTCAAGAAACCGCGTGGAGGGGAGGGCGATGAGATGAGGGATGCTGGC
CGCGGTGATGGACTACTTCAGCACCTGCTGGGGCCCGCGGTCTCGTGCGG
GGCACAGGGGCAAGGGCTCCGACGCCGCCGGCCGGCAGGACGGCCTCCTC
TGGTACAAGGACGCCGGGCAGCTCGTCACCGGGGGGTTCTCCATGGCCGT
GGTGCAGGCCAACCAGCTGCTTGAGGACCAGAGCCAGGTGGAGTCCGGAT
CGCTCTCCCTGGCTGACTACGGCCCGCAGGGCACCTTCGTCGGCGTCTAT
GATGGCCATGGCGGCCCGGAGACGTCCCGGTTCATCAATGACCACCTCTT
CAACCATCTCAGGAGATTTGCAACTGAGCACAAGTCCATGTCACGAGACG
TGATCCGGAAAGCTTTCCAAGAAACTGAGGAGGGCTTTCTTTCTCTAGTC
ATCAAGGAATGGTCTTTCAAGCCTCAGATTGCATCAGTTGGCTCCTGTTG
CCTTGTTGGTGTAATCTGTGCTGGGACTCTGTATGTTGCAAACCTGGGCG
ACTCCCGTGCAGTTCTTGGAAGGCTTGTTAAGGCAACTGGAGAGGTTCTG
GCCACGCAGTTGTCAGCGGAGCACAATGCATGCTATGAAGAAGTTAGACA
AGAGCTGCAGTCATCACATCCTGATGATCCACGTATTGTGGTTCTAAAAC
ATAACGTTTGGCGAGTGAAGGGTCTCATCCAGATCTCAAGATCTATCGGA
GATGTATATCTAAAGAAACCGGAGTATAACAGAGAACCTCTTCACAGCAA
GTTTCGGCTTCGAGAAACCTTCCAGAAGCCGATTCTTAGTTCTGAACCTC
AAATTACTGAACACCGAATACAGCCAAACGATCAGTTTGTTATATTTGCT
TCTGATGGTCTATGGGAGCACCTCAGCAATCAGGAAGCTGTTGACCTTGT
CCAAAGTAGTCCCCGTAATGGAATCGCTCGGAGACTAGTGAAAGCCGCGA
TGCAAGAAGCTGCCAAGAAGAGGGAGATGAGATACTCAGACCTCAAGAAG
ATCGACCGTGGCGTGAGGAGGCATTTCCACGACGATATAACCGTCGTCGT
GGTGTTCCTCGACTCGGATGCCATGAGCAAAGCTAGCTGGAGCAAGAGCC
CCTCGGTTTCTCTCCGAGGGGCGGCGTCACCCTTCCCGCCAAGTCCCTC
GCACCCTTCTCGGCTCCGGCACAGTTGAACGGCACCCACTGAAGCTGCTA
CTGCTCTTGAAAAGGGGCACAGTGCAGATCTGCTAGAGATGATGAGAGAA
GCAGCAATCAAGTCAAGTGTAGCTGTTGCTCGTACACCTGCTGTGCTGTT
GCTGTTTGCAAAGCTGCCGTCTTGACTCCGCCTGGTAATTAGTGTACTGA
TAGCGAGGTATAGAAATTAGGTTATTTGTTAGCGACGCAAATCCTTTCTT
TTTTTTCTTCTTCTCTCTGTTCTTATCCCTTTTCTCTTCATCATGGAG
GAAACAGGTGGCTGTAAATTTGTCCAGAACGTGTTTTCCCTAATAGCCCA
TCATATCCCGCTATTTTTCTTGTTAAAAAAAAAA
```

The ZM65086957 cDNA is translated into the following amino acid sequence (SEQ ID NO:32):

```
MLAAVMDYFSTCWGPRSRAGHRGKGSDAAGRQDGLLWYKDAGQLVTGGFS
MAVVQANQLLEDQSQVESGSLSLADYGPQGTFVGVYDGHGGPETSRFIND
HLFNHLRRFATEHKSMSADVIRKAFQETEEGFLSLVIKEWSFKPQIASVG
SCCLVGVICAGTLYVANLGDSRAVLGRLVKATGEVLATQLSAEHNACYEE
VRQELQSSHPDDPRIVVLKHNVWRVKGLIQISRSIGDVYLKKPEYNREPL
HSKFRLRETFQKPILSSEPQITEHRIQPNDQFVIFASDGLWEHLSNQEAV
DLVQSSPRNGIARRLVKAAMQEAAKKREMRYSDLKKIDRGVRRHFHDDIT
VVVVFLDSDAMSKASWSKSPSVSLRGGGVTLPAKSLAPFSAPAQLNGTH
``` cDNA sequence of ZM68587657 from corn (SEQ ID NO:33):

GGACGCCGGGCAACATGTCAATGGGGAGTTCTCCATGGCTGTTGTTCAGG
CAAATAACTTACTTGAGGACCAGTGTCAGATCGAGTCGGGCCCACTGAGT
TTTCTAGATTCTGGACCATATGGCACTTTCGTTGGTGTTTACGATGGGCA
TGGTGGTCCAGAGACGGCCTGCTATATCAATGATCATCTTTTCCAGAATC
TGAAAAGTAA
CTTGCTAACCTTTAAATCTGTGCAGTAGCACTATTCCCGTTTCTTAGCAC
TATATCTGCATTTGGCTTTCAGTTTGCACATAAAGGAGATCATCCATTTT
TTCATGGCTTGTATTTAGGATTTGCATCTGAGCAGAATGCAATGTCTGCT
GATGTACTGAAGAAGGCATATGAAGCTACAGAAGATGGATTCTTCTCCAT
TGTTACCAAA
CAATGGCCTGTAAAGCCTCAGATAGCAGCTGTCGGCTCATGCTGCCTGGT
CGGTGTAATTTGTGGTGGCATGCTTTATGTTGCCAATGTTGGGGATTCCC
GTGTCGTTTTAGGAAAACATGTTAAGGCCACTGGAGAAGTTTTGGCTGTC
CAACTGTCAGCAGAACATAATGTTAGTATTGCGTCCGTGAGAAAAGAACT
GCAGTCAATG
CACCCAGAAGATAGGCACATTGTTGTTCTCAAGCACAATGTTTGGCGTGT
TAAAGGACTAATTCAGGTTTGTAGATCAATTGGTGATGCATATCTCAAAA
AGCAAGAGTTCAACAGGGAACCCCTATATGCAAAATTTCGCCTCCGTGAA
CCTTTTCACAAGCCAATACTAAGTTCAGAACCATCAATCAGTGTGCAACC
ACTACAACCA
CACGACCAGTTTCTCATATTTGCATCTGATGGACTTTGGGAGCAGTTAAC
CAACCAAGAGGCAGTTGATATTGTTCGAAGTAGCCCCCGCAGTGGCTGTG
CTAGGAGGCTGATAAGAGCGGCACTGCAAGAGGCAGCCAAGAAAAGAGAG
ATGAGGTACTCGGACCTCAAGAAGATTGACCGCGGTGTTCGCCGCCACTT
CCACGACGACATAACAGTCATAGTAGTGTTCCTTGACTCCGGCCTCGTAA
GCCAGGCGAGCACACACCGAGGTCCAACTCTTTCCTTGCGAGGCGGTGGC
GGCAGCGCTGGCCTGCGCAGCAACACACTTGCACCTACGTGACTATAAAG
TGCCTGGTGGAGTGGAGGCTACTGACTGAAGGTGGTTTTCTTTCCTTGTG
TCGAATGTGTTATATATGTACTTGTACCAGCCAAGATCATTCATCCCCCC
CCCTAAAATGGTGTAAAGAAGTAGGAGAGGCGCCGAAGTTCCTCACCAGC
GTATCTGAATGCCCTCAATGGTGTCAAGTTGTGGACTCAAGTGGATAGCT
TCGCTGAATCTTCTGATGATGCTCTGTGGAAAGCTCGAATCCTTTCCACC
TGAAAAAGCAAGTAATATGTCTTCCAGTGCTGGAATTAACCCCTAGTGCA
TATATATATGTATGAAATAATAATAAGGCAAAAGGAGGAGTAACTTATTT
AACTAATGCTGTGAGGTGTATTTATGTTTTGTATGTGTACTGCTTTTGAC
TGCTACTGCATCTACTGTTGTTAATTGAAAAAAAAAAAAAAAA

The ZM68587657 cDNA is translated into the following amino acid sequence (SEQ ID NO:34):

MSADVLKKAYEATEDGFFSIVTKQWPVKPQIAAVGSCCLVGVICGGMLYV
ANVGDSRVVLGKHVKATGEVLAVQLSAEHNVSIASVRKELQSMHPEDRHI
VVLKHNVWRVKGLIQVCRSIGDAYLKKQEFNREPLYAKFRLREPFHKPIL
SSEPSISVQPLQPHDQFLIFASDGLWEQLTNQEAVDIVRSSPRSGCARRL
IRAALQEAAKKREMRYSDLKKIDRGVRRHFHDDITVIVVFLDSGLVSQAS
THRGPTLSLRGGGGSAGLRSNTLAPT cDNA sequence of EST390 from moss (SEQ ID NO:35):

ATCCCGGGTGGAGCCCTTTCAAGCCTCACGCATTCTGGATTCGCTCCCGG
CTTCGAATGCTTGAGTGGTTCTAAGTGATGAGATAGCGCCGTCTAGGGAG
AATTTCGAATTTGCGCTAGAACATGGGTGGTTATTCCATCAGTGTGGCAG
CGCCCACAGATATTGCAGTGAAAGGTTGAACACAACGACCCAAGGACAAC
CTGCACCTTCCAACAGTCAGCGTGAGGTGAAAAGATAGGCCAGTTTTCAG
CTGCACATAACCTTCACTTCTGCAGGCGCAGAACACGTGCGGTACTGAGC
AATGGGGTCCTCTAAGGCAGAAGAGAATTTGGCCTTACGGCTGGGCCTCA
CTGCAGCGTCAGCCATGGCGTCGGAGTCTGTGACCTTCCCAATCGATATC
ACGAAAACCCGCCTGCAGCTCCAAGGCGAAATGGGTGCCACAGCTGGCGC
ACCCAAGCGAGGAGCGATCAGCATGGCGATCTCTATAGGCAAGGAGGAGG
GCATTGCCGGTCTTTATAGGGGCCTTTCTCCGGCACTTTTGCGTCATGTA
TTTTACACAAGCATTCGTATTGTTGCGTATGAAAATCTACGTACCGCCCT
CAGTCATGGCGAACACCCGGAAAATCTGTCCGTTGCAAAAAAGGCTTTCA
TCGGTGGCACTTCCGGTATTATTGGGCAGGTGATAGCGAGTCCAGCGGAT
TTGGTGAAGGTGCGCATGCAAGCGGATGGGAGGCTGGTGAAGCTTGGGCA
GCAGCCACGCTACACCGGAGTAGCTGACGCATTCACCAAGATTGCCCGAG
CCGAGGGTGTGACAGGGCTGTGGCGTGGAGTGGGACCCAATGCTCAACGT
GCCTTCCTCGTCAACATGGGGGAGCTTGCATGCTACGACCAGTCGAAGCA
ATGGATCATAGGACGCGGCATTGCTGCCGACAACATCGGAGCTCACACGC
TTGCATCAGTGATGTCTGGGTTATCAGCTACTATTCTGAGCTGCCCTGCC
GATGTGGTGAAGACCCGGATGATGAACCAAGGCGCTGCAGGTGCCGTGTA
CCGCAACTCTCTGGATTGTCTCACCAAAACCGTGAAGGCTGAAGGCGTGA
TGGCGCTGTGGAAGGGCTTCTTCCCGACGTGGACAAGGCTGGGCCCTTGG
CAATTCGTGTTTGGGTCTCATATGAGCAGCTCCGCCGCATCAGCGGTCT
ATCATCCTTCTAATAAGTAAAGCCTCGCAGTTGTTTTGGGTGTGAAACTT
ACATGGCATTCAGCTCTTACAAAGATTTCACATGCTTGAAGATTTTGAGG
TGCTGTTTTTTTTATCATTTTTGTTCCTTCTCTTTTCTGCCTCAATTGGA
TGTCATAGCT
GAGGCTATGAAGCTTAGTTTCATTGACAAATGTTTACATTTGTTAGCAAT
GTGTAGTAGTGCACTTGCGTTAACCG

The EST390 cDNA is translated into the following amino acid sequence (SEQ ID NO:36):

MGSSKAEENLALRLGLTAASAMASESVTFPIDITKTRLQLQGEMGATAGA
PKRGAISMAISIGKEEGIAGLYRGLSPALLRHVFYTSIRIVAYENLRTAL
SHGEHPENLSVAKKAFIGGTSGIIGQVIASPADLVKVRMQADGRLVKLGQ
QPRYTGVADAFTKIARAEGVTGLWRGVGPNAQRAFLVNMGELACYDQSKQ
WIIGRGIAADNIGAHTLASVMSGLSATILSCPADVVKTRMMNQGAAGAVY
RNSLDCLTKTVKAEGVMALWKGFFPTWTRLGPWQFVFWVSYEQLRRISGL
SSF cDNA sequence of BN51363030 from canola (SEQ ID NO:37):

AGAAAACAAATAAAAATCAAATCGTTACAGCAATGGGCGTCAAAAGTTTC
GTGGAAGGTGGGATTGCCCCTGTAGTCGCCGGCTGCTCCACTCACCCTCT
CGATCTCATCAAGGTTCGCCTTCAGCTCCACGGCGAAGCTTCCGCCGTCA
CTCTCCTCCGCCCAGCTCTCGCTTTCCACAATTCTCCCCCAGCTTTTCTG
GAGACGACTC
ATTCGGTCCCTAAAGTAGGACCCATCTCCCTCGGAATCAACCTCGTCAAA
ACCGAAGGCGCCGCCGCGCTTTTCTCCGGCGTCTCCGCCACACTCCTCCG
TCAGACTCTCTACTCCACCACCAGGATGGGTCTCTACGAGGTGTTGAAAA
ACAAATGGACTGATCCCGAGTCCGGTAAGCTGAGTCTCACTCGTAAAATC
GCCGCGGGGCTAGTCGGTGGCGGGATCGGAGCCGCCGTCGGGAACCCAGC
CGACGTGGCGATGGTAAGGATGCAAGCCGACGGGAGGCTTCCCGTGGCAG
AGCGTCGTAACTACGCGGGCGTAGGAGACGCGATCAAGAGGATGGCGAAG
CAAGAAGGCGTGGTGAGCCTGTGGCGCGGCTCGGCTCTGACGATCAACAG
GGCGATGATAGTGACGGCGGCGCAGCTCGCGTCGTACGATCAGTTCAAGG
AAGGGATGGTGGAGAGCGGGGGATGAAAGATGGGCTCGGGACTCACGTG
GTGGCGAGCTTCGCGGCGGGATCGTGGCGGCTGTTGCGTCGAATCCGGT
GGATGTGATAAAGACGAGGGTGATGAATATGAAGGTGGATGCGCGTGGTG
GGGAGGCTCAGTACAAAGGCGCGTGGGATTGTGCGGTGAAGACGGTTAGA
GCTGAAGGACCGATGGCTCTTTATAAAGGGTTTGTTCCTACGGTTTGCAG
GCAAGGACCTTTCACTGTTGTGCTCTTTGTTACGTTGGAGCAAGTCAAGA
AGCTGCTTCGTGATTTTTGATTATCATTTGAAGGTTATGATGATGAGGAC
GACTAAGAATAAGAATGCTAGTAGTATTGATTTGATAGGGATTTTTCGTA
TTGGGTTATTCATTTTCG

The BN51363030 cDNA is translated into the following amino acid sequence (SEQ ID NO:38):

MGVKSFVEGGIAPVVAGCSTHPLDLIKVRLQLHGEASAVTLLRPALAFHN
SPPAFLETTHSVPKVGPISLGINLVKTEGAAALFSGVSATLLRQTLYSTT
RMGLYEVLKNKWTDPESGKLSLTRKIAAGLVGGGIGAAVGNPADVAMVRM
QADGRLPVAERRNYAGVGDAIKRMAKQEGVVSLWRGSALTINRAMIVTAA
QLASYDQFKEGMVESGGMKDGLGTHVVASFAAGIVAAVASNPVDVIKTRV
MNMKVDARGGEAQYKGAWDCAVKTVRAEGPMALYKGFVPTVCRQGPFTVV
LFVTLEQVKKLLRDF cDNA sequence of BN42986056 from canola (SEQ ID NO:39):

TCTAAAAAAACTTTTTGTCTGAACGGCATATGTCTCAGAGACCTCAAGTT
CCTCATTCTTCTTCTATAGCTTTCGGTCTCCATTCTCATCTCCTAATCTC
CAGTGAGATCAGCTCCAATTCCAACTGGTCTCTCTAAGAAAAAAATAATC
AAACCTTTTCAAAATTTTCTCTCGGATTTTCTCGGAATAAAAATCTAACC
TTTCTGACTTTTTTGATTTTCGATTTGATAAAAACAAGAAATGGGTCTTA
AGGGTTTCGCTGAAGGAGGCATCGCATCGATCGTAGCGGGATGTTCGACC
CACCCGCTTGATCTAATCAAGGTCTGAATGCAGCTCCAAGGGGAATCAGC
CTCGATTCAGACAAATCTCCGACCAGCTCTTGCTTTCCAGACTTCCTCCG
CCGTTCACGCGCCTTCGCCTCCTCCGCGCGTGGGTATAATCACCATCGGA
TCTCGCATCATCAGACAAGAAGGCACGTGCACTCTCTTCTCCGGCATCTC
CGCCACCTCCGCCACCGTTCTCCGCCAGACTCTCTACTCGACGACTCGCA
TGGGTCTATACGACATCCTGAAAACCAAATGGACCGACCCGGAAACCAAA
ACCATACCTTTGACCCGCAAACTCGCCGCCGGGTTCATCGCCGGAGGTAT
CGGCGCCGCCGTCGGGAACCCGGCGGATGTCGCCATGGTGCGCATGCAAG
CCGACGGGAGGCTCCCGGTGGTCGACCGGAGGAACTACAAGAGCGTTTTG
GACGCGATCGCGCAGATGGTTCGCGGCGAAGGCGTCACGTCGCTGTGGAG
AGGTTCGTCGATGACGATCAACAGAGCGATGCTCGTGACG
GCGTCGCAGCTGGCTACGTACGACTCGGTGAAAGAGACGATTTTGGAGAA
AGGGTTGATGAGGGACGGGCTCGGGACTCACGTGACGTCGAGCTTCGCGG
CGGGGTTTGTGGCTTCGGTCGCGTCGAACCCCGTGGATGTGATCAAGACG
AGAGTGATGAATATGAAAGTGGAGGCGGGGAAAACGGCGCCGTATAAGGG
AGCGGTTGATTGCGCGTTGAAGACGGTGAGAGCGGAAGGGATCATGGCTT
TATACAAAGGGTTTCTGCCGACGGTGTCGAGACAAGCACCGTTCACGGTG
ATTATGTTTGTGACACTTGAACAAGTTAAGAAGGTGTTCAAGGACTTTGA
CTTTTGAGACAAGAGTTAAAGATGATGGTGGCGATAATTTGCTTTAAACT
AAATAAATTTTGTTTTTTTTTATTGTATTTTCTTT

The BN42986056 cDNA is translated into the following amino acid sequence (SEQ ID NO:40):

MQLQGESASIQTNLRPALAFQTSSAVHAPSPPPRVGIITIGSRIIRQEGT
CTLFSGISATSATVLRQTLYSTTRMGLYDILKTKWTDPETKTIPLTRKLA
AGFIAGGIGAAVGNPADVAMVRMQADGRLPVVDRRNYKSVLDAIAQMVRG
EGVTSLWRGSSMTINRAMLVTASQLATYDSVKETILEKGLMRDGLGTHVT
SSFAAGFVASVASNPVDVIKTRVMNMKVEAGKTAPYKGAVDCALKTVRAE
GIMALYKGFLPTVSRQAPFTVIMFVTLEQVKKVFKDFDF cDNA sequence of BN49389066 from canola (SEQ ID NO:41):

CGACGATTTCGTTTAATATAAACATCACCAAGTGAATCTCTCCGCCTCTC

TCTCTCTTTCTCTGCGGAATCTCTTCGTCTCGTTGCGTTCGAGAGTTCCG

TACGATTCCCAACAAGAAAGGGAAGAGATGGCGGAGGAGAAGAAAGTAGC

TCCGATTGGTATCTGGACTGCCGTGAAGCCTTTCGTCAATGGCGGTGCCT

CTGGTATGCT

CGCCACTTGCGTTATCCAGCCTATTGACATGATCAAGGTGAGGATTCAAC

TAGGTCAGGGATCTGCAGCTAGTGTGACCACCACCATGTTGAAGAATGAA

GGTATCGGTGCCTTCTACAAGGGATTATCAGCTGGTTTGCTGAGGCAAGC

AACTTACACCACAGCTCGTCTTGGATCATTCAAGATGCTGACTGCGAAAG

CAAGCGAGGCTAACGATGGGAAGCCACTACCGCTGTATCAAAAGCTCTA

TGTGGTCTGACAGCTGGTGCTATCGGTGCCTGCGTTGGTAGTCCAGCCGA

TTTAGCGCTTATCAGAATGCAAGCTGATAACACTTTGCCGTTAGCTCAGC

GCAGGAACTATACCAACGCCTTCCATGCGCTTTACCGTATTAGCGCTGAT

GAAGGAGTTTTGGCGCTTTGGAAAGGTTGTGGGCCAACTGTGGTCAGAGC

AATGGCTTTGAACATGGGGATGCTTGCGTCTTATGATCAAAGTGCTGAGT

ATATGAGAGATAATCTTGGTCTTGGGGAGACATCCACAGTCGTAGGAGCA

AGTGCTGTTTGGGATTCTGCGCTGCGGCTTGCATCTTCCATTTGACTTTG

TCAAAACACAGATCCAAAAAATGCAACCCGACGCTCAGGGTAAATATCCA

TACACTGGTTCGCAGGACTGTGCGATGCAAACAGGAGGACCTTTGAAAT

TCTACACAGGCTTTCCGGTATACTGCGTCAGGATCGCCCCTCACGTCATG

GTGACATGGATCTTCCTGAACCAGATTACAAAGTTCCAAAAGAACATTGG

GATGTGATCTTCAAGCAAACCTTATGAAGTGCGCGGTG

AAAATATGATGAGAAGAATTCATTTGCTTTTAATCATATACATGATTAG

The BN49389066 cDNA is translated into the following amino acid sequence (SEQ ID NO:42):

MAEEKKVAPIGIWTAVKPFVNGGASGMLATCVIQPIDMIKVRIQLGQGSA

ASVTTTMLKNEGIGAFYKGLSAGLLRQATYTTARLGSFKMLTAKASEAND

GKPLPLYQKALCGLTAGAIGACVGSPADLALIRMQADNTLPLAQRRNYTN

AFHALYRISADEGVLALWKGCGPTVVRAMALNMGMLASYDQSAEYMRDNL

GLGETSTVVGASAVLGFCAAACSLPFDFVKTQIQKMQPDAQGKYPYTGSQ

DCAMQNRRTFEILHRLSGILRQDRPSRHGDMDLPEPDYKVPKEHWD-VIF

KQTL cDNA sequence of BN51339479 from canola (SEQ ID NO:43):

CTTTCTCCGCCTATCTCTTTCTCTCCGCGGATTCTCTTCTTCTCGTTTCG

ACTCCGTACGATCCCCAAAGAAAAAAAGAGATGGCGGAAGAGAAAAAAGT

AGCTCCGATTGGTGTCTGGATACCGTGAAGCCCTTCGTCAATGGCGGTGC

CTCCGGTATGCTCGCCACTTGCGTTATCCAGCCGATCGACATGATCAAGG

TGAGGATTC

AACTAGGTCAGGGATCTGCAGTCAGTGTGACCAAGAACATGTTGAAGAAT

GATGGTATTGGTGCTTTCTACAAGGGATTGTCTGCTGGTTTGCTAAGGCA

AGCAACTTACACCACAGCCCGTCTTGGATCCTTCAAGATGCTGACTGCAA

AGCAATTGAGGCTAACGATGGGAAGCCGCTACCTCTGTACCAGAAGGCTC

TATGTGGTC

TGACAGCTGGTGCAATCGGTGCTTGCGTTGGTAGTCCAGCTGACTTGGCG

CTTATCAGAATGCAAGCTGATAACACCTTGCCGTTAGCTCAGCGCAGGAA

CTATACCAATGCCTTCCATGCGCTTTACCGTATTAGCGCTGATGAAGGAG

TTTTGGCACTTTGGAAAGGTTGTGGTCCTACTGTGGTCAGAGCTATGGCT

TTGAACATGG

GAATGCTTGCTTCTTATGATCAAAGTGCTGAGTACATGAGAGATAATCTC

GGTCTTGGGGAGACTTCTACGGTCGTAGGAGCAAGTGCTGTTTCTGGATT

CTGCGCTGCGGCTTGCAGTCTTCCATTTGACTTTGTCAAAACTCAGATCC

AGAAGATGCAACCTGACGCTCAGGGGAAGTATCCATACACGGGTTCGCTT

GACTGTGCCA

TGCAAACCTTGAAGTCAGGAGGACCTCTTAAATTCTACACAGGTTTCCCT

GTTTACTGCGTCAGGATCGCCCCTCACGTCATGATGACATGGATCTTCCT

GAACCAGATTACAAAGTTTCAAAAGACCATTGGTCTGTGAGCTTCAAGCA

TTGTGAAGTGCGCGCTGAGAATAAGTTGAAAACGAAAACGCAATTGGAAT

TGTGTTAGAT

TTGCTTTTTATTCAATATACATGATCGCATGCCTTAACGCATTATTTGAA

GTGTTGGAGACTTTA

The BN51339479 cDNA is translated into the following amino acid sequence (SEQ ID NO:44):

MAEEKKVAPIGVWNTVKPFVNGGASGMLATCVIQPIDMIKVRIQLGQGSA

VSVTKNMLKNDGIGAFYKGLSAGLLRQATYTTARLGSFKMLTAKAIEAND

GKPLPLYQKALCGLTAGAIGACVGSPADLALIRMQADNTLPLAQRRNYTN

AFHALYRISADEGVLALWKGCGPTVVRAMALNMGMLASYDQSAEYMRDNL

GLGETSTVVGASAVSGFCAAACSLPFDFVKTQIQKMQPDAQGKYPYTGSL

DCAMQTLKSGGPLKFYTGFPVYCVRIAPHVMMTWIFLNQITKFQKTIGL cDNA sequence of ZM57651070 from corn (SEQ ID NO:45):

CTAGCACGTGAAAATTCCTTCGGCTCCAGTTATTACGGAGGATTAGGTTG

GTGAACTGGTGACTGGAGCTGGAATCGCATTTCTTGCTCTTTGGTCTCTC

CAGAATCATCCTCCGGCCAGCCGTTCTTGGAATCCTCCCGAGATTCGCTT

GCCCGCCCTTTTCTTTTCAAGTGGATCTGAACTTGGGAGGGAACCCCGAT

GCAGCCGCGG

TACGGAGAAGCACGACAACCGCTGCCGGGCGGTACGCGCTGTACCACTT

CGGCACCAGCGGCGCCGCCGTCGCCGCCGCCACCGCCGTGACCCATCCGT

-continued

```
TCGATGTTATCAAAGTCAGGCTTCAAATGCAGCTTGCTGGGCAAAGAGGA

AACTTAGTTGGAATGGGAACAATATTTACACAAATGGTTGAAAGGGAAGG

GACTCGGTCACTCTACCTGGGACTTGCACCAGCGTTGGCGAGAGCTGTTG

TCTATGGTGGCCTTCGGTTTGGACTGTATGAGCCCTGCAAGCATGTCTGC

AGTTATGCATTTGGTTCAACAAACTTTGCTTTTAAATTTGCATCTGGAGT

CATTGCTGGGGCCTTGCAACTGCTTTAACAAATCCCATGGAAGTTTTGA

AGGTGAGGCTGCAGATGAGTAAAAGCAGTACCAGTACAATAAGAGAGATG

AGAAAAGTTATAGCGCACGAAGGGTTTAAAGCACTTTGGAAAGGAGTCGG

CCCAGCAATGACAAGAGCAGGTTGCCTTACTGCATCACAAATGGCGACTT

ACGATGAGGCCAAACAGGCCTTAATGAAGTGGACACCACTTGAAGAAGGT

TTTCAGTTACATCTCATCTCGAGTTTCATAGCTGGAACAGCTGGTACTCT

TGTGACCTCACCTGTAGACATGATCAAAACACGGTTAATGCTGCAACAGG

AGTCCAAAGGCGCCAGAGTATACAGGAACGGATTCCATTGTGCTTCCCAG

GTTGTGGTGACAGAGGGTGTGAAATCACTTTATAAAGGTGGATTTGCCAC

ATTCGCGAGAGTAGGCCCTCAGACAACGATTACCTTTATCGTGTGCGAGA

AACTGCGCGAACTTGCAGGAATGACTGCCATCTAGTGCCACCCCAAATTG

CATAATGTGTGGGGTCCAACGGTTGAACAGCATACTCTACCCGAGTTTTC

ACACCATTCTTTATTCACTATTCATGATGAGAAGGGAGAAGATAAGCACC

CACTGGGATGTCTAAGGATTGGGAAGCCCAGAGCTCCTTCAGATTTATCA

TACCTCATTTGAAATTTCGAAATAGCGTGATTGTTCTTATGTTTGCTCTA

AGACTTACTCATCATATCTCCAATCTCATCTTGTATTTCAAACTACACTC

TACAAACAATACAGTCTGTAGTGTAAAAACATTATTTTGGGTGACCATAT

GGGTAACCTGCTGTA-CAAAAAAAAAA
```

The ZM57651070 cDNA is translated into the following amino acid sequence (SEQ ID NO:46):

```
MQPRYGEARQPLPGRYALYHFGTSGAAVAAATAVTHPFDVIKVRLQMQLA

GQRGNLVGMGTIFTQMVEREGTRSLYLGLAPALARAVVYGGLRFGLYEPC

KHVCSYAFGSTNFAFKFASGVIAGGLATALTNPMEVLKVRLQMSKSSTST

IREMRKVIAHEGFKALWKGVGPAMTRAGCLTASQMATYDEAKQALMKWTP

LEEGFQLHLISSFIAGTAGTLVTSPVDMIKTRLMLQQESKGARVYRNGFH

CASQVVVTEGVKSLYKGGFATFARVGPQTTITFIVCEKLRELAGMTAI
``` cDNA sequence of ZM62073276 from corn (SEQ ID NO:47):

```
GCCGCCTCTCCTACTGCATCTCCCTCGCTCTCGTCGCCTCGTTCGCTTCG

CCTCCGCCCCGCCCCGCCCCGAGCAGAGCGCAGCCCTATCCGGAGCTGGG

ATGGCGGACGCGAAGCAGCAGCAGCAGCAGCAGCAGCAGCCACAGCAGGC

GGCAGCGGCAGCCACCGGCGTGTGGAAGACGGTCAAGCCCTTCGTTAACG

GCGAGGCCTCTGGGATGCTCGCGACCTGCGTCATCCAGCCTATCGACATG

GTCAAGGTGAGGATCCAGTTGGGTGAGGGCTCTGCTGGTCAGGTCACAAG

GAACATGCTTGCAAATGAGGGTGTCCGTTCTTTCTACAAGGGTTTGTCCG

CCGGATTGCTGAGGCAAGCGACGTACACGACTGCTCGTCTTGGATCCTTT

AGGGTTCTAACTAACAAAGCAGTTGAAAAGAATGAAGGGAAGCCATTGCC

TCTATTTCAGAAAGCTTTTATTGGTCTGACTGCTGGTGCAATTGGTGCTT

GTGTTGGTAGTCCTGCTGATCTGGCACTCATTAGAATGCAAGCCGATTCG

ACCCTGCCAGTTGCACAACGACGCAACTATAAGAATGCTTTCCATGCACT

CTACCGTATCAGTGGTGATGAGGGAGTCCTTGCGCTTTGGAAGGGTGCAG

GTCCAACTGTGGTGAGAGCTATGGCACTCAATATGGGTATGCTTGCTTCC

TATGACCAGAGTGTCGAGCTATTTAGGGACAAATTTGGCGCAGGAGAAAT

TTCTACTGTTGTTGGAGCCAGCGCTGTTTCTGGATTCTTTGCCTCAGCAT

GCAGTTTGCCCTTTGACTATGTGAAGACACAGATTCAGAA

GATGCAACCTGATGCGAATGGCAAGTACCCATACACAGGGTCTTTGGACT

GTGCTGTGAAGACCTTCAAGAGCGGTGGCCCATTCAAGTTCTACACTGGT

TTCCCGGTGTACTGCGTCAGGATTGCACCCCATGTCATGATGACCTGGAT

ATTCTTGAATCAGATCCAGAAGTTTGAGAAGAAGATCGGCATATAGGATT

CCCATCGGAC

GGATACAGGGTTGACAGTTCTATGCTATTACTGCTTGACTCTGTAATAAC

ATTCCAGCTGCTTTCGCACCATGGTAGTTGGTTTTGGTAGAGACAAGTCT

GTTACAATTTTTTACCTTAGCTTTCCAATTATTGTGTTGCAATAATCGAA

TTAATTGTTGCTGGGGATTTTTTTGGGGGGTTGGGAGGGTGGCATGCTT

TTGTTGGCTG

GGATGTAGCCATAAGGAGAGGGGGATACTGCCTAGTTATGTCATTGAATG

GAATTGGACCATATTTTATACAGATTTTTACCTTCAAAAAAAAAAAAAA
```

The ZM62073276 cDNA is translated into the following amino acid sequence (SEQ ID NO:48):

```
MADAKQQQQQQQQPQQAAAAATGVWKTVKPFVNGEASGMLATCVIQPIDM

VKVRIQLGEGSAGQVTRNMLANEGVRSFYKGLSAGLLRQATYTTARLGSF

RVLTNKAVEKNEGKPLPLFQKAFIGLTAGAIGACVGSPADLALIRMQADS

TLPVAQRRNYKNAFHALYRISGDEGVLALWKGAGPTVVRAMALNMGMLAS

YDQSVELFRDKFGAGEISTVVGASAVSGFFASACSLPFDYVKTQIQKMQP

DANGKYPYTGSLDCAVKTFKSGGPFKFYTGFPVYCVRIAPHVMMTWIFLN

QIQKFEKKIGI
``` cDNA sequence of EST257 from moss (SEQ ID NO:49):

```
CCCGGGGATTCAGCAGTACTTCACAAGAAGAATAGCATGGTGCGTGCAGA

TCTTGTCAACCTTGCGGACTTAGATACTGCTCTAAACAGAGTTCATAATA

AGCTACCTAATTCCATAGAAACAGCTAGTGCAGAGCCTCCTGCTCCTCCA

GAAGAATGGGAAATAAATCCTCGAGAGATCACTTTGAAGCATATGATTGC

GCGTGGCACCTTTGGGACTGTCCACAAAGGAGTGTACAAAGGTCAGGATG

TCGCAGTTAAGCTACTTGAGTGGGGCGAGGAGAATACCATGAAGAAAACA
```

-continued
```
GAGGTTCAATACTACAGAAACCAATTCAGACAAGAGGTTGCTGTGTGGCA

TAAACTCGACCACCCTAATGTCACGAAGTTCATCGGAGCCTCGATGGGA

ACTCAGATTTGCGGATTCCCTCAGCCGTGGATGGTGATGATGGATTCCAT

CATGTGCCGAACAATGCTTGTTGTGTTGTCGTTGAGTACCTTGCAGGCGG

GACTCTTAAAGATCATCTCATTCGCAGCCGGCGGAAAAAACTCTCGTACA

AGGTGGTCGTGCAATTAGCCTTGGATGTTTCTAGAGGGCTTGCATACCTC

CATTCTCAGAAGATCGCTCATCGTGACGTGAAGACAGAGAACATGTTGCT

CGATAAACAGATGAGGGTCAAAATTGCAGATTTCGGAGTTGCACGAGTGG

AGGCATCCAATCCCAAGGACATGACTGGTGATACTGGTACCCCAGGATAC

ATGGCTCCGGAGATTCTCGACGGCAAGCCCTACAACAAGAAGTGCGATGT

GTACAGCTTCGGGATCTGTTTGTGGGAAGTTTATTGCTGCGACATGCCGT

ACTTGGACCTCTCCTTTGCGGACATGACATCGGCAGTTGTGCATCAGAAT

TTGAGACCCGAGGTGCCCAAGTGCTGCCCTCAGGGACTCGCGGATATCAT

GAGGCAGTGTTGGGATGCAAATCCTGAGAAACGGCCTGCCATGGCTGATG

TGGTGCAGATGCTGGAGGCTCTAGACACCTCCAAAGGTGGAGGTATGATA

CCAACAGACGCCCAGCCGCATGGGTGTCTCTGTTTTGGGAGATTCAAGGG

CCCATAGCACGTTTTTGGTTTTTTTTTTCCTTAATTGTGGTTTTACATTT

TATTTATATTTTTCCCTTTTTTAATGTAGGGATGACATGATAATAAGTGT

GCAAACATTTTGTTGTCTCCCCTGGTTTCGTTTCAAGCGTAGCTGCTTGA

CTTGCAATTTCAGTAACCTGGTGCAGGACCCGTTAAC
```

The EST257 cDNA is translated into the following amino acid sequence (SEQ ID NO:50):

```
MVRADLVNLADLDTALNRVHNKLPNSIETASAEPPAPPEEWEINPREITL

KHMIARGTFGTVHKGVYKGQDVAVKLLEWGEENTMKKTEVQYYRNQFRQE

VAVWHKLDHPNVTKFIGASMGNSDLRIPSAVDGDDGFHHVPNNACCVVVE

YLAGGTLKDHLIRSRRKKLSYKVVVQLALDVSRGLAYLHSQKIAHRDVKT

ENMLLDKQMRVKIADFGVARVEASNPKDMTGDTGTPGYMAPEILDGKPYN

KKCDVYSFGICLWEVYCCDMPYLDLSFADMTSAVVHQNLRPEVPKCCPQG

LADIMRQCWDANPEKRPAMADVVQMLEALDTSKGGGMIPTDAQPHGCLCF

GRFKGP
``` cDNA sequence of LU61665952 from linseed (SEQ ID NO:51):

```
AGGGTGATCACGAGGGAGGTATGAATTCTAAGGTGAAGGGAAATGGAAGT

GTTAGTAGAAAAGATATGATTTTTCGAGCGGATCGAATCGATTTGAAGAT

CCTGGATGTACAGCTAGAGAAGCACCTGAGTAGGGTGTGGTCGAGGAACA

CCACAGACAACGCTAAGCCTAAAGAAGAGTGGGAGATTGATTTGTCTAAG

TTGGACATCAAAACCCAGATAGCTCGTGGTACTTATGGCACTGTTTATAA

AGGCACTTATGATAATCAAGATGTTGCAGTGAAAGTGTTGGATTGGGGGG

AAGATGGTATGACTACAGTATCTGAAGCTGCTTCTCTTGAGCATCATTT

CGTCAAGAGGTTGCTGTTTGGCATAAGCTTGACCATCCTAATGTTACCAA
```

```
ATTCGTTGGAGCATCGATGGGAACTTCAAATCTCAAGGTTTCAAATAATA

AATCTGATGGTCAGCATACTGCTAGAGCATGTTGTGTTGTGGTTGAGTAT

CAACCTGGTGGAACACTAAAGCAGTACTTGATAAGAAATAGGCGAAAGAA

ACTTCCTTATAAAGTTGTAATACAACTTGCTTTGGATCTCTCTAGGGGTT

TGAGTTACCTACATTCGAAGAAAATTGTGCACCGTGATGTGAAGTCGGAA

AACATGTTGCTTGATAATCATAGAAATCTTAGGATTGCGGATTTTGGTGT

TGCTCGAGTCGAAGCTCAAAATCCAAGTGATATGACTGGTGAAACTGGTA

CCCTTGGATACATGGCACCTGAGGTCCTTGATGGCAAGCCATATAACAGA

AGGTGTGATGTTTATAGCTTCGGCATATGTTTATGGGAAATCTATTGTTG

TGATATGCCATATCCAGATCTTAGCTTTGCTGATGTGACGTCCGCGGTTG

TTCGACAAACTTGAGCCGGGAGATTCCGAGATGTTGTCCAAGTTCACTA

GGAAGCATCATGAAGAAATGTTGGGATGCACAATCAGAGAACCGTCCAGA

AATGGCTGAAGTGGTGAAGATGTTGGAAGCCATTGATACAAGTAAAGGAG

GAGGAATGATCCCTGAAGACCAGAACCCTGGTTGTTTCTGCTTCGCCCCA

ACCCGTGGCCCTTAAACCCCCTTATTAATTTACTCCCCAAACAGTCCTCA

TCCATCTATGTGTGCACAAATTTCAATTTCTTTATATTTGAGTTGTTTTC

TTTGTTTATCATTTTCTTGTGTTCTTCACTTCTGCACATATTTTGATTTT

GAACTACCTAAAGGGAGTGAAAGGATTAATGTTATAAGTAAAAAAAAAAA

AAAA
```

The LU61665952 cDNA is translated into the following amino acid sequence (SEQ ID NO:52):

```
MNSKVKGNGSVSRKDMIFRADRIDLKILDVQLEKHLSRVWSRNTTDNAKP

KEEWEIDLSKLDIKTQIARGTYGTVYKGTYDNQDVAVKVLDWGEDGMTTV

SEAASLRASFRQEVAVWHKLDHPNVTKFVGASMGTSNLKVSNNKSDGQHT

ARACCVVVEYQPGGTLKQYLIRNRRKKLPYKVVIQLALDLSRGLSYLHSK

KIVHRDVKSENMLLDNHRNLRIADFGVARVEAQNPSDMTGETGTLGYMAP

EVLDGKPYNRRCDVYSFGICLWEIYCCDMPYPDLSFADVTSAVVRQNLRP

EIPRCCPSSLGSIMKKCWDAQSENRPEMAEVVKMLEAIDTSKGGGMIPED

QNPGCFCFAPTRGP
``` cDNA sequence of TA56863186 from wheat (SEQ ID NO:53):

```
AGCACTGACAACTACAACCTCGCTGGTGGCTCCGTTACCATGTCAGTGGA

CAACAGCAGCGTGGGCTCGAACGAGTCCCGCACCGTCATACTTAAGCACC

CGGGCCTCCGTGATGCTCCAACCGCAAGCTACTCGGTTGGCAACAGTGTC

TTTCGTCCCAACCGTGTGGCTGCGCACACCCTAAATGAAGATGCATTGGC

CAGGGTTCTGATGGACCCAAATCATCCAACAGAGATACTTAGCAAGTACC

AGCAGTGGGCCATTGATCTGGGGAGGTTGGATATGGGGGTTCCCTTTGCA

CAGGGAGCCTTTGGGAAGCTGTACCGGGGAACATATATTGGAGAAGATGT

TGCCATTAAGCTGCTGGAGAAGCCTGACAATGATATCGAGAGAGCACAAT
```

```
CGTTGGAACAGCAGTTTGTGCAAGAAGTTATGATGTTATCTACCCTAAGG
CACCCAAATATAGTAAGATTTATAGGGGCTTGCAGGAAGTCAATTGTGTG
GTGCATTATTACTGAGTATGCAAAAGGTGGCTCAGTCAGGCAGTTCCTGG
CAAAAAGGCAGAACAAGTCGGTACCTTTGAGGCTGGCTGTCAAACAAGCA
TTGGATGTAGCGAGGGGAATGGCGTATGTGCATGCTCTGGGATTTATCCA
TAGGGACCTGAAGTCGGATAATCTTCTAATTGCAGCAGACAGATCCATTA
AGATTGCTGACTTTGGAGTTGCTCGAATTGAAGTGAAAACAGAGGGGATG
ACACCAGAGACAGGAACCTACCGCTGGATGGCACCGGAAATGATCCAGCA
CAGGCCTTATGATCATAAGGTTGATGTCTACAGCTTTGGGATTGTCTTGT
GGGAGCTTATAACTGGCATGCTTCCTTTCACAAACATGACAGCTGTTCAG
GCGGCTTTTGCTGTTGTAAATAAGGGTGCTCGTCCAGCGATCCCACATGA
CTGCCTGCCTTCCCTAACCCACATCATGACGCGCTGTTGGGATGCAAACC
CTGAAGTTCGCCCACCATTCACCGAGATCGTCTGCATGCTTGAGAACGCC
GAGATGGAGGTCGTGAGCCATGTCCGTAAAGCGCGCTTCCGCTGCTGCGT
TGCTGACCCATGACCACCGACTGAAACTAAAGCAGGTTAGACTATCGCAG
CGGGCATTAGGGAAGAAAACAGGTAAGGATGAAGAAAAGAGGCAATGCCA
ATGTGTTCATCGTTGTCAGTGCGTGGGGTCTGTGTGCCTTTACCAGTGCG
CATTCTGTCTTGTGTAAGTTGCACACCTCAAGTAAAAGTAATTTCGTATA
GATGTTGCCTTGTATGCTAACAAAGACCTAATGGAGCTTTTCCGTGTTAA
TAATATCCGCTTGCTCTTGTACTCGTGCAAGTTTGTGCCAAAAAAAAAAA
AAAA
```

The TA56863186 cDNA is translated into the following amino acid sequence (SEQ ID NO:54):

```
MSVDNSSVGSNESRTVILKHPGLRDAPTASYSVGNSVFRPNRVAAHTLNE
DALARVLMDPNHPTEILSKYQQWAIDLGRLDMGVPFAQGAFGKLYRGTYI
GEDVAIKLLEKPDNDIERAQSLEQQFVQEVMMLSTLRHPNIVRFIGACRK
SIVWCIITEYAKGGSVRQFLAKRQNKSVPLRLAVKQALDVARGMAYVHAL
GFIHRDLKSDNLLIAADRSIKIADFGVARIEVKTEGMTPETGTYRWMAPE
MIQHRPYDHKVDVYSFGIVLWELITGMLPFTNMTAVQAAFAVVNKGARPA
IPHDCLPSLTHIMTRCWDANPEVRPPFTEIVCMLENAEMEVVSHVRKARF
RCCVAEPMTTD
``` cDNA sequence of ZM62026837 from corn (SEQ ID NO:55):

```
CGCGCGGCCAAACTCCTGTTCTTCCACCTGCTGGCTGCTCCTGCCTCCCC
TGCGCCCCAAACCCACCCGCCTCGCCGTCCCCGCAGGCCGCAGCCTGCTC
TCGGCTCCCGCCGCCGTCTACCGCGTCCTGCGGCTGCGGTGTTGCGTCAC
CTCGGGTTCGCCTTAACTTCCACAATCCTCGCCGTCCTGGTGCTCCGCCG
CCCCTCCCTT
TGTACTCGCGCTGGAGCTGCAGATCCACCGCGACCTGGCGACCAATTCCT
CCTCCCGCTGAAGAATTGGCGACCTTGGCCTCCGCCCCCGCGGCGCGGAG
GAGTCAACTGTGGTAGCAACCACCGCGGAGGCTGCAAGCCTTCGGTAAGG
GAGGAAAGTTGACTTGTTGGAAGCCGGTCCAGGGCCGCGATGACGTCGAC
CGCCGCCGGCGCGTCGTCGTCGGCGGCGAAGAGCGAGTCCTACCTGCGGG
CCGACAAGATCGACCTCGAGAGCCTGGACATCCAGCTGGAGAAGCAGCTG
GCCAAGACCTGGGAGAAGCACAAGGGGTCGTACAACCAGGGGCCCAGGGA
GGACTGGGAGATCGACCTCGCCAAGCTCGAGATTCGCTACGTCATAGCGC
AGGGCACCTACGGCACGGTGTATCGCGGCACGTATGATGGGCAGGACGTC
GCAGTAAAACTATTGGATTGGGGTGAAGATGGCTTTGCGTCAGAAACTGA
AACTGCCACACTGCGAGCATCATTTAAGCAGGAGGTTGCTGTCTGGCATG
AGCTCAACCATCCGAATGTTACAAAGTTTGTTGGTGCATCAATGGGTACT
ACAGACCTTAAGATTCCAGCCAATAGTTCTAACAGTGGTGGGCGCACTGA
GCTGCCGCCAAAAGCATGTGTGTTGTGGTCGAATATCTCGCTGGAGGAT
CACTGAAGCAGTATTTAATAAAGAACAGGCGAAGGAAGCTTGCATACAAG
GTTGTTGTTCAGATAGCACTGGATCTTGCCAGAGGATTGAACTATCTACA
TTCAAGAAAGATAGTACATCGGGATGTAAAAACTGAAAATATGCTGCTCG
ATACACAGCGAAACCTTAAGATTGCTGATTTTGGTGTTGCTCGTGTTGAG
GCTCAGAATCCAAAGGACATGACAGGCGCGACTGGGACACTTGGCTACAT
GGCCCCAGAGGTGCTTGAAGGCAAGCCATACAACAGAAAGTGTGATGTCT
ACAGTTTTGGCATATGCTTATGGGAAATATACTGCTGTGACATGCCATAT
CCAGACCTCAGTTTTGCAGACGTCTCGTCCGCCGTCGTTCACCAGAACCT
GCGGCCTGACATCCCTCGCTGCTGCCCAAGCCCAATGGCGAACATCATGC
GGAAGTGCTGGGACGCAAACCCGGATAAGCGCCCTGACATGGACGACGTG
GTGCGGTTCCTGGAGGCCCTCGACACGAGCAAGGGCGGTGGCATGATACC
AGAAGGCCAGGCAGGCGGGTGCTTGTGTTTCTTCAGAGCCCGTGGTCCTT
AGAACCAACCAACCCTTTCCAGCCATCCTCTACTTGTCTCTGCCATACTA
CAGTATTGGAGCCAGATGTAGGCCTTTGTTGTTCATCGGATAGGGGATTG
CAGATAACTTGATGACAATCTTTGTGATTGGTTGACACTTGTTATACGTT
CTATAGTGATGTGAATACCAGTGAGGAGTCCATAATACAGAGTGAAAAAA
AAAA
```

The ZM62026837 cDNA is translated into the following amino acid sequence (SEQ ID NO:56):

```
MTSTAAGASSSAAKSESYLRADKIDLESLDIQLEKQLAKTWEKHKGSYNQ
GPREDWEIDLAKLEIRYVIAQGTYGTVYRGTYDGQDVAVKLLDWGEDGFA
SETETATLRASFKQEVAVWHELNHPNVTKFVGASMGTTDLKIPANSSNSG
GRTELPPKACCVVVEYLAGGSLKQYLIKNRRRKLAYKVVVQIALDLARGL
NYLHSRKIVHRDVKTENMLLDTQRNLKIADFGVARVEAQNPKDMTGATGT
LGYMAPEVLEGKPYNRKCDVYSFGICLWEIYCCDMPYPDLSFADVSSAVV
HQNLRPDIPRCCPSPMANIMRKCWDANPDKRPDMDDVVRFLEALDTSKGG
GMIPEGQAGGCLCFFRARGP
``` cDNA sequence of ZM65457595 from corn (SEQ ID NO:57):

```
ACCTCGCCACCCTCCTGCCTCCTCCGCATCCGCGCCCCCTCGCTTAGCCT
AAACCGCGGGGCAGCTAGTCTCGCCACCGCAGGCCGCACCGGTCATCACA
CCGAAGCGCACGCGGGGAGCCCCCGTAGAGTTCCGGGGCGACCAGGCCAA
CTAACGCCATGAAGGAGGAAGGCGGCGGCGGGGACGCGGGGTTCGTGCGG
GCGGACCAGATCGACCTCAAGAGCCTGGACGAGCAGCTGGAGCGCCATCT
CACCCGCGCCTGGACCATGGAGAAGCGCAAGGAGGAGGCCTCCGCCGGCG
CTGGCGCCGGCGCCAGGCAGCACCAGCAGTCCCGGCGCCCGCGGAGGGAG
GACTGGGAGATCGACCCCGCCAAGCTTGTCGTCAAGGGCGTCATCGCCCG
CGGCACCTTTGGCACCGTCCACCGCGGCATCTACGACGCTCACGACGTCG
CAGTGAAACTACTTGATTGGGGAGAGGATGGGCATAGATCAGAACAAGAC
ATTGCAGCACTAAGAGCAGCTTTTTCACAAGAGGTCTCTGTTTGGCATAA
GCTTGACCATCCAAATGTAACCAAGTTTATTGGAGCTATAATGGGTGCAA
GGGATCTGAATATTCAAACGGAAAACGGCCACATTGGCATGCCAACTAAT
ATCTGCTGTGTCGTTGTGGAGTACCTTCCTGGTGGTGCACTAAAATCATT
TCTGATAAAGAACAGGAGAAAGAAGCTAGCTTTTAAGGTCGTTGTTCAAA
TCGCTCTTGACCTTGCCAGGGGATTAAGCTATCTCCATTCCAAGAAGATT
GTGCACCGTGATGTGAAGACTGAAAATATGCTTCTTGACAAAACGAGAAC
CGTGAAGATCGCTGATTTTGGTGTTGCTCGCCTTGAAGCTTCAAATCCCA
GTGACATGACGGGCGAAACTGGAACGCTTGGTTACATGACACCTGAGGTT
CTCAATGGAAATCCCTACAACAGGAAATGCGATGTTTACAGCTTCGGAT
CTGTTTGTGGGAGATATACTGCTGTGATATGCCATATCCTGACTTGAGCT
TTTCTGAGGTCACGTCTGCGGTTGTCCGTCAGAACCTGAGGCCGGAGATA
CCACGCTGCTGCCCGAGCTCTCTATCGAACGTGATGAAGCGCTGCTGGGA
CGCCAACCCCGACAAGCGACCTGAGATGGCCGAGGCGGTGTCCATGCTGG
AGGCGATCGACACGTCGAAGGGTGGAGGCATGATCCCTGTGGACCAGCGG
CCAGGATGCCTTGCGTGCTTCCGGCAGTACAGAGGTCCATGACAGATAGG
TGGAAACCTGTTGGAGCTGCGGCCTCTAGATCTCGTGGATGCCGATCGAT
CGCGTGTTGTTTTCTGGGGAAGCAAACTGGTTAATGGAGCTAGCCCGCCT
TACCGGCTCGTGTAAATCCTCTGTCCATCAATTCGTAACTCTGTTTTAT
CGATTAATGAAAAGAACCGGGCTTGCTCGAAAAAAAAAAAAAAA
```

The ZM65457595 cDNA is translated into the following amino acid sequence (SEQ ID NO:58):

```
MKEEGGGGDAGFVRADQIDLKSLDEQLERHLTRAWTMEKRKEEASAGAGA
GARQHQQSRRPRREDWEIDPAKLVVKGVIARGTFGTVHRGIYDAHDVAVK
LLDWGEDGHRSEQDIAALRAAFSQEVSVWHKLDHPNVTKFIGAIMGARDL
NIQTENGHIGMPTNICCVVVEYLPGGALKSFLIKNRRKKLAFKVVVQIAL
DLARGLSYLHSKKIVHRDVKTENMLLDKTRTVKIADFGVARLEASNPSDM
TGETGTLGYMTPEVLNGNPYNRKCDVYSFGICLWEIYCCDMPYPDLSFSE
VTSAVVRQNLRPEIPRCCPSSLSNVMKRCWDANPDKRPEMAEAVSMLEAI
DTSKGGGMIPVDQRPGCLACFRQYRGP
``` cDNA sequence of ZM67230154 from corn (SEQ ID NO:59):

```
CGGCAACCCACTATCTCATGCGCTCACATGGAGACTCCCGCACGAACTGG
AATCATCTCCGCCTCGCCACCTCTTCATCTTCTTCCCCAGTAGCCGCCGC
CACCACCACTGCAGCAGCCAAACCACGTGACACCTCCCGCGCCGCTCAAC
CCCACAGCATCCGTTGCCACCGCCGCTCACCTCCCCGGCGCTCCCGGCTA
CAACCACTGC
AAGCATGAGGCAGCCAACCAGCGCGGGCGGCGACGCTGGGTTCTTGCGCG
CGGACCAGATCGACCTCAAGAGCCTGGACGAGCAGCTCGAGCGCCACCTC
GGACATCCCGCGGAGCGGGTAGTTGGCCCAGTCTCTGGGACAGGGAGCCG
CCGCGGCGAAACGGCCAAGCTGGGTCCGGAGGAGCTGACGCCACTGCAGC
GGTGCCGTGAGGACTGGGAGATCGACCCTACCAAGCTCATCATCAAGGGC
GTCATCGCGCGCGGCACCTTTGGCACCGTCCACCGCGGCGTCTACGACGG
CCAGGACGTCGCTGTAAAATTGCTTGACTGGGGCGAAGATGGCCATAGAT
CAGAACAAGAAATTGGTGCACTAAGAGCAGCGTTTGCACAAGAGGTCGCT
GTCTGGCATAAGCTTGAGCATCCAAACGTTACTAAGTTTATTGGGGCTAT
AATGGGCGCAAGAGATTTAAATATACAAACGGAACATGGACAGCTTGGCA
TGCCAAGCAATATTTGCTGTGTTGTTGTTGAGTACCTTGCTGGAGGTGCG
CTGAAAAATTTTCTGATAAAGAACAGGAGAAGGAAACTTGCCTTTAAAGT
TGTGGTCCAAATAGCTCTTGACCTTGCCAGGGGATTATGCTACCTCCACT
CAAAGAAAATAGTGCACCGTGATGTCAAGACTGAAAACATGCTTCTGGAC
AAGACGAGAACGGTAAAGATCGCTGATTTTGGTGTTGCTCGAGTCGAGGC
TTCAAATCCTAGCGATATGACGGGAGAAACAGGGACGCTTGGTTACATGG
CTCCTGAGGTTCTCAATGGCCATGCTTACAACAGGAAGTGTGACGTGTAC
AGCTTTGGGATCTGCCTGTGGGAGATATACTGCTGTGACATGCCGTACCC
TGATCTCAGTTTTTCTGAGGTCACCTCTGCCGTCGTTCGCCAGAATCTGA
GGCCTGAGATACCGCGCTGCTGCCCGAGCTCGCTAGCGAATGTGATGAAG
CGATGCTGGGACGCGAACCCGGACAAGCGTCCCGAGATGGCGGAGGTGGT
GTCCATGCTGGAGGCGATCGACACGTCCAAGGGTGGCGGCATGATCCCTA
AGGACCAGACGCAGGGCTGCCTCTCGTGCTTCCGCCAGTACCGAGGTCCC
TAACGCAGGGTTGTTTATTTATACCCGGTGAAATGATGATATTGGTCTCT
ACACTACAACTCAGTGTAATCTAATCGCAGAAGTGGCTATATAATGGAGA
AGCTTATCATTGCTTGCCATGGGTGTAAATGGATGGGGCGGGGTGGTTGA
CGATTGGTGTGCTTGTATGCTCGCTTCGAGTTATAATGCTTGCTGTAAGT
TAAGGTGTGGAAAAAAAAAAAAAAA
```

The ZM67230154 cDNA is translated into the following amino acid sequence (SEQ ID NO:60):

MRQPTSAGGDAGFLRADQIDLKSLDEQLERHLGHPAERVVGPVSGTGSRR
GETAKLGPEELTPLQRCREDWEIDPTKLIIKGVIARGTFGTVHRGVYDGQ
DVAVKLLDWGEDGHRSEQEIGALRAAFAQEVAVWHKLEHPNVTKFIGAIM
GARDLNIQTEHGQLGMPSNICCVVVEYLAGGALKNFLIKNRRKLAFKVV
VQIALDLARGLCYLHSKKIVHRDVKTENMLLDKTRTVKIADFGVARVEAS
NPSDMTGETGTLGYMAPEVLNGHAYNRKCDVYSFGICLWEIYCCDMPYPD
LSFSEVTSAVVRQNLRPEIPRCCPSSLANVMKRCWDANPDKRPEMAEVVS
MLEAIDTSKGGGMIPKDQTQGCLSCFRQYRGP cDNA sequence of EST465 from moss (SEQ ID NO:61):

GGGCCTCCTTCCTAGCCTTCATCTGCTGCGACGATGGAGGAGCTCGCCTC
ATCTGATGTTCCGAACAAGTTGAAGAAGAAGGAATCTAAGATGAAGAAGA
GGGTTATAACTCCAGGGGCCTTGCTGAAGGCAGTAGTAAGGTCTGGAGAG
GGGACTAAACGTCCTGTAGAAGGTGATCAGATTATCTTCCATTATGTCAC
ACGAACAAATCAGGGAGTGGTGGTTGAGACATCGCGATCTGACTTTGGAG
GAAAGGGAGTTCCTCTTAGACTTGTTCTGGGAAAAAGCAAATGATTGCT
GGATGGGAGGAAGGCATCACCACCATGGCCAAAGGTGAAATAGCTATGCT
GAAAGTGCAACCTGAATTACATTATGGTGACCCGGAGTGTCCTGTACCAG
TGCCCGAGAACTTTCCAGTTTCTGATGAGCTCCTTTACGAAGTGGAGTTG
TTCAACTTCTGTAAGGCGAAGATTATCACAGAGGATCTTGGTGTGACAAA
AGTGGTCTTAGAAGAGGGTGAGGGCTGGGAAACTGCAAGGCCTCCGTACG
AGGTGAAGCTTTGGATTACAGGCCGGATCTTAGGTGGGTCCACATTTTTT
ACTCATAAAGAGTGCGATCCCATTCATGTTGAATTCGGCAAGGAACAGTT
GCCAGAAGGACTTGAGAAGGCAGTCGGCACTATGACGAGGAAAGAAAAGT
CAATTATCTACATTTCAAGTTCATACTGTACGAATTCTTCAAATGCATAC
AAATTGAATATATCTCCTCAAGCGCAAGAACTAGAATTTGAAGTGCAGTT
GGTGCAGCTCATTCAGGTAAGAGACATGTTTGGAGATGGAGGATTGATTA
AGAGACGCCTGCGAGACGGACTAGGTGAATTTCCTGTGGACTGTCCTCTG
CAAGATAGTGTGCTTAGAGTCCACTATAAGGCTATGCTACCTGATGATGG
CGGCAGAATATTTATTGACACCAGAAGTAATGGAGGGGAGCCTGTTGAGT
TTGCTTCTGGTGAGGGTGTGGTACCAGAGGGACTTGAGGCAAGTTTGAGG
TTGATGCTTCCGGGGGAGCTCGCACTGATCAACAGCGTCTCTAAGTACGC
ATATGACAAATTTCAAAGGCCAGAGAGTGTTCCAGAGGGAGCTTCAGTCC
AATGGGAAGTGGAATTACTGGAATTTGAGAGTGCAAAGGATTGGACGGGC
CTTAATTTTCAAGAGATCATGGCTGAAGCTGATTCCATAAAGACCACAGG
TAACCGGTTATTTAAGGAGGGCAAGCACGAGCTGGCTAAAGCTAAGTACG
AAAAGGTGTTGAGGGATTTCAGACATGTAAACCCTGGCAGTGATGAAGAA
GCAAAGGAACTACAAGACACCAATAACGCACTGCGGCTTAATGTAGCAGC
TTGTTATCATAAAACTCCATGAGTACATCAAATGCATAGAAACATGCAACA

AGGTGCTAGAAGGTAACCCGCATCATGTCAAAGGGTTATTTCGCCGAGGA
ACTGCTTACATGGAAACGGGGGACTTTGATGAAGCTAGAGCTGATTTCAA
GCAGATGATAACAGTTGACAAGGCTGTCACAGTTGATGCAACTGCTGCTT
TACAGAAGCTCAAGCAAAAGAACGGGAAGCTGAGCTGAAAGCTAAGAAA
CAGTTCAAAGGGCTATTTGACTTAAAACCTGGAGAACTCTCTGAGGGGCT
AGAAGAGGTAAAGCCCGTAAGCGAAATCCATGAGAAGACTGTTGTCAACG
AGGAACTTCCGATAGCATCTATGGATCAACATCAACACTCAAAGCACGAA
ACAGAGGAAGGGAGCCATGAATCGCCCAGGGCAAGCAGCCGATTGTTAAG
ACTTCTGAAAGGTGGAGAGCACCTGATAAGGACAGTCACTTTTGGGAAGT
GTACGATTCTTTAATTTTTCATATTGCTACTGCTAGGATCTCCCCTTTTT
ACTGTACTGGTGACTACCTTATGCTCATTTACATTTCTAAGCCGTTATAG
CTGTTATTAACCATTCGATAATGTACTATGAACAATATTCCACTAGCGTT
TTATGGCTATTTTTCATTAAGTCCTCGTGCCGTTA

The EST465 cDNA is translated into the following amino acid sequence (SEQ ID NO:62):

MEELASSDVPNKLKKKESKMKKRVITPGALLKAVVRSGEGTKRPVEGDQI
IFHYVTRTNQGVVVETSRSDFGGKGVPLRLVLGKSKMIAGWEEGITTMAK
GEIAMLKVQPELHYGDPECPVPVPENFPVSDELLYEVELFNFCKAKIITE
DLGVTKVVLEEGEGWETARPPYEVKLWITGRILGGSTFFTHKECDPIHVE
FGKEQLPEGLEKAVGTMTRKEKSIIYISSSYCTNSSNAYKLNISPQAQEL
EFEVQLVQLIQVRDMFGDGGLIKRRLRDGLGEFPVDCPLQDSVLRVHYKA
MLPDDGGRIFIDTRSNGGEPVEFASGEGVVPEGLEASLRLMLPGELALIN
SVSKYAYDKFQRPESVPEGASVQWEVELLEFESAKDWTGLNFQEIMAEAD
SIKTTGNRLFKEGKHELAKAKYEKVLRDFRHVNPGSDEEAKELQDTNNAL
RLNVAACYHKLHEYIKCIETCNKVLEGNPHHVKGLFRRGTAYMETGDFDE
ARADFKQMITVDKAVTVDATAALQKLKQKEREAELKAKKQFKGLFDLKPG
ELSEGLEEVKPVSEIHEKTVVNEELPIASMDQHQHSKHETEEGSHESPRA
SSRLLRLLKGGEHLIRTVTFGKCTIL cDNA sequence of YBL109w from yeast (SEQ ID NO:63):

ATGTCCCTACGGCCTTGTCTAACACCATCCAGCATGCAATACAGTGACAT
ATATATATACCCTAACACTACCCTAACCCTACCCTATTTCAACCCTTCCA
ACCTGTCTCTCAACTTACCCTCACATTACCCTACCTCTCCACTTGTTACC
CTGTCCCATTCAACCATACCACTCCCAACCACCATCCATCCCTCTACTTA
CTACCACCAATCAACCGTCCACCATAACCGTTACCCTCCAATTAGCCATA
TTCAACTTCACTACCACTTACCCTGCCATTACTCTACCATCCACCATCTG
CTACTCACCATACTGTTGTTCTACCCTCCATATTAA

The YBL109w cDNA is translated into the following amino acid sequence (SEQ ID NO:64):

MSLRPCLTPSSMQYSDIYIYPNTTLTLPYFNPSNLSLNLPSHYPTSPLVT
LSHSTIPLPTTIHPSTYYHQSTVHHNRYPPISHIQLHYHLPCHYSTIHHL
LLTILLFYPPY cDNA sequence of YBL100c from yeast (SEQ ID NO:65):

ATGTTGTTCAAACCAAAAACACGAGCAATACCATCACCGACTGCAAGAAC
TCTACCAGTTTCGTTCAAATTGGCCTCGTCGGACACACCCTTAATTCTTT
CCTCTAAGATGGAGGAAACTTCTGTGGGTTGTGCCTTGGTGGAAGCCAAT
CTTCTGGTGGAAGCCAAAGCAGCAGCGGCAGGTCTTGCGGCCTTGGTAGA
GTTAATTAGAGTTCTCGATAGAGAACGAATAGCAGCAGTACGAGCCAACA
TTATTATATGTGCGTGTTTTTTTATTTATTTTGTTACTGTTCTTGCGAT
AGTTATGAGAGCTAA

The YBL100c cDNA is translated into the following amino acid sequence (SEQ ID NO:66):

MLFKPKTRAIPSPTARTLPVSFKLASSDTPLILSSKMEETSVGCALVEAN
LLVEAKAAAAGLAALVELIRVLDRERIAAVRANIIICACFFYLFCYCSCD
SYES cDNA sequence of YKL184w from yeast (SEQ ID NO:67):

ATGTCTAGTACTCAAGTAGGAAATGCTCTATCTAGTTCCACTACTACTTT
AGTGGACTTGTCTAATTCTACGGTTACCCAAAAGAAGCAATATTATAAAG
ATGGCGAGACGCTGCACAATCTTTTGCTTGAACTAAAGAATAACCAAGAT
TTGGAACTTTTACCGCATGAACAAGCGCATCCTAAAATATTTCAAGCGCT
CAAGGCTCGTATTGGTAGAATTAATAATGAAACGTGCGACCCCGGTGAGG
AGAACTCGTTTTTCATATGCGATTTGGGAGAAGTCAAGAGATTATTCAAC
AACTGGGTGAAGGAGCTTCCTAGAATTAAGCCATTTTATGCCGTCAAATG
TAATCCTGATACCAAGGTTTTGTCATTATTAGCAGAGTTGGGCGTTAATT
TCGATTGCGCTTCCAAAGTGGAAATTGACAGAGTATTATCGATGAACATC
TCGCCGGATAGAATTGTTTACGCTAATCCTTGTAAAGTAGCATCTTTCAT
TAGATATGCAGCTTCAAAAAATGTAATGAAGTCTACTTTTGACAATGTAG
AAGAATTGCATAAAATCAAAAAGTTTCATCCTGAGTCTCAGTTGTTATTA
AGAATCGCTACCGATGACTCTACCGCTCAATGTCGACTTTCCACCAAATA
TGGCTGTGAAATGGAAAACGTAGACGTTTTATTAAAGGCTATAAAGGAAC
TAGGTTTAAACCTGGCTGTGTTTCTTTCCACGTCGGTTCAGGCGCTTCT
GATTTTACAAGCTTATACAAAGCCGTTAGAGATGCAAGAACGGTATTTGA
CAAAGCTGCTAACGAATACGGGTTGCCCCCTTTGAAGATTTTGGATGTAG
GTGGTGGATTTCAATTTGAATCCTTCAAAGAATCAACTGCTGTTTTGCGT
CTAGCGCTAGAGGAATTTTTCCCTGTAGGTTGTGGTGTTGATATAATTGC
AGAGCCTGGCAGATACTTTGTAGCTACAGCGTTCACTTTGGCATCTCATG
TGATTGCGAAGAGAAAACTGTCTGAGAATGAAGCAATGATTTACACTAAC
GATGGTGTATACGGGAACATGAATTGTATTTTATTCGATCATCAAGAGCC
CCATCCAAGAACCCTTTATCATAATTTGGAATTTCATTACGACGATTTTG
AATCCACTACTGCGGTCCTCGACTCTATCAACAAAACAAGATCTGAGTAT
CCATATAAAGTTTCCATCTGGGGACCCACATGTGATGGTTTGGATTGTAT
TGCCAAAGAGTATTACATGAAGCATGATGTTATAGTCGGTGATTGGTTTT
ATTTTCCTGCCCTGGGTGCCTACACATCATCGGCGGCTACTCAATTCAAC
GGCTTTGAGCAGACTGCGGATATAGTATACATAGACTCTGAACTCGATTA
A

The YKL184w cDNA is translated into the following amino acid sequence (SEQ ID NO:68):

MSSTQVGNALSSSTTTLVDLSNSTVTQKKQYYKDGETLHNLLLELKNNQD
LELLPHEQAHPKIFQALKARIGRINNETCDPGEENSFFICDLGEVKRLFN
NWVKELPRIKPFYAVKCNPDTKVLSLLAELGVNFDCASKVEIDRVLSMNI
SPDRIVYANPCKVASFIRYAASKNVMKSTFDNVEELHKIKKFHPESQLLL
RIATDDSTAQCRLSTKYGCEMENVDVLLKAIKELGLNLAGVSFHVGSGAS
DFTSLYKAVRDARTVFDKAANEYGLPPLKILDVGGGFQFESFKESTAVLR
LALEEFFPVGCGVDIIAEPGRYFVATAFTLASHVIAKRKLSENEAMIYTN
DGVYGNMNCILFDHQEPHPRTLYHNLEFHYDDFESTTAVLDSINKTRSEY
PYKVSIWGPTCDGLDCIAKEYYMKHDVIVGDWFYFPALGAYTSSAATQFN
GFEQTADIVYIDSELD cDNA sequence of YPL091w from yeast (SEQ ID NO:69):

ATGCTTTCTGCAACCAAACAAACATTTAGAAGTCTACAGATAAGAACTAT
GTCCACGAACACCAAGCATTACGATTACCTCGTCATCGGGGGTGGCTCAG
GGGGTGTTGCTTCCGCAAGAAGAGCTGCATCTTATGGTGCGAAGACATTA
CTAGTTGAAGCTAAGGCTCTTGGTGGTACCTGTGTTAACGTGGGTTGTGT
TCCGAAGAAAGTCATGTGGTATGCTTCTGACCTCGCTACTAGAGTATCCC
ATGCAAATGAATATGGATTATATCAGAATCTTCCATTAGATAAAGAGCAT
TTGACTTTTAATTGGCCAGAATTTAAGCAGAAAAGGGATGCTTATGTCCA
TAGGTTGAACGGTATATACCAGAAGAATTTAGAAAAAGAAAAGTGGATG
TTTGTATTTGGATGGGCTAGATTCAATAAGGACGGTAATGTTGAAGTTCAG
AAAAGGGATAATACTACTGAAGTTTACTCCGCTAACCATATTTTAGTTGC
GACCGGTGGAAAGGCTATTTTCCCCGAAAACATTCCAGGTTTCGAATTAG
GTACTGATTCTGATGGGTTCTTTAGATTGGAAGAACAACCTAAGAAAGTT
GTTGTTGTTGGCGCTGGTTATATTGGTATTGAGCTAGCAGGTGTGTTCCA
TGGGCTGGGATCCGAAACGCACTTGGTAATTAGAGGTGAAACTGTCTTGA
GAAAATTTGATGAATGCATCCAGAACACTATTACTGACCATTACGTAAAG
GAAGGCATCAACGTTCATAAACTATCCAAATTGTTAAGGTGGAGAAAAA
TGTAGAAACTGACAAACTGAAAATACATATGAATGACTCAAAGTCCATCG

-continued

ATGACGTTGACGAATTAATTTGGACAATTGGACGTAAATCCCATCTAGGT

ATGGGTTCAGAAAATGTAGGTATAAAGCTGAACTCTCATGACCAAATAAT

TGCTGATGAATATCAGAACACCAATGTTCCAAACATTTATTCTCTAGGTG

ACGTTGTTGGAAAAGTTGAATTGACACCTGTCGCTATTGCAGCGGGCAGA

AAGCTGTCTAATAGACTTTTTGGTCCAGAGAAATTCCGTAATGACAAACT

AGATTACGAGAACGTCCCCAGCGTAATTTTCTCACATCCTGAAGCCGGTT

CCATTGGTATTTCTGAGAAGGAAGCCATTGAAAAGTACGGTAAGGAGAAT

ATAAAGGTCTACAATTCCAAATTTACCGCCATGTACTATGCTATGTTGAG

TGAGAAATCACCCACAAGATATAAAATTGTTTGTGCGGGACCAAATGAAA

AGGTTGTCGGTCTGCACATTGTTGGTGATTCCTCTGCAGAAATCTTGCAA

GGGTTCGGTGTTGCTATAAAGATGGGTGCCACTAAGGCTGATTTCGATAA

TTGTGTTGCTATTCATCCGACTAGCGCAGAAGAATTGGTTACTATGAGAT

AA

The YPL091w cDNA is translated into the following amino acid sequence (SEQ ID NO:70):

MLSATKQTFRSLQIRTMSTNTKHYDYLVIGGGSGGVASARRAASYGAKTL

LVEAKALGGTCVNVGCVPKKVMWYASDLATRVSHANEYGLYQNLPLDKEH

LTFNWPEFKQKRDAYVHRLNGIYQKNLEKEKVDVVFGWARFNKDGNVEVQ

KRDNTTEVYSANHILVATGGKAIFPENIPGFELGTDSDGFFRLEEQPKKV

VVVGAGYIGIELAGVFHGLGSETHLVIRGETVLRKFDECIQNTITDHYVK

EGINVHKLSKIVKVEKNVETDKLKIHMNDSKSIDDVDELIWTIGRKSHLG

MGSENVGIKLNSHDQIIADEYQNTNVPNIYSLGDVVGKVELTPVAIAAGR

KLSNRLFGPEKFRNDKLDYENVPSVIFSHPEAGSIGISEKEAIEKYGKEN

IKVYNSKFTAMYYAMLSEKSPTRYKIVCAGPNEKVVGLHIVGDSSAEILQ

GFGVAIKMGATKADFDNCVAIHPTSAEELVTMR cDNA sequence of TA54587433 from wheat (SEQ ID NO:71):

ATGGCGGTCATGTCACGGTTGAAGAGGCTGGCGGCGCCCGCGCTGCTGGT

GCTGCTTGCGCTGGCGGCGTCCGCGGCCGTGGCGGCGAAGACGACCCAGG

ACGGCGCGGAGGCGGCGCCGGGCAAGGATGAAGAGTCGTGGACGGGGTGG

GCCAAGGACAAGATCTCCGAGGGGCTGGGGCTCAAGCACGACGCTGACGA

GGAGGCCGCGCGCGAGACCGTCCAGCACACCGCCTCCGAGACGGGGAGTC

AGGTGAGCGGCAAGGCAGCGGACGCCAAGGAGGCGGCCAAGGGAACGGTC

GGGGAGAAGCTCGGGGAGGTGAAGGACAAGGTCACCGGCGCAGCAGCCGA

CGGCAAGGACAAGACGCACCGCAAGGATGACTTGCTGTGA

The TA54587433 cDNA is translated into the following amino acid sequence (SEQ ID NO:72):

MAVMSRLKRLAAPALLVLLALAASAAVAAKTTQDGAEAAPGKDEESWTGW

AKDKISEGLGLKHDADEEAARETVQHTASETGSQVSGKAADAKEAAKGTV

GEKLGEVKDKVTGAAADGKDKTHRKDDLL cDNA sequence of ZM68532504 from corn (SEQ ID NO:73):

ATGCCGTCGCACGGGGATCTGGACCGGCAGATCGCGCAGCTGCGCGACTG

CAAGTACCTGCCCGAGGCGGAGGTCAAGGCGCTCTGCGAGCAGGCCAAGG

CCATCCTTATGGAGGAGTGGAACGTGCAGCCCGTGCGCTGTCCTGTCACC

GTCTGTGGCGACATCCACGGCCAGTTCTATGACCTCATCGAGCTCTTCCG

CATCGGCGGCGACGCTCCCGACACCAACTACCTCTTCATGGGCGACTACG

TCGATCGTGGGTACTATTCAGTTGAAACAGTTTCTCTGTTAGTGGCTTTG

AAAGTCCGTTACAGAGATAGAATTACAATACTTAGAGGAAATCATGAGAG

CAGACAAATCACTCAAGTATATGGCTTCTATGATGAATGCTTAAGAAAGT

ATGGAAATGCAAATGTCTGGAAGTATTTTACAGACTTGTTTGATTTTTTG

CCTCTCACAGCTCTTATAGAAAATCAGGTCTTCTGTCTTCACGGTGGCCT

CTCTCCGTCATTGGACACGTTGGATAATATTCGTTCTCTTGATCGCGTAC

AGGAGGTTCCTCATGAAGGACCCATGTGTGATCTTTTGTGGTCTGACCCA

GATGACCGATGTGGATGGGAATTTCACCAAGAGGAGCAGGTTACACATT

TGGGCAAGACATTGCGCAGCAGTTCAACCATACAAATGGTCTTTCTCTCA

TTTCAAGGGCCCATCAACTTGTAATGGAAGGATTTAATTGGTGCCAGGAT

AAGAATGTAGTCACAGTCTTCAGCGCGCCTAATTATTGTTACCGCTGTGG

TAACATGGCTGCTATTCTTGAAATCGGGGAAAACATGGACCAGAACTTCC

TTCAATTCGACCCGGCACCTCGGCAAATTGAGCCAGACACAACTCGGAAA

ACCCCAGACTACTTTTTGTAA

The ZM68532504 cDNA is translated into the following amino acid sequence (SEQ ID NO:74):

MPSHGDLDRQIAQLRDCKYLPEAEVKALCEQAKAILMEEWNVQPVRCPVT

VCGDIHGQFYDLIELFRIGGDAPDTNYLFMGDYVDRGYYSVETVSLLVAL

KVRYRDRITILRGNHESRQITQVYGFYDECLRKYGNANVWKYFTDLFDFL

PLTALIENQVFCLHGGLSPSLDTLDNIRSLDRVQEVPHEGPMCDLLWSDP

DDRCGWGISPRGAGYTFGQDIAQQFNHTNGLSLISRAHQLVMEGFNWCQD

KNVVTVFSAPNYCYRCGNMAAILEIGENMDQNFLQFDPAPRQIEPDTTRK

TPDYFL cDNA sequence of BN42856089 from canola (SEQ ID NO:75):

AAAACTCCAAAAACAAACCATTTTCCATCTCTCAGGCCAAAAAAACCAGA

GATTTGATCTCTCTGGCGATTCATCATCCTCTTCATCCACCACACGCCGT

ATAAGTTAAAGGATCGGTGGTGGTCTCTCGATGCCGCCGAACGGAGATCT

AGACCGTCAGATCTCCCAGCTGATGGAGTGTAAACCGCTATCTGAGGCCG

ATGTGAAGACGCTCTGCGATCAAGCGAGGGCCATCCTCGTCGAGGAGTGG

AACGTTCAGCCCGTGAAGTGTCCTGTCACCGTCTGCGGCGATATCCACGG

ACAGTTCTATGACCTTATCGAGCTCTTTCGAATCGGTGGGAATCCTCCGG

ATACTAACTACCTCTTCATGGGAGACTATGTAGACCGTGGCTACTATTCA

GTAGAAACAGTTTCTCTATTGGTGGCACTGAAAGTGCGATACAGGGATAG

GATTACAATCTTGCGAGGGAATCACGAGAGTCGGCAGATTACTCAAGTCT

ATGGGTTTTATGATGAATGTTTGAGGAAGTATGGAAATGCAAATGTCTGG

AAGTTTTTCACGGACCTTTTCGATTATCTTCCTCTTACTGCTCTCATAGA

GAGTCAGGTTTTCTGCTTGCATGGAGGGCTTTCACCTTCTCTGGACACCC

TTGATAATATCCGAAGCTTGGATCGTATACAAGAGGTTCCACATGAAGGA

CCAATGTGTGATTTATTATGGTCTGATCCCGATGATCGATGTGGGTGGGG

AATATCTCCACGAGGTGCTGGTTATACATTTGGACAAGACATCGCAACTC

AGTTTAATCACAACAATGGACTCAGTCTCATATCAAGAGCACATCAACTT

GTCATGGAAGGCTTTAACTGGTGTCAGGACAAAAATGTTGTGACGGTGTT

TAGTGCACCAAACTATTGCTACCGGTGTGGAAACATGGCAGCTATTCTAG

AGATAGGAGAGAACATGGACCAGAACTTCCTCCAGTTCGATCCAGCTCCT

CGTCAAGTCGAACCAGATACTACCCGCAAGACCCCTGATTATTTTTGTG

ATTTATTTGCATTTTTTTTCTTTTGTTCCCAACCATTTATAATTTTTAA

AAAATCTGTTTTATCTTGCTTATGAATAATCATTCTAGTGTCTCTTCAAA

AAAAAAAAAAAA

The BN42856089 cDNA is translated into the following amino acid sequence (SEQ ID NO:76):

MPPNGDLDRQISQLMECKPLSEADVKTLCDQARAILVEEWNVQPVKCPVT

VCGDIHGQFYDLIELFRIGGNPPDTNYLFMGDYVDRGYYSVETVSLLVAL

KVRYRDRITILRGNHESRQITQVYGFYDECLRKYGNANVWKFFTDLFDYL

PLTALIESQVFCLHGGLSPSLDTLDNIRSLDRIQEVPHEGPMCDLLWSDP

DDRCGWGISPRGAGYTFGQDIATQFNHNNGLSLISRAHQLVMEGFNWCQD

KNVVTVFSAPNYCYRCGNMAAILEIGENMDQNFLQFDPAPRQVEPDTTRK

T-PDYFL cDNA sequence of BN43206527 from canola (SEQ ID NO:77):

CCAAAGACCATTTGATCTCTGGCGATTTCATCTTCCGATATGCCGCCGAA

CGGAGATCTAGACCGTCAGATCGAGCATCTGATGGAGTGCAAACCTTTAT

CGGAGGAGGATGTGAGGACGCTCTGCGATCAAGCTAAGGCCATCCTCGTC

GAGGAATGGAACGTCCAGCCCGTGAAATGCCCCGTCACCGTCTGCGGCGA

TATCCACGGCCAGTTCTATGACCTTATCGAGCTTTTCCGAATCGGTGGTA

ACGCCCCCGATACGAATTACCTCTTCATGGGTGACTATGTAGACCGTGGC

TACTATTCAGTGGAAACGGTTTCTTTATTGGTGGCATTGAAAGTCAGATA

CAGGGATAGGATTACAATCTTGCGAGGGAACCACGAGAGTCGTCAGATCA

CCCAAGTATATGGTTTTATGACGAGTGCTTGAGGAAGTACGGAAACGCA

AATGTGTGGAAGTATTTCACAGACCTTTTCGATTATCTTCCTCTTACTGC

TCTTATCGAGAGTCAGGTTTTCTGTTTGCATGGAGGGCTATCACCTTCTC

TGGATACACTTGATAATATCCGAAGCTTGGATCGTATACAAGAGGTTCCA

CACGAAGGACCAATGTGTGATTTACTATGGTCTGATCCAGATGATCGATG

CGGGTGGGGAATATCTCCAAGAGGTGCTGGTTATACATTTGGACAGGATA

TAGCAACTCAGTTTAATCACAACAATGGACTCAGTCTCATATCAAGAGCG

CATCAGCTTGTCATGGAAGGTTTTAACTGGTGTCAGGATAAGAATGTGGT

GACGGTGTTTAGTGCACCAAACTATTGCTACCGGTGTGGAAACATGGCAG

CGATTCTAGAGATAAGTGAGAACATGGAGCAGAACTTCCTTCAGTTTGAT

CCAGCTCCAAGACAAGTCGAACCTGATACTACCCGTAAGACCCCTGATTA

TTTTTTGTGATTTTATTTGTATTTTTTTTCTTCTAAGCGGAGTTCGAGT

TTCCCTCAAAACGAAAGAAAGAAACAAACATCATTTTGTTGTTGATG

TGATTGCTGAGAACAAAGTTTGTAGTAGAAGCGTCTATATATAGAATAGT

GTCTTCTCATTGTCATTTCACTTGTTACTGCATAGAGGAATGAGGTTTCG

AACCCTGCCCGCCACTTTCATTTCAGTTTCATTTATAAAATATGAGTTTG

ATACCGAAAAAAAAAAAAAAA

The BN43206527 cDNA is translated into the following amino acid sequence (SEQ ID NO:78):

MPPNGDLDRQIEHLMECKPLSEEDVRTLCDQAKAILVEEWNVQPVKCPVT

VCGDIHGQFYDLIELFRIGGNAPDTNYLFMGDYVDRGYYSVETVSLLVAL

KVRYRDRITILRGNHESRQITQVYGFYDECLRKYGNANVWKYFTDLFDYL

PLTALIESQVFCLHGGLSPSLDTLDNIRSLDRIQEVPHEGPMCDLLWSDP

DDRCGWGISPRGAGYTFGQDIATQFNHNNGLSLISRAHQLVMEGFNWCQD

KNVVTVFSAPNYCYRCGNMAAILEISENMEQNFLQFDPAPRQVEPDTTRK

T-PDYFL cDNA sequence of HA66872964 from sunflower (SEQ ID NO:79):

CTAAAAATATCTTTAACCGCCGGCTGCCATGACGGAACCCTAAGCAACTT

CTCCGGCGACTCCGGCGGAGCTCCGTTCAACCTAAATGCGAATCATTCTT

CCAGATCTTCAAATCCGAACACACAAATCACGTAACAATGCCGTCGCAAT

CGGATCTGGACCGTCAGATCGAGCACTTGATGGACTGTAAACCGCTGCCG

GAGGCGGAGGTGCGGACGTTGTGTGATCAGGCGAGGACGATTTGGTCGA

GGAGTGGAATGTGCAGCCGGTGAAGTGTCCGGTGACTGTTTGCGGTGATA

TTCATGGGCAGTTTCATGATTTGCTTGAGCTGTTTCGGATCGGAGGAAGT

GCTCCGGACACGAATTACTTGTTTATGGGAGATTATGTTGATCGAGGCTA

TTACTCGGTGGAGACTGTTACGCTTCTTGTGGCATTGAAAGTTCGTTACA

GAGATAGGATTACTATTCTCAGAGGAAACCATGAGAGCAGGCAGATAACT

CAAGTGTATGGATTTTACGATGAATGCTTGAGGAAGTACGGAAACGCAAA

TGTATGGAAACATTTCACTGACCTTTTTGATTATCTACCTCTCACTGCCC

TTATCGAGAGTCAGATATTCTGTCTCCATGGTGGCTTGTCTCCATCTTTG

GATACACTAGATAACATACGTGCTTTAGATCGCATACAAGAGGTTCCTCA

TGAGGGGCCAATGTGTGACCTTTTGTGGTCTGATCCTGATGACCGGTGTG

GTTGGGGAATATCTCCTCGTGGAGCCGGTTACACTTTCGGGCAGGATATA

```
GCCGCACAGTTTAACCATACAAACGGGCTCTCGCTTATTTCTCGGGCTCA

CCAGCTTGTCATGGAAGGTTACAATTGGTCTCAGGAGAACAACGTTGTAA

CCATATTTAGTGCACCAAACTACTGCTATAGATGCGGGAATATGGCTGCG

ATACTTGAGGTTGGAGAGAATATGGACCAGAATTTCTTACAATTTGACCC

AGCCCCTCGTCAGGTTGAGCCCGATGTTGCACGAAGAACTCCGGATTACT

TCCTGTAAATTTGTGTTGGATAATATGACCTTTGCATGCATCCTATTTAT

GTTGTTATAGTTTTCGCTTTCCCCTGCTAGAGAGTCCCCCTATTCTTGAG

AATTAAAGACAATATGTATGATTGTTTGTCCCTTGTTCTATTTGAGATTA

TTTGTTTAAAAAAAAAAAAAA
```

The HA66872964 cDNA is translated into the following amino acid sequence (SEQ ID NO:80):

```
MPSQSDLDRQIEHLMDCKPLPEAEVRTLCDQARTILVEEWNVQPVKCPVT

VCGDIHGQFHDLLELFRIGGSAPDTNYLFMGDYVDRGYYSVETVTLLVAL

KVRYRDRITILRGNHESRQITQVYGFYDECLRKYGNANVWKHFTDLFDYL

PLTALIESQIFCLHGGLSPSLDTLDNIRALDRIQEVPHEGPMCDLLWSDP

DDRCGWGISPRGAGYTFGQDIAAQFNHTNGLSLISRAHQLVMEGYNWSQE

NNVVTIFSAPNYCYRCGNMAAILEVGENMDQNFLQFDPAPRQVEPDVARR

T-PDYFL
``` cDNA sequence of LU61662612 from linseed (SEQ ID NO:81):

```
CATCTCTCTTTCTCTCTCTTCCATTTTCGTTCTTTTGAATCTCCGTTAGC

CCTACAAATCCATGGTCATGGCCTGAGAGAGATAGAGGGATAGAGCTCTC

AGTTCCTAATCACCTTACCTGACCTAACCCCACGGACATATTATCGAAGG

TCTGCGAGCAGGAGAGCGCAGGAGGAAGAGTGGGGCCAGGGTACGATGCC

GTCCCACGCCGATCTGGACCGTCAGATCGAGCACTTGATGCAGTGCAAGC

CACTTTCTGAGGCCGAAGTGAAGGCTCTCTGCGAGCAGGCCAGGGCCGTC

CTCGTCGAGGAATGGAACGTCCAGCCGGTCAAGTGTCCGGTGACTGTCTG

CGGCGACATCCACGGCCAGTTTCACGATCTTGTCGAGCTCTTTCGAATCG

GAGGAAACGCCCCTGACACGAACTACCTCTTCATGGGCGACTATGTAGAT

CGAGGGTATTATTCGGTGGAGACTGTCACCCTTCTAGTCGCCTTGAAAGT

AAGATATAGAGATAGGATCACAATTCTGAGAGGAAATCATGAAAGTCGTC

AAATAACTCAAGTGTATGGATTCTATGATGAGTGCTTGAGAAAATATGGA

AATGCCAATGTGTGGAAACATTTTACCGATCTCTTTGATTATCTACCACT

TACAGCTCTGATTGAGAGTCAGGTCTTCTGCTTACATGGTGGACTTTCCC

CTTCACTAGACACGCTAGACAACATTCGCTCCCTGATCGTATCCAAGAG

GTTCCGCACGAGGGTCCTATGTGCGACCTCCTATGGTCGGACCCGGATGA

CCGTTGCGGGTGGGGATCTCTCCTCGTGGAGCTGGCTACACCTTTGCAC

AGGACATATCTCAACAGTTCAACCACACGAACGGCCTTTCTCTCATATCC

AGAGCTCACCAGCTGGTCATGGAAGGTTACAATTGGGCCCAGGACAAGAA

TGTGGTGACGGTGTTCAGCGCCCCGAACTACTGCTACCGGTGTGGGAACA

TGGCGGCCATTCTCGAGATCGGAGAGAACATGGAGCAGAACTTCCTGCAG

TTCGACCCAGCTCCTCGACAGATCGAACCGGAGACGACTCGCAGAACACC

CGATTATTTTTTGTGAAATGCATAGCTTCTTCTTCCTCCCTCCTTCTTGC

TTGGAAATGGGATCCGTGTCCATTTTTTCTAATCGCCTGCCCTGCTATGT

GCTTATGTTTTTTGTAGATGCATTCATCATCATCATATCCAGAATAGAGA

AGAAATTTTGGTGTTTGCTTTGATTGAGAAAAGGCGGGGAGGGAAAAATC

GGCCTCTAGAGATGCTGGGTGTTGTCATTTTTCTTCTTCTTCTTCCTCCT

TTTGGGATGGTTTCGTTTTTACTTTTTCTTTTGGGTTTCTATTGTTTATC

CTGCATTCATTTGAGTTTAACAAAGTTTATTATTTACAGTCTGGGTGTGT

TATTAATATTATTCACTGTGGTCTTGTACCAAAAAAAAAAAAAAA
```

The LU61662612 cDNA is translated into the following amino acid sequence (SEQ ID NO:82):

```
MPSHADLDRQIEHLMQCKPLSEAEVKALCEQARAVLVEEWNVQPVKCPVT

VCGDIHGQFHDLVELFRIGGNAPDTNYLFMGDYVDRGYYSVETVTLLVAL

KVRYRDRITILRGNHESRQITQVYGFYDECLRKYGNANVWKHFTDLFDYL

PLTALIESQVFCLHGGLSPSLDTLDNIRSLDRIQEVPHEGPMCDLLWSDP

DDRCGWGISPRGAGYTFGQDISQQFNHTNGLSLISRAHQLVMEGYNWAQD

KNVVTVFSAPNYCYRCGNMAAILEIGENMEQNFLQFDPAPRQIEPETTRR

TPDYFL
``` cDNA sequence of OS32806943 from rice (SEQ ID NO:83):

```
GAGGCTTGAGCTCCACCTCCACCTCCTCCACCTCCAACCCCCGATCCCCC

GCAAACCCTAGCCCTCTCCCCCACCCTCCTCGCCGGCGGCGAGCGGCGGC

GGCGCGCGGCGGGACCCGGAGCCCCCAGTAGCGCCTCCTCGTCCTCCCCT

CCCTGAGGTGCGGGGGAGAGGATGCCGTCGTCGCACGGGGATCTGGACCG

GCAGATCGCGCAGCTGCGGGAGTGCAAGCACCTGGCGGAGGGGGAGGTGA

GGGCGCTGTGCGAGCAGGCGAAGGCCATCCTCATGGAGGAGTGGAACGTG

CAGCCGGTGCGGTGCCCCGTCACGGTCTGCGGCGACATCCACGGCCAGTT

CTACGACCTCATCGAGCTCTTCCGCATCGGCGGCGAGGCGCCCGACACCA

ACTACCTCTTCATGGGCGACTACGTCGACCGTGGCTACTACTCAGTGGAG

ACTGTTTCGTTGTTGGTGGCTTTGAAAGTACGCTACAGAGATCGAATTAC

AATATTGAGGAAATCATGAGAGCAGACAAATCACTCAAGTGTACGGCT

TCTACGATGAATGCTTGAGAAAGTATGGAAATGCAAATGTATGGAAATAC

TTTACAGACTTGTTTGATTATTTGCCTCTCACAGCTCTTATAGAAACCA

GGTGTTCTGCCTTCACGGTGGTCTCTCTCCATCATTGGATACTTTAGATA

ACATCCGTGCTCTTGATCGTATACAAGAGGTTCCTCATGAAGGACCCATG

TGTGATCTTTTGTGGTCTGACCCAGATGACAGATGCGGGTGGGGAATTTC

ACCGAGAGGAGCAGGTTATACATTTGGGCAAGATATCGCTCAACAGTTTA

ACCATACAAATGGTCTATCTCTCATCTCAAGGGCACATCAACTTGTAATG

GAAGGATTTAATTGGTGTCAGGACAAGAATGTTGTGACGGTCTTCAGTGC
```

ACCAAACTACTGTTATCGCTGTGGTAACATGGCTGCAATTCTTGAGATTG

GCGAAAACATGGATCAGAACTTCCTCCAATTTGATCCAGCTCCTCGGCAA

ATTGAACCAGACACAACACGCAAGACTCCCGACTACTTTTTGTAATTTGT

GGTGTTGACAATTTTAACTCACCTGTGTTGATGCTCCTCTCCTCCGCGGT

GTCGGGGTCTGTAGATCTTCTGTCCTTAGATACGGGTTCCACGAGCCCGG

CTGTATGTCTCTCAATTCTTTTGTTTGGAGATTTTGTTGCTGCTTCTCAA

CCTTTATACAAGACGTTAAAAGTTACATGCACTGGATTTTTTCTCAAAA

AAAAAAAAAAAAAAAAAAAAAAAAAAGAAAAAAAAAAAAAA

The OS32806943 cDNA is translated into the following amino acid sequence (SEQ ID NO:84):

MPSSHGDLDRQIAQLRECKHLAEGEVRALCEQAKAILMEEWNVQPVRCPV

TVCGDIHGQFYDLIELFRIGGEAPDTNYLFMGDYVDRGYYSVETVSLLVA

LKVRYRDRITILRGNHESRQITQVYGFYDECLRKYGNANVWKYFTDLFDY

LPLTALIENQVFCLHGGLSPSLDTLDNIRALDRIQEVPHEGPMCDLLWSD

PDDRCGWGISPRGAGYTFGQDIAQQFNHTNGLSLISRAHQLVMEGFNWCQ

DKNVVTVFSAPNYCYRCGNMAAILEIGENMDQNFLQFDPAPRQIEPDTTR

KTPDYFL cDNA sequence of OS34738749 from rice (SEQ ID NO:85):

GGTCGACGCCGTCACCGTCGCGCCAACTGCCGCAAACCGAATAAACCGAA

TCGATCTGAGAGAAGAAGAAGAAGAAGACGCGATCTCGGAGGTGGGAGCG

AAACGAAACGATGCCGTCTCACGCGGATGTGAACGACAGATCGAGCAGC

TGATGGAGTGCAAGCCTCTGTCGGAGTCGGAGGTGAAGGCGCTGTGTGAT

CAAGCGAGGGCGATTCTCGTGGAGGAATGGAACGTGCAACCGGTGAAGTG

CCCCGTCACCGTCTGCGGCGATATTCACGGCCAGTTTTACGATCTCATCG

AGCTGTTTCGGATTGGAGGGAACGCACCCGATACCAATTATCTCTTCATG

GGTGATTATGTAGATCGTGGATACTATTCAGTGGAGACTGTTACACTTTT

GGTGGCTTTGAAAGTCCGTTACAGAGATAGAATCACAATTCTCAGGGGAA

ATCATGAAAGTCGTCAAATTACTCAAGTGTATGGCTTCTATGATGAATGC

TTGAGAAAATATGGAAATGCCAATGTCTGGAAATACTTTACAGACTTGTT

TGATTATTTACCTCTGACTGCCCTCATTGAGAGTCAGATTTTCTGCTTGC

ATGGAGGTCTCTCACCTTCTTTGGATACACTGGATAACATCAGAGCATTG

GATCGTATACAAGAGGTTCCACATGAAGGACCAATGTGTGATCTCTTGTG

GTCTGACCCTGATGATCGCTGTGGATGGGAATATCTCCACGTGGTGCAG

GATACACATTTGGACAGGATATAGCTGCTCAGTTTAATCATACCAATGGT

CTCTCCCTGATATCGAGAGCTCATCAGCTTGTTATGGAAGGATTCAATTG

GTGCCAGGACAAAAATGTGGTGACTGTATTTAGTGCACCAAATTACTGTT

ACCGATGTGGGAATATGGCTGCTATACTAGAAATAGGAGAGAATATGGAT

CAGAATTTCCTTCAGTTTGATCCAGCGCCCAGGCAAATTGAGCCTGACAC

CACACGCAAGACTCCAGATTATTTTTTATAATTTCATTTATCTGCCTGTT

TGTAGTTACTGCTCTCTGCCATTACTGTAGATGTGTCTTTAAGGAAAGGA

GTTTTGCTGTTTAAGTGGAGGGTGGTCATCAACATAATTCTTTCTTTTGG

AGTTTACCTCCTGCTGCTGCCGCTGCCGCTGCCTTATTTGTACAAGAAAC

CAATAGAACTGACACAAGCCACCAATTGGGGTTGTATATTTTTGGGAGGA

AGCGGTAATAACATGGTATATCTTGTTCTGTAATCCTTTTTCTTTAAATT

GAATCTCAAGTTAGAGAGCAAAAAAAAAAAAAA

The OS34738749 cDNA is translated into the following amino acid sequence (SEQ ID NO:86):

MPSHADLERQIEQLMECKPLSESEVKALCDQARAILVEEWNVQPVKCPVT

VCGDIHGQFYDLIELFRIGGNAPDTNYLFMGDYVDRGYYSVETVTLLVAL

KVRYRDRITILRGNHESRQITQVYGFYDECLRKYGNANVWKYFTDLFDYL

PLTALIESQIFCLHGGLSPSLDTLDNIRALDRIQEVPHEGPMCDLLWSDP

DDRCGWGISPRGAGYTFGQDIAAQFNHTNGLSLISRAHQLVMEGFNWCQD

KNVVTVFSAPNYCYRCGNMAAILEIGENMDQNFLQFDPAPRQIEPDTTRK

TP-DYFL cDNA sequence of ZM59400933 from corn (SEQ ID NO:87):

CTGACCGCAGCGGGCCCGCAGGCCGGAGAAGGAGTCGGAGTCGCCCCCAC

CCACCCACCCTCTGCCGCGGGCGGGGAGCGGGCGGCGGACGAGATGCCGT

CGCACGGGGATCTGGACCGGCAGATCGCGCAGCTGCGCGACTGCAAGTAC

CTCGGGCAGGCGGAGGTCAAGGTGCTCTGCGAGCAGGCCAAGGCCATCCT

CATGGAGGAATGGAACGTGCAGCCCGTGCGCTGCCCCGTCACCGTCTGCG

GCGACATCCACGGCCAGTTCTATGACCTCATCGAGCTCTTCCGCATCGGC

GGCGACTCTCCCGACACAACTACCTCTTCATGGGCGACTACGTCGATCGT

GGCTATTATTCAGTTGAAACGGTTTCTCTGTTAGTGGCTTTGAAAGTCCG

TTACAGAGATAGAATTACAATACTTCGAGGAAATCATGAGAGCAGACAAA

TCACTCAAGTGTACGGCTTCTATGATGAATGCTTAAGAAAATATGGAAAT

GCAAATGTATGGAAGTATTTTACAGACTTGTTTGATTATTTGCCTCTCAC

AGCTCTTATAGAAAATCAGGTCTTCTGTCTTCATGGAGGCCTCTCTCCGT

CATTGGACACATTGGATAACATTCGTTCTCTTGATCGCATACAGGAGGTA

CCTCATGAAGGACCCATGTGTGATCTTTTGTGGTCTGACCCAGATGACCG

ATGTGGGTGGGAATTTCACCCAGAGGAGCAGGTTACACATTTGGGCAAG

ACATTGCACAGCAGTTCAACCATACAAATGGTCTCTCTCTCATTTCAAGG

GCCCATCAACTTGTAATGGAAGGATTTAATTGGTGCCAGGATAAGAATGT

AGTCACAGTCTTCAGTGCGCCTAATTACTGTTACCGCTGTGGTAACATGG

CTGCTATTCTTGAAATCGGGGAAAACATGGACCAGAACTTCCTTCAATTC

AACCCCGCACCTCGGCAAATTGAGCCAGACACAACTCGCAAAACCCCAGA

CTACTTTCTGTAATTGTGGTGGTGACCTTAACTTTCTGGTGTTTGATGCT

CCTCTCTTCCGCAGCATCAGGGTATGTAGATCTTGTCCTTAGATATGGGT

```
-continued
CCCATGTGCCCGGCCTTAACGTCTCCCTATTCTTTTGTTTGGAGATTTTG

TTTCTGCTTCTCGATCTTGATACAAGATGTTAGAAGTTGAATGCCAGTGT

ATTTTTTT-CAAAAAAAAAAA
```

The ZM59400933 cDNA is translated into the following amino acid sequence (SEQ ID NO:88):

```
MPSHGDLDRQIAQLRDCKYLPEAEVKVLCEQAKAILMEEWNVQPVRCPVT

VCGDIHGQFYDLIELFRIGGDSPDTNYLFMGDYVDRGYYSVETVSLLVAL

KVRYRDRITILRGNHESRQITQVYGFYDECLRKYGNANVWKYFTDLFDYL

PLTALIENQVFCLHGGLSPSLDTLDNIRSLDRIQEVPHEGPMCDLLWSDP

DDRCGWGISPRGAGYTFGQDIAQQFNHTNGLSLISRAHQLVMEGFNWCQD

KNVVTVFSAPNYCYRCGNMAAILEIGENMDQNFLQFNPAPRQIEPDTTRK

TP-DYFL
``` cDNA sequence of ZM62132060 from corn (SEQ ID NO:89):

```
AATCGTCGCTCCACCTCCTCCTCGTCTATCGCCGATCTCCCCCAAACCCT

AGCCCCGACCTGACCGCCGGCGGGCCCGCCGGCCGGAGAAGGAGTCGCTC

CCACCCATCCAACTTCTGCGGCGGAAGGGGAGCGGGCGGCGGACGAGATG

CCGTCGCACGGGGATCTGGACCGGCAGATCGCGCAGCTGCGCGACTGCAA

GTACCTGCCCGAGGCGGAGGTCAAGGCGCTCTGCGAGCAGGCCAAGGCCA

TCCTTATGGAGGAGTGGAACGTGCAGCCCGTGCGCTGTCCTGTCACCGTC

TGTGGCGACATCCACGGCCAGTTCTATGACCTCATCGAGCTCTTCCGCAT

CGGCGGCGACGCTCCCGACACCAACTACCTCTTCATGGGCGACTACGTCG

ATCGTGGGTACTATTCAGTTGAAACAGTTTCTCTGTTAGTGGCTTTGAAA

GTCCGTTACAGAGATAGAATTACAATACTTAGAGGAAATCATGAGAGCAG

ACAAATCACTCAAGTATATGGCTTCTATGATGAATGCTTAAGAAAGTATG

GAAATGCAAATGTCTGGAAGTATTTTACAGACTTGTTTGATTTTTTGCCT

CTCACAGCTCTTATAGAAAATCAGGTCTTCTGTCTTCACGGTGGCCTCTC

TCCGTCATTGGACACGTTGGATAATATTCGTTCTCTTGATCGCGTACAGG

AGGTTCCTCATGAAGGACCCATGTGTGATCTTTTGTGGTCTGACCCAGAT

GACCGATGTGGATGGGGAATTTCACCAAGAGGAGCAGGTTACACATTTGG

GCAAGACATTGCGCAGCAGTTCAACCATACAAATGGTCTTTCTCTCATTT

CAAGGGCCCATCAACTTGTAATGGAAGGATTTAATTGGTGCCAGGATAAG

AATGTAGTCACAGTCTTCAGCGCGCCTAATTATTGTTACCGCTGTGGTAA

CATGGCTGCTATTCTTGAAATCGGGAAAAACATGGACCAGAACTTCCTTC

AATTCGACCCGGCACCTCGGCAAATTGAGCCAGACACAACTCGGAAAACC

CCAGACTACTTTTTGTAATTGTGGTGGTGACATTAACTTACTGGTGTTGA

TGCTCCTCTTTTCCGCAGCATCAGGGTCTGTAGATCATCTGTCCTTAGAT

ATGGGTTCCATGAGCCCGACCTGTACGTCTCCCAATTCTTTTGTTTGGAG

ATTTTGTTGCCGCTTAACGATCTTTATACAATATGTTAAAAAGTTAAATG

CCATTGGATTTTTCTCCAAAAAAAAAAAA
```

The ZM62132060 cDNA is translated into the following amino acid sequence (SEQ ID NO:90):

```
MPSHGDLDRQIAQLRDCKYLPEAEVKALCEQAKAILMEEWNVQPVRCPVT

VCGDIHGQFYDLIELFRIGGDAPDTNYLFMGDYVDRGYYSVETVSLLVAL

KVRYRDRITILRGNHESRQITQVYGFYDECLRKYGNANVWKYFTDLFDFL

PLTALIENQVFCLHGGLSPSLDTLDNIRSLDRVQEVPHEGPMCDLLWSDP

DDRCGWGISPRGAGYTFGQDIAQQFNHTNGLSLISRAHQLVMEGFNWCQD

KNVVTVFSAPNYCYRCGNMAAILEIGKNMDQNFLQFDPAPRQIEPDTTRK

TPDYFL
``` cDNA sequence of ZM59202533 from corn (SEQ ID NO:91):

```
ATGAAGGGGAAGAAGCCGGTCAAGGAGCTCAAGCTCACCGTGCCGGCGCA

GGAGACCCCGGTAGACAAGTTCCTGACGGCAAGTGGCACGTTCAAGGATG

GTGAGCTGAGGCTCAATCAGAGCGGCTTGCGGCTTATCTCTGAGGAAACG

GGGGATGAAGATGAATCTACAAAGCTGAAGGTGGAAGATGTGCAGTTATC

AATGGATGATCTTGAGATGATTCAAGTCATTGGCAAAGGAAGCGGTGGTG

TTGTCCAGCTAGTGAGGCACAAATGGGTGGGACATTGTTTGCCTTAAAG

GGTATTCAAATGAACATTCAGGAGTCAGTTCGTAAACAAATAGTACAGGA

GCTCAAAATAAACCAAGCAACACAGAGCCCTCATATAGTTATGTGCCATC

AATCTTTTTACCACAATGGTGTAATATATCTTGTTCTTGAGTACATGGAC

CGTGGATCGCTTGCAGACATTGTTAAGCAAGTGAAGACTATTCTGGAGCC

ATACCTTGCAGTACTTTGTAAGCAGGTCTTGGAGGGTTTATTGTATCTTC

ATCATCAAAGGCACGTGATTCACAGGGACATAAAACCATCTAACTTGTTG

GTCAACCGTAAAGGTGAAGTCAAGATTACCGACTTCGGAGTGAGTGCTGT

GCTAGCAAGCTCAATAGGTCAGCGAGATACATTTGTTGGAACCTACAACT

ATATGGCGCCTGAGCGGATTAGTGGTAGCACTTATGACTACAAAAGTGAC

ATATGGAGTTTGGGCTTAGTTATACTTGAGTGTGCCATTGGCCGGTTCCC

TTATATACCTTCGGAAGGTGAAGGTTGGTTAAGCTTTTATGAACTTCTGG

AGGCCATTGTCGATCAGCCACCACCTTCTGCACCTGCAGATCAGTTCTCT

CCAGAATTCTGCTCATTTATCTCCTCTTGCATACAGAAAGATCCGGCTCA

GAGGATGTCTGCTTCAGAACTCTTGAATCACCCTTTTTTGAAGAAGTTCG

AGGATAAGGACTTAAACCTGGGGATTCTTGTGGAGAACCTGGAACCTCCA

ATGAATATACCCGAATAG
```

The ZM59202533 cDNA is translated into the following amino acid sequence (SEQ ID NO:92):

```
MKGKKPVKELKLTVPAQETPVDKFLTASGTFKDGELRLNQSGLRLISEEN

GDEDESTKLKVEDVQLSMDDLEMIQVIGKGSGGVVQLVRHKWVGTLFALK

GIQMNIQESVRKQIVQELKINQATQSPHIVMGHQSFYHNGVIYLVLEYMD

RGSLADIVKQVKTILEPYLAVLCKQVLEGLLYLHHQRHVIHRDIKPSNLL

VNRKGEVKITDFGVSAVLASSIGQRDTFVGTYNYMAPERISGSTYDYKSD
```

IWSLGLVILECAIGRFPYIPSEGEGWLSFYELLEAIVDQPPPSAPADQFS
PEFCSFISSCIQKDPAQRMSASELLNHPFLKKFEDKDLNLGILVENLEPP
MNIPE cDNA sequence of BN41901422 from canola (SEQ ID NO:93):

GTCATTCTTCTAATTTCTCTGACCTCTGCTACTGTCTATCCGTTCGTGTT
GCTTTGATCTCTCTAATCAGACATGAAGAGAGGCAGCTTGAGTCTTAATC
CCATCTCTCTCCCTCCTCCTGAGCAATCCATCTCCAAATTCTTAACACAG
AGCGGAACGTTCAAGGATGGAGACCTTCAAGTGAACAAAGATGGAATCCA
GACAGTATCTCATTCTGAGCCTGGAGCTCCACCACCTATTGATCCATTGG
ACAACCAGTTGAGTTTGGCTGACCTTGAAGTGATCAAAGTCATTGGCAAA
GGAAGCAGTGGTAGTGTTCAGCTGGTTAAACACAAACTAACTCAACAGTT
TTTCGCTACTAAGGTTATTCAGTTAAACACAGAAGAGTCCACATGTCGAG
CCATTTCTCAGGAGCTGAGGATAAACTTGGCATCTCAATGTCCATATCTC
GTCTCATGTTATCAGTCTTTCTACCATAACGGTCTCGTCTCAATCGTAAT
GGAGTTCATGGACGGTGGATCTCTTTTGGATTTGTTGAAGAAAGTCCAGA
CAGTTCCTGAAAACATGCTCGCTGCCATCTCCAAGCGAGTGCTCCGAGGC
TTGTGCTATATTCACGATGAGAGGCGAATCATTCACCGGGACTTGAAGCC
TTCCAACTTGCTAATCAATCACAGAGGTGAAGTCAAGATCGCAGACTTTG
GTGTCAGCAAGATCTTGTCTAGCACAAGCAGTCTAGCGCATACCTTCGTG
GGCACAGACTTCTATATGTCGCCAGAGAGAATCAGTGGGAAAGCGTATGG
GAACAAGTGTGATATTTGGAGTTTGGGAGTGGTTCTGCTCGAATGTGCAA
CGGGTAAGTTTCCGTATACTCCTCCTGAAAACATGAAGGGATGGACTAGC
ATGTATGAGCTAGTTGACGCCATTGTTGAAAACCCGCCTCCTCGTGCACC
TTCCCACCTGTTCTCTCCAGAGTTTTGCTCCTTCATCTCGCAATGTGTAC
AAAAAGATCCAAGGGACCGGAAATCAGCAATGGAGCTTCTGGACCATAGG
TTCGTAAACATGTTTGAAGATGTGGATGTGGATCTCTCGTCTTACTTCAC
CGCCGCAGGATCTTTGATTCCCCCACTAGCCAACAGCTAGAACCGAGTTT
GAACAATCCTTTTAACACCAAGTTATATATATGTATTTTATATCCACTGG
AAGAGACGATATTTACGAGATGTTGCGACTTATGAGAGAATTCTCTTGAT
AGACATTTATATTTTCAAGTATTGAATTTATTTGGGTAAAAAAAAAAAA
AAA

The BN41901422 cDNA is translated into the following amino acid sequence (SEQ ID NO:94):

MKRGSLSLNPISLPPPEQSISKFLTQSGTFKDGDLQVNKDGIQTVSHSEP
GAPPPIDPLDNQLSLADLEVIKVIGKGSSGSVQLVKHKLTQQFFATKVIQ
LNTEESTCRAISQELRINLASQCPYLVSCYQSFYHNGLVSIVMEFMDGGS
LLDLLKKVQRVPENMLAAISKRVLRGLCYIHDERRIIHRDLKPSNLLINH
RGEVKIADFGVSKILSSTSSLAHTFVGTDFYMSPERISGKAYGNKCDIWS
LGVVLLECATGKFPYTPPENMKGWTSMYELVDAIVENPPPRAPSHLFSPE
FCSFISQCVQKDPRDRKSAMELLDHRFVNMFEDVDVDLSSYFTAAGSLIP
PLANS cDNA sequence of BN47868329 from canola (SEQ ID NO:95):

CCAGATCGTTAAACCATAATCCAAACCAAGCTTGCAAAAACTTTTGATCC
TAAACCGAGATGAAACCAATCCAACCGCCACCAGGAGTAATCGGTCCGGT
TAAGAACCGCCCTCGCCGCCGTCCAGACCTCTCCTTACCACTTCCTCACC
GCGACGTTTCCCTCGCCGTACCTCTCCCCCTCCCACCAACTTCCGGCGGC
GGTTCCACCACCTCAGAGCCTAAAAGCTACTCAGACTTAGTACGTGGCAA
CCGGATCGGAAGCGGAGCCGGTGGAACGGTTTACAGAGTAGTCCACCGTC
CAACCTCCCGCGTATACGCACTCAAGATAATCAACGGTAACCACGATGAC
ACTGTTCGTGGCCAGATCTGCAGAGAGATCAAGATTCTCCGAGACGTGAA
TCACCCCAACGTGGTGAAATGCCACGAGATGTTCGATCAAAACGGAGAGA
TCCAGGTCTTGCTCGAGCTCATGGACCAAGGATCTTTAGAAGGTGCTCAT
ATCTCGAACGAGCAACAGTTATCTGACCTATCTCGTCAGATACTAAACGG
TTTGGCTTATCTTCACGGCCGTCATATAGTCCATAGAGACATAAAGCCAT
CGAATCTACTTATAAACTCGGACAATAACGTCAAGATTGCTGATTTTGGA
GTGAGCAGGGTCTTGGCTCAGACCCTGTCTCCGTGTAAGTCCTCTGTTGG
GACTATTGCTTACATGAGTCCTGAGAGGATCAACACGGATTTGAATCAGG
GGATGTATGATGGTTGCGCTGGGGATATTTGGAGCTTCGGTGTTAGTGTT
CTTGAGTTTTTCTTGGGGAGGTTTCCTTTTAATGTGAATAGGCTAGGTGA
TTGGGCTAGTCTTATGTGTGCTATTTGTATGTCTAAGCCGCCTGAAGCTC
CTGCCACGGCGTCTCCGGAGTTTAGACACTTTGTTTCGTGTTGTTTGCAG
AGAGAACCGGGGAGGAGGCAAACTGCTGTTCAGCTTTTGCAACATCCTTT
TGTGCGTAGAGGGCGATTCAGAGTCAGAATAGGTCTCCTCAGAATCTAC
ATCAACTCTTGCCTCCTCCACACTAAAGGTTTAGTTTTGTCTGATAATGT
TTCTACACTAAAGGTTGATCATGTCTTGCTGTTTAGACAAACTATATCAT
TGTCTTGTACTTAGCTGAAAGCAAAGCGTATATAGTTTGAATCACTTTGC
ACCTCATGATGGTTAATTTCACTAAGTAATTCAGTAGTAGAGTCATTAAA
TGTAAAAAAAAAAAAAAA

The BN47868329 cDNA is translated into the following amino acid sequence (SEQ ID NO:96):

MKPIQPPPGVIGPVKNRPRRRPDLSLPLPHRDVSLAVPLPLPPTSGGGST
TSEPKSYSDLVRGNRIGSGAGGTVYRVVHRPTSRVYALKIINGNHDDTVR
GQICREIKILRDVNHPNVVKCHEMFDQNGEIQVLLELMDQGSLEGAHISN
EQQLSDLSRQILNGLAYLHGRHIVHRDIKPSNLLINSDNNVKIADFGVSR
VLAQTLSPCKSSVGTIAYMSPERINTDLNQGMYDGCAGDIWSFGVSVLEF
FLGRFPFNVNRLGDWASLMCAICMSKPPEAPATASPEFRHFVSCCLQREP
GRRQTAVQLLQHPFVRRGAIQSQNRSPQNLHQLLPPPH cDNA sequence of BN42671700 from canola (SEQ ID NO:97):

CTGCAAACTAAAATCTAGAACCGGAACAGATCTAAACCAAACCAAACCGA
ACCGGGTGTCTTTGTTTGTAACTCTCCAAATGGTGAAGAAAGCGATGAAG
GAGGAAGAAGAAGCAGAGATGAGAAACTCGTCGATGCAGTCAAAGTACAA
AGGCGTGAGGAAGAGGAAGTGGGGCAAATGGGTTTCGGAGATCAGACTTC
CCAACAGCAGAGAGCGAATCTGGCTAGGCTCTTTCGACACTCCCGAGAAG
GCGGCGCGTGCCTTCGACGCCGCCCAGTTTTGTCTCCGCGGCTGCCAATC
CGGTTTCAATTTCCCCGATAATCCGCCGTCGATCTCCGGCGGAAGGTCGC
TGACGCCTCCGGAGATCCGGGAAGCGGCTGCTCGATACGCAAACGCTCAG
GACGACGATATTATCATCACCACCGGAGAAGAAGAATCGGTTTTGTCCGA
AACCCGACCGGAGTCTCCTTCAACAACCTCCGTGTCTGAAGCAGATACGT
CGCTGGATTGCGATCTATCGTTCTTAGACACGCTTCCTAATGATTTCGGG
ATGTTTTCTGTGTTTGATGACTTCTCCGACGGCTTCTCCGGCGATCAGTT
TACAGAGGTTTTACCCGTTGAAGATTACGGAGATGTGATTTTTGATGAGT
CTCTGTTTCTTTGGGATTTTTAAATGTGTAAAGAGTTTTGAATTGTTGTT
TATTCGGGTCATGGAGAGTAATCTGGATATTTTTGTAAGTCGGAGCTCCA
GCGACCCGGGAACTTGATCATTCTTGCTTTGGTTGATGATATCTATCATT
CCTTCATTTTTTGTTGTTATTAATGAAAATATTTGGATAAAATAGCAATT
ACAGAAAAAAAAAAAAAAAAA

The BN42671700 cDNA is translated into the following amino acid sequence (SEQ ID NO:98):

MVKKAMKEEEEAEMRNSSMQSKYKGVRKRKWGKWVSEIRLPNSRERIWLG
SFDTPEKAARAFDAAQFCLRGCQSGFNFPDNPPSISGGRSLTPPEIREAA
ARYANAQDDDIIITTGEEESVLSETRPESPSTTSVSEADTSLDGDLSFLD
TLPNDFGMESVFDDFSDGFSGDQFTEVLPVEDYGDVIFDESLFLWDF cDNA sequence of ZM68416988 from corn (SEQ ID NO:99):

CTCGCCTCGCCTTCCTCCGAGCCCCGGCGAGGAAGAGGAACCCGCCGCCG
CCGCCGCCGGACGCACTTCCGATGGCGACGCCACGGAAGCCGATCAAGCT
CACGCTGCCGTCCCACGAGACCACCATCGGCAAGTTCCTGACGCACAGCG
GGACGTTCACGGACGGGGATCTGCGCGTGAACAAGGACGGCCTCCGCATC
GTCTCGCGGAGGGAGGGAGGCGAGGCTCCTCCTATAGAGCCGTTGGATAG
TCAACTGAGCTTAGATGATCTAGACGTTATAAAAGTGATCGGGAAAGGTA
GCAGCGGAAATGTGCAATTGGTCCGCCACAAATTTACTGGCCAGTTTTTT
GCTCTGAAGGTTATTCAACTAAATATTGATGAGAGTATACGCAAACAGAT
TGCCAAGGAGTTGAAGATAAACTTATCAACACAGTGCCAATATGTTGTTG
TGTTCTATCAGTGTTTCTATTTCAATGGTGCCATTTCTATTGTTTTGGAA
TACATGGATGGTGGCTCCCTTGCAGATTTCCTGAAGACTGTTAAAACCAT
TCCAGAGGCCTACCTCGCTGCTATCTGTACGCAGATGCTAAAAGGACTGA
TCTATTTGCATAACGAGAAGCGCGTTATACACCGAGATCTGAAACCATCA
AATATATTGATAAATCATAGGGGTGAAGTAAAAATATCAGATTTTGGTGT
GAGTGCCATTATATCTAGTTCCTCTTCGCAACGAGATACATTTATTGGCA
CACGCAACTACATGGCGCCAGAAGAATCGATGGAAAGAAACATGGTTCT
ATGAGTGATATCTGGAGTTTGGGACTAGTGATACTGGAATGTGCAACCGG
CATCTTTCCATTTCCTCCTTGTGAAAGCTTCTACGAACTTCTCGTGGCTG
TTGTTGATCAACCGCCACCTTCTGCGCCGCCGGATCAGTTTTCACCAGAA
TTCTGTGGGTTCATTTCTGCATGTCTCCAGAAGGATGCTAATGACAGGTC
ATCAGCCCAAGCCTTATTGGACCATCCGTTCCTGAGCATGTATGATGACC
TGCATGTAGATCTTGCTTCGTACTTCACGACAGCAGGATCTCCTCTCGCC
ACCTTCAATTCCAGGCAACTCTAATTTTTTTGTCCTCCTTATTACGCGAA
CGGTGTGGCGACAAATTTCTCTTTTTGGACAAGGCTTGGATTGTGTACTG
AGCTGTAATGATCTTGTGTGTGTCAGGTCGGTGATTGGCTCCATCACTTT
ACATATATGACATACATGTACAGCCTTTTAGGATAAAAATGAGCACTGAA
GTTTTGCCTATCTGTATATCGGCAGCAAACGTTTGGTCATGTTTGTTTCA
CCTTGTAATGTATTGACTCAGATATGGGATTGGTCATTGTCTCTAAAAAA
AAAAA

The ZM68416988 cDNA is translated into the following amino acid sequence (SEQ ID NO:100):

MATPRKPIKLTLPSHETTIGKFLTHSGTFTDGDLRVNKDGLRIVSRREGG
EAPPIEPLDSQLSLDDLDVIKVIGKGSSGNVQLVRHKFTGQFFALKVIQL
NIDESIRKQIAKELKINLSTQCQYVVVFYQCFYFNGAISIVLEYMDGGSL
ADFLKTVKTIPEAYLAAICTQMLKGLIYLHNEKRVIHRDLKPSNILINHR
GEVKISDFGVSAIISSSSSQRDTFIGTRNYMAPERIDGKKHGSMSDIWSL
GLVILEGATGIFPFPPCESFYELLVAVVDQPPPSAPPDQFSPEFCGFISA
CLQKDANDRSSAQALLDHPFLSMYDDLHVDLASYFTTAGSPLATFNSRQL

---

The invention claimed is:

1. A transgenic plant transformed with an expression cassette comprising an isolated polynucleotide encoding a full-length polypeptide comprising SEQ ID NO: 16.

2. An isolated polynucleotide comprising of SEQ ID NO: 15.

3. A method of producing a transgenic plant, said method comprising the steps of:

(a) introducing into a plant cell an expression vector comprising a polynucleotide comprising SEQ ID NO: 15, and (b) generating from the plant cell a transgenic plant that expresses the polynucleotide.

* * * * *

SEQUENCE LISTING

<160> NUMBER OF SEQ ID NOS: 100

<210> SEQ ID NO 1
<211> LENGTH: 906
<212> TYPE: DNA
<213> ORGANISM: Arabidopsis thaliana

```
<220> FEATURE:
<221> NAME/KEY: CDS
<222> LOCATION: (1)..(906)
<223> OTHER INFORMATION: CAAX amino terminal protease (at2g20725)

<400> SEQUENCE: 1 atg att cta ggc cga tgg gtt tcc ttc agt tgc gga aac acg ccg gtg        48
Met Ile Leu Gly Arg Trp Val Ser Phe Ser Cys Gly Asn Thr Pro Val
1               5                   10                  15 act aat tgt tcc gaa cga cga cga cat acg gag ttt cgt cgt ctc tcc        96
Thr Asn Cys Ser Glu Arg Arg Arg His Thr Glu Phe Arg Arg Leu Ser
            20                  25                  30 tct gct agt act tgt cga cct tct ctc ata tgc tct tgt ctc aaa agc       144
Ser Ala Ser Thr Cys Arg Pro Ser Leu Ile Cys Ser Cys Leu Lys Ser
        35                  40                  45 aaa tcc tcc caa gaa act act cag att gaa cag ttg ggg aat gga gaa       192
Lys Ser Ser Gln Glu Thr Thr Gln Ile Glu Gln Leu Gly Asn Gly Glu
50                  55                  60 ggg ttc tca gtt ttg gca tca gag att cca tgg gag gat gat aac ata       240
Gly Phe Ser Val Leu Ala Ser Glu Ile Pro Trp Glu Asp Asp Asn Ile
65                  70                  75                  80 tgg agc aca ttt gct ctt tac atg ttc tct ctg cat att cct ctc agt       288
Trp Ser Thr Phe Ala Leu Tyr Met Phe Ser Leu His Ile Pro Leu Ser
                85                  90                  95 ttt ggg ggt tta tcc att gtt gcc aac ata ctc cac cgg cag gtt ctt       336
Phe Gly Gly Leu Ser Ile Val Ala Asn Ile Leu His Arg Gln Val Leu
            100                 105                 110 gat cct cag acc caa gtg cta tca ctt gtg gtt ctc caa atg gta gaa       384
Asp Pro Gln Thr Gln Val Leu Ser Leu Val Val Leu Gln Met Val Glu
        115                 120                 125 ctt gca ggg aca gtc ttg ctg ctg agg acc aca gcg aag cct cag tgc       432
Leu Ala Gly Thr Val Leu Leu Leu Arg Thr Thr Ala Lys Pro Gln Cys
    130                 135                 140 aaa tca atc aac ttt cta aag ggt aat aac gaa aca agg gaa gga aga       480
Lys Ser Ile Asn Phe Leu Lys Gly Asn Asn Glu Thr Arg Glu Gly Arg
145                 150                 155                 160 aac tgt gtg gtt ggc tca gca ttg ggt ttg gga tgt ctt gtg ggc ttt       528
Asn Cys Val Val Gly Ser Ala Leu Gly Leu Gly Cys Leu Val Gly Phe
                165                 170                 175 atc ttc gtc acg tcg ctt gta gct gat caa ctc ttt ggc cct aag gct       576
Ile Phe Val Thr Ser Leu Val Ala Asp Gln Leu Phe Gly Pro Lys Ala
            180                 185                 190 gta cat gaa tca gaa ttg gag aag ata atg gtg agc ggg gaa gtg gcg       624
Val His Glu Ser Glu Leu Glu Lys Ile Met Val Ser Gly Glu Val Ala
        195                 200                 205 aga agc gga tgt ttt gct ctc tac tgc gta gta gct ccc atc ctt gag       672
Arg Ser Gly Cys Phe Ala Leu Tyr Cys Val Val Ala Pro Ile Leu Glu
    210                 215                 220 gag ata gtg tac aga cgc ttt ctc ctg acc tcc tta gcg tcg aga atg       720
Glu Ile Val Tyr Arg Arg Phe Leu Leu Thr Ser Leu Ala Ser Arg Met
225                 230                 235                 240 gaa tgg tgg aag gca cta gtg atc agc tca gga gta ttt gct gca ggt       768
Glu Trp Trp Lys Ala Leu Val Ile Ser Ser Gly Val Phe Ala Ala Gly
                245                 250                 255 cac ttc tca ggt gag gat ttt gtg cag ctg ttt ggg ata ggt tgc ggt       816
His Phe Ser Gly Glu Asp Phe Val Gln Leu Phe Gly Ile Gly Cys Gly
            260                 265                 270 ctc ggg tta tgt tac agc tgg tca ggg aac tta gcc tca tca gtg ctc       864
Leu Gly Leu Cys Tyr Ser Trp Ser Gly Asn Leu Ala Ser Ser Val Leu
        275                 280                 285 gtc cac tcc ttg tac aat gca ttg aca ctt ctc ttc tct tag             906
Val His Ser Leu Tyr Asn Ala Leu Thr Leu Leu Phe Ser
    290                 295                 300
```

```
Val His Ser Leu Tyr Asn Ala Leu Thr Leu Leu Phe Ser
290                 295                 300

<210> SEQ ID NO 2
<211> LENGTH: 301
<212> TYPE: PRT
<213> ORGANISM: Arabidopsis thaliana

<400> SEQUENCE: 2

Met Ile Leu Gly Arg Trp Val Ser Phe Ser Cys Gly Asn Thr Pro Val
1               5                   10                  15

Thr Asn Cys Ser Glu Arg Arg His Thr Glu Phe Arg Leu Ser
            20                  25                  30

Ser Ala Ser Thr Cys Arg Pro Ser Leu Ile Cys Ser Cys Leu Lys Ser
                35                  40                  45

Lys Ser Ser Gln Glu Thr Thr Gln Ile Glu Gln Leu Gly Asn Gly Glu
        50                  55                  60

Gly Phe Ser Val Leu Ala Ser Glu Ile Pro Trp Glu Asp Asp Asn Ile
65                  70                  75                  80

Trp Ser Thr Phe Ala Leu Tyr Met Phe Ser Leu His Ile Pro Leu Ser
                85                  90                  95

Phe Gly Gly Leu Ser Ile Val Ala Asn Ile Leu His Arg Gln Val Leu
            100                 105                 110

Asp Pro Gln Thr Gln Val Leu Ser Leu Val Val Leu Gln Met Val Glu
        115                 120                 125

Leu Ala Gly Thr Val Leu Leu Leu Arg Thr Thr Ala Lys Pro Gln Cys
130                 135                 140

Lys Ser Ile Asn Phe Leu Lys Gly Asn Asn Glu Thr Arg Glu Gly Arg
145                 150                 155                 160

Asn Cys Val Val Gly Ser Ala Leu Gly Leu Gly Cys Leu Val Gly Phe
                165                 170                 175

Ile Phe Val Thr Ser Leu Val Ala Asp Gln Leu Phe Gly Pro Lys Ala
            180                 185                 190

Val His Glu Ser Glu Leu Glu Lys Ile Met Val Ser Gly Glu Val Ala
        195                 200                 205

Arg Ser Gly Cys Phe Ala Leu Tyr Cys Val Val Ala Pro Ile Leu Glu
210                 215                 220

Glu Ile Val Tyr Arg Arg Phe Leu Leu Thr Ser Leu Ala Ser Arg Met
225                 230                 235                 240

Glu Trp Trp Lys Ala Leu Val Ile Ser Ser Gly Val Phe Ala Ala Gly
                245                 250                 255

His Phe Ser Gly Glu Asp Phe Val Gln Leu Phe Gly Ile Gly Cys Gly
            260                 265                 270

Leu Gly Leu Cys Tyr Ser Trp Ser Gly Asn Leu Ala Ser Ser Val Leu
        275                 280                 285

Val His Ser Leu Tyr Asn Ala Leu Thr Leu Leu Phe Ser
290                 295                 300

<210> SEQ ID NO 3
<211> LENGTH: 882
<212> TYPE: DNA
<213> ORGANISM: Arabidopsis thaliana
<220> FEATURE:
<221> NAME/KEY: CDS
<222> LOCATION: (1)..(882)
<223> OTHER INFORMATION: CAAX amino terminal protease (at3g26085)

<400> SEQUENCE: 3
```

```
atg ggt tcc atc gct ctg caa tct tgg agc aga gga gct tca act tct    48
Met Gly Ser Ile Ala Leu Gln Ser Trp Ser Arg Gly Ala Ser Thr Ser
1               5                   10                  15 ctt cat ctc ctt ttt cgt cca gtt ggc tcg aac cct aag cta tat gat    96
Leu His Leu Leu Phe Arg Pro Val Gly Ser Asn Pro Lys Leu Tyr Asp
            20                  25                  30 gct cga aga gta caa ttt gat gta aga gcc tct tca agt cgt aaa tca   144
Ala Arg Arg Val Gln Phe Asp Val Arg Ala Ser Ser Ser Arg Lys Ser
        35                  40                  45 ctt aag aaa ctc aaa aga gag tca caa caa ggt aaa gac ata ggc tta   192
Leu Lys Lys Leu Lys Arg Glu Ser Gln Gln Gly Lys Asp Ile Gly Leu
50                  55                  60 aga aat gtt aca gat gaa gaa gtt tct tct cca aga ttt gag gaa gct   240
Arg Asn Val Thr Asp Glu Glu Val Ser Ser Pro Arg Phe Glu Glu Ala
65                  70                  75                  80 caa gtt gat tct tca act tca aag gac tcc att gat gtt ttt gtt gct   288
Gln Val Asp Ser Ser Thr Ser Lys Asp Ser Ile Asp Val Phe Val Ala
                85                  90                  95 gct cct cga gac aaa gtg ctt cag gct tgc act gta act tcc ggt ttg   336
Ala Pro Arg Asp Lys Val Leu Gln Ala Cys Thr Val Thr Ser Gly Leu
            100                 105                 110 atg gct gca cta ggt ctg atc atc aga aag gcg tct cat gtt gct tcg   384
Met Ala Ala Leu Gly Leu Ile Ile Arg Lys Ala Ser His Val Ala Ser
        115                 120                 125 act gaa gga tta ctg gtt cca gac tgc tct ata gat gta cca ttt ggg   432
Thr Glu Gly Leu Leu Val Pro Asp Cys Ser Ile Asp Val Pro Phe Gly
130                 135                 140 ttt gaa act tgg cat ctc ggt tta att gct gga atc gtt gtg ttt ata   480
Phe Glu Thr Trp His Leu Gly Leu Ile Ala Gly Ile Val Val Phe Ile
145                 150                 155                 160 tcg tca agt agg ttc ttg cta ctt aaa tct tgg cca gat ttt gct gat   528
Ser Ser Ser Arg Phe Leu Leu Leu Lys Ser Trp Pro Asp Phe Ala Asp
                165                 170                 175 tct agt gaa gca gca aac cga cag att ctc act tcc ctc gaa cct cta   576
Ser Ser Glu Ala Ala Asn Arg Gln Ile Leu Thr Ser Leu Glu Pro Leu
            180                 185                 190 gat tac ctt gtt gtt gca atg tta ccg gga ata agt gag gag ctg ctg   624
Asp Tyr Leu Val Val Ala Met Leu Pro Gly Ile Ser Glu Glu Leu Leu
        195                 200                 205 ttt aga ggt gca tta atg cct ttg ttc gga act aat tgg aat ggt att   672
Phe Arg Gly Ala Leu Met Pro Leu Phe Gly Thr Asn Trp Asn Gly Ile
210                 215                 220 gta gcg gtt ggc ctc att ttc ggt tta ctt cat ctc ggg agc gga aga   720
Val Ala Val Gly Leu Ile Phe Gly Leu Leu His Leu Gly Ser Gly Arg
225                 230                 235                 240 aag tat tct ttt gca gtt tgg gct tcg att gtc ggt ata gtc tac ggt   768
Lys Tyr Ser Phe Ala Val Trp Ala Ser Ile Val Gly Ile Val Tyr Gly
                245                 250                 255 tat gca gct gtt ttg tcg tcg agt ctt atc gtt cca atg gcc tcg cac   816
Tyr Ala Ala Val Leu Ser Ser Ser Leu Ile Val Pro Met Ala Ser His
            260                 265                 270 gca ctc aac aat ttg gtg gga ggt ctg ttg tgg cga tat agt tcc aag   864
Ala Leu Asn Asn Leu Val Gly Gly Leu Leu Trp Arg Tyr Ser Ser Lys
        275                 280                 285 atc aag tca ttg gag taa                                            882
Ile Lys Ser Leu Glu
        290

<210> SEQ ID NO 4
<211> LENGTH: 293
<212> TYPE: PRT
```

<213> ORGANISM: Arabidopsis thaliana

<400> SEQUENCE: 4

```
Met Gly Ser Ile Ala Leu Gln Ser Trp Ser Arg Gly Ala Ser Thr Ser
1               5                   10                  15
Leu His Leu Leu Phe Arg Pro Val Gly Ser Asn Pro Lys Leu Tyr Asp
            20                  25                  30
Ala Arg Arg Val Gln Phe Asp Val Arg Ala Ser Ser Ser Arg Lys Ser
        35                  40                  45
Leu Lys Lys Leu Lys Arg Glu Ser Gln Gln Gly Lys Asp Ile Gly Leu
    50                  55                  60
Arg Asn Val Thr Asp Glu Glu Val Ser Ser Pro Arg Phe Glu Glu Ala
65                  70                  75                  80
Gln Val Asp Ser Ser Thr Ser Lys Asp Ser Ile Asp Val Phe Val Ala
                85                  90                  95
Ala Pro Arg Asp Lys Val Leu Gln Ala Cys Thr Val Thr Ser Gly Leu
            100                 105                 110
Met Ala Ala Leu Gly Leu Ile Ile Arg Lys Ala Ser His Val Ala Ser
        115                 120                 125
Thr Glu Gly Leu Leu Val Pro Asp Cys Ser Ile Asp Val Pro Phe Gly
    130                 135                 140
Phe Glu Thr Trp His Leu Gly Leu Ile Ala Gly Ile Val Val Phe Ile
145                 150                 155                 160
Ser Ser Ser Arg Phe Leu Leu Lys Ser Trp Pro Asp Phe Ala Asp
                165                 170                 175
Ser Ser Glu Ala Ala Asn Arg Gln Ile Leu Thr Ser Leu Glu Pro Leu
            180                 185                 190
Asp Tyr Leu Val Val Ala Met Leu Pro Gly Ile Ser Glu Glu Leu Leu
        195                 200                 205
Phe Arg Gly Ala Leu Met Pro Leu Phe Gly Thr Asn Trp Asn Gly Ile
    210                 215                 220
Val Ala Val Gly Leu Ile Phe Gly Leu Leu His Leu Gly Ser Gly Arg
225                 230                 235                 240
Lys Tyr Ser Phe Ala Val Trp Ala Ser Ile Val Gly Ile Val Tyr Gly
                245                 250                 255
Tyr Ala Ala Val Leu Ser Ser Ser Leu Ile Val Pro Met Ala Ser His
            260                 265                 270
Ala Leu Asn Asn Leu Val Gly Gly Leu Leu Trp Arg Tyr Ser Ser Lys
        275                 280                 285
Ile Lys Ser Leu Glu
    290
```

<210> SEQ ID NO 5
<211> LENGTH: 936
<212> TYPE: DNA
<213> ORGANISM: Arabidopsis thaliana
<220> FEATURE:
<221> NAME/KEY: CDS
<222> LOCATION: (1)..(936)
<223> OTHER INFORMATION: CAAX amino terminal protease (AtFACE-2)

<400> SEQUENCE: 5

```
atg gcc acc gat ggc gag agt atc tcg atg tcg ttg gcg gtg gct acc      48
Met Ala Thr Asp Gly Glu Ser Ile Ser Met Ser Leu Ala Val Ala Thr
1               5                   10                  15
tgc gtc gcg atg gca cta ttc tac gtt ttg atc ctt tac gtt ccc acc      96
Cys Val Ala Met Ala Leu Phe Tyr Val Leu Ile Leu Tyr Val Pro Thr
            20                  25                  30
```

| | | | | | | | | | | | | | | |
|---|---|---|---|---|---|---|---|---|---|---|---|---|---|---|
| gtg | ata | ctc | cgt | ctc | ccg | tcg | gct | tct | tct | tac | acc | gaa | ttc | atg | att | 144 |
| Val | Ile | Leu | Arg | Leu | Pro | Ser | Ala | Ser | Ser | Tyr | Thr | Glu | Phe | Met | Ile | |
| | | 35 | | | | | 40 | | | | | 45 | | | | |

```
gtg ata ctc cgt ctc ccg tcg gct tct tct tac acc gaa ttc atg att      144
Val Ile Leu Arg Leu Pro Ser Ala Ser Ser Tyr Thr Glu Phe Met Ile
        35                  40                  45 cgg cga ttc atc tgc gcg gcc att tgt act gta gca tct ctc gtc ttc      192
Arg Arg Phe Ile Cys Ala Ala Ile Cys Thr Val Ala Ser Leu Val Phe
 50                  55                  60 aca gct ttt ata ctt ccg ata aaa agc tgg gag gcc tct tat ata ctt      240
Thr Ala Phe Ile Leu Pro Ile Lys Ser Trp Glu Ala Ser Tyr Ile Leu
65                  70                  75                  80 gga gtt tat ggc ata agg aaa gat cat ctg tgg caa gga gtg gtg tat      288
Gly Val Tyr Gly Ile Arg Lys Asp His Leu Trp Gln Gly Val Val Tyr
                85                  90                  95 cct ctt cta ttg acc tcg ctc gtt tat gct ggg tct ttg gtg ttg aag      336
Pro Leu Leu Leu Thr Ser Leu Val Tyr Ala Gly Ser Leu Val Leu Lys
            100                 105                 110 ttg ttt act ctc ctg gaa tca tgg aag gaa aat ggc gga gga tgt agt      384
Leu Phe Thr Leu Leu Glu Ser Trp Lys Glu Asn Gly Gly Gly Cys Ser
        115                 120                 125 tcc ttt aat tac atc aga agc ttt ttc caa aca atc cct gct tcg gta      432
Ser Phe Asn Tyr Ile Arg Ser Phe Phe Gln Thr Ile Pro Ala Ser Val
130                 135                 140 ttg aca agt gct tct aat gtt tcc gtt tgg cgc aat ttt atc gtg gca      480
Leu Thr Ser Ala Ser Asn Val Ser Val Trp Arg Asn Phe Ile Val Ala
145                 150                 155                 160 cca gta act gag gag ctg gtt ttc cga tca tgt atg ata cct ttg ctt      528
Pro Val Thr Glu Glu Leu Val Phe Arg Ser Cys Met Ile Pro Leu Leu
                165                 170                 175 ctg tgt gct ggg ttt agg att aac act gcc atc ttt ctg tgc cca gtt      576
Leu Cys Ala Gly Phe Arg Ile Asn Thr Ala Ile Phe Leu Cys Pro Val
            180                 185                 190 ctc ttt agc ttg gct cac tta aac cat ttt aga gag atg tac atc agg      624
Leu Phe Ser Leu Ala His Leu Asn His Phe Arg Glu Met Tyr Ile Arg
        195                 200                 205 cat aac cgc agc tat ctc cgg gct tca ctt att gtt ggt ctt cag ctt      672
His Asn Arg Ser Tyr Leu Arg Ala Ser Leu Ile Val Gly Leu Gln Leu
210                 215                 220 ggc tac aca gtc att ttt ggt gca tat gca tcg ttt ctc ttc atc aga      720
Gly Tyr Thr Val Ile Phe Gly Ala Tyr Ala Ser Phe Leu Phe Ile Arg
225                 230                 235                 240 acc gga cat ctt gct gct cct ttg ttt gct cat ata ttt tgc aac tac      768
Thr Gly His Leu Ala Ala Pro Leu Phe Ala His Ile Phe Cys Asn Tyr
                245                 250                 255 atg gga ttg cct gtg cta tac gca aat gga aaa ggt ttg gtg agt gca      816
Met Gly Leu Pro Val Leu Tyr Ala Asn Gly Lys Gly Leu Val Ser Ala
            260                 265                 270 gcg ttc tta ggc ggt gtg gtt ggg ttc gtc tta ctt ctc ttt cct tta      864
Ala Phe Leu Gly Gly Val Val Gly Phe Val Leu Leu Leu Phe Pro Leu
        275                 280                 285 aca aag cct ctc atg tac aac gat agt acc aac gat tgt ccg tgt tgg      912
Thr Lys Pro Leu Met Tyr Asn Asp Ser Thr Asn Asp Cys Pro Cys Trp
290                 295                 300 ctt ggc tat tgt ttg tgg aat tga                                       936
Leu Gly Tyr Cys Leu Trp Asn
305                 310
```

<210> SEQ ID NO 6
<211> LENGTH: 311
<212> TYPE: PRT
<213> ORGANISM: Arabidopsis thaliana

<400> SEQUENCE: 6

```
Met Ala Thr Asp Gly Glu Ser Ile Ser Met Ser Leu Ala Val Ala Thr
1               5                   10                  15

Cys Val Ala Met Ala Leu Phe Tyr Val Leu Ile Leu Tyr Val Pro Thr
            20                  25                  30

Val Ile Leu Arg Leu Pro Ser Ala Ser Ser Tyr Thr Glu Phe Met Ile
        35                  40                  45

Arg Arg Phe Ile Cys Ala Ala Ile Cys Thr Val Ala Ser Leu Val Phe
    50                  55                  60

Thr Ala Phe Ile Leu Pro Ile Lys Ser Trp Glu Ala Ser Tyr Ile Leu
65                  70                  75                  80

Gly Val Tyr Gly Ile Arg Lys Asp His Leu Trp Gln Gly Val Val Tyr
                85                  90                  95

Pro Leu Leu Leu Thr Ser Leu Val Tyr Ala Gly Ser Leu Val Leu Lys
            100                 105                 110

Leu Phe Thr Leu Leu Glu Ser Trp Lys Glu Asn Gly Gly Gly Cys Ser
        115                 120                 125

Ser Phe Asn Tyr Ile Arg Ser Phe Phe Gln Thr Ile Pro Ala Ser Val
    130                 135                 140

Leu Thr Ser Ala Ser Asn Val Ser Val Trp Arg Asn Phe Ile Val Ala
145                 150                 155                 160

Pro Val Thr Glu Glu Leu Val Phe Arg Ser Cys Met Ile Pro Leu Leu
                165                 170                 175

Leu Cys Ala Gly Phe Arg Ile Asn Thr Ala Ile Phe Leu Cys Pro Val
            180                 185                 190

Leu Phe Ser Leu Ala His Leu Asn His Phe Arg Glu Met Tyr Ile Arg
        195                 200                 205

His Asn Arg Ser Tyr Leu Arg Ala Ser Leu Ile Val Gly Leu Gln Leu
    210                 215                 220

Gly Tyr Thr Val Ile Phe Gly Ala Tyr Ala Ser Phe Leu Phe Ile Arg
225                 230                 235                 240

Thr Gly His Leu Ala Ala Pro Leu Phe Ala His Ile Phe Cys Asn Tyr
                245                 250                 255

Met Gly Leu Pro Val Leu Tyr Ala Asn Gly Lys Gly Leu Val Ser Ala
            260                 265                 270

Ala Phe Leu Gly Gly Val Val Gly Phe Val Leu Leu Leu Phe Pro Leu
        275                 280                 285

Thr Lys Pro Leu Met Tyr Asn Asp Ser Thr Asn Asp Cys Pro Cys Trp
    290                 295                 300

Leu Gly Tyr Cys Leu Trp Asn
305                 310
```

<210> SEQ ID NO 7
<211> LENGTH: 1451
<212> TYPE: DNA
<213> ORGANISM: Zea mays
<220> FEATURE:
<221> NAME/KEY: CDS
<222> LOCATION: (101)..(1039)
<223> OTHER INFORMATION: CAAX amino terminal protease (ZM57353913)

<400> SEQUENCE: 7

```
cgaagccacg cgaccgactg tgttacgatc ccaaatcttc actcccgacg aaatctagaa    60
tccaatgagc aatctcgact gacgcctgct tcaccagatt atg gcg acg ccg gcg   115
                                              Met Ala Thr Pro Ala
                                              1               5 ggc ctc ctt ctc gcc tcg ccg ccg gtg ata tca ggt gtc gcg gcg atg   163
```

-continued

| | | | | | | | | | | | | | | | | |
|---|---|---|---|---|---|---|---|---|---|---|---|---|---|---|---|---|
| Gly | Leu | Leu | Leu | Ala | Ser | Pro | Val | Ile | Ser | Gly | Val | Ala | Ala | Met | | |
| | | | 10 | | | | 15 | | | | 20 | | | | | |

| gcg | gcg | tgc | gcc | gca | atg | gca | gta | ttc | tac | gtc | gct | gtc | ctc | tat | gcc | 211 |
|---|---|---|---|---|---|---|---|---|---|---|---|---|---|---|---|---|
| Ala | Ala | Cys | Ala | Ala | Met | Ala | Val | Phe | Tyr | Val | Ala | Val | Leu | Tyr | Ala | |
| | | 25 | | | | | 30 | | | | | 35 | | | | |

| ccg | acg | gtc | atc | ctc | cgg | ttc | cca | ccc | cca | acc | tca | ctc | cgc | acc | ttc | 259 |
|---|---|---|---|---|---|---|---|---|---|---|---|---|---|---|---|---|
| Pro | Thr | Val | Ile | Leu | Arg | Phe | Pro | Pro | Pro | Thr | Ser | Leu | Arg | Thr | Phe | |
| | | 40 | | | | | 45 | | | | | 50 | | | | |

| ctc | cac | cgt | cgc | ttc | gcc | tgt | gcc | gcc | gtc | gca | tcc | gcc | gcc | tcc | gtc | 307 |
|---|---|---|---|---|---|---|---|---|---|---|---|---|---|---|---|---|
| Leu | His | Arg | Arg | Phe | Ala | Cys | Ala | Ala | Val | Ala | Ser | Ala | Ala | Ser | Val | |
| | 55 | | | | | 60 | | | | | 65 | | | | | |

| ctt | gcc | act | gcg | tcc | ctc | ctc | cga | gtc | tgg | agc | ctc | agc | gac | ttc | gct | 355 |
|---|---|---|---|---|---|---|---|---|---|---|---|---|---|---|---|---|
| Leu | Ala | Thr | Ala | Ser | Leu | Leu | Arg | Val | Trp | Ser | Leu | Ser | Asp | Phe | Ala | |
| 70 | | | | | 75 | | | | | 80 | | | | | 85 | |

| gat | atg | ttt | gct | gtg | ttc | ggc | att | agg | aag | gat | cac | ttg | att | cag | gcc | 403 |
|---|---|---|---|---|---|---|---|---|---|---|---|---|---|---|---|---|
| Asp | Met | Phe | Ala | Val | Phe | Gly | Ile | Arg | Lys | Asp | His | Leu | Ile | Gln | Ala | |
| | | | | 90 | | | | | 95 | | | | | 100 | | |

| gtg | gct | att | cca | ctt | ctc | ctg | aca | tcc | cta | gtg | tat | gct | ggg | tca | ttc | 451 |
|---|---|---|---|---|---|---|---|---|---|---|---|---|---|---|---|---|
| Val | Ala | Ile | Pro | Leu | Leu | Leu | Thr | Ser | Leu | Val | Tyr | Ala | Gly | Ser | Phe | |
| | | | 105 | | | | | 110 | | | | | 115 | | | |

| gtc | gct | aga | gtg | tgg | ctc | cta | gtg | agc | tcg | tgg | ggc | ggt | ggc | gat | gag | 499 |
|---|---|---|---|---|---|---|---|---|---|---|---|---|---|---|---|---|
| Val | Ala | Arg | Val | Trp | Leu | Leu | Val | Ser | Ser | Trp | Gly | Gly | Gly | Asp | Glu | |
| | | 120 | | | | | 125 | | | | | 130 | | | | |

| gtg | gag | ata | ggc | tgc | gca | cag | agg | ctt | gca | caa | tgg | atc | caa | gct | gct | 547 |
|---|---|---|---|---|---|---|---|---|---|---|---|---|---|---|---|---|
| Val | Glu | Ile | Gly | Cys | Ala | Gln | Arg | Leu | Ala | Gln | Trp | Ile | Gln | Ala | Ala | |
| | 135 | | | | | 140 | | | | | 145 | | | | | |

| gtt | gcg | gat | gtt | atg | gtt | tgg | cgg | aac | tat | gta | gtg | gca | cca | ttt | act | 595 |
|---|---|---|---|---|---|---|---|---|---|---|---|---|---|---|---|---|
| Val | Ala | Asp | Val | Met | Val | Trp | Arg | Asn | Tyr | Val | Val | Ala | Pro | Phe | Thr | |
| 150 | | | | | 155 | | | | | 160 | | | | | 165 | |

| gag | gag | ctg | gtt | ttc | agg | gca | tgc | atg | ata | cct | ctt | ctg | ctc | tgt | ggg | 643 |
|---|---|---|---|---|---|---|---|---|---|---|---|---|---|---|---|---|
| Glu | Glu | Leu | Val | Phe | Arg | Ala | Cys | Met | Ile | Pro | Leu | Leu | Leu | Cys | Gly | |
| | | | | 170 | | | | | 175 | | | | | 180 | | |

| gga | ttc | aaa | atg | tct | aca | att | ata | ttt | ctg | agt | cca | atc | ttc | ttc | agt | 691 |
|---|---|---|---|---|---|---|---|---|---|---|---|---|---|---|---|---|
| Gly | Phe | Lys | Met | Ser | Thr | Ile | Ile | Phe | Leu | Ser | Pro | Ile | Phe | Phe | Ser | |
| | | | 185 | | | | | 190 | | | | | 195 | | | |

| cta | gcg | cac | ttg | aac | cat | ttt | ttc | gaa | cta | cac | cag | cag | gga | tgt | aac | 739 |
|---|---|---|---|---|---|---|---|---|---|---|---|---|---|---|---|---|
| Leu | Ala | His | Leu | Asn | His | Phe | Phe | Glu | Leu | His | Gln | Gln | Gly | Cys | Asn | |
| | | 200 | | | | | 205 | | | | | 210 | | | | |

| ttt | atg | aga | gcg | cta | ttg | att | gta | ggt | gtc | cag | tta | ggc | tac | act | gtc | 787 |
|---|---|---|---|---|---|---|---|---|---|---|---|---|---|---|---|---|
| Phe | Met | Arg | Ala | Leu | Leu | Ile | Val | Gly | Val | Gln | Leu | Gly | Tyr | Thr | Val | |
| | 215 | | | | | 220 | | | | | 225 | | | | | |

| att | ttt | ggg | tgg | tat | gca | aca | ttc | ttg | tta | atc | cga | aca | ggg | aat | ctg | 835 |
|---|---|---|---|---|---|---|---|---|---|---|---|---|---|---|---|---|
| Ile | Phe | Gly | Trp | Tyr | Ala | Thr | Phe | Leu | Leu | Ile | Arg | Thr | Gly | Asn | Leu | |
| 230 | | | | | 235 | | | | | 240 | | | | | 245 | |

| tta | tgt | cca | att | att | gct | cac | gtc | ttc | tgt | aat | atg | atg | ggt | tta | cct | 883 |
|---|---|---|---|---|---|---|---|---|---|---|---|---|---|---|---|---|
| Leu | Cys | Pro | Ile | Ile | Ala | His | Val | Phe | Cys | Asn | Met | Met | Gly | Leu | Pro | |
| | | | | 250 | | | | | 255 | | | | | 260 | | |

| gtt | ttc | tcg | tca | cca | cga | aca | aaa | gga | gcg | gca | ttg | gta | gcg | ttt | ctg | 931 |
|---|---|---|---|---|---|---|---|---|---|---|---|---|---|---|---|---|
| Val | Phe | Ser | Ser | Pro | Arg | Thr | Lys | Gly | Ala | Ala | Leu | Val | Ala | Phe | Leu | |
| | | | 265 | | | | | 270 | | | | | 275 | | | |

| gct | ggt | tca | ata | gcc | ttc | ttt | tgg | ctg | ctt | ttc | cct | gca | aca | agt | cct | 979 |
|---|---|---|---|---|---|---|---|---|---|---|---|---|---|---|---|---|
| Ala | Gly | Ser | Ile | Ala | Phe | Phe | Trp | Leu | Leu | Phe | Pro | Ala | Thr | Ser | Pro | |
| | | 280 | | | | | 285 | | | | | 290 | | | | |

| gaa | ctg | tac | aac | agc | agt | ttt | gat | cgc | tgc | agt | tgc | tgg | cat | ggc | ttt | 1027 |
|---|---|---|---|---|---|---|---|---|---|---|---|---|---|---|---|---|
| Glu | Leu | Tyr | Asn | Ser | Ser | Phe | Asp | Arg | Cys | Ser | Cys | Trp | His | Gly | Phe | |
| | 295 | | | | | 300 | | | | | 305 | | | | | |

| tgc | aat | tgg | aaa | taacatagaa ctagattgga aagcaatggg tcctaacttg | 1079 |
|---|---|---|---|---|---|
| Cys | Asn | Trp | Lys | | |
| 310 | | | | | | aagctactaa caattgaaac ctccaggccc tagctgacac ttctgacgga ttttctattt     1139

```
gcagaaactc catatgaatg tcttaaaacg ttttgtagaa atgtgtccct tgttttagct      1199
taagactcaa gagcttaaac tagcaaaaga ttgtattttg ccacttgtta aatacgtgct      1259
gatcatgaaa tcgctgtcaa tcccttctca aagtggaatt tgactttgtt gagctgcttt      1319
tatttatatt gtgcttgcta ctgcagcgcc tagagtttgt agattacaca tcatggaccc      1379
gtctgatatt gtaaacgaga gacatgtttc taagttaata tgctccctcc atttatttaa      1439
aaaaaaaaaa aa                                                         1451

<210> SEQ ID NO 8
<211> LENGTH: 313
<212> TYPE: PRT
<213> ORGANISM: Zea mays

<400> SEQUENCE: 8
```

Met Ala Thr Pro Ala Gly Leu Leu Ala Ser Pro Val Ile Ser
1               5                   10                  15

Gly Val Ala Ala Met Ala Ala Cys Ala Ala Met Ala Val Phe Tyr Val
                20                  25                  30

Ala Val Leu Tyr Ala Pro Thr Val Ile Leu Arg Phe Pro Pro Thr
        35                  40                  45

Ser Leu Arg Thr Phe Leu His Arg Arg Phe Ala Cys Ala Val Ala
    50                  55                  60

Ser Ala Ala Ser Val Leu Ala Thr Ala Ser Leu Leu Arg Val Trp Ser
65                  70                  75                  80

Leu Ser Asp Phe Ala Asp Met Phe Ala Val Phe Gly Ile Arg Lys Asp
                85                  90                  95

His Leu Ile Gln Ala Val Ala Ile Pro Leu Leu Leu Thr Ser Leu Val
            100                 105                 110

Tyr Ala Gly Ser Phe Val Ala Arg Val Trp Leu Leu Val Ser Ser Trp
        115                 120                 125

Gly Gly Gly Asp Glu Val Glu Ile Gly Cys Ala Gln Arg Leu Ala Gln
    130                 135                 140

Trp Ile Gln Ala Ala Val Ala Asp Val Met Val Trp Arg Asn Tyr Val
145                 150                 155                 160

Val Ala Pro Phe Thr Glu Glu Leu Val Phe Arg Ala Cys Met Ile Pro
                165                 170                 175

Leu Leu Leu Cys Gly Gly Phe Lys Met Ser Thr Ile Ile Phe Leu Ser
            180                 185                 190

Pro Ile Phe Phe Ser Leu Ala His Leu Asn His Phe Glu Leu His
        195                 200                 205

Gln Gln Gly Cys Asn Phe Met Arg Ala Leu Leu Ile Val Gly Val Gln
    210                 215                 220

Leu Gly Tyr Thr Val Ile Phe Gly Trp Tyr Ala Thr Phe Leu Leu Ile
225                 230                 235                 240

Arg Thr Gly Asn Leu Leu Cys Pro Ile Ile Ala His Val Phe Cys Asn
                245                 250                 255

Met Met Gly Leu Pro Val Phe Ser Ser Pro Arg Thr Lys Gly Ala Ala
            260                 265                 270

Leu Val Ala Phe Leu Ala Gly Ser Ile Ala Phe Phe Trp Leu Leu Phe
        275                 280                 285

Pro Ala Thr Ser Pro Glu Leu Tyr Asn Ser Ser Phe Asp Arg Cys Ser
    290                 295                 300

Cys Trp His Gly Phe Cys Asn Trp Lys
305                 310

<210> SEQ ID NO 9
<211> LENGTH: 1215
<212> TYPE: DNA
<213> ORGANISM: Zea mays
<220> FEATURE:
<221> NAME/KEY: CDS
<222> LOCATION: (128)..(934)
<223> OTHER INFORMATION: CAAX amino terminal protease (ZM59252659)

<400> SEQUENCE: 9

```
cccaaatctt catttccgac gaaatcgaga atccaatgtg caatctcgac tgacgcctgc       60
ttcaacagat tatggcgacg cggtgggtct ccttctcgcc tcgccgccgg aatatcaggg      120 tcgcgcg atg ggt cgt gcg cca acg gaa gga ttc tac gtc gct gtc ctc       169
        Met Gly Arg Ala Pro Thr Glu Gly Phe Tyr Val Ala Val Leu
        1               5                   10 tat gcc ccg acg gtc atc ctc cgg gtc cca ccc cca agc tca ctc cgc       217
Tyr Ala Pro Thr Val Ile Leu Arg Val Pro Pro Pro Ser Ser Leu Arg
15                  20                  25                  30 acc ttc ctc cac cgt cgc ttc gcc tgt gcc gcc gtc gca tcc gcc gcc       265
Thr Phe Leu His Arg Arg Phe Ala Cys Ala Ala Val Ala Ser Ala Ala
                35                  40                  45 tcc gtc ctt gcc act gcg tcc ctc ctc cga atc tgg agc ctc agc gac       313
Ser Val Leu Ala Thr Ala Ser Leu Leu Arg Ile Trp Ser Leu Ser Asp
        50                  55                  60 ttc gct gat atg ttt gct gtg ttc ggc att agg aag gat cac ttg att       361
Phe Ala Asp Met Phe Ala Val Phe Gly Ile Arg Lys Asp His Leu Ile
65                  70                  75 cag gcc gtg gct att cca ctt ctc ctg aca tcc cta gtg tat gct ggg       409
Gln Ala Val Ala Ile Pro Leu Leu Leu Thr Ser Leu Val Tyr Ala Gly
        80                  85                  90 tca ttc gtc gct aga gtg tgg ctc cta gtg agc tcg tgg ggc ggt ggc       457
Ser Phe Val Ala Arg Val Trp Leu Leu Val Ser Ser Trp Gly Gly Gly
95                  100                 105                 110 gat gag gtg gag ata ggc tgc gca cag agg ctt gca caa tgg atc caa       505
Asp Glu Val Glu Ile Gly Cys Ala Gln Arg Leu Ala Gln Trp Ile Gln
                115                 120                 125 gct gct gtt gcg gat gtt atg gtt tgg cgg aac tat gta gtg gca cca       553
Ala Ala Val Ala Asp Val Met Val Trp Arg Asn Tyr Val Val Ala Pro
        130                 135                 140 ttt act gag gag ctg gtt ttc agg gca tgc atg ata cct ctt ctg ctc       601
Phe Thr Glu Glu Leu Val Phe Arg Ala Cys Met Ile Pro Leu Leu Leu
145                 150                 155 tgt ggg gga ttc aaa atg tct aca att ata ttt ctg agt cca atc ttc       649
Cys Gly Gly Phe Lys Met Ser Thr Ile Ile Phe Leu Ser Pro Ile Phe
        160                 165                 170 ttc agt cta ggt gtc cag tta ggc tac act gtc att ttt ggg tgg tat       697
Phe Ser Leu Gly Val Gln Leu Gly Tyr Thr Val Ile Phe Gly Trp Tyr
175                 180                 185                 190 gca aca ttc ttg tta atc cga aca ggg aat ctg tta tgt cca att act       745
Ala Thr Phe Leu Leu Ile Arg Thr Gly Asn Leu Leu Cys Pro Ile Thr
                195                 200                 205 gct cac gtc ttc tgt aat atg atg ggt tta cct gtt ttc tcg tca cca       793
Ala His Val Phe Cys Asn Met Met Gly Leu Pro Val Phe Ser Ser Pro
        210                 215                 220 cga aca aaa gga gcg gca ttg gta gcg ttt ctg gct ggt tca ata gcc       841
Arg Thr Lys Gly Ala Ala Leu Val Ala Phe Leu Ala Gly Ser Ile Ala
225                 230                 235 ttc ttt tgg ctg ctt ttc cct gca aca agt cct gaa ctg tac aac agc       889
Phe Phe Trp Leu Leu Phe Pro Ala Thr Ser Pro Glu Leu Tyr Asn Ser
        240                 245                 250
```

```
agt ttt gat cgc tgc agt tgc tgg cat ggc ttt tgc aat tgg aaa      934
Ser Phe Asp Arg Cys Ser Cys Trp His Gly Phe Cys Asn Trp Lys
255             260                 265 taacatagaa ctagattgga aagcaatggg tcctaacttg aagctactaa caattgaaac    994
ctccaggccc tagctgacac tgctgacgga ttttctattt gcagaaactc catatgaatg   1054
tcttaaaacg ttttgtagaa atgtgtccct tgttttagct taagactcga gcttaaacta   1114 gcaaagatt gtattttgcc acttgttaaa tacgtgctga tcatgaaatc gctgtcaatc    1174
ccttctcaaa gtggaatttg actttgttgt aaaaaaaaaa a                      1215
```

<210> SEQ ID NO 10
<211> LENGTH: 269
<212> TYPE: PRT
<213> ORGANISM: Zea mays

<400> SEQUENCE: 10

```
Met Gly Arg Ala Pro Thr Glu Gly Phe Tyr Val Ala Val Leu Tyr Ala
1               5                   10                  15

Pro Thr Val Ile Leu Arg Val Pro Pro Ser Ser Leu Arg Thr Phe
            20                  25                  30

Leu His Arg Arg Phe Ala Cys Ala Ala Val Ala Ser Ala Ala Ser Val
        35                  40                  45

Leu Ala Thr Ala Ser Leu Leu Arg Ile Trp Ser Leu Ser Asp Phe Ala
    50                  55                  60

Asp Met Phe Ala Val Phe Gly Ile Arg Lys Asp His Leu Ile Gln Ala
65                  70                  75                  80

Val Ala Ile Pro Leu Leu Leu Thr Ser Leu Val Tyr Ala Gly Ser Phe
                85                  90                  95

Val Ala Arg Val Trp Leu Leu Val Ser Ser Trp Gly Gly Gly Asp Glu
            100                 105                 110

Val Glu Ile Gly Cys Ala Gln Arg Leu Ala Gln Trp Ile Gln Ala Ala
        115                 120                 125

Val Ala Asp Val Met Val Trp Arg Asn Tyr Val Val Ala Pro Phe Thr
    130                 135                 140

Glu Glu Leu Val Phe Arg Ala Cys Met Ile Pro Leu Leu Leu Cys Gly
145                 150                 155                 160

Gly Phe Lys Met Ser Thr Ile Ile Phe Leu Ser Pro Ile Phe Phe Ser
                165                 170                 175

Leu Gly Val Gln Leu Gly Tyr Thr Val Ile Phe Gly Trp Tyr Ala Thr
            180                 185                 190

Phe Leu Leu Ile Arg Thr Gly Asn Leu Leu Cys Pro Ile Thr Ala His
        195                 200                 205

Val Phe Cys Asn Met Met Gly Leu Pro Val Phe Ser Ser Pro Arg Thr
    210                 215                 220

Lys Gly Ala Ala Leu Val Ala Phe Leu Ala Gly Ser Ile Ala Phe Phe
225                 230                 235                 240

Trp Leu Leu Phe Pro Ala Thr Ser Pro Glu Leu Tyr Asn Ser Ser Phe
                245                 250                 255

Asp Arg Cys Ser Cys Trp His Gly Phe Cys Asn Trp Lys
            260                 265
```

<210> SEQ ID NO 11
<211> LENGTH: 258
<212> TYPE: DNA
<213> ORGANISM: Capsicum annuum
<220> FEATURE:

-continued

```
<221> NAME/KEY: CDS
<222> LOCATION: (1)..(258)
<223> OTHER INFORMATION: SAR8.2 protein precursor (CASAR82A)

<400> SEQUENCE: 11 atg gtg tct aag tcc tca atc ttc att tgc ctg agc ctt atc atc ctc      48
Met Val Ser Lys Ser Ser Ile Phe Ile Cys Leu Ser Leu Ile Ile Leu
1               5                   10                  15 gtg atc atg tct acc cag atc gtg gct aga gag atg acc agt gaa gct      96
Val Ile Met Ser Thr Gln Ile Val Ala Arg Glu Met Thr Ser Glu Ala
            20                  25                  30 tct gct tca ctc aca cag gca atg aac ggg aac aat atc tct gag acc     144
Ser Ala Ser Leu Thr Gln Ala Met Asn Gly Asn Asn Ile Ser Glu Thr
        35                  40                  45 aag aaa gtg ggt cgt cac ttg gtg aag ggc ttg gat aag atc ttc aag     192
Lys Lys Val Gly Arg His Leu Val Lys Gly Leu Asp Lys Ile Phe Lys
    50                  55                  60 gct gga aag gtg atc tac tgc aag acc tgc aaa acc tgc cac ggt cgc     240
Ala Gly Lys Val Ile Tyr Cys Lys Thr Cys Lys Thr Cys His Gly Arg
65                  70                  75                  80 tgc gat tac tgt tgc gcc                                             258
Cys Asp Tyr Cys Cys Ala
                85

<210> SEQ ID NO 12
<211> LENGTH: 86
<212> TYPE: PRT
<213> ORGANISM: Capsicum annuum

<400> SEQUENCE: 12

Met Val Ser Lys Ser Ser Ile Phe Ile Cys Leu Ser Leu Ile Ile Leu
1               5                   10                  15

Val Ile Met Ser Thr Gln Ile Val Ala Arg Glu Met Thr Ser Glu Ala
            20                  25                  30

Ser Ala Ser Leu Thr Gln Ala Met Asn Gly Asn Asn Ile Ser Glu Thr
        35                  40                  45

Lys Lys Val Gly Arg His Leu Val Lys Gly Leu Asp Lys Ile Phe Lys
    50                  55                  60

Ala Gly Lys Val Ile Tyr Cys Lys Thr Cys Lys Thr Cys His Gly Arg
65                  70                  75                  80

Cys Asp Tyr Cys Cys Ala
                85

<210> SEQ ID NO 13
<211> LENGTH: 2091
<212> TYPE: DNA
<213> ORGANISM: Escherichia coli
<220> FEATURE:
<221> NAME/KEY: CDS
<222> LOCATION: (1)..(2091)
<223> OTHER INFORMATION: putative membrane protein (b3358)

<400> SEQUENCE: 13 atg tgg cgc aga ctg att tat cac ccc gat atc aac tat gca ctt cga      48
Met Trp Arg Arg Leu Ile Tyr His Pro Asp Ile Asn Tyr Ala Leu Arg
1               5                   10                  15 caa acg ctg gtg cta tgt ttg ccc gtg gcc gtt ggg tta atg ctt ggc      96
Gln Thr Leu Val Leu Cys Leu Pro Val Ala Val Gly Leu Met Leu Gly
            20                  25                  30 gaa tta cga ttc ggt ctg ctc ttc tcc ctc gtt cct gcc tgt tgc aat     144
Glu Leu Arg Phe Gly Leu Leu Phe Ser Leu Val Pro Ala Cys Cys Asn
        35                  40                  45
```

```
att gcg ggc ctt gat acg cct cat aaa cgt ttt ttc aaa cgc tta atc      192
Ile Ala Gly Leu Asp Thr Pro His Lys Arg Phe Phe Lys Arg Leu Ile
    50                  55                  60 att ggt gcg tcg ctg ttt gcc acc tgt agc ttg ctg aca cag cta cta      240
Ile Gly Ala Ser Leu Phe Ala Thr Cys Ser Leu Leu Thr Gln Leu Leu
65                  70                  75                  80 ctg gca aaa gat gtt ccc ctg ccc ttt ttg ctg acc gga tta acg ctg      288
Leu Ala Lys Asp Val Pro Leu Pro Phe Leu Leu Thr Gly Leu Thr Leu
                85                  90                  95 gta ctt ggc gtc act gct gag ctg ggg cca ttg cac gca aaa ttg ctt      336
Val Leu Gly Val Thr Ala Glu Leu Gly Pro Leu His Ala Lys Leu Leu
            100                 105                 110 cct gca tcg ctg ctc gcc gcc att ttt acc ctc agt ttg gcg gga tac      384
Pro Ala Ser Leu Leu Ala Ala Ile Phe Thr Leu Ser Leu Ala Gly Tyr
        115                 120                 125 atg ccg gtc tgg gaa ccg ttg ctc atc tat gcg ttg ggc act ctc tgg      432
Met Pro Val Trp Glu Pro Leu Leu Ile Tyr Ala Leu Gly Thr Leu Trp
    130                 135                 140 tac gga ttg ttt aac tgg ttt tgg ttc tgg atc tgg cgc gaa caa ccg      480
Tyr Gly Leu Phe Asn Trp Phe Trp Phe Trp Ile Trp Arg Glu Gln Pro
145                 150                 155                 160 ctg cgc gag tca cta agt ctg ctg tac cgt gaa ctg gca gat tat tgt      528
Leu Arg Glu Ser Leu Ser Leu Leu Tyr Arg Glu Leu Ala Asp Tyr Cys
                165                 170                 175 gaa gcc aaa tac agc ctg ctt acc cag cac acc gac cct gaa aaa gcg      576
Glu Ala Lys Tyr Ser Leu Leu Thr Gln His Thr Asp Pro Glu Lys Ala
            180                 185                 190 ctg ccg ccg ctg ctg gtg cgc cag caa aaa gcg gtc gat cta att acc      624
Leu Pro Pro Leu Leu Val Arg Gln Gln Lys Ala Val Asp Leu Ile Thr
        195                 200                 205 cag tgc tat cag caa atg cat atg ctt tcc gcg caa aat aat act gac      672
Gln Cys Tyr Gln Gln Met His Met Leu Ser Ala Gln Asn Asn Thr Asp
    210                 215                 220 tac aag cgg atg ctg cgt att ttc cag gag gcg ctg gat tta cag gaa      720
Tyr Lys Arg Met Leu Arg Ile Phe Gln Glu Ala Leu Asp Leu Gln Glu
225                 230                 235                 240 cat att tcg gtc agt ttg cat cag ccg gaa gag gtg caa aag ctg gtc      768
His Ile Ser Val Ser Leu His Gln Pro Glu Glu Val Gln Lys Leu Val
                245                 250                 255 gag cgt agc cat gcg gaa gaa gtt atc cgc tgg aat gcg caa acc gtc      816
Glu Arg Ser His Ala Glu Glu Val Ile Arg Trp Asn Ala Gln Thr Val
            260                 265                 270 gcc gct cgc ctg cgc gtg ctg gct gat gac att ctt tac cat cgc ctg      864
Ala Ala Arg Leu Arg Val Leu Ala Asp Asp Ile Leu Tyr His Arg Leu
        275                 280                 285 cca acg cgt ttt acg atg gaa aag caa att ggc gca ctg gaa aaa atc      912
Pro Thr Arg Phe Thr Met Glu Lys Gln Ile Gly Ala Leu Glu Lys Ile
    290                 295                 300 gcc cgc cag cat ccg gat aat ccg gtt ggg caa ttc tgc tac tgg cat      960
Ala Arg Gln His Pro Asp Asn Pro Val Gly Gln Phe Cys Tyr Trp His
305                 310                 315                 320 ttc agc cgc atc gcc cgc gtg ctg cgc acc caa aaa ccg ctc tat gcc     1008
Phe Ser Arg Ile Ala Arg Val Leu Arg Thr Gln Lys Pro Leu Tyr Ala
                325                 330                 335 cgt gac tta ctg gcc gat aaa cag cgg cga atg cca tta ctt ccg gcg     1056
Arg Asp Leu Leu Ala Asp Lys Gln Arg Arg Met Pro Leu Leu Pro Ala
            340                 345                 350 ctg aaa agt tat ctg tca cta aag tct ccg gcg cta cgc aat gcc gga     1104
Leu Lys Ser Tyr Leu Ser Leu Lys Ser Pro Ala Leu Arg Asn Ala Gly
        355                 360                 365
```

```
cga ctc agt gtg atg tta agc gtt gcc agc ctg atg ggc acc gcg ctg      1152
Arg Leu Ser Val Met Leu Ser Val Ala Ser Leu Met Gly Thr Ala Leu
    370             375                 380 cat ctg ccg aag tcg tac tgg atc ctg atg acg gta ttg ctg gtg aca      1200
His Leu Pro Lys Ser Tyr Trp Ile Leu Met Thr Val Leu Leu Val Thr
385                 390                 395                 400 caa aat ggc tat ggc gca acc cgt ctg agg att gtg aat cgc tcc gtg      1248
Gln Asn Gly Tyr Gly Ala Thr Arg Leu Arg Ile Val Asn Arg Ser Val
                405                 410                 415 gga acc gtg gtc ggg tta atc att gcg ggc gtg gcg ctg cac ttt aaa      1296
Gly Thr Val Val Gly Leu Ile Ile Ala Gly Val Ala Leu His Phe Lys
        420                 425                 430 att ccc gaa ggt tac acc ctg acg ttg atg ctg att acc acc ctc gcc      1344
Ile Pro Glu Gly Tyr Thr Leu Thr Leu Met Leu Ile Thr Thr Leu Ala
            435                 440                 445 agc tac ctg ata ttg cgc aaa aac tac ggc tgg gcg acg gtc ggt ttt      1392
Ser Tyr Leu Ile Leu Arg Lys Asn Tyr Gly Trp Ala Thr Val Gly Phe
    450                 455                 460 act att acc gca gtg tat acc ctg caa cta ttg tgg ttg aac ggc gag      1440
Thr Ile Thr Ala Val Tyr Thr Leu Gln Leu Leu Trp Leu Asn Gly Glu
465                 470                 475                 480 caa tac atc ctt ccg cgt ctt atc gat acc att att ggt tgt tta att      1488
Gln Tyr Ile Leu Pro Arg Leu Ile Asp Thr Ile Ile Gly Cys Leu Ile
                485                 490                 495 gct ttc ggc ggt act gtc tgg ctg tgg ccg cag tgg cag agc ggg tta      1536
Ala Phe Gly Gly Thr Val Trp Leu Trp Pro Gln Trp Gln Ser Gly Leu
        500                 505                 510 ttg cgt aaa aac gcc cat gat gct tta gaa gcc tat cag gaa gcg att      1584
Leu Arg Lys Asn Ala His Asp Ala Leu Glu Ala Tyr Gln Glu Ala Ile
            515                 520                 525 cgc ttg att ctt agc gag gat ccg caa cct acg cca ctg gcc tgg cag      1632
Arg Leu Ile Leu Ser Glu Asp Pro Gln Pro Thr Pro Leu Ala Trp Gln
    530                 535                 540 cga atg cgg gta aat cag gca cat aac act ctg tat aac tca ttg aat      1680
Arg Met Arg Val Asn Gln Ala His Asn Thr Leu Tyr Asn Ser Leu Asn
545                 550                 555                 560 cag gcg atg cag gaa ccg gcg ttt aac agc cat tat ctg gca gat atg      1728
Gln Ala Met Gln Glu Pro Ala Phe Asn Ser His Tyr Leu Ala Asp Met
                565                 570                 575 aaa ctg tgg gta acg cac agc cag ttt att gtt gag cat att aat gcc      1776
Lys Leu Trp Val Thr His Ser Gln Phe Ile Val Glu His Ile Asn Ala
        580                 585                 590 atg acc acg ctg gcg cgg gaa cac cgg gca ttg cca cct gaa ctg gca      1824
Met Thr Thr Leu Ala Arg Glu His Arg Ala Leu Pro Pro Glu Leu Ala
            595                 600                 605 caa gag tat tta cag tct tgt gaa atc gcc att cag cgt tgt cag cag      1872
Gln Glu Tyr Leu Gln Ser Cys Glu Ile Ala Ile Gln Arg Cys Gln Gln
    610                 615                 620 cga ctg gag tat gac gaa ccg gtt agt tct ggc gat gcc aat atc atg      1920
Arg Leu Glu Tyr Asp Glu Pro Val Ser Ser Gly Asp Ala Asn Ile Met
625                 630                 635                 640 gat gcg ccg gag atg cag ccg cac gaa ggc gcg gca ggt acg ctg gag      1968
Asp Ala Pro Glu Met Gln Pro His Glu Gly Ala Ala Gly Thr Leu Glu
                645                 650                 655 cag cat tta cag cgg gtt att ggt cat ctg aac acc atg cac acc att      2016
Gln His Leu Gln Arg Val Ile Gly His Leu Asn Thr Met His Thr Ile
        660                 665                 670 tcg tcg atg gca tgg cgt cag cga ccg cat cac ggg att tgg ctg agt      2064
Ser Ser Met Ala Trp Arg Gln Arg Pro His His Gly Ile Trp Leu Ser
            675                 680                 685
```

```
cgc aag ttg cgg gat tcg aag gcg taa                              2091
Arg Lys Leu Arg Asp Ser Lys Ala
    690             695

<210> SEQ ID NO 14
<211> LENGTH: 696
<212> TYPE: PRT
<213> ORGANISM: Escherichia coli

<400> SEQUENCE: 14

Met Trp Arg Arg Leu Ile Tyr His Pro Asp Ile Asn Tyr Ala Leu Arg
1               5                   10                  15

Gln Thr Leu Val Leu Cys Leu Pro Val Ala Val Gly Leu Met Leu Gly
            20                  25                  30

Glu Leu Arg Phe Gly Leu Leu Phe Ser Leu Val Pro Ala Cys Cys Asn
        35                  40                  45

Ile Ala Gly Leu Asp Thr Pro His Lys Arg Phe Phe Lys Arg Leu Ile
    50                  55                  60

Ile Gly Ala Ser Leu Phe Ala Thr Cys Ser Leu Leu Thr Gln Leu Leu
65                  70                  75                  80

Leu Ala Lys Asp Val Pro Leu Pro Phe Leu Thr Gly Leu Thr Leu
                85                  90                  95

Val Leu Gly Val Thr Ala Glu Leu Gly Pro Leu His Ala Lys Leu Leu
            100                 105                 110

Pro Ala Ser Leu Leu Ala Ala Ile Phe Thr Leu Ser Leu Ala Gly Tyr
        115                 120                 125

Met Pro Val Trp Glu Pro Leu Leu Ile Tyr Ala Leu Gly Thr Leu Trp
    130                 135                 140

Tyr Gly Leu Phe Asn Trp Phe Trp Phe Trp Ile Trp Arg Glu Gln Pro
145                 150                 155                 160

Leu Arg Glu Ser Leu Ser Leu Leu Tyr Arg Glu Leu Ala Asp Tyr Cys
                165                 170                 175

Glu Ala Lys Tyr Ser Leu Leu Thr Gln His Thr Asp Pro Glu Lys Ala
            180                 185                 190

Leu Pro Pro Leu Leu Val Arg Gln Gln Lys Ala Val Asp Leu Ile Thr
        195                 200                 205

Gln Cys Tyr Gln Gln Met His Met Leu Ser Ala Gln Asn Asn Thr Asp
    210                 215                 220

Tyr Lys Arg Met Leu Arg Ile Phe Gln Glu Ala Leu Asp Leu Gln Glu
225                 230                 235                 240

His Ile Ser Val Ser Leu His Gln Pro Glu Glu Val Gln Lys Leu Val
                245                 250                 255

Glu Arg Ser His Ala Glu Glu Val Ile Arg Trp Asn Ala Gln Thr Val
            260                 265                 270

Ala Ala Arg Leu Arg Val Leu Ala Asp Asp Ile Leu Tyr His Arg Leu
        275                 280                 285

Pro Thr Arg Phe Thr Met Glu Lys Gln Ile Gly Ala Leu Glu Lys Ile
    290                 295                 300

Ala Arg Gln His Pro Asp Asn Pro Val Gly Gln Phe Cys Tyr Trp His
305                 310                 315                 320

Phe Ser Arg Ile Ala Arg Val Leu Arg Thr Gln Lys Pro Leu Tyr Ala
                325                 330                 335

Arg Asp Leu Leu Ala Asp Lys Gln Arg Arg Met Pro Leu Leu Pro Ala
            340                 345                 350

Leu Lys Ser Tyr Leu Ser Leu Lys Ser Pro Ala Leu Arg Asn Ala Gly
        355                 360                 365
```

```
Arg Leu Ser Val Met Leu Ser Val Ala Ser Leu Met Gly Thr Ala Leu
        370                 375                 380

His Leu Pro Lys Ser Tyr Trp Ile Leu Met Thr Val Leu Leu Val Thr
385                 390                 395                 400

Gln Asn Gly Tyr Gly Ala Thr Arg Leu Arg Ile Val Asn Arg Ser Val
                405                 410                 415

Gly Thr Val Val Gly Leu Ile Ile Ala Gly Val Ala Leu His Phe Lys
            420                 425                 430

Ile Pro Glu Gly Tyr Thr Leu Thr Leu Met Leu Ile Thr Thr Leu Ala
        435                 440                 445

Ser Tyr Leu Ile Leu Arg Lys Asn Tyr Gly Trp Ala Thr Val Gly Phe
450                 455                 460

Thr Ile Thr Ala Val Tyr Thr Leu Gln Leu Leu Trp Leu Asn Gly Glu
465                 470                 475                 480

Gln Tyr Ile Leu Pro Arg Leu Ile Asp Thr Ile Ile Gly Cys Leu Ile
                485                 490                 495

Ala Phe Gly Gly Thr Val Trp Leu Trp Pro Gln Trp Gln Ser Gly Leu
            500                 505                 510

Leu Arg Lys Asn Ala His Asp Ala Leu Glu Ala Tyr Gln Glu Ala Ile
        515                 520                 525

Arg Leu Ile Leu Ser Glu Asp Pro Gln Pro Thr Pro Leu Ala Trp Gln
530                 535                 540

Arg Met Arg Val Asn Gln Ala His Asn Thr Leu Tyr Asn Ser Leu Asn
545                 550                 555                 560

Gln Ala Met Gln Glu Pro Ala Phe Asn Ser His Tyr Leu Ala Asp Met
                565                 570                 575

Lys Leu Trp Val Thr His Ser Gln Phe Ile Val Glu His Ile Asn Ala
            580                 585                 590

Met Thr Thr Leu Ala Arg Glu His Arg Ala Leu Pro Pro Glu Leu Ala
        595                 600                 605

Gln Glu Tyr Leu Gln Ser Cys Glu Ile Ala Ile Gln Arg Cys Gln Gln
610                 615                 620

Arg Leu Glu Tyr Asp Glu Pro Gly Ser Ser Gly Asp Ala Asn Ile Met
625                 630                 635                 640

Asp Ala Pro Glu Met Gln Pro His Glu Gly Ala Ala Gly Thr Leu Glu
                645                 650                 655

Gln His Leu Gln Arg Val Ile Gly His Leu Asn Thr Met His Thr Ile
            660                 665                 670

Ser Ser Met Ala Trp Arg Gln Arg Pro His His Gly Ile Trp Leu Ser
        675                 680                 685

Arg Lys Leu Arg Asp Ser Lys Ala
690                 695

<210> SEQ ID NO 15
<211> LENGTH: 855
<212> TYPE: DNA
<213> ORGANISM: Physcomitrella patens
<220> FEATURE:
<221> NAME/KEY: CDS
<222> LOCATION: (1)..(855)
<223> OTHER INFORMATION: protein phosphatase 2C (EST564)

<400> SEQUENCE: 15 atg tca tgc gac gtt ctc tgc caa tct ttc aag gag gta gag ggc aag     48
Met Ser Cys Asp Val Leu Cys Gln Ser Phe Lys Glu Val Glu Gly Lys
1               5                   10                  15
```

| | | |
|---|---|---|
| ttc ttg gaa atc gtc gaa agg gct tgg gcc gtc aag ccg caa att gcc<br>Phe Leu Glu Ile Val Glu Arg Ala Trp Ala Val Lys Pro Gln Ile Ala<br>20 25 30 | | 96 |
| gct gtt gga tct tgt tgt ttg gtg gga gcc gta tgg gat tcc aaa ctg<br>Ala Val Gly Ser Cys Cys Leu Val Gly Ala Val Trp Asp Ser Lys Leu<br>35 40 45 | | 144 |
| tac atc gct agt ctt gga gat tct cga gct gtt tta ggt agt tgc tct<br>Tyr Ile Ala Ser Leu Gly Asp Ser Arg Ala Val Leu Gly Ser Cys Ser<br>50 55 60 | | 192 |
| cgt gac act ggc ctt cca gtt gct aag caa att tca aca gag cac aac<br>Arg Asp Thr Gly Leu Pro Val Ala Lys Gln Ile Ser Thr Glu His Asn<br>65 70 75 80 | | 240 |
| gca agc atc gag tct atc cgg aat gag ttg ttc gca aag cat agt gat<br>Ala Ser Ile Glu Ser Ile Arg Asn Glu Leu Phe Ala Lys His Ser Asp<br>85 90 95 | | 288 |
| gat ccg cag atc gtg gtt ttg aag cat gga gtg tgg cgt gtg aag ggt<br>Asp Pro Gln Ile Val Val Leu Lys His Gly Val Trp Arg Val Lys Gly<br>100 105 110 | | 336 |
| att att cag att tca cgc tca att ggt gat ttt tac ttg aag aaa gcc<br>Ile Ile Gln Ile Ser Arg Ser Ile Gly Asp Phe Tyr Leu Lys Lys Ala<br>115 120 125 | | 384 |
| gaa ttt aat cag ccg cct ctt ata gcc agg ttc cgg ctt cca gat ccc<br>Glu Phe Asn Gln Pro Pro Leu Ile Ala Arg Phe Arg Leu Pro Asp Pro<br>130 135 140 | | 432 |
| ctc aag aga cct gtc ata agc tca gag ccg gag tgc aac gtc att aca<br>Leu Lys Arg Pro Val Ile Ser Ser Glu Pro Glu Cys Asn Val Ile Thr<br>145 150 155 160 | | 480 |
| ctc ggc ccg gat gac gaa ttc gtc att ttt gca tct gat ggc ctt tgg<br>Leu Gly Pro Asp Asp Glu Phe Val Ile Phe Ala Ser Asp Gly Leu Trp<br>165 170 175 | | 528 |
| gag cac ttg agc agc aaa gag gcc gta gac att gtg tat agt cat ccc<br>Glu His Leu Ser Ser Lys Glu Ala Val Asp Ile Val Tyr Ser His Pro<br>180 185 190 | | 576 |
| cgg gct ggg att gcc agg cgt ctg atc aaa gct gct ctt caa aaa gct<br>Arg Ala Gly Ile Ala Arg Arg Leu Ile Lys Ala Ala Leu Gln Lys Ala<br>195 200 205 | | 624 |
| gct act aaa cgt gaa atg cgg tac tct gat ttg aaa ggg att gag cgc<br>Ala Thr Lys Arg Glu Met Arg Tyr Ser Asp Leu Lys Gly Ile Glu Arg<br>210 215 220 | | 672 |
| ggg ata cga cgg cat ttt cat gat gac ata act gtt gtg gtt ctt tat<br>Gly Ile Arg Arg His Phe His Asp Asp Ile Thr Val Val Val Leu Tyr<br>225 230 235 240 | | 720 |
| ttg gac act aaa ctg ctc aac aga ggt ggt agt att tct aat cat att<br>Leu Asp Thr Lys Leu Leu Asn Arg Gly Gly Ser Ile Ser Asn His Ile<br>245 250 255 | | 768 |
| tct tcg aaa tgt cca att gac atg cca aaa ggc gat aac cct ccg tcg<br>Ser Ser Lys Cys Pro Ile Asp Met Pro Lys Gly Asp Asn Pro Pro Ser<br>260 265 270 | | 816 |
| tta gtt agc tct aac atg aac tta gct ttt aac aaa taa<br>Leu Val Ser Ser Asn Met Asn Leu Ala Phe Asn Lys<br>275 280 | | 855 |

<210> SEQ ID NO 16
<211> LENGTH: 284
<212> TYPE: PRT
<213> ORGANISM: Physcomitrella patens

<400> SEQUENCE: 16

Met Ser Cys Asp Val Leu Cys Gln Ser Phe Lys Glu Val Glu Gly Lys
1               5                   10                  15

Phe Leu Glu Ile Val Glu Arg Ala Trp Ala Val Lys Pro Gln Ile Ala

```
                        20                  25                  30
    Ala Val Gly Ser Cys Cys Leu Val Gly Ala Val Trp Asp Ser Lys Leu
             35                  40                  45

Tyr Ile Ala Ser Leu Gly Asp Ser Arg Ala Val Leu Gly Ser Cys Ser
     50                  55                  60

Arg Asp Thr Gly Leu Pro Val Ala Lys Gln Ile Ser Thr Glu His Asn
    65                  70                  75                  80

Ala Ser Ile Glu Ser Ile Arg Asn Glu Leu Phe Ala Lys His Ser Asp
                     85                  90                  95

Asp Pro Gln Ile Val Val Leu Lys His Gly Val Trp Arg Val Lys Gly
                100                 105                 110

Ile Ile Gln Ile Ser Arg Ser Ile Gly Asp Phe Tyr Leu Lys Lys Ala
                115                 120                 125

Glu Phe Asn Gln Pro Pro Leu Ile Ala Arg Phe Arg Leu Pro Asp Pro
            130                 135                 140

Leu Lys Arg Pro Val Ile Ser Ser Glu Pro Glu Cys Asn Val Ile Thr
    145                 150                 155                 160

Leu Gly Pro Asp Asp Glu Phe Val Ile Phe Ala Ser Asp Gly Leu Trp
                    165                 170                 175

Glu His Leu Ser Ser Lys Glu Ala Val Asp Ile Val Tyr Ser His Pro
                180                 185                 190

Arg Ala Gly Ile Ala Arg Arg Leu Ile Lys Ala Ala Leu Gln Lys Ala
                195                 200                 205

Ala Thr Lys Arg Glu Met Arg Tyr Ser Asp Leu Lys Gly Ile Glu Arg
            210                 215                 220

Gly Ile Arg Arg His Phe His Asp Asp Ile Thr Val Val Val Leu Tyr
    225                 230                 235                 240

Leu Asp Thr Lys Leu Leu Asn Arg Gly Gly Ser Ile Ser Asn His Ile
                    245                 250                 255

Ser Ser Lys Cys Pro Ile Asp Met Pro Lys Gly Asp Asn Pro Pro Ser
                260                 265                 270

Leu Val Ser Ser Asn Met Asn Leu Ala Phe Asn Lys
            275                 280

<210> SEQ ID NO 17
<211> LENGTH: 1473
<212> TYPE: DNA
<213> ORGANISM: Brassica napus
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: CDS
<222> LOCATION: (102)..(1253)
<223> OTHER INFORMATION: protein phosphatase 2C (BN49502266)

<400> SEQUENCE: 17
ccaataatca aatcaaaacc ctttcgatca gttgttncag gaaaaaaaaa aacccttcg          60 atctcattcc atttcgaatc agaaaaccct agcaattgac g atg ttg cga gct tta      116
                                            Met Leu Arg Ala Leu
                                              1               5 gcg cgg cct ctc gaa cgg tgt tta gga agc aga gcg agc ggc gac ggt        164
Ala Arg Pro Leu Glu Arg Cys Leu Gly Ser Arg Ala Ser Gly Asp Gly
            10                  15                  20 ttg ctc tgg caa tcg gag ttg aaa cca cac gcc ggc gga gat tac tcg        212
Leu Leu Trp Gln Ser Glu Leu Lys Pro His Ala Gly Gly Asp Tyr Ser
        25                  30                  35
```

| | | |
|---|---|---|
| atc gcg gtg gtt caa gcc aat tct agc cta gag gat cag agt cag gtg<br>Ile Ala Val Val Gln Ala Asn Ser Ser Leu Glu Asp Gln Ser Gln Val<br>40 45 50 | 260 | |
| ttc acg tct tcc tcc gct act tac gtc ggc gtc tac gac ggc cat ggc<br>Phe Thr Ser Ser Ser Ala Thr Tyr Val Gly Val Tyr Asp Gly His Gly<br>55 60 65 | 308 | |
| gga ccc gaa gct tct aga ttc gtt aac aga cat ctc ttt cct tat att<br>Gly Pro Glu Ala Ser Arg Phe Val Asn Arg His Leu Phe Pro Tyr Ile<br>70 75 80 85 | 356 | |
| cag aag ttc gca aaa gaa cat gga gga ctg tct gca gac gtt att aaa<br>Gln Lys Phe Ala Lys Glu His Gly Gly Leu Ser Ala Asp Val Ile Lys<br>90 95 100 | 404 | |
| aaa gca ttc aaa gaa act gaa gag gat ttt tgc ggt atg gtt aaa cgc<br>Lys Ala Phe Lys Glu Thr Glu Glu Asp Phe Cys Gly Met Val Lys Arg<br>105 110 115 | 452 | |
| tca ctt ccc atg aag cca cag atg gct act gta gga tct tgc tgt ctc<br>Ser Leu Pro Met Lys Pro Gln Met Ala Thr Val Gly Ser Cys Cys Leu<br>120 125 130 | 500 | |
| ttt ggt gcc atc tct aac ggc acg ctc tat gtc gcg aat ctt gga gac<br>Phe Gly Ala Ile Ser Asn Gly Thr Leu Tyr Val Ala Asn Leu Gly Asp<br>135 140 145 | 548 | |
| tcg aga gcc gtt ctt ggg agc gtt gtt gca ggg gat gat agt aat agt<br>Ser Arg Ala Val Leu Gly Ser Val Val Ala Gly Asp Asp Ser Asn Ser<br>150 155 160 165 | 596 | |
| agt aac aag ggt gct gca gct gaa cgg ttg tcc act gat cat aac gtt<br>Ser Asn Lys Gly Ala Ala Ala Glu Arg Leu Ser Thr Asp His Asn Val<br>170 175 180 | 644 | |
| gct gtt gaa gaa gtg agg aag gag gtt aag gaa ctt aac ccg gat gat<br>Ala Val Glu Glu Val Arg Lys Glu Val Lys Glu Leu Asn Pro Asp Asp<br>185 190 195 | 692 | |
| tcg cag atc gtc atg tac att cgt gga gtt tgg agg att aaa ggc att<br>Ser Gln Ile Val Met Tyr Ile Arg Gly Val Trp Arg Ile Lys Gly Ile<br>200 205 210 | 740 | |
| att cag gta tct aga tca att ggg gat gtt tac ttg aag aaa ccg gag<br>Ile Gln Val Ser Arg Ser Ile Gly Asp Val Tyr Leu Lys Lys Pro Glu<br>215 220 225 | 788 | |
| ttt tac agg gat ccg ata ttc cag caa cat gga aat cac att cct ttg<br>Phe Tyr Arg Asp Pro Ile Phe Gln Gln His Gly Asn His Ile Pro Leu<br>230 235 240 245 | 836 | |
| agg aga ccc gcg atg aca gct gaa ccg tcc att ata gta agg aag ctt<br>Arg Arg Pro Ala Met Thr Ala Glu Pro Ser Ile Ile Val Arg Lys Leu<br>250 255 260 | 884 | |
| aag ccg caa gac ttg ttt ctg ata ttt gca tca gat ggt ctc tgg gag<br>Lys Pro Gln Asp Leu Phe Leu Ile Phe Ala Ser Asp Gly Leu Trp Glu<br>265 270 275 | 932 | |
| cat ctt agt gat gaa gca gca gta gaa att gta ctc aaa cac cca aga<br>His Leu Ser Asp Glu Ala Ala Val Glu Ile Val Leu Lys His Pro Arg<br>280 285 290 | 980 | |
| act ggg att gca aga aaa ctt gta aga gca gct ctt gaa gaa gca gca<br>Thr Gly Ile Ala Arg Lys Leu Val Arg Ala Ala Leu Glu Glu Ala Ala<br>295 300 305 | 1028 | |
| agg aag aga gaa atg aga tat gga gat ata aag aaa ata gcc aaa ggg<br>Arg Lys Arg Glu Met Arg Tyr Gly Asp Ile Lys Lys Ile Ala Lys Gly<br>310 315 320 325 | 1076 | |
| gtt aga aga cat ttc cat gac gac ata agc gtc gtt gta gtt tat ctt<br>Val Arg Arg His Phe His Asp Asp Ile Ser Val Val Val Val Tyr Leu<br>330 335 340 | 1124 | |
| gat caa caa aaa acc act tct tca tcg aat gat aga ttg atc cag aaa<br>Asp Gln Gln Lys Thr Thr Ser Ser Ser Asn Asp Arg Leu Ile Gln Lys<br>345 350 355 | 1172 | |

```
gga gga atc act gct cca ccg gat atc tac tcg tta cgt tca gat gaa     1220
Gly Gly Ile Thr Ala Pro Pro Asp Ile Tyr Ser Leu Arg Ser Asp Glu
        360                 365                 370 gct gag caa cga cgg cta ctc aat gtg tta tat tgatactctc tggttagagg   1273
Ala Glu Gln Arg Arg Leu Leu Asn Val Leu Tyr
    375                 380 gatacaactt gtttacatat ttgtttaatc ttttacaaag aatgtttgtt cttttttctt   1333
tcttttttta atatttggag ttggatttgt atattctttt taccagcaag gaacgaaaac   1393
ccttctcttt tgggggcaaa acagttttgg ttttgacaaa caatataaag tgaaaccgtt   1453
tgcaaaaaaa aaaaaaaaaa                                               1473

<210> SEQ ID NO 18
<211> LENGTH: 384
<212> TYPE: PRT
<213> ORGANISM: Brassica napus

<400> SEQUENCE: 18

Met Leu Arg Ala Leu Ala Arg Pro Leu Glu Arg Cys Leu Gly Ser Arg
1               5                   10                  15

Ala Ser Gly Asp Gly Leu Leu Trp Gln Ser Glu Leu Lys Pro His Ala
            20                  25                  30

Gly Gly Asp Tyr Ser Ile Ala Val Val Gln Ala Asn Ser Ser Leu Glu
        35                  40                  45

Asp Gln Ser Gln Val Phe Thr Ser Ser Ala Thr Tyr Val Gly Val
    50                  55                  60

Tyr Asp Gly His Gly Gly Pro Glu Ala Ser Arg Phe Val Asn Arg His
65                  70                  75                  80

Leu Phe Pro Tyr Ile Gln Lys Phe Ala Lys Glu His Gly Gly Leu Ser
                85                  90                  95

Ala Asp Val Ile Lys Lys Ala Phe Lys Glu Thr Glu Glu Asp Phe Cys
            100                 105                 110

Gly Met Val Lys Arg Ser Leu Pro Met Lys Pro Gln Met Ala Thr Val
        115                 120                 125

Gly Ser Cys Cys Leu Phe Gly Ala Ile Ser Asn Gly Thr Leu Tyr Val
    130                 135                 140

Ala Asn Leu Gly Asp Ser Arg Ala Val Leu Gly Ser Val Val Ala Gly
145                 150                 155                 160

Asp Asp Ser Asn Ser Ser Asn Lys Gly Ala Ala Ala Glu Arg Leu Ser
                165                 170                 175

Thr Asp His Asn Val Ala Val Glu Val Arg Lys Glu Val Lys Glu
            180                 185                 190

Leu Asn Pro Asp Asp Ser Gln Ile Val Met Tyr Ile Arg Gly Val Trp
        195                 200                 205

Arg Ile Lys Gly Ile Ile Gln Val Ser Arg Ser Ile Gly Asp Val Tyr
    210                 215                 220

Leu Lys Lys Pro Glu Phe Tyr Arg Asp Pro Ile Phe Gln Gln His Gly
225                 230                 235                 240

Asn His Ile Pro Leu Arg Arg Pro Ala Met Thr Ala Glu Pro Ser Ile
                245                 250                 255

Ile Val Arg Lys Leu Lys Pro Gln Asp Leu Phe Leu Ile Phe Ala Ser
            260                 265                 270

Asp Gly Leu Trp Glu His Leu Ser Asp Glu Ala Ala Val Glu Ile Val
        275                 280                 285

Leu Lys His Pro Arg Thr Gly Ile Ala Arg Lys Leu Val Arg Ala Ala
    290                 295                 300
```

```
Leu Glu Glu Ala Ala Arg Lys Arg Glu Met Arg Tyr Gly Asp Ile Lys
305                 310                 315                 320

Lys Ile Ala Lys Gly Val Arg Arg His Phe His Asp Asp Ile Ser Val
            325                 330                 335

Val Val Val Tyr Leu Asp Gln Gln Lys Thr Thr Ser Ser Ser Asn Asp
                340                 345                 350

Arg Leu Ile Gln Lys Gly Gly Ile Thr Ala Pro Pro Asp Ile Tyr Ser
            355                 360                 365

Leu Arg Ser Asp Glu Ala Glu Gln Arg Arg Leu Leu Asn Val Leu Tyr
        370                 375                 380

<210> SEQ ID NO 19
<211> LENGTH: 1321
<212> TYPE: DNA
<213> ORGANISM: Glycine max
<220> FEATURE:
<221> NAME/KEY: CDS
<222> LOCATION: (91)..(1125)
<223> OTHER INFORMATION: protein phosphatase 2C (GM49788080)

<400> SEQUENCE: 19
tcccgggtcg acgatttcgt ggttacgggg cggaaggaag ggctgctgtg gtacaaggat        60
gcggggcagc acttgtttgg tgaatactca atg gct gtt gtc cag gcc aac aac       114
                                   Met Ala Val Val Gln Ala Asn Asn
                                     1               5 ctg ctc gag gac cag agc cag att gag tct ggt cct ctc agc ctg ctt        162
Leu Leu Glu Asp Gln Ser Gln Ile Glu Ser Gly Pro Leu Ser Leu Leu
     10                  15                  20 gac act ggc cct tat ggg acc ttt gtt ggt gta tat gat gga cac ggt        210
Asp Thr Gly Pro Tyr Gly Thr Phe Val Gly Val Tyr Asp Gly His Gly
 25                  30                  35                  40 ggg ccc gag acg tcg cgc tac gtc tgt gat cat ctc ttc caa cat cta        258
Gly Pro Glu Thr Ser Arg Tyr Val Cys Asp His Leu Phe Gln His Leu
                 45                  50                  55 aaa cga ttt gca tct gag cag aag tcc atg tct atg gag gtt att cgg        306
Lys Arg Phe Ala Ser Glu Gln Lys Ser Met Ser Met Glu Val Ile Arg
             60                  65                  70 aag gca tac caa gcc aca gaa gaa ggt ttt ttg tca gtg gtt acc aaa        354
Lys Ala Tyr Gln Ala Thr Glu Glu Gly Phe Leu Ser Val Val Thr Lys
         75                  80                  85 cag tgg ccc atg aat ccc caa att gct gct gtg gga tct tgt tgt ttg        402
Gln Trp Pro Met Asn Pro Gln Ile Ala Ala Val Gly Ser Cys Cys Leu
     90                  95                 100 gtt ggt gtg att tgt ggt ggt atc ctc tat att gct aac ctt ggt gat        450
Val Gly Val Ile Cys Gly Gly Ile Leu Tyr Ile Ala Asn Leu Gly Asp
105                 110                 115                 120 tcc cgt gct gtg ctt ggc cgg gtg gtc aga gca act ggg gag gtt ttg        498
Ser Arg Ala Val Leu Gly Arg Val Val Arg Ala Thr Gly Glu Val Leu
                125                 130                 135 gcg atc cag ctt tcg tca gag cat aat gtg gcc ata gaa tct gtg aga        546
Ala Ile Gln Leu Ser Ser Glu His Asn Val Ala Ile Glu Ser Val Arg
            140                 145                 150 caa gag atg cat tct ttg cat ccg gat gac tca aaa att gtg gtt cta        594
Gln Glu Met His Ser Leu His Pro Asp Asp Ser Lys Ile Val Val Leu
        155                 160                 165 aag cac aat gta tgg cgg gtg aag ggt ctg ata cag att tct aga tcc        642
Lys His Asn Val Trp Arg Val Lys Gly Leu Ile Gln Ile Ser Arg Ser
    170                 175                 180 att ggc gat gta tac cta aaa aag gct gaa ttt aac aag gaa ccg ttg        690
Ile Gly Asp Val Tyr Leu Lys Lys Ala Glu Phe Asn Lys Glu Pro Leu
```

```
tat gct aag ttt cgt gtg cgg gaa ggt ttt aag agg ccc att ttg agc    738
Tyr Ala Lys Phe Arg Val Arg Glu Gly Phe Lys Arg Pro Ile Leu Ser
            205                 210                 215 tct gac cca tca att tct gtc cat gaa ctt caa cag cat gat caa ttt    786
Ser Asp Pro Ser Ile Ser Val His Glu Leu Gln Gln His Asp Gln Phe
            220                 225                 230 ctc ata ttt gct tct gat ggt ctt tgg gaa cac ctt agc aat cag gat    834
Leu Ile Phe Ala Ser Asp Gly Leu Trp Glu His Leu Ser Asn Gln Asp
            235                 240                 245 gcc gtt gat ata gtt caa aac aac cca cac aat gga att gct cgg agg    882
Ala Val Asp Ile Val Gln Asn Asn Pro His Asn Gly Ile Ala Arg Arg
            250                 255                 260 ctc atc aaa gct gcg ttg caa gaa gca gca aaa aag aga gag atg agg    930
Leu Ile Lys Ala Ala Leu Gln Glu Ala Ala Lys Lys Arg Glu Met Arg
265                 270                 275                 280 tac tct gat ttg aag aaa att gac cgt ggt gtc cgc cgg cat ttc cat    978
Tyr Ser Asp Leu Lys Lys Ile Asp Arg Gly Val Arg Arg His Phe His
            285                 290                 295 gat gac atc aca gtt gta gtt gta ttt ctt gac tcc aat ctt gtc agc   1026
Asp Asp Ile Thr Val Val Val Val Phe Leu Asp Ser Asn Leu Val Ser
            300                 305                 310 aga gcc agc tca gta aga ggt cct cct tta tcg gtg aga gga ggt ggt   1074
Arg Ala Ser Ser Val Arg Gly Pro Pro Leu Ser Val Arg Gly Gly Gly
            315                 320                 325 gtt ccc cta cct tct aga act ttg gct ccc tgt gct gca cct atg gaa   1122
Val Pro Leu Pro Ser Arg Thr Leu Ala Pro Cys Ala Ala Pro Met Glu
330                 335                 340 act tagttcaggt tgatgaagct ggctgtatga tctgttatgc ttctatttag         1175
Thr
345 tgttgtaccc ttagcagaca ttgagctctg gtgatccacc agattgtata tccaatttaa  1235 cagagattga aaaatgttc gttcaattag tacaatgtta caagtgactt ggggtatgta   1295 gcttgcgtga gtaaagcatc atggaa                                       1321

<210> SEQ ID NO 20
<211> LENGTH: 345
<212> TYPE: PRT
<213> ORGANISM: Glycine max

<400> SEQUENCE: 20

Met Ala Val Val Gln Ala Asn Asn Leu Leu Glu Asp Gln Ser Gln Ile
1               5                   10                  15

Glu Ser Gly Pro Leu Ser Leu Leu Asp Thr Gly Pro Tyr Gly Thr Phe
            20                  25                  30

Val Gly Val Tyr Asp Gly His Gly Gly Pro Glu Thr Ser Arg Tyr Val
        35                  40                  45

Cys Asp His Leu Phe Gln His Leu Lys Arg Phe Ala Ser Glu Gln Lys
    50                  55                  60

Ser Met Ser Met Glu Val Ile Arg Lys Ala Tyr Gln Ala Thr Glu Glu
65                  70                  75                  80

Gly Phe Leu Ser Val Val Thr Lys Gln Trp Pro Met Asn Pro Gln Ile
                85                  90                  95

Ala Ala Val Gly Ser Cys Cys Leu Val Gly Val Ile Cys Gly Gly Ile
            100                 105                 110

Leu Tyr Ile Ala Asn Leu Gly Asp Ser Arg Ala Val Leu Gly Arg Val
        115                 120                 125
```

```
Val Arg Ala Thr Gly Glu Val Leu Ala Ile Gln Leu Ser Ser Glu His
        130                 135                 140

Asn Val Ala Ile Glu Ser Val Arg Gln Glu Met His Ser Leu His Pro
145                 150                 155                 160

Asp Asp Ser Lys Ile Val Val Leu Lys His Asn Val Trp Arg Val Lys
                165                 170                 175

Gly Leu Ile Gln Ile Ser Arg Ser Ile Gly Asp Val Tyr Leu Lys Lys
                180                 185                 190

Ala Glu Phe Asn Lys Glu Pro Leu Tyr Ala Lys Phe Arg Val Arg Glu
            195                 200                 205

Gly Phe Lys Arg Pro Ile Leu Ser Ser Asp Pro Ser Ile Ser Val His
210                 215                 220

Glu Leu Gln Gln His Asp Gln Phe Leu Ile Phe Ala Ser Asp Gly Leu
225                 230                 235                 240

Trp Glu His Leu Ser Asn Gln Asp Ala Val Asp Ile Val Gln Asn Asn
                245                 250                 255

Pro His Asn Gly Ile Ala Arg Arg Leu Ile Lys Ala Ala Leu Gln Glu
                260                 265                 270

Ala Ala Lys Lys Arg Glu Met Arg Tyr Ser Asp Leu Lys Lys Ile Asp
            275                 280                 285

Arg Gly Val Arg Arg His Phe His Asp Asp Ile Thr Val Val Val Val
290                 295                 300

Phe Leu Asp Ser Asn Leu Val Ser Arg Ala Ser Ser Val Arg Gly Pro
305                 310                 315                 320

Pro Leu Ser Val Arg Gly Gly Val Pro Leu Pro Ser Arg Thr Leu
                325                 330                 335

Ala Pro Cys Ala Ala Pro Met Glu Thr
            340                 345

<210> SEQ ID NO 21
<211> LENGTH: 1700
<212> TYPE: DNA
<213> ORGANISM: Glycine max
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: CDS
<222> LOCATION: (215)..(1339)
<223> OTHER INFORMATION: protein phosphatase 2C (GM53049821)

<400> SEQUENCE: 21
tgctcctcta ccaccgaaca canccccggc caccaccgaa cgctaacgtg cgccccttcc      60
ttaccctgcg cctcggcact ctcccttatt cccccctcctt cataagctcc gcgttaaccg    120
tcctctctct ctctctctct cggatcggag cgagactggc ggctccggcg ttgggggcgt    180
tagggttagg gttagggttt ccaagagatg tggt atg ctc cag gca ttg atg aat    235
                                      Met Leu Gln Ala Leu Met Asn
                                        1               5 ctg ttc tcg ctg tgt tgg aag cca ttt ggc cgc gat gct gct gat cga    283
Leu Phe Ser Leu Cys Trp Lys Pro Phe Gly Arg Asp Ala Ala Asp Arg
        10                  15                  20 atc gat tcc atc gga gtt acc gga aga gaa ggc aaa gac ggc ttg ctt    331
Ile Asp Ser Ile Gly Val Thr Gly Arg Glu Gly Lys Asp Gly Leu Leu
    25                  30                  35 tgg ttc cgc gac ggc gga aaa tat ggc tct ggc gat ttc tcc atg gcc    379
Trp Phe Arg Asp Gly Gly Lys Tyr Gly Ser Gly Asp Phe Ser Met Ala
40                  45                  50                  55
```

```
gtc gtt cag gcc aac cag gtt ctc gaa gac cag agc cag atc gag tct   427
Val Val Gln Ala Asn Gln Val Leu Glu Asp Gln Ser Gln Ile Glu Ser
         60                  65                  70 ggt cct ctc ggc acc ttc gtc ggc atc tac gac ggt cac gga gga ccc   475
Gly Pro Leu Gly Thr Phe Val Gly Ile Tyr Asp Gly His Gly Gly Pro
     75                  80                  85 gac gcc tca aga tac gtt tgc gat cac ttg ttt cgc cat ttt caa gca   523
Asp Ala Ser Arg Tyr Val Cys Asp His Leu Phe Arg His Phe Gln Ala
             90                  95                 100 ata tca gct gag tca cgc ggg gtt gtg aca act gag aca atc gaa aga   571
Ile Ser Ala Glu Ser Arg Gly Val Val Thr Thr Glu Thr Ile Glu Arg
        105                 110                 115 gca ttt cgc caa aca gaa gag ggg tac atg gcc ctc gtg tca ggc tcg   619
Ala Phe Arg Gln Thr Glu Glu Gly Tyr Met Ala Leu Val Ser Gly Ser
120                 125                 130                 135 tgg aat gct cga cct cat att gca agt gct ggg acc tgt tgt cta gtt   667
Trp Asn Ala Arg Pro His Ile Ala Ser Ala Gly Thr Cys Cys Leu Val
                140                 145                 150 gga gtg ata ttt cag cag aca ctc ttt gtg gca aac gct gga gat tcc   715
Gly Val Ile Phe Gln Gln Thr Leu Phe Val Ala Asn Ala Gly Asp Ser
            155                 160                 165 cgt gtt gta ttg ggt aag aaa gtt ggc aac act gga ggt atg gct gca   763
Arg Val Val Leu Gly Lys Lys Val Gly Asn Thr Gly Gly Met Ala Ala
        170                 175                 180 att cag ctg tct aca gaa cac aat gca aat ctt gag gct gtt agg cag   811
Ile Gln Leu Ser Thr Glu His Asn Ala Asn Leu Glu Ala Val Arg Gln
    185                 190                 195 gaa ctt aaa gaa tta cat cct cat gat ccc caa att gtt gtc ctc aaa   859
Glu Leu Lys Glu Leu His Pro His Asp Pro Gln Ile Val Val Leu Lys
200                 205                 210                 215 cat gga gtg tgg aga gta aaa ggc att att cag gtt tct aga tct ata   907
His Gly Val Trp Arg Val Lys Gly Ile Ile Gln Val Ser Arg Ser Ile
                220                 225                 230 ggt gat gta tat ttg aag cat gca cag ttt aac cga gaa cca ctt aat   955
Gly Asp Val Tyr Leu Lys His Ala Gln Phe Asn Arg Glu Pro Leu Asn
            235                 240                 245 gca aaa ttc aga ctt cct gaa ccg atg aac atg cct atc ttg agt gct  1003
Ala Lys Phe Arg Leu Pro Glu Pro Met Asn Met Pro Ile Leu Ser Ala
        250                 255                 260 aat ccc act att ctt tct cat gct ctc caa cca aat gat tcc ttc ctt  1051
Asn Pro Thr Ile Leu Ser His Ala Leu Gln Pro Asn Asp Ser Phe Leu
    265                 270                 275 ata ttt gca tct gat ggt tta tgg gag cat ttg agt aac gag aaa gct  1099
Ile Phe Ala Ser Asp Gly Leu Trp Glu His Leu Ser Asn Glu Lys Ala
280                 285                 290                 295 gtg gat att gta aac agc aat cca cat gcg ggt agt gcc aag aga ctt  1147
Val Asp Ile Val Asn Ser Asn Pro His Ala Gly Ser Ala Lys Arg Leu
                300                 305                 310 atc aag gct gct ctc cat gaa gca gca aga aaa cga gaa atg cga tat  1195
Ile Lys Ala Ala Leu His Glu Ala Ala Arg Lys Arg Glu Met Arg Tyr
            315                 320                 325 tca gac ctc cgt aag att gac aag aaa gtt cga cgc cat ttt cat gat  1243
Ser Asp Leu Arg Lys Ile Asp Lys Lys Val Arg Arg His Phe His Asp
        330                 335                 340 gat ata tcc gtt att gtt tta ttc tta aat cac gac ctt att tcc aga  1291
Asp Ile Ser Val Ile Val Leu Phe Leu Asn His Asp Leu Ile Ser Arg
    345                 350                 355 ggc aca gtg cta gac ccg aca ctt tca att cga agc gct ctc gat cac  1339
Gly Thr Val Leu Asp Pro Thr Leu Ser Ile Arg Ser Ala Leu Asp His
360                 365                 370                 375
```

-continued

```
tgacttgtat cactgtaagc agtcttgtac gagttttgg caactgtacc gatacctgaa    1399
gcattggtag gtacctggct ataatatgtc atttctatgg cacatatggc ttctggtacc    1459
gacatcattc ttgaggcacg agaatttatt aagttataac atattattag aaatttattc    1519
ataaagagga aaaaataaa tacaaaaata tcttattccc ttttctaacc ttatagtttt     1579
acccgaaata ctggatttta tttatttgtt tgttttttg gctgaacata gctaatcgaa     1639
cagcatgttg attgaattca aagttatttt acaacaaatt atatggaaaa aaaaaaaaa    1699 a                                                                    1700
```

<210> SEQ ID NO 22
<211> LENGTH: 375
<212> TYPE: PRT
<213> ORGANISM: Glycine max

<400> SEQUENCE: 22

```
Met Leu Gln Ala Leu Met Asn Leu Phe Ser Leu Cys Trp Lys Pro Phe
1               5                   10                  15

Gly Arg Asp Ala Ala Asp Arg Ile Asp Ser Ile Gly Val Thr Gly Arg
            20                  25                  30

Glu Gly Lys Asp Gly Leu Leu Trp Phe Arg Asp Gly Lys Tyr Gly
        35                  40                  45

Ser Gly Asp Phe Ser Met Ala Val Val Gln Ala Asn Gln Val Leu Glu
    50                  55                  60

Asp Gln Ser Gln Ile Glu Ser Gly Pro Leu Gly Thr Phe Val Gly Ile
65                  70                  75                  80

Tyr Asp Gly His Gly Gly Pro Asp Ala Ser Arg Tyr Val Cys Asp His
                85                  90                  95

Leu Phe Arg His Phe Gln Ala Ile Ser Ala Glu Ser Arg Gly Val Val
            100                 105                 110

Thr Thr Glu Thr Ile Glu Arg Ala Phe Arg Gln Thr Glu Glu Gly Tyr
        115                 120                 125

Met Ala Leu Val Ser Gly Ser Trp Asn Ala Arg Pro His Ile Ala Ser
    130                 135                 140

Ala Gly Thr Cys Cys Leu Val Gly Val Ile Phe Gln Gln Thr Leu Phe
145                 150                 155                 160

Val Ala Asn Ala Gly Asp Ser Arg Val Val Leu Gly Lys Lys Val Gly
                165                 170                 175

Asn Thr Gly Gly Met Ala Ala Ile Gln Leu Ser Thr Glu His Asn Ala
            180                 185                 190

Asn Leu Glu Ala Val Arg Gln Glu Leu Lys Glu Leu His Pro His Asp
        195                 200                 205

Pro Gln Ile Val Val Leu Lys His Gly Val Trp Arg Val Lys Gly Ile
    210                 215                 220

Ile Gln Val Ser Arg Ser Ile Gly Asp Val Tyr Leu Lys His Ala Gln
225                 230                 235                 240

Phe Asn Arg Glu Pro Leu Asn Ala Lys Phe Arg Leu Pro Glu Pro Met
                245                 250                 255

Asn Met Pro Ile Leu Ser Ala Asn Pro Thr Ile Leu Ser His Ala Leu
            260                 265                 270

Gln Pro Asn Asp Ser Phe Leu Ile Phe Ala Ser Asp Gly Leu Trp Glu
        275                 280                 285

His Leu Ser Asn Glu Lys Ala Val Asp Ile Val Asn Ser Asn Pro His
    290                 295                 300

Ala Gly Ser Ala Lys Arg Leu Ile Lys Ala Ala Leu His Glu Ala Ala
```

```
                305                 310                 315                 320
Arg Lys Arg Glu Met Arg Tyr Ser Asp Leu Arg Lys Ile Asp Lys Lys
                    325                 330                 335

Val Arg Arg His Phe His Asp Asp Ile Ser Val Ile Val Leu Phe Leu
                    340                 345                 350

Asn His Asp Leu Ile Ser Arg Gly Thr Val Leu Asp Pro Thr Leu Ser
                    355                 360                 365

Ile Arg Ser Ala Leu Asp His
                    370                 375

<210> SEQ ID NO 23
<211> LENGTH: 1868
<212> TYPE: DNA
<213> ORGANISM: Zea mays
<220> FEATURE:
<221> NAME/KEY: CDS
<222> LOCATION: (215)..(1384)
<223> OTHER INFORMATION: protein phosphatase 2C (ZM58462719)

<400> SEQUENCE: 23
cgtggcgacg cccaaatcga gcgacctgat cgaggcccct cgcccctact cgctgaatcc     60
caatccgagc ccgccaattg ggcgcccccc cccgcccacg caaaggacag atagaagaaa    120
attattggcg ctctgacaaa tccaactgag gttttcttgg actacagatg aagcgggctc    180
gaagggcgta tgtgcaagag atgactgatg aggg atg cta gtg aaa ttg atg aac    235
                                    Met Leu Val Lys Leu Met Asn
                                      1               5 ttg tta cgg gcg tgc tgg cga ccg tca tcg aac cgg cat gcc cga aca    283
Leu Leu Arg Ala Cys Trp Arg Pro Ser Ser Asn Arg His Ala Arg Thr
            10                  15                  20 ggc tca gat gtt acc ggt agg cag gat gga ctt cta tgg tac aag gac    331
Gly Ser Asp Val Thr Gly Arg Gln Asp Gly Leu Leu Trp Tyr Lys Asp
 25                  30                  35 gcc ggg caa cat gtc aat ggg gag ttc tcc atg gct gtt gtt cag gca    379
Ala Gly Gln His Val Asn Gly Glu Phe Ser Met Ala Val Val Gln Ala
 40                  45                  50                  55 aat aac tta ctt gag gac cag tgt cag atc gag tcg ggc cca ctg agt    427
Asn Asn Leu Leu Glu Asp Gln Cys Gln Ile Glu Ser Gly Pro Leu Ser
                60                  65                  70 ttt cta gat tct gga cca tat ggc act ttc gtt ggt gtt tac gat ggg    475
Phe Leu Asp Ser Gly Pro Tyr Gly Thr Phe Val Gly Val Tyr Asp Gly
         75                  80                  85 cat ggt ggt cca gag acg gcc tgc tat atc aat gat cat ctt ttc cag    523
His Gly Gly Pro Glu Thr Ala Cys Tyr Ile Asn Asp His Leu Phe Gln
     90                  95                 100 aat ctg aaa aga ttt gca tct gaa cag aat gca atg tct gct gat gta    571
Asn Leu Lys Arg Phe Ala Ser Glu Gln Asn Ala Met Ser Ala Asp Val
105                 110                 115 ctg aag aag gca tat gaa gct aca gaa gat gga ttc ttc tcc att gtt    619
Leu Lys Lys Ala Tyr Glu Ala Thr Glu Asp Gly Phe Phe Ser Ile Val
120                 125                 130                 135 acc aaa caa tgg cct gta aag cct cag ata gca gct gtc ggc tca tgc    667
Thr Lys Gln Trp Pro Val Lys Pro Gln Ile Ala Ala Val Gly Ser Cys
                140                 145                 150 tgc ctg gtc ggt gta att tgt ggt ggc atg ctt tat gtt gcc aat gtt    715
Cys Leu Val Gly Val Ile Cys Gly Gly Met Leu Tyr Val Ala Asn Val
        155                 160                 165 ggg gat tcc cgt gtc gtt tta gga aaa cat gtt aag gcc act gga gaa    763
Gly Asp Ser Arg Val Val Leu Gly Lys His Val Lys Ala Thr Gly Glu
    170                 175                 180
```

| | | |
|---|---|---|
| gtt ttg gct gtc caa ctg tca gca gaa cat aat gtt agt att gcg tcc<br>Val Leu Ala Val Gln Leu Ser Ala Glu His Asn Val Ser Ile Ala Ser<br>185 190 195 | 811 | |
| gtg aga aaa gaa ctg cag tca atg cac cca gaa gat agg cac att gtt<br>Val Arg Lys Glu Leu Gln Ser Met His Pro Glu Asp Arg His Ile Val<br>200 205 210 215 | 859 | |
| gtt ctc aag cac aat gtt tgg cgt gtt aaa gga cta att cag gtt tgt<br>Val Leu Lys His Asn Val Trp Arg Val Lys Gly Leu Ile Gln Val Cys<br>220 225 230 | 907 | |
| aga tca att ggt gat gca tat ctc aaa aag caa gag ttc aac agg gaa<br>Arg Ser Ile Gly Asp Ala Tyr Leu Lys Lys Gln Glu Phe Asn Arg Glu<br>235 240 245 | 955 | |
| ccc cta tat gca aaa ttt cgc ctc cgt gaa cct ttt cac aag cca ata<br>Pro Leu Tyr Ala Lys Phe Arg Leu Arg Glu Pro Phe His Lys Pro Ile<br>250 255 260 | 1003 | |
| cta agt tca gaa cca tca atc agt gtg caa cca cta caa cca cac gac<br>Leu Ser Ser Glu Pro Ser Ile Ser Val Gln Pro Leu Gln Pro His Asp<br>265 270 275 | 1051 | |
| cag ttt ctc ata ttt gca tct gat gga ctt tgg gag cag tta acc aac<br>Gln Phe Leu Ile Phe Ala Ser Asp Gly Leu Trp Glu Gln Leu Thr Asn<br>280 285 290 295 | 1099 | |
| caa gag gca gtt gat att gtt cga agt agc ccc cgc agt ggc tgt gct<br>Gln Glu Ala Val Asp Ile Val Arg Ser Ser Pro Arg Ser Gly Cys Ala<br>300 305 310 | 1147 | |
| agg agg ctg ata aga gcg gca ctg caa gag gca gcc aag aaa aga gag<br>Arg Arg Leu Ile Arg Ala Ala Leu Gln Glu Ala Ala Lys Lys Arg Glu<br>315 320 325 | 1195 | |
| atg agg tac tcg gac ctc aag aag att gac cgc ggt gtt cgc cgc cac<br>Met Arg Tyr Ser Asp Leu Lys Lys Ile Asp Arg Gly Val Arg Arg His<br>330 335 340 | 1243 | |
| ttc cac gac gac ata aca gtc ata gta gtg ttc ctt gac tcc ggc ctc<br>Phe His Asp Asp Ile Thr Val Ile Val Val Phe Leu Asp Ser Gly Leu<br>345 350 355 | 1291 | |
| gta agc cag gcg agc aca cac cga ggt cca act ctt tcc ttg cga ggc<br>Val Ser Gln Ala Ser Thr His Arg Gly Pro Thr Leu Ser Leu Arg Gly<br>360 365 370 375 | 1339 | |
| ggt ggc ggc agc gct ggc ctg cgc agc aac aca ctt gca cct acg<br>Gly Gly Gly Ser Ala Gly Leu Arg Ser Asn Thr Leu Ala Pro Thr<br>380 385 390 | 1384 | |
| tgactataaa gtgcctggtg gagtggaggc tactgactga aggtggtttt ctttccttgt | 1444 | |
| gtcgaatgtg ttatatatgt acttgtacca gccaagatca ttcatccccc cccctaaaat | 1504 | |
| ggtgtaaaga agtaggagag gcgccgaagt tcctcaccag cgtatctgaa tgccctcaat | 1564 | |
| ggtgtcaagt tgtggactca agtggatagc ttcgctgaat cttctgatga tgctctgtgg | 1624 | |
| aaagctcgaa tcctttccac ctgaaaaagc aagtaatatg tcttccagtg ctggaattaa | 1684 | |
| cccctagtgc atatatatat gtatgaaata ataataaggc aaaaggagga gtaacttatt | 1744 | |
| taactaatgc tgtgaggtgt atttatgttt tgtatgtgta ctgcttttga ctgctactgc | 1804 | |
| atctactgtt gttaattgac cactggtgaa gtgaaatcac tggtttcgta aaaaaaaaaa | 1864 | |
| aaaa | 1868 | |

<210> SEQ ID NO 24
<211> LENGTH: 390
<212> TYPE: PRT
<213> ORGANISM: Zea mays

<400> SEQUENCE: 24

Met Leu Val Lys Leu Met Asn Leu Leu Arg Ala Cys Trp Arg Pro Ser
1               5                   10                  15

-continued

Ser Asn Arg His Ala Arg Thr Gly Ser Asp Val Thr Gly Arg Gln Asp
            20                  25                  30

Gly Leu Leu Trp Tyr Lys Asp Ala Gly Gln His Val Asn Gly Glu Phe
        35                  40                  45

Ser Met Ala Val Val Gln Ala Asn Asn Leu Leu Glu Asp Gln Cys Gln
    50                  55                  60

Ile Glu Ser Gly Pro Leu Ser Phe Leu Asp Ser Gly Pro Tyr Gly Thr
65                  70                  75                  80

Phe Val Gly Val Tyr Asp Gly His Gly Gly Pro Glu Thr Ala Cys Tyr
                85                  90                  95

Ile Asn Asp His Leu Phe Gln Asn Leu Lys Arg Phe Ala Ser Glu Gln
            100                 105                 110

Asn Ala Met Ser Ala Asp Val Leu Lys Lys Ala Tyr Glu Ala Thr Glu
        115                 120                 125

Asp Gly Phe Phe Ser Ile Val Thr Lys Gln Trp Pro Val Lys Pro Gln
    130                 135                 140

Ile Ala Ala Val Gly Ser Cys Cys Leu Val Gly Val Ile Cys Gly Gly
145                 150                 155                 160

Met Leu Tyr Val Ala Asn Val Gly Asp Ser Arg Val Val Leu Gly Lys
                165                 170                 175

His Val Lys Ala Thr Gly Glu Val Leu Ala Val Gln Leu Ser Ala Glu
            180                 185                 190

His Asn Val Ser Ile Ala Ser Val Arg Lys Glu Leu Gln Ser Met His
        195                 200                 205

Pro Glu Asp Arg His Ile Val Val Leu Lys His Asn Val Trp Arg Val
    210                 215                 220

Lys Gly Leu Ile Gln Val Cys Arg Ser Ile Gly Asp Ala Tyr Leu Lys
225                 230                 235                 240

Lys Gln Glu Phe Asn Arg Glu Pro Leu Tyr Ala Lys Phe Arg Leu Arg
                245                 250                 255

Glu Pro Phe His Lys Pro Ile Leu Ser Ser Glu Pro Ser Ile Ser Val
            260                 265                 270

Gln Pro Leu Gln Pro His Asp Gln Phe Leu Ile Phe Ala Ser Asp Gly
        275                 280                 285

Leu Trp Glu Gln Leu Thr Asn Gln Glu Ala Val Asp Ile Val Arg Ser
    290                 295                 300

Ser Pro Arg Ser Gly Cys Ala Arg Arg Leu Ile Arg Ala Ala Leu Gln
305                 310                 315                 320

Glu Ala Ala Lys Lys Arg Glu Met Arg Tyr Ser Asp Leu Lys Lys Ile
                325                 330                 335

Asp Arg Gly Val Arg Arg His Phe His Asp Ile Thr Val Ile Val
            340                 345                 350

Val Phe Leu Asp Ser Gly Leu Val Ser Gln Ala Ser Thr His Arg Gly
        355                 360                 365

Pro Thr Leu Ser Leu Arg Gly Gly Gly Ser Ala Gly Leu Arg Ser
    370                 375                 380

Asn Thr Leu Ala Pro Thr
385                 390

<210> SEQ ID NO 25
<211> LENGTH: 2015
<212> TYPE: DNA
<213> ORGANISM: Zea mays
<220> FEATURE:
<221> NAME/KEY: CDS
<222> LOCATION: (485)..(1678)
<223> OTHER INFORMATION: protein phosphatase 2C (ZM61092633)

<400> SEQUENCE: 25

```
agcttcctcc ctcttccctg gtctggtcgc ttctcctgta gctgtaattt ttgagagtcc      60
ctctcaaact ttgcttgctt gcgctctcca tatatcctgt ggatcggaga ggatgctctg     120
atctacctgt ctgttcttcg atcgagtctg agagatttgg gaggaggagg gaaacaaagc     180
gaaagagccc atctttttg tcttttggt tcggtttcgt ggttgcttct tttggacccc      240
gcggaggagc ccaccgtttc tacaaaaacc caatctttgc tgccttctca gcggtcgaga     300
tcgataggtt tccagatctg aggctccgtg ttctggctgt gagatcggag gcgcagcaat     360
ccgagcacgc agctagtagg gaaagtatcc gagaaaagtt gcagattttg ctgggggcaa     420
cggagcgaga acaagttact gcagaaggaa agggcaaagg tggggaggc gccggagatg     480
```

| | | | | | | | | | | | | | | | | |
|---|---|---|---|---|---|---|---|---|---|---|---|---|---|---|---|---|
| aggg | atg | cta | tca | gct | ctg | atg | gat | tat | ttg | aaa | tct | tgc | tgg | ggt | ccg | 529 |
| | Met | Leu | Ser | Ala | Leu | Met | Asp | Tyr | Leu | Lys | Ser | Cys | Trp | Gly | Pro | |
| | 1 | | | 5 | | | | | 10 | | | | | 15 | | |

| gca | tca | ccg | gct | ggg | cgt | ccc | cgc | aaa | gga | tcg | gat | gcc | acc | ggc | cgc | 577 |
|---|---|---|---|---|---|---|---|---|---|---|---|---|---|---|---|---|
| Ala | Ser | Pro | Ala | Gly | Arg | Pro | Arg | Lys | Gly | Ser | Asp | Ala | Thr | Gly | Arg | |
| | | | 20 | | | | | 25 | | | | | 30 | | | |

| cag | gac | ggg | ctc | ctg | tgg | tac | aag | gac | ggc | ggg | cag | gtc | gtc | gat | ggt | 625 |
|---|---|---|---|---|---|---|---|---|---|---|---|---|---|---|---|---|
| Gln | Asp | Gly | Leu | Leu | Trp | Tyr | Lys | Asp | Gly | Gly | Gln | Val | Val | Asp | Gly | |
| | | 35 | | | | | 40 | | | | | 45 | | | | |

| gag | ttc | tcc | atg | gcc | gtg | gtc | cag | gcc | aat | aac | cta | ttg | gag | gac | cat | 673 |
|---|---|---|---|---|---|---|---|---|---|---|---|---|---|---|---|---|
| Glu | Phe | Ser | Met | Ala | Val | Val | Gln | Ala | Asn | Asn | Leu | Leu | Glu | Asp | His | |
| | 50 | | | | | 55 | | | | | 60 | | | | | |

| agc | cag | gtt | gaa | tcc | ggg | ccg | ctt | agc | aca | tcg | gag | cct | gga | ctg | caa | 721 |
|---|---|---|---|---|---|---|---|---|---|---|---|---|---|---|---|---|
| Ser | Gln | Val | Glu | Ser | Gly | Pro | Leu | Ser | Thr | Ser | Glu | Pro | Gly | Leu | Gln | |
| 65 | | | | | 70 | | | | | 75 | | | | | | |

| ggc | acc | ttc | gtc | ggg | gtc | tac | gat | ggg | cac | ggt | ggc | ccg | gag | aca | gcg | 769 |
|---|---|---|---|---|---|---|---|---|---|---|---|---|---|---|---|---|
| Gly | Thr | Phe | Val | Gly | Val | Tyr | Asp | Gly | His | Gly | Gly | Pro | Glu | Thr | Ala | |
| 80 | | | | 85 | | | | | 90 | | | | | 95 | | |

| cgt | tac | atc | aat | gac | cat | ctc | ttc | aac | cac | ttg | agg | aga | ttc | gca | tct | 817 |
|---|---|---|---|---|---|---|---|---|---|---|---|---|---|---|---|---|
| Arg | Tyr | Ile | Asn | Asp | His | Leu | Phe | Asn | His | Leu | Arg | Arg | Phe | Ala | Ser | |
| | | | 100 | | | | | 105 | | | | | 110 | | | |

| gag | cac | aag | tgc | atg | tca | gcg | gat | gtg | att | cgg | aag | gca | ttc | cga | gcg | 865 |
|---|---|---|---|---|---|---|---|---|---|---|---|---|---|---|---|---|
| Glu | His | Lys | Cys | Met | Ser | Ala | Asp | Val | Ile | Arg | Lys | Ala | Phe | Arg | Ala | |
| | | | 115 | | | | | 120 | | | | | 125 | | | |

| act | gag | gag | ggt | ttc | att | tct | gtg | gtt | agt | aac | caa | tgg | tca | ttg | aga | 913 |
|---|---|---|---|---|---|---|---|---|---|---|---|---|---|---|---|---|
| Thr | Glu | Glu | Gly | Phe | Ile | Ser | Val | Val | Ser | Asn | Gln | Trp | Ser | Leu | Arg | |
| | | 130 | | | | | 135 | | | | | 140 | | | | |

| cct | caa | tta | gca | gct | gta | ggc | tct | tgc | tgt | cta | gtt | ggt | gtg | gtt | tgc | 961 |
|---|---|---|---|---|---|---|---|---|---|---|---|---|---|---|---|---|
| Pro | Gln | Leu | Ala | Ala | Val | Gly | Ser | Cys | Cys | Leu | Val | Gly | Val | Val | Cys | |
| 145 | | | | | 150 | | | | | 155 | | | | | | |

| agc | gga | act | cta | tat | gtt | gca | aac | ctt | ggg | gac | tcc | cgt | gct | gtt | ctg | 1009 |
|---|---|---|---|---|---|---|---|---|---|---|---|---|---|---|---|---|
| Ser | Gly | Thr | Leu | Tyr | Val | Ala | Asn | Leu | Gly | Asp | Ser | Arg | Ala | Val | Leu | |
| 160 | | | | | 165 | | | | | 170 | | | | | 175 | |

| ggg | aga | ctt | gtc | aag | gga | act | ggg | gag | gtt | ttg | gca | atg | cag | ctc | tca | 1057 |
|---|---|---|---|---|---|---|---|---|---|---|---|---|---|---|---|---|
| Gly | Arg | Leu | Val | Lys | Gly | Thr | Gly | Glu | Val | Leu | Ala | Met | Gln | Leu | Ser | |
| | | | | 180 | | | | | 185 | | | | | 190 | | |

| gca | gaa | cac | aat | gca | tcc | tat | gag | gag | gtt | aga | cga | gag | ctg | cag | gca | 1105 |
|---|---|---|---|---|---|---|---|---|---|---|---|---|---|---|---|---|
| Ala | Glu | His | Asn | Ala | Ser | Tyr | Glu | Glu | Val | Arg | Arg | Glu | Leu | Gln | Ala | |
| | | | 195 | | | | | 200 | | | | | 205 | | | |

| tca | cat | cct | gat | gat | ccc | cat | att | gtg | gtc | cta | aaa | cac | aat | gtt | tgg | 1153 |
|---|---|---|---|---|---|---|---|---|---|---|---|---|---|---|---|---|
| Ser | His | Pro | Asp | Asp | Pro | His | Ile | Val | Val | Leu | Lys | His | Asn | Val | Trp | |
| | 210 | | | | | 215 | | | | | 220 | | | | | |

| cgt | gta | aag | ggt | att | atc | cag | ata | aca | agg | tca | att | gga | gat | gtg | tat | 1201 |
|---|---|---|---|---|---|---|---|---|---|---|---|---|---|---|---|---|
| Arg | Val | Lys | Gly | Ile | Ile | Gln | Ile | Thr | Arg | Ser | Ile | Gly | Asp | Val | Tyr | |
| 225 | | | | | 230 | | | | | 235 | | | | | | |

```
ctg aag aaa cca gaa ttt aat aga gaa cct ttg cac agc aag ttt cgt    1249
Leu Lys Lys Pro Glu Phe Asn Arg Glu Pro Leu His Ser Lys Phe Arg
240             245                 250                 255 ctt cag gaa act ttt agg aga cca ctt ctt agt tct gat cca gca att    1297
Leu Gln Glu Thr Phe Arg Arg Pro Leu Leu Ser Ser Asp Pro Ala Ile
                260                 265                 270 act gtc cac caa ata cag cca act gat aag ttc atc att ttt gca tct    1345
Thr Val His Gln Ile Gln Pro Thr Asp Lys Phe Ile Ile Phe Ala Ser
            275                 280                 285 gat gga ctc tgg gaa cat ctt agt aat cag gaa gtg gtt gac atg gtc    1393
Asp Gly Leu Trp Glu His Leu Ser Asn Gln Glu Val Val Asp Met Val
        290                 295                 300 caa agt agc ccg cgt aat gga atc gca cga aag tta gta aag tct gca    1441
Gln Ser Ser Pro Arg Asn Gly Ile Ala Arg Lys Leu Val Lys Ser Ala
305                 310                 315 gtg cag gaa gca gcg aag aag agg gag atg cgg tat tca gac ctc aag    1489
Val Gln Glu Ala Ala Lys Lys Arg Glu Met Arg Tyr Ser Asp Leu Lys
320                 325                 330                 335 aaa gtt gat cgg ggg gtg agg cgg cac ttc cac gac gat ata act gtc    1537
Lys Val Asp Arg Gly Val Arg Arg His Phe His Asp Asp Ile Thr Val
                340                 345                 350 att gtg gta ttt ttc gat tca aac gcc atg aca act gct gcc tgg agc    1585
Ile Val Val Phe Phe Asp Ser Asn Ala Met Thr Thr Ala Ala Trp Ser
            355                 360                 365 aga ccc tcg gtc tct ctc cga ggg ggt ggg ttt cca atc cat tca aac    1633
Arg Pro Ser Val Ser Leu Arg Gly Gly Gly Phe Pro Ile His Ser Asn
        370                 375                 380 acc ctt gct cca ttc tcg gtt cct aca gag cta aac aac tcc tac        1678
Thr Leu Ala Pro Phe Ser Val Pro Thr Glu Leu Asn Asn Ser Tyr
385                 390                 395 tgaaaccacg cggtatgtga aggagccagg caagaggata aaaaaaagt aaaggaaaac   1738 ggagaaggaa aaacagctgt tgtgatcagt tgtagtgtat ttcaccgttc atgttcattt   1798
aaaacatttt ttagattctc aagtctcaac ctggtgacca gtgcactgat agcaaggtat   1858
aagattagat tattccttagc ttttttatcc tcttttttt ttctcgtcct taccctttag   1918
attcactcat gggatatccg atatcaggtg cttgtacatt ctttggttca acttgtgata   1978
atagttcatc gccccctct tttcgcaaaa aaaaaa                              2015

<210> SEQ ID NO 26
<211> LENGTH: 398
<212> TYPE: PRT
<213> ORGANISM: Zea mays

<400> SEQUENCE: 26

Met Leu Ser Ala Leu Met Asp Tyr Leu Lys Ser Cys Trp Gly Pro Ala
1               5                   10                  15

Ser Pro Ala Gly Arg Pro Arg Lys Gly Ser Asp Ala Thr Gly Arg Gln
            20                  25                  30

Asp Gly Leu Leu Trp Tyr Lys Asp Gly Gly Gln Val Val Asp Gly Glu
        35                  40                  45

Phe Ser Met Ala Val Val Gln Ala Asn Asn Leu Leu Glu Asp His Ser
    50                  55                  60

Gln Val Glu Ser Gly Pro Leu Thr Ser Glu Pro Gly Leu Gln Gly
65                  70                  75                  80

Thr Phe Val Gly Val Tyr Asp Gly His Gly Gly Pro Glu Thr Ala Arg
                85                  90                  95

Tyr Ile Asn Asp His Leu Phe Asn His Leu Arg Arg Phe Ala Ser Glu
```

```
                100              105              110
His Lys Cys Met Ser Ala Asp Val Ile Arg Lys Ala Phe Arg Ala Thr
            115              120              125
Glu Glu Gly Phe Ile Ser Val Val Ser Asn Gln Trp Ser Leu Arg Pro
        130              135              140
Gln Leu Ala Ala Val Gly Ser Cys Cys Leu Val Gly Val Val Cys Ser
145              150              155              160
Gly Thr Leu Tyr Val Ala Asn Leu Gly Asp Ser Arg Ala Val Leu Gly
                165              170              175
Arg Leu Val Lys Gly Thr Gly Glu Val Leu Ala Met Gln Leu Ser Ala
            180              185              190
Glu His Asn Ala Ser Tyr Glu Glu Val Arg Arg Glu Leu Gln Ala Ser
        195              200              205
His Pro Asp Asp Pro His Ile Val Leu Lys His Asn Val Trp Arg
210              215              220
Val Lys Gly Ile Ile Gln Ile Thr Arg Ser Ile Gly Asp Val Tyr Leu
225              230              235              240
Lys Lys Pro Glu Phe Asn Arg Glu Pro Leu His Ser Lys Phe Arg Leu
                245              250              255
Gln Glu Thr Phe Arg Arg Pro Leu Leu Ser Ser Asp Pro Ala Ile Thr
            260              265              270
Val His Gln Ile Gln Pro Thr Asp Lys Phe Ile Ile Phe Ala Ser Asp
        275              280              285
Gly Leu Trp Glu His Leu Ser Asn Gln Glu Val Val Asp Met Val Gln
    290              295              300
Ser Ser Pro Arg Asn Gly Ile Ala Arg Lys Leu Val Lys Ser Ala Val
305              310              315              320
Gln Glu Ala Ala Lys Lys Arg Glu Met Arg Tyr Ser Asp Leu Lys Lys
                325              330              335
Val Asp Arg Gly Val Arg Arg His Phe His Asp Ile Thr Val Ile
            340              345              350
Val Val Phe Phe Asp Ser Asn Ala Met Thr Thr Ala Ala Trp Ser Arg
        355              360              365
Pro Ser Val Ser Leu Arg Gly Gly Phe Pro Ile His Ser Asn Thr
370              375              380
Leu Ala Pro Phe Ser Val Pro Thr Glu Leu Asn Asn Ser Tyr
385              390              395
```

<210> SEQ ID NO 27
<211> LENGTH: 1744
<212> TYPE: DNA
<213> ORGANISM: Zea mays
<220> FEATURE:
<221> NAME/KEY: CDS
<222> LOCATION: (229)..(1425)
<223> OTHER INFORMATION: protein phosphatase 2C (ZM62016485)

<400> SEQUENCE: 27

```
tgtcttgctg ctggcgcgcc ggggctccga ttgcgctcca gatctgaggc acctgctcgg      60
tggattccag gaatccgagc accaactcga caggggagtt ctcagggtaa agaggctgag     120
agcgcgttgg agatttggac tataagagcg agcgagcgag ctgggtgcct tgctgccttg     180
aggacgccgt caagaaaccg cgtggagggg agggcgatga gatgaggg atg ctg gcc     237
                                                    Met Leu Ala
                                                      1 gcg gtg atg gac tac ttc agc acc tgc tgg ggc ccg cgg tct cgt gcg     285
Ala Val Met Asp Tyr Phe Ser Thr Cys Trp Gly Pro Arg Ser Arg Ala
```

```
                5                   10                  15
ggg cac cgg ggc aag ggc tcc gac gcc gcc ggc cgg cag gac ggc ctc       333
Gly His Arg Gly Lys Gly Ser Asp Ala Ala Gly Arg Gln Asp Gly Leu
20                  25                  30                  35 ctc tgg tac aag gac gcc ggg cag ctc gtc acc ggg ggg ttc tcc atg       381
Leu Trp Tyr Lys Asp Ala Gly Gln Leu Val Thr Gly Gly Phe Ser Met
        40                  45                  50 gcc gtg gtg cag gcc aac cag ctg ctt gag gac cag agc cag gtg gag       429
Ala Val Val Gln Ala Asn Gln Leu Leu Glu Asp Gln Ser Gln Val Glu
            55                  60                  65 tcc gga tcg ctc tcc ctg gct gac tac ggc ccg cag ggc acc ttc gtc       477
Ser Gly Ser Leu Ser Leu Ala Asp Tyr Gly Pro Gln Gly Thr Phe Val
                70                  75                  80 ggc gtc tat gat ggc cat ggc ggc ccg gag acg tcc cgg ttc atc aat       525
Gly Val Tyr Asp Gly His Gly Gly Pro Glu Thr Ser Arg Phe Ile Asn
85                  90                  95 gac cac ctc ttc aac cat ctc agg aga ttc gca act gag cac aag tcc       573
Asp His Leu Phe Asn His Leu Arg Arg Phe Ala Thr Glu His Lys Ser
100                 105                 110                 115 atg tca gca gac gtg atc cgg aaa gct ttc caa gaa act gag gag ggc       621
Met Ser Ala Asp Val Ile Arg Lys Ala Phe Gln Glu Thr Glu Glu Gly
                120                 125                 130 ttt ctt tct cta gtc atc aag gaa tgg tct ttc aag cct cag att gca       669
Phe Leu Ser Leu Val Ile Lys Glu Trp Ser Phe Lys Pro Gln Ile Ala
                135                 140                 145 tca gtt ggc tcc tgt tgc ctt gtt ggt gta atc tgt gct ggg act ctc       717
Ser Val Gly Ser Cys Cys Leu Val Gly Val Ile Cys Ala Gly Thr Leu
                150                 155                 160 tat gtt gca aac ctg ggc gac tcg cgt gca gtt ctt gga agg ctt gtg       765
Tyr Val Ala Asn Leu Gly Asp Ser Arg Ala Val Leu Gly Arg Leu Val
165                 170                 175 aaa gca act gga gag gtt ctg gcc act cag ttg tca gcg gag cac aat       813
Lys Ala Thr Gly Glu Val Leu Ala Thr Gln Leu Ser Ala Glu His Asn
180                 185                 190                 195 gca tgc tat gaa gaa gtt aga caa gag ctg cag tca tca cat cct gat       861
Ala Cys Tyr Glu Glu Val Arg Gln Glu Leu Gln Ser Ser His Pro Asp
                200                 205                 210 gat cca cgt att gtg gtt ctc aaa cat aac gtt tgg cga gtg aag ggt       909
Asp Pro Arg Ile Val Val Leu Lys His Asn Val Trp Arg Val Lys Gly
                215                 220                 225 ctc atc cag atc tca aga tct atc gga gat gta tat cta aag aaa ccg       957
Leu Ile Gln Ile Ser Arg Ser Ile Gly Asp Val Tyr Leu Lys Lys Pro
                230                 235                 240 gag tat aac aga gaa cct ctt cac agc aag ttt cgg ctt cga gaa acc      1005
Glu Tyr Asn Arg Glu Pro Leu His Ser Lys Phe Arg Leu Arg Glu Thr
245                 250                 255 ttc cag aag ccg att ctt agt tct gaa cct caa att act gaa cac cga      1053
Phe Gln Lys Pro Ile Leu Ser Ser Glu Pro Gln Ile Thr Glu His Arg
260                 265                 270                 275 ata cag cca aac gat cag ttt gtt ata ttt gct tcc gat ggt cta tgg      1101
Ile Gln Pro Asn Asp Gln Phe Val Ile Phe Ala Ser Asp Gly Leu Trp
                280                 285                 290 gag cac ctc agc aat cag gaa gct gtt gac ctt gtc caa agt agt ccc      1149
Glu His Leu Ser Asn Gln Glu Ala Val Asp Leu Val Gln Ser Ser Pro
                295                 300                 305 cgt aat gga atc gct cgg aga cta gtg aaa gcc gcg atg caa gaa gct      1197
Arg Asn Gly Ile Ala Arg Arg Leu Val Lys Ala Ala Met Gln Glu Ala
            310                 315                 320 gcc aag aag agg gag atg aga tac tca gac ctc aag aag atc gac cgt      1245
Ala Lys Lys Arg Glu Met Arg Tyr Ser Asp Leu Lys Lys Ile Asp Arg
```

```
                325                 330                 335
ggc gtg agg agg cat ttc cac gac gat ata acc gtc gtc gtg gtg ttc      1293
Gly Val Arg Arg His Phe His Asp Asp Ile Thr Val Val Val Val Phe
340                 345                 350                 355 ctc gac tcg gat gcc atg agc aaa gct agc tgg agc aag agc ccc tcg      1341
Leu Asp Ser Asp Ala Met Ser Lys Ala Ser Trp Ser Lys Ser Pro Ser
                360                 365                 370 ttt tct ctc cga ggg ggc ggc gtc acc ctt ccc gcc aag tcc ctc gca      1389
Phe Ser Leu Arg Gly Gly Gly Val Thr Leu Pro Ala Lys Ser Leu Ala
            375                 380                 385 ccc ttc tcg gct ccg gca cag ttg aac ggc acc cac tgaagctgct           1435
Pro Phe Ser Ala Pro Ala Gln Leu Asn Gly Thr His
        390                 395 actgctcttg aaagaaggg cacagtgcag atcgctaga gatgatgaga gaagcagcaa      1495
tcaagtgtag ctgttgctcg tacacctgct gtgctgttgc tgtttgcaaa gctgccgtct    1555
tgactccgcc tggtaattag tgtactgata gcgaggtata gaaattaggt tatttgttag    1615
cgacgcaaat cctttctttt tttttcttct ccctctgttc ttatctcttt tctcttcatc    1675
atggaggaaa caggtggctg taaatttgtc cagaacatgt tttccctaat agcccaacaa    1735
aaaaaaaaa                                                            1744

<210> SEQ ID NO 28
<211> LENGTH: 399
<212> TYPE: PRT
<213> ORGANISM: Zea mays

<400> SEQUENCE: 28

Met Leu Ala Ala Val Met Asp Tyr Phe Ser Thr Cys Trp Gly Pro Arg
1               5                   10                  15

Ser Arg Ala Gly His Arg Gly Lys Gly Ser Asp Ala Ala Gly Arg Gln
                20                  25                  30

Asp Gly Leu Leu Trp Tyr Lys Asp Ala Gly Gln Leu Val Thr Gly Gly
            35                  40                  45

Phe Ser Met Ala Val Val Gln Ala Asn Gln Leu Leu Glu Asp Gln Ser
        50                  55                  60

Gln Val Glu Ser Gly Ser Leu Ser Leu Ala Asp Tyr Gly Pro Gln Gly
65                  70                  75                  80

Thr Phe Val Gly Val Tyr Asp Gly His Gly Gly Pro Glu Thr Ser Arg
                85                  90                  95

Phe Ile Asn Asp His Leu Phe Asn His Leu Arg Arg Phe Ala Thr Glu
            100                 105                 110

His Lys Ser Met Ser Ala Asp Val Ile Arg Lys Ala Phe Gln Glu Thr
        115                 120                 125

Glu Glu Gly Phe Leu Ser Leu Val Ile Lys Glu Trp Ser Phe Lys Pro
    130                 135                 140

Gln Ile Ala Ser Val Gly Ser Cys Cys Leu Val Gly Val Ile Cys Ala
145                 150                 155                 160

Gly Thr Leu Tyr Val Ala Asn Leu Gly Asp Ser Arg Ala Val Leu Gly
                165                 170                 175

Arg Leu Val Lys Ala Thr Gly Glu Val Leu Ala Thr Gln Leu Ser Ala
            180                 185                 190

Glu His Asn Ala Cys Tyr Glu Glu Val Arg Gln Glu Leu Gln Ser Ser
        195                 200                 205

His Pro Asp Asp Pro Arg Ile Val Val Leu Lys His Asn Val Trp Arg
    210                 215                 220
```

```
Val Lys Gly Leu Ile Gln Ile Ser Arg Ser Ile Gly Asp Val Tyr Leu
225                 230                 235                 240

Lys Lys Pro Glu Tyr Asn Arg Glu Pro Leu His Ser Lys Phe Arg Leu
            245                 250                 255

Arg Glu Thr Phe Gln Lys Pro Ile Leu Ser Ser Glu Pro Gln Ile Thr
        260                 265                 270

Glu His Arg Ile Gln Pro Asn Asp Gln Phe Val Ile Phe Ala Ser Asp
    275                 280                 285

Gly Leu Trp Glu His Leu Ser Asn Gln Glu Ala Val Asp Leu Val Gln
290                 295                 300

Ser Ser Pro Arg Asn Gly Ile Ala Arg Leu Val Lys Ala Ala Met
305                 310                 315                 320

Gln Glu Ala Ala Lys Lys Arg Glu Met Arg Tyr Ser Asp Leu Lys Lys
                325                 330                 335

Ile Asp Arg Gly Val Arg Arg His Phe His Asp Asp Ile Thr Val Val
            340                 345                 350

Val Val Phe Leu Asp Ser Asp Ala Met Ser Lys Ala Ser Trp Ser Lys
        355                 360                 365

Ser Pro Ser Phe Ser Leu Arg Gly Gly Val Thr Leu Pro Ala Lys
370                 375                 380

Ser Leu Ala Pro Phe Ser Ala Pro Ala Gln Leu Asn Gly Thr His
385                 390                 395

<210> SEQ ID NO 29
<211> LENGTH: 1840
<212> TYPE: DNA
<213> ORGANISM: Zea mays
<220> FEATURE:
<221> NAME/KEY: CDS
<222> LOCATION: (296)..(1492)
<223> OTHER INFORMATION: protein phosphatase 2C (ZM62051019)

<400> SEQUENCE: 29 tttctctta tccagcttct tagcatgatt ctctttgatc ccggagagca gccaccggtc      60
caactagtcc ttgctgttgg tctgccggaa cttttgattg ctctccagat ctgaggcacc    120
tgctgggtgg attccaggaa cccgagcacg aagttgacag gtgagttctc agggaaaaag    180
gggaggaagg aagaggctga aagggcggtg gagagagaaa gactataagg gcagctgag    240 tcccttgagg atgccgtcaa gaaaccgcgt ggagaggagg gcgatgagat gaggg atg    298
                                                              Met
                                                              1 ctg gcc gcg gtg atg gac tac ttc agc tcc tgc tgg ggc ccg cga tcg    346
Leu Ala Ala Val Met Asp Tyr Phe Ser Ser Cys Trp Gly Pro Arg Ser
        5                   10                  15 ggc gcc ggg cac cgg ggc aag ggc tcc gac gcc gcc ggc cgg cag gac    394
Gly Ala Gly His Arg Gly Lys Gly Ser Asp Ala Ala Gly Arg Gln Asp
    20                  25                  30 ggt ctc ctc tgg tac aag gac gcc ggc cag ctc gtc act ggg gag ttc    442
Gly Leu Leu Trp Tyr Lys Asp Ala Gly Gln Leu Val Thr Gly Glu Phe
35                  40                  45 tcc atg gcc gtg gtg cag gcc aac cag ctc ctc gag gac cag agc caa    490
Ser Met Ala Val Val Gln Ala Asn Gln Leu Leu Glu Asp Gln Ser Gln
50                  55                  60                  65 gta gag tcc gga tcg ctc tcc ctg gct gac ccg ggc cca cag ggc acc    538
Val Glu Ser Gly Ser Leu Ser Leu Ala Asp Pro Gly Pro Gln Gly Thr
                70                  75                  80 ttc gtc ggc gtc tat gat ggc cat ggc ggc ccg gag acg tcc cgg ttc    586
Phe Val Gly Val Tyr Asp Gly His Gly Gly Pro Glu Thr Ser Arg Phe
            85                  90                  95
```

| | | | | | | | | | | | | | | |
|---|---|---|---|---|---|---|---|---|---|---|---|---|---|---|
| atc | aat | gac | cac | ctc | ttc | aac | cat | ctc | aga | agg | ttt | gca | act | gag | cac | 634 |
| Ile | Asn | Asp | His | Leu | Phe | Asn | His | Leu | Arg | Arg | Phe | Ala | Thr | Glu | His |
|   |   | 100 |   |   |   | 105 |   |   |   |   | 110 |   |   |   |   |

| aag | ttt | atg | tca | gcg | gac | gtg | atc | cgg | aaa | gct | ttc | caa | gca | act | gag | 682 |
| Lys | Phe | Met | Ser | Ala | Asp | Val | Ile | Arg | Lys | Ala | Phe | Gln | Ala | Thr | Glu |
| 115 | | | | | 120 | | | | | 125 | | | | | |

| gag | ggc | ttt | ctt | tct | cta | gtc | agc | aag | gaa | tgg | tct | ttg | aag | cct | cag | 730 |
| Glu | Gly | Phe | Leu | Ser | Leu | Val | Ser | Lys | Glu | Trp | Ser | Leu | Lys | Pro | Gln |
| 130 | | | | 135 | | | | | 140 | | | | | 145 | |

| att | gct | tca | gtg | ggc | tcc | tgc | tgc | ctt | gtt | ggt | gta | atc | tgt | gct | ggg | 778 |
| Ile | Ala | Ser | Val | Gly | Ser | Cys | Cys | Leu | Val | Gly | Val | Ile | Cys | Ala | Gly |
| | | | | 150 | | | | | 155 | | | | | 160 | |

| act | ctc | tat | gtt | gca | aac | gtg | ggc | gac | tca | cgt | gca | gtt | ctt | gga | agg | 826 |
| Thr | Leu | Tyr | Val | Ala | Asn | Val | Gly | Asp | Ser | Arg | Ala | Val | Leu | Gly | Arg |
| | | | 165 | | | | | 170 | | | | | 175 | | |

| ctt | gtt | aag | gca | act | gga | gag | gtt | gtg | gcc | atg | cag | ttg | tca | tcg | gag | 874 |
| Leu | Val | Lys | Ala | Thr | Gly | Glu | Val | Val | Ala | Met | Gln | Leu | Ser | Ser | Glu |
| | | 180 | | | | | 185 | | | | | 190 | | | |

| cac | aat | gcg | tgc | tat | gag | gaa | gtt | aga | caa | gaa | ctg | cag | tca | tca | cat | 922 |
| His | Asn | Ala | Cys | Tyr | Glu | Glu | Val | Arg | Gln | Glu | Leu | Gln | Ser | Ser | His |
| | 195 | | | | | 200 | | | | | 205 | | | | |

| cct | gac | gat | cca | cat | att | gtg | gtt | ctc | aaa | cac | aat | gtt | tgg | cga | gtg | 970 |
| Pro | Asp | Asp | Pro | His | Ile | Val | Val | Leu | Lys | His | Asn | Val | Trp | Arg | Val |
| 210 | | | | | 215 | | | | | 220 | | | | | 225 |

| aag | ggt | ctc | atc | cag | atc | tca | aga | tct | att | gga | gat | gta | tat | cta | aag | 1018 |
| Lys | Gly | Leu | Ile | Gln | Ile | Ser | Arg | Ser | Ile | Gly | Asp | Val | Tyr | Leu | Lys |
| | | | | 230 | | | | | 235 | | | | | 240 | |

| aaa | cca | gag | tac | aac | aga | gaa | cca | ctt | cac | agc | aag | ttt | cgg | ctt | cga | 1066 |
| Lys | Pro | Glu | Tyr | Asn | Arg | Glu | Pro | Leu | His | Ser | Lys | Phe | Arg | Leu | Arg |
| | | | 245 | | | | | 250 | | | | | 255 | | |

| gaa | acc | ttc | cag | agg | ccg | acc | ctt | agt | tct | gaa | cct | caa | att | act | gaa | 1114 |
| Glu | Thr | Phe | Gln | Arg | Pro | Thr | Leu | Ser | Ser | Glu | Pro | Gln | Ile | Thr | Glu |
| | | 260 | | | | | 265 | | | | | 270 | | | |

| cat | cga | ata | cag | ccg | aac | gat | caa | ttt | gtt | ata | ttt | gct | tct | gat | ggt | 1162 |
| His | Arg | Ile | Gln | Pro | Asn | Asp | Gln | Phe | Val | Ile | Phe | Ala | Ser | Asp | Gly |
| | 275 | | | | | 280 | | | | | 285 | | | | |

| cta | tgg | gag | cac | ctc | agc | aat | aag | gaa | gca | gtt | gac | ctt | gtc | caa | agt | 1210 |
| Leu | Trp | Glu | His | Leu | Ser | Asn | Lys | Glu | Ala | Val | Asp | Leu | Val | Gln | Ser |
| 290 | | | | | 295 | | | | | 300 | | | | | 305 |

| agt | ccc | cga | aat | gga | atc | gct | cgg | agg | cta | gtg | aaa | gcc | gcg | atg | caa | 1258 |
| Ser | Pro | Arg | Asn | Gly | Ile | Ala | Arg | Arg | Leu | Val | Lys | Ala | Ala | Met | Gln |
| | | | | 310 | | | | | 315 | | | | | 320 | |

| gaa | gct | gcc | aag | aag | agg | gag | atg | aga | tac | tca | gac | ctc | aag | aag | atc | 1306 |
| Glu | Ala | Ala | Lys | Lys | Arg | Glu | Met | Arg | Tyr | Ser | Asp | Leu | Lys | Lys | Ile |
| | | | 325 | | | | | 330 | | | | | 335 | | |

| gac | cgt | ggt | gtg | aga | agg | cat | ttc | cac | gac | gat | ata | act | gtc | gtc | gtg | 1354 |
| Asp | Arg | Gly | Val | Arg | Arg | His | Phe | His | Asp | Asp | Ile | Thr | Val | Val | Val |
| | | 340 | | | | | 345 | | | | | 350 | | | |

| gta | ttc | ctc | gat | tcg | gat | gcc | atg | agc | aaa | gct | agc | tgg | agc | aaa | agc | 1402 |
| Val | Phe | Leu | Asp | Ser | Asp | Ala | Met | Ser | Lys | Ala | Ser | Trp | Ser | Lys | Ser |
| | 355 | | | | | 360 | | | | | 365 | | | | |

| ccc | tcg | gtt | tct | ctc | cga | ggg | ggc | ggt | gtc | gcc | ctc | cct | gcg | aag | tcc | 1450 |
| Pro | Ser | Val | Ser | Leu | Arg | Gly | Gly | Gly | Val | Ala | Leu | Pro | Ala | Lys | Ser |
| 370 | | | | 375 | | | | | 380 | | | | | 385 | |

| ctc | gca | cct | ttc | tca | gct | ccg | gca | cgg | ctg | aac | agc | acc | tac | | | 1492 |
| Leu | Ala | Pro | Phe | Ser | Ala | Pro | Ala | Arg | Leu | Asn | Ser | Thr | Tyr |
| | | | 390 | | | | | 395 | | | | | |

| tgaagttgct | accactcttg | aaaggaagaa | cacagtgcag | atctgcagtg | gtgagagaga | 1552 |

| gagagaaaac | agcaaccaag | tgtagcgtta | cagttacacc | tgctgtgttg | ttgctctttg | 1612 |

```
caaaactact gtctagactc cgcctggtaa ttagtgtact gatagcgagg taaaaaaagt   1672
tagattattt gttagcgaca cacatccttt caccttctct tctctccctc gattcctatc   1732
ccttttctct tcatccttga gagaacaggt ggatgtaaat tgttcagaac atgttttccc   1792
ttatagtcca tcatatcccg ctttttttcgt gttgaaaaaa aaaaaaaa              1840

<210> SEQ ID NO 30
<211> LENGTH: 399
<212> TYPE: PRT
<213> ORGANISM: Zea mays

<400> SEQUENCE: 30
```

| | | | | | | | | | | | | | | |
|---|---|---|---|---|---|---|---|---|---|---|---|---|---|---|
| Met | Leu | Ala | Ala | Val | Met | Asp | Tyr | Phe | Ser | Ser | Cys | Trp | Gly | Pro | Arg |
| 1 | | | | 5 | | | | | 10 | | | | | 15 | |
| Ser | Gly | Ala | Gly | His | Arg | Gly | Lys | Gly | Ser | Asp | Ala | Ala | Gly | Arg | Gln |
| | | | 20 | | | | | 25 | | | | | 30 | | |
| Asp | Gly | Leu | Leu | Trp | Tyr | Lys | Asp | Ala | Gly | Gln | Leu | Val | Thr | Gly | Glu |
| | | | 35 | | | | | 40 | | | | | 45 | | |
| Phe | Ser | Met | Ala | Val | Val | Gln | Ala | Asn | Gln | Leu | Leu | Glu | Asp | Gln | Ser |
| | 50 | | | | | 55 | | | | | 60 | | | | |
| Gln | Val | Glu | Ser | Gly | Ser | Leu | Ser | Leu | Ala | Asp | Pro | Gly | Pro | Gln | Gly |
| 65 | | | | | 70 | | | | | 75 | | | | | 80 |
| Thr | Phe | Val | Gly | Val | Tyr | Asp | Gly | His | Gly | Gly | Pro | Glu | Thr | Ser | Arg |
| | | | | 85 | | | | | 90 | | | | | 95 | |
| Phe | Ile | Asn | Asp | His | Leu | Phe | Asn | His | Leu | Arg | Arg | Phe | Ala | Thr | Glu |
| | | | 100 | | | | | 105 | | | | | 110 | | |
| His | Lys | Phe | Met | Ser | Ala | Asp | Val | Ile | Arg | Lys | Ala | Phe | Gln | Ala | Thr |
| | | 115 | | | | | 120 | | | | | 125 | | | |
| Glu | Glu | Gly | Phe | Leu | Ser | Leu | Val | Ser | Lys | Glu | Trp | Ser | Leu | Lys | Pro |
| | 130 | | | | | 135 | | | | | 140 | | | | |
| Gln | Ile | Ala | Ser | Val | Gly | Ser | Cys | Cys | Leu | Val | Gly | Val | Ile | Cys | Ala |
| 145 | | | | | 150 | | | | | 155 | | | | | 160 |
| Gly | Thr | Leu | Tyr | Val | Ala | Asn | Val | Gly | Asp | Ser | Arg | Ala | Val | Leu | Gly |
| | | | | 165 | | | | | 170 | | | | | 175 | |
| Arg | Leu | Val | Lys | Ala | Thr | Gly | Glu | Val | Val | Ala | Met | Gln | Leu | Ser | Ser |
| | | | 180 | | | | | 185 | | | | | 190 | | |
| Glu | His | Asn | Ala | Cys | Tyr | Glu | Val | Arg | Gln | Glu | Leu | Gln | Ser | Ser |
| | | 195 | | | | | 200 | | | | | 205 | | | |
| His | Pro | Asp | Asp | Pro | His | Ile | Val | Val | Leu | Lys | His | Asn | Val | Trp | Arg |
| | 210 | | | | | 215 | | | | | 220 | | | | |
| Val | Lys | Gly | Leu | Ile | Gln | Ile | Ser | Arg | Ser | Ile | Gly | Asp | Val | Tyr | Leu |
| 225 | | | | | 230 | | | | | 235 | | | | | 240 |
| Lys | Lys | Pro | Glu | Tyr | Asn | Arg | Glu | Pro | Leu | His | Ser | Lys | Phe | Arg | Leu |
| | | | | 245 | | | | | 250 | | | | | 255 | |
| Arg | Glu | Thr | Phe | Gln | Arg | Pro | Thr | Leu | Ser | Ser | Glu | Pro | Gln | Ile | Thr |
| | | | 260 | | | | | 265 | | | | | 270 | | |
| Glu | His | Arg | Ile | Gln | Pro | Asn | Asp | Gln | Phe | Val | Ile | Phe | Ala | Ser | Asp |
| | | 275 | | | | | 280 | | | | | 285 | | | |
| Gly | Leu | Trp | Glu | His | Leu | Ser | Asn | Lys | Glu | Ala | Val | Asp | Leu | Val | Gln |
| | 290 | | | | | 295 | | | | | 300 | | | | |
| Ser | Ser | Pro | Arg | Asn | Gly | Ile | Ala | Arg | Arg | Leu | Val | Lys | Ala | Ala | Met |
| 305 | | | | | 310 | | | | | 315 | | | | | 320 |
| Gln | Glu | Ala | Ala | Lys | Lys | Arg | Glu | Met | Arg | Tyr | Ser | Asp | Leu | Lys | Lys |
| | | | | 325 | | | | | 330 | | | | | 335 | |

-continued

```
Ile Asp Arg Gly Val Arg Arg His Phe His Asp Asp Ile Thr Val Val
            340                 345                 350

Val Val Phe Leu Asp Ser Asp Ala Met Ser Lys Ala Ser Trp Ser Lys
        355                 360                 365

Ser Pro Ser Val Ser Leu Arg Gly Gly Val Ala Leu Pro Ala Lys
370                 375                 380

Ser Leu Ala Pro Phe Ser Ala Pro Ala Arg Leu Asn Ser Thr Tyr
385                 390                 395
```

<210> SEQ ID NO 31
<211> LENGTH: 2144
<212> TYPE: DNA
<213> ORGANISM: Zea mays
<220> FEATURE:
<221> NAME/KEY: CDS
<222> LOCATION: (603)..(1799)
<223> OTHER INFORMATION: protein phosphatase 2C (ZM65086957)

<400> SEQUENCE: 31

| | |
|---|---:|
| ctctgtctcc ttggatttgc gcttgtgctc gtctggccgc atactagtat ccgcaccaga | 60 |
| gaggagacac ctccgactcc gacctgctct tgcatataga ttggacagag agtgagggag | 120 |
| agagagagcg cgcgcgctga aggggtgcca aaggagatt ttttttttt aatccagctt | 180 |
| cttagcctga ctgactctct tgatcccgg agagcagccg ccagcccaac taatccttgc | 240 |
| tgctggcgcg ccggggctct gattgcgctc cagatctgag gcacctgctc ggtggattcc | 300 |
| aggaatccga gcaccaactc gacagggaga gttctcaggg taaggacga cgcttgatgc | 360 |
| acacgggacg ggacaacgag ttggccgcaa gttttgtttg cacacgcaca cgacccacca | 420 |
| gctcacgcgt tttttttttt tttttgctt cttaactcgc tttgattgca tctgttgttt | 480 |
| cggaaggaag aggctgagag cgcgttggag atttggacta taagagcgag cgagcgagcg | 540 |
| agctgggtgc cttgaggacg ccgtcaagaa accgcgtgga ggggagggcg atgagatgag | 600 |

```
gg atg ctg gcc gcg gtg atg gac tac ttc agc acc tgc tgg ggc ccg          647
   Met Leu Ala Ala Val Met Asp Tyr Phe Ser Thr Cys Trp Gly Pro
   1               5                  10                  15 cgg tct cgt gcg ggg cac agg ggc aag ggc tcc gac gcc gcc ggc cgg          695
Arg Ser Arg Ala Gly His Arg Gly Lys Gly Ser Asp Ala Ala Gly Arg
            20                  25                  30 cag gac ggc ctc ctc tgg tac aag gac gcc ggg cag ctc gtc acc ggg          743
Gln Asp Gly Leu Leu Trp Tyr Lys Asp Ala Gly Gln Leu Val Thr Gly
        35                  40                  45 ggg ttc tcc atg gcc gtg gtg cag gcc aac cag ctg ctt gag gac cag          791
Gly Phe Ser Met Ala Val Val Gln Ala Asn Gln Leu Leu Glu Asp Gln
    50                  55                  60 agc cag gtg gag tcc gga tcg ctc tcc ctg gct gac tac ggc ccg cag          839
Ser Gln Val Glu Ser Gly Ser Leu Ser Leu Ala Asp Tyr Gly Pro Gln
65                  70                  75 ggc acc ttc gtc ggc gtc tat gat ggc cat ggc ggc ccg gag acg tcc          887
Gly Thr Phe Val Gly Val Tyr Asp Gly His Gly Gly Pro Glu Thr Ser
80                  85                  90                  95 cgg ttc atc aat gac cac ctc ttc aac cat ctc agg aga ttt gca act          935
Arg Phe Ile Asn Asp His Leu Phe Asn His Leu Arg Arg Phe Ala Thr
                100                 105                 110 gag cac aag tcc atg tca gca gac gtg atc cgg aaa gct ttc caa gaa          983
Glu His Lys Ser Met Ser Ala Asp Val Ile Arg Lys Ala Phe Gln Glu
            115                 120                 125 act gag gag ggc ttt ctt tct cta gtc atc aag gaa tgg tct ttc aag        1031
Thr Glu Glu Gly Phe Leu Ser Leu Val Ile Lys Glu Trp Ser Phe Lys
        130                 135                 140
```

```
cct cag att gca tca gtt ggc tcc tgt tgc ctt gtt ggt gta atc tgt     1079
Pro Gln Ile Ala Ser Val Gly Ser Cys Cys Leu Val Gly Val Ile Cys
    145                 150                 155 gct ggg act ctc tat gtt gca aac ctg ggc gac tcc cgt gca gtt ctt     1127
Ala Gly Thr Leu Tyr Val Ala Asn Leu Gly Asp Ser Arg Ala Val Leu
160                 165                 170                 175 gga agg ctt gtt aag gca act gga gag gtt ctg gcc acg cag ttg tca     1175
Gly Arg Leu Val Lys Ala Thr Gly Glu Val Leu Ala Thr Gln Leu Ser
            180                 185                 190 gcg gag cac aat gca tgc tat gaa gaa gtt aga caa gag ctg cag tca     1223
Ala Glu His Asn Ala Cys Tyr Glu Glu Val Arg Gln Glu Leu Gln Ser
        195                 200                 205 tca cat cct gat gat cca cgt att gtg gtt cta aaa cat aac gtt tgg     1271
Ser His Pro Asp Asp Pro Arg Ile Val Val Leu Lys His Asn Val Trp
    210                 215                 220 cga gtg aag ggt ctc atc cag atc tca aga tct atc gga gat gta tat     1319
Arg Val Lys Gly Leu Ile Gln Ile Ser Arg Ser Ile Gly Asp Val Tyr
225                 230                 235 cta aag aaa ccg gag tat aac aga gaa cct ctt cac agc aag ttt cgg     1367
Leu Lys Lys Pro Glu Tyr Asn Arg Glu Pro Leu His Ser Lys Phe Arg
240                 245                 250                 255 ctt cga gaa acc ttc cag aag ccg att ctt agt tct gaa cct caa att     1415
Leu Arg Glu Thr Phe Gln Lys Pro Ile Leu Ser Ser Glu Pro Gln Ile
            260                 265                 270 act gaa cac cga ata cag cca aac gat cag ttt gtt ata ttt gct tct     1463
Thr Glu His Arg Ile Gln Pro Asn Asp Gln Phe Val Ile Phe Ala Ser
        275                 280                 285 gat ggt cta tgg gag cac ctc agc aat cag gaa gct gtt gac ctt gtc     1511
Asp Gly Leu Trp Glu His Leu Ser Asn Gln Glu Ala Val Asp Leu Val
    290                 295                 300 caa agt agt ccc cgt aat gga atc gct cgg aga cta gtg aaa gcc gcg     1559
Gln Ser Ser Pro Arg Asn Gly Ile Ala Arg Arg Leu Val Lys Ala Ala
305                 310                 315 atg caa gaa gct gcc aag aag agg gag atg aga tac tca gac ctc aag     1607
Met Gln Glu Ala Ala Lys Lys Arg Glu Met Arg Tyr Ser Asp Leu Lys
320                 325                 330                 335 aag atc gac cgt ggc gtg agg agg cat ttc cac gac gat ata acc gtc     1655
Lys Ile Asp Arg Gly Val Arg Arg His Phe His Asp Asp Ile Thr Val
            340                 345                 350 gtc gtg gtg ttc ctc gac tcg gat gcc atg agc aaa gct agc tgg agc     1703
Val Val Val Phe Leu Asp Ser Asp Ala Met Ser Lys Ala Ser Trp Ser
        355                 360                 365 aag agc ccc tcg gtt tct ctc cga ggg ggc ggc gtc acc ctt ccc gcc     1751
Lys Ser Pro Ser Val Ser Leu Arg Gly Gly Gly Val Thr Leu Pro Ala
    370                 375                 380 aag tcc ctc gca ccc ttc tcg gct ccg gca cag ttg aac ggc acc cac     1799
Lys Ser Leu Ala Pro Phe Ser Ala Pro Ala Gln Leu Asn Gly Thr His
385                 390                 395 tgaagctgct actgctcttg aaaaggggca cagtgcagat ctgctagaga tgatgagaga   1859
agcagcaatc aagtcaagtg tagctgttgc tcgtacacct gctgtgctgt tgctgtttgc   1919
aaagctgccg tcttgactcc gcctggtaat tagtgtactg atagcgaggt atagaaatta   1979
ggttatttgt tagcgacgca aatcctttct tttttttctt cttctctctc tgttcttatc   2039
ccttttctct tcatcatgga ggaaacaggt ggctgtaaat ttgtccagaa cgtgttttcc   2099
ctaatagccc atcatatccc gctatttttc ttgttaaaaa aaaaa                   2144

<210> SEQ ID NO 32
<211> LENGTH: 399
<212> TYPE: PRT
```

<213> ORGANISM: Zea mays

<400> SEQUENCE: 32

```
Met Leu Ala Ala Val Met Asp Tyr Phe Ser Thr Cys Trp Gly Pro Arg
1               5                   10                  15

Ser Arg Ala Gly His Arg Gly Lys Gly Ser Asp Ala Ala Gly Arg Gln
            20                  25                  30

Asp Gly Leu Leu Trp Tyr Lys Asp Ala Gly Gln Leu Val Thr Gly Gly
        35                  40                  45

Phe Ser Met Ala Val Val Gln Ala Asn Gln Leu Leu Glu Asp Gln Ser
    50                  55                  60

Gln Val Glu Ser Gly Ser Leu Ser Leu Ala Asp Tyr Gly Pro Gln Gly
65                  70                  75                  80

Thr Phe Val Gly Val Tyr Asp Gly His Gly Gly Pro Glu Thr Ser Arg
                85                  90                  95

Phe Ile Asn Asp His Leu Phe Asn His Leu Arg Arg Phe Ala Thr Glu
            100                 105                 110

His Lys Ser Met Ser Ala Asp Val Ile Arg Lys Ala Phe Gln Glu Thr
        115                 120                 125

Glu Glu Gly Phe Leu Ser Leu Val Ile Lys Glu Trp Ser Phe Lys Pro
130                 135                 140

Gln Ile Ala Ser Val Gly Ser Cys Cys Leu Val Gly Val Ile Cys Ala
145                 150                 155                 160

Gly Thr Leu Tyr Val Ala Asn Leu Gly Asp Ser Arg Ala Val Leu Gly
                165                 170                 175

Arg Leu Val Lys Ala Thr Gly Glu Val Leu Ala Thr Gln Leu Ser Ala
            180                 185                 190

Glu His Asn Ala Cys Tyr Glu Val Arg Gln Glu Leu Gln Ser Ser
        195                 200                 205

His Pro Asp Asp Pro Arg Ile Val Val Leu Lys His Asn Val Trp Arg
    210                 215                 220

Val Lys Gly Leu Ile Gln Ile Ser Arg Ser Ile Gly Asp Val Tyr Leu
225                 230                 235                 240

Lys Lys Pro Glu Tyr Asn Arg Glu Pro Leu His Ser Lys Phe Arg Leu
                245                 250                 255

Arg Glu Thr Phe Gln Lys Pro Ile Leu Ser Ser Glu Pro Gln Ile Thr
            260                 265                 270

Glu His Arg Ile Gln Pro Asn Asp Gln Phe Val Ile Phe Ala Ser Asp
        275                 280                 285

Gly Leu Trp Glu His Leu Ser Asn Gln Glu Ala Val Asp Leu Val Gln
    290                 295                 300

Ser Ser Pro Arg Asn Gly Ile Ala Arg Leu Val Lys Ala Ala Met
305                 310                 315                 320

Gln Glu Ala Ala Lys Lys Arg Glu Met Arg Tyr Ser Asp Leu Lys Lys
                325                 330                 335

Ile Asp Arg Gly Val Arg Arg His Phe His Asp Ile Thr Val Val
            340                 345                 350

Val Val Phe Leu Asp Ser Asp Ala Met Ser Lys Ala Ser Trp Ser Lys
        355                 360                 365

Ser Pro Ser Val Ser Leu Arg Gly Gly Val Thr Leu Pro Ala Lys
    370                 375                 380

Ser Leu Ala Pro Phe Ser Ala Pro Ala Gln Leu Asn Gly Thr His
385                 390                 395
```

```
<210> SEQ ID NO 33
<211> LENGTH: 1632
<212> TYPE: DNA
<213> ORGANISM: Zea mays
<220> FEATURE:
<221> NAME/KEY: CDS
<222> LOCATION: (352)..(1179)
<223> OTHER INFORMATION: protein phosphatase 2C (ZM68587657)

<400> SEQUENCE: 33
ggacgccggg caacatgtca atggggagtt ctccatggct gttgttcagg caaataactt      60
acttgaggac cagtgtcaga tcgagtcggg cccactgagt tttctagatt ctggaccata     120
tggcactttc gttggtgttt acgatgggca tggtggtcca gagacggcct gctatatcaa     180
tgatcatctt ttccagaatc tgaaaagtaa cttgctaacc tttaaatctg tgcagtagca     240
ctattcccgt ttcttagcac tatatctgca tttggctttc agtttgcaca taaggagat      300 catccatttt ttcatggctt gtatttagga tttgcatctg agcagaatgc a atg tct     357
                                                          Met Ser
                                                            1
```

| | | | | | | | | | | | | | | | |
|---|---|---|---|---|---|---|---|---|---|---|---|---|---|---|---|
| gct | gat | gta | ctg | aag | aag | gca | tat | gaa | gct | aca | gaa | gat | gga | ttc | ttc | 405 |
| Ala | Asp | Val | Leu | Lys | Lys | Ala | Tyr | Glu | Ala | Thr | Glu | Asp | Gly | Phe | Phe | |
| | | 5 | | | | | 10 | | | | | 15 | | | | |

```
tcc att gtt acc aaa caa tgg cct gta aag cct cag ata gca gct gtc     453
Ser Ile Val Thr Lys Gln Trp Pro Val Lys Pro Gln Ile Ala Ala Val
     20                  25                  30 ggc tca tgc tgc ctg gtc ggt gta att tgt ggt ggc atg ctt tat gtt     501
Gly Ser Cys Cys Leu Val Gly Val Ile Cys Gly Gly Met Leu Tyr Val
 35              40                  45                  50 gcc aat gtt ggg gat tcc cgt gtc gtt tta gga aaa cat gtt aag gcc     549
Ala Asn Val Gly Asp Ser Arg Val Val Leu Gly Lys His Val Lys Ala
             55                  60                  65 act gga gaa gtt ttg gct gtc caa ctg tca gca gaa cat aat gtt agt     597
Thr Gly Glu Val Leu Ala Val Gln Leu Ser Ala Glu His Asn Val Ser
         70                  75                  80 att gcg tcc gtg aga aaa gaa ctg cag tca atg cac cca gaa gat agg     645
Ile Ala Ser Val Arg Lys Glu Leu Gln Ser Met His Pro Glu Asp Arg
     85                  90                  95 cac att gtt gtt ctc aag cac aat gtt tgg cgt gtt aaa gga cta att     693
His Ile Val Val Leu Lys His Asn Val Trp Arg Val Lys Gly Leu Ile
 100                 105                 110 cag gtt tgt aga tca att ggt gat gca tat ctc aaa aag caa gag ttc     741
Gln Val Cys Arg Ser Ile Gly Asp Ala Tyr Leu Lys Lys Gln Glu Phe
115                 120                 125                 130 aac agg gaa ccc cta tat gca aaa ttt cgc ctc cgt gaa cct ttt cac     789
Asn Arg Glu Pro Leu Tyr Ala Lys Phe Arg Leu Arg Glu Pro Phe His
                135                 140                 145 aag cca ata cta agt tca gaa cca tca atc agt gtg caa cca cta caa     837
Lys Pro Ile Leu Ser Ser Glu Pro Ser Ile Ser Val Gln Pro Leu Gln
            150                 155                 160 cca cac gac cag ttt ctc ata ttt gca tct gat gga ctt tgg gag cag     885
Pro His Asp Gln Phe Leu Ile Phe Ala Ser Asp Gly Leu Trp Glu Gln
        165                 170                 175 tta acc aac caa gag gca gtt gat att gtt cga agt agc ccc cgc agt     933
Leu Thr Asn Gln Glu Ala Val Asp Ile Val Arg Ser Ser Pro Arg Ser
    180                 185                 190 ggc tgt gct agg agg ctg ata aga gcg gca ctg caa gag gca gcc aag     981
Gly Cys Ala Arg Arg Leu Ile Arg Ala Ala Leu Gln Glu Ala Ala Lys
195                 200                 205                 210 aaa aga gag atg agg tac tcg gac ctc aag aag att gac cgc ggt gtt    1029
Lys Arg Glu Met Arg Tyr Ser Asp Leu Lys Lys Ile Asp Arg Gly Val
                215                 220                 225
```

-continued

```
cgc cgc cac ttc cac gac gac ata aca gtc ata gta gtg ttc ctt gac   1077
Arg Arg His Phe His Asp Asp Ile Thr Val Ile Val Val Phe Leu Asp
        230                 235                 240 tcc ggc ctc gta agc cag gcg agc aca cac cga ggt cca act ctt tcc   1125
Ser Gly Leu Val Ser Gln Ala Ser Thr His Arg Gly Pro Thr Leu Ser
245                 250                 255 ttg cga ggc ggt ggc ggc agc gct ggc ctg cgc agc aac aca ctt gca   1173
Leu Arg Gly Gly Gly Gly Ser Ala Gly Leu Arg Ser Asn Thr Leu Ala
    260                 265                 270 cct acg tgactataaa gtgcctggtg gagtggaggc tactgactga aggtggtttt   1229
Pro Thr
275 ctttccttgt gtcgaatgtg ttatatatgt acttgtacca gccaagatca ttcatccccc   1289 cccctaaaat ggtgtaaaga agtaggagag gcgccgaagt tcctcaccag cgtatctgaa   1349 tgccctcaat ggtgtcaagt tgtggactca agtggatagc ttcgctgaat cttctgatga   1409 tgctctgtgg aaagctcgaa tcctttccac ctgaaaaagc aagtaatatg tcttccagtg   1469 ctggaattaa ccccctagtgc atatatatat gtatgaaata ataataaggc aaaaggagga   1529 gtaacttatt taactaatgc tgtgaggtgt atttatgttt tgtatgtgta ctgcttttga   1589 ctgctactgc atctactgtt gttaattgaa aaaaaaaaa aaa                     1632
```

<210> SEQ ID NO 34
<211> LENGTH: 276
<212> TYPE: PRT
<213> ORGANISM: Zea mays

<400> SEQUENCE: 34

```
Met Ser Ala Asp Val Leu Lys Lys Ala Tyr Glu Ala Thr Glu Asp Gly
1               5                   10                  15

Phe Phe Ser Ile Val Thr Lys Gln Trp Pro Val Lys Pro Gln Ile Ala
            20                  25                  30

Ala Val Gly Ser Cys Cys Leu Val Gly Val Ile Cys Gly Gly Met Leu
        35                  40                  45

Tyr Val Ala Asn Val Gly Asp Ser Arg Val Val Leu Gly Lys His Val
    50                  55                  60

Lys Ala Thr Gly Glu Val Leu Ala Val Gln Leu Ser Ala Glu His Asn
65                  70                  75                  80

Val Ser Ile Ala Ser Val Arg Lys Glu Leu Gln Ser Met His Pro Glu
                85                  90                  95

Asp Arg His Ile Val Val Leu Lys His Asn Val Trp Arg Val Lys Gly
            100                 105                 110

Leu Ile Gln Val Cys Arg Ser Ile Gly Asp Ala Tyr Leu Lys Lys Gln
        115                 120                 125

Glu Phe Asn Arg Glu Pro Leu Tyr Ala Lys Phe Arg Leu Arg Glu Pro
    130                 135                 140

Phe His Lys Pro Ile Leu Ser Ser Glu Pro Ser Ile Ser Val Gln Pro
145                 150                 155                 160

Leu Gln Pro His Asp Gln Phe Leu Ile Phe Ala Ser Asp Gly Leu Trp
                165                 170                 175

Glu Gln Leu Thr Asn Gln Glu Ala Val Asp Ile Val Arg Ser Ser Pro
            180                 185                 190

Arg Ser Gly Cys Ala Arg Arg Leu Ile Arg Ala Ala Leu Gln Glu Ala
        195                 200                 205

Ala Lys Lys Arg Glu Met Arg Tyr Ser Asp Leu Lys Lys Ile Asp Arg
    210                 215                 220
```

```
Gly Val Arg Arg His Phe His Asp Asp Ile Thr Val Ile Val Val Phe
225                 230                 235                 240

Leu Asp Ser Gly Leu Val Ser Gln Ala Ser Thr His Arg Gly Pro Thr
            245                 250                 255

Leu Ser Leu Arg Gly Gly Gly Ser Ala Gly Leu Arg Ser Asn Thr
            260                 265                 270

Leu Ala Pro Thr
        275

<210> SEQ ID NO 35
<211> LENGTH: 1436
<212> TYPE: DNA
<213> ORGANISM: Physcomitrella patens
<220> FEATURE:
<221> NAME/KEY: CDS
<222> LOCATION: (302)..(1210)
<223> OTHER INFORMATION: mitochondrial carrier protein (EST390)

<400> SEQUENCE: 35
atcccgggtg gagcccttc aagcctcacg cattctggat tcgctcccgg cttcgaatgc      60
ttgagtggtt ctaagtgatg agatagcgcc gtctagggag aatttcgaat ttgcgctaga    120
acatgggtgg ttattccatc agtgtggcag cgcccacaga tattgcagtg aaaggttgaa    180
cacaacgacc caaggacaac ctgcaccttc aacagtcag cgtgaggtga aaagataggc     240
cagttttcag ctgcacataa ccttcacttc tgcaggcgca gaacacgtgc ggtactgagc    300 a atg ggg tcc tct aag gca gaa gag aat ttg gcc tta cgg ctg ggc ctc   349
  Met Gly Ser Ser Lys Ala Glu Glu Asn Leu Ala Leu Arg Leu Gly Leu
  1               5                   10                  15 act gca gcg tca gcc atg gcg tcg gag tct gtg acc ttc cca atc gat    397
Thr Ala Ala Ser Ala Met Ala Ser Glu Ser Val Thr Phe Pro Ile Asp
            20                  25                  30 atc acg aaa acc cgc ctg cag ctc caa ggc gaa atg ggt gcc aca gct    445
Ile Thr Lys Thr Arg Leu Gln Leu Gln Gly Glu Met Gly Ala Thr Ala
        35                  40                  45 ggc gca ccc aag cga gga gcg atc agc atg gcg atc tct ata ggc aag    493
Gly Ala Pro Lys Arg Gly Ala Ile Ser Met Ala Ile Ser Ile Gly Lys
    50                  55                  60 gag gag ggc att gcc ggt ctt tat agg ggc ctt tct ccg gca ctt ttg    541
Glu Glu Gly Ile Ala Gly Leu Tyr Arg Gly Leu Ser Pro Ala Leu Leu
65                  70                  75                  80 cgt cat gta ttt tac aca agc att cgt att gtt gcg tat gaa aat cta    589
Arg His Val Phe Tyr Thr Ser Ile Arg Ile Val Ala Tyr Glu Asn Leu
                85                  90                  95 cgt acc gcc ctc agt cat ggc gaa cac ccg gaa aat ctg tcc gtt gca    637
Arg Thr Ala Leu Ser His Gly Glu His Pro Glu Asn Leu Ser Val Ala
            100                 105                 110 aaa aag gct ttc atc ggt ggc act tcc ggt att att ggg cag gtg ata    685
Lys Lys Ala Phe Ile Gly Gly Thr Ser Gly Ile Ile Gly Gln Val Ile
        115                 120                 125 gcg agt cca gcg gat ttg gtg aag gtg cgc atg caa gcg gat ggg agg    733
Ala Ser Pro Ala Asp Leu Val Lys Val Arg Met Gln Ala Asp Gly Arg
    130                 135                 140 ctg gtg aag ctt ggg cag cag cca cgc tac acc gga gta gct gac gca    781
Leu Val Lys Leu Gly Gln Gln Pro Arg Tyr Thr Gly Val Ala Asp Ala
145                 150                 155                 160 ttc acc aag att gcc cga gcc gag ggt gtg aca ggg ctg tgg cgt gga    829
Phe Thr Lys Ile Ala Arg Ala Glu Gly Val Thr Gly Leu Trp Arg Gly
                165                 170                 175 gtg gga ccc aat gct caa cgt gcc ttc ctc gtc aac atg ggg gag ctt    877
```

```
Val Gly Pro Asn Ala Gln Arg Ala Phe Leu Val Asn Met Gly Glu Leu
            180                 185                 190 gca tgc tac gac cag tcg aag caa tgg atc ata gga cgc ggc att gct    925
Ala Cys Tyr Asp Gln Ser Lys Gln Trp Ile Ile Gly Arg Gly Ile Ala
        195                 200                 205 gcc gac aac atc gga gct cac acg ctt gca tca gtg atg tct ggg tta    973
Ala Asp Asn Ile Gly Ala His Thr Leu Ala Ser Val Met Ser Gly Leu
    210                 215                 220 tca gct act att ctg agc tgc cct gcc gat gtg gtg aag acc cgg atg   1021
Ser Ala Thr Ile Leu Ser Cys Pro Ala Asp Val Val Lys Thr Arg Met
225                 230                 235                 240 atg aac caa ggc gct gca ggt gcc gtg tac cgc aac tct ctg gat tgt   1069
Met Asn Gln Gly Ala Ala Gly Ala Val Tyr Arg Asn Ser Leu Asp Cys
                245                 250                 255 ctc acc aaa acc gtg aag gct gaa ggc gtg atg gcg ctg tgg aag ggc   1117
Leu Thr Lys Thr Val Lys Ala Glu Gly Val Met Ala Leu Trp Lys Gly
            260                 265                 270 ttc ttc ccg acg tgg aca agg ctg ggc cct tgg caa ttc gtg ttt tgg   1165
Phe Phe Pro Thr Trp Thr Arg Leu Gly Pro Trp Gln Phe Val Phe Trp
        275                 280                 285 gtc tca tat gag cag ctc cgc cgc atc agc ggt cta tca tcc ttc       1210
Val Ser Tyr Glu Gln Leu Arg Arg Ile Ser Gly Leu Ser Ser Phe
    290                 295                 300 taataagtaa agcctcgcag ttgttttggg tgtgaaactt acatggcatt cagctcttac  1270
aaagatttca catgcttgaa gattttgagg tgctgttttt tttatcattt tgttccttc   1330 tcttttctgc ctcaattgga tgtcatagct gaggctatga agcttagttt cattgacaaa  1390
tgtttacatt tgttagcaat gtgtagtagt gcacttgcgt taaccg                 1436

<210> SEQ ID NO 36
<211> LENGTH: 303
<212> TYPE: PRT
<213> ORGANISM: Physcomitrella patens

<400> SEQUENCE: 36

Met Gly Ser Ser Lys Ala Glu Glu Asn Leu Ala Leu Arg Leu Gly Leu
1               5                   10                  15

Thr Ala Ala Ser Ala Met Ala Ser Glu Ser Val Thr Phe Pro Ile Asp
                20                  25                  30

Ile Thr Lys Thr Arg Leu Gln Leu Gln Gly Glu Met Gly Ala Thr Ala
            35                  40                  45

Gly Ala Pro Lys Arg Gly Ala Ile Ser Met Ala Ile Ser Ile Gly Lys
        50                  55                  60

Glu Glu Gly Ile Ala Gly Leu Tyr Arg Gly Leu Ser Pro Ala Leu Leu
65                  70                  75                  80

Arg His Val Phe Tyr Thr Ser Ile Arg Ile Val Ala Tyr Glu Asn Leu
                85                  90                  95

Arg Thr Ala Leu Ser His Gly Glu His Pro Glu Asn Leu Ser Val Ala
            100                 105                 110

Lys Lys Ala Phe Ile Gly Gly Thr Ser Gly Ile Ile Gly Gln Val Ile
        115                 120                 125

Ala Ser Pro Ala Asp Leu Val Lys Val Arg Met Gln Ala Asp Gly Arg
    130                 135                 140

Leu Val Lys Leu Gly Gln Gln Pro Arg Tyr Thr Gly Val Ala Asp Ala
145                 150                 155                 160

Phe Thr Lys Ile Ala Arg Ala Glu Gly Val Thr Gly Leu Trp Arg Gly
                165                 170                 175
```

```
Val Gly Pro Asn Ala Gln Arg Ala Phe Leu Val Asn Met Gly Glu Leu
            180                 185                 190

Ala Cys Tyr Asp Gln Ser Lys Gln Trp Ile Ile Gly Arg Gly Ile Ala
        195                 200                 205

Ala Asp Asn Ile Gly Ala His Thr Leu Ala Ser Val Met Ser Gly Leu
210                 215                 220

Ser Ala Thr Ile Leu Ser Cys Pro Ala Asp Val Val Lys Thr Arg Met
225                 230                 235                 240

Met Asn Gln Gly Ala Ala Gly Ala Val Tyr Arg Asn Ser Leu Asp Cys
                245                 250                 255

Leu Thr Lys Thr Val Lys Ala Glu Gly Val Met Ala Leu Trp Lys Gly
            260                 265                 270

Phe Phe Pro Thr Trp Thr Arg Leu Gly Pro Trp Gln Phe Val Phe Trp
        275                 280                 285

Val Ser Tyr Glu Gln Leu Arg Arg Ile Ser Gly Leu Ser Ser Phe
    290                 295                 300

<210> SEQ ID NO 37
<211> LENGTH: 1078
<212> TYPE: DNA
<213> ORGANISM: Brassica napus
<220> FEATURE:
<221> NAME/KEY: CDS
<222> LOCATION: (33)..(977)
<223> OTHER INFORMATION: mitochondrial carrier protein (BN51363030)

<400> SEQUENCE: 37
agaaaacaaa taaaaatcaa atcgttacag ca atg ggc gtc aaa agt ttc gtg      53
                                    Met Gly Val Lys Ser Phe Val
                                    1               5 gaa ggt ggg att gcc cct gta gtc gcc ggc tgc tcc act cac cct ctc     101
Glu Gly Gly Ile Ala Pro Val Val Ala Gly Cys Ser Thr His Pro Leu
    10                  15                  20 gat ctc atc aag gtt cgc ctt cag ctc cac gga gaa gct tcc gcc gtc     149
Asp Leu Ile Lys Val Arg Leu Gln Leu His Gly Glu Ala Ser Ala Val
    25                  30                  35 act ctc ctc cgc cca gct ctc gct ttc cac aat tct ccc cca gct ttt     197
Thr Leu Leu Arg Pro Ala Leu Ala Phe His Asn Ser Pro Pro Ala Phe
40                  45                  50                  55 ctg gag acg act cat tcg gtc cct aaa gta gga ccc atc tcc ctc gga     245
Leu Glu Thr Thr His Ser Val Pro Lys Val Gly Pro Ile Ser Leu Gly
                60                  65                  70 atc aac ctc gtc aaa acc gaa ggc gcc gcc gcg ctt ttc tcc ggc gtc     293
Ile Asn Leu Val Lys Thr Glu Gly Ala Ala Ala Leu Phe Ser Gly Val
            75                  80                  85 tcc gcc aca ctc ctc cgt cag act ctc tac tcc acc acc agg atg ggt     341
Ser Ala Thr Leu Leu Arg Gln Thr Leu Tyr Ser Thr Thr Arg Met Gly
        90                  95                  100 ctc tac gag gtg ttg aaa aac aaa tgg act gat ccc gag tcc ggt aag     389
Leu Tyr Glu Val Leu Lys Asn Lys Trp Thr Asp Pro Glu Ser Gly Lys
    105                 110                 115 ctg agt ctc act cgt aaa atc gcc gcg ggg cta gtc ggt ggc ggg atc     437
Leu Ser Leu Thr Arg Lys Ile Ala Ala Gly Leu Val Gly Gly Gly Ile
120                 125                 130                 135 gga gcc gcc gtc ggg aac cca gcc gac gtg gcg atg gta agg atg caa     485
Gly Ala Ala Val Gly Asn Pro Ala Asp Val Ala Met Val Arg Met Gln
                140                 145                 150 gcc gac ggg agg ctt ccc gtg gca gag cgt cgt aac tac gcg ggc gta     533
Ala Asp Gly Arg Leu Pro Val Ala Glu Arg Arg Asn Tyr Ala Gly Val
            155                 160                 165
```

```
gga gac gcg atc aag agg atg gcg aag caa gaa ggc gtg gtg agc ctg    581
Gly Asp Ala Ile Lys Arg Met Ala Lys Gln Glu Gly Val Val Ser Leu
        170                 175                 180 tgg cgc ggc tcg gct ctg acg atc aac agg gcg atg ata gtg acg gcg    629
Trp Arg Gly Ser Ala Leu Thr Ile Asn Arg Ala Met Ile Val Thr Ala
    185                 190                 195 gcg cag ctc gcg tcg tac gat cag ttc aag gaa ggg atg gtg gag agc    677
Ala Gln Leu Ala Ser Tyr Asp Gln Phe Lys Glu Gly Met Val Glu Ser
200                 205                 210                 215 ggg ggg atg aaa gat ggg ctc ggg act cac gtg gtg gcg agc ttc gcg    725
Gly Gly Met Lys Asp Gly Leu Gly Thr His Val Val Ala Ser Phe Ala
            220                 225                 230 gcg ggg atc gtg gcg gct gtt gcg tcg aat ccg gtg gat gtg ata aag    773
Ala Gly Ile Val Ala Ala Val Ala Ser Asn Pro Val Asp Val Ile Lys
            235                 240                 245 acg agg gtg atg aat atg aag gtg gat gcg cgt ggt ggg gag gct cag    821
Thr Arg Val Met Asn Met Lys Val Asp Ala Arg Gly Gly Glu Ala Gln
        250                 255                 260 tac aaa ggc gcg tgg gat tgt gcg gtg aag acg gtt aga gct gaa gga    869
Tyr Lys Gly Ala Trp Asp Cys Ala Val Lys Thr Val Arg Ala Glu Gly
    265                 270                 275 ccg atg gct ctt tat aaa ggg ttt gtt cct acg gtt tgc agg caa gga    917
Pro Met Ala Leu Tyr Lys Gly Phe Val Pro Thr Val Cys Arg Gln Gly
280                 285                 290                 295 cct ttc act gtt gtg ctc ttt gtt acg ttg gag caa gtc aag aag ctg    965
Pro Phe Thr Val Val Leu Phe Val Thr Leu Glu Gln Val Lys Lys Leu
            300                 305                 310 ctt cgt gat ttt tgattatcat ttgaaggtta tgatgatgag gacgactaag       1017
Leu Arg Asp Phe
            315 aataagaatg ctagtagtat tgatttgata gggatttttc gtattgggtt attcattttc 1077 g                                                                 1078

<210> SEQ ID NO 38
<211> LENGTH: 315
<212> TYPE: PRT
<213> ORGANISM: Brassica napus

<400> SEQUENCE: 38

Met Gly Val Lys Ser Phe Val Glu Gly Gly Ile Ala Pro Val Val Ala
1               5                   10                  15

Gly Cys Ser Thr His Pro Leu Asp Leu Ile Lys Val Arg Leu Gln Leu
            20                  25                  30

His Gly Glu Ala Ser Ala Val Thr Leu Leu Arg Pro Ala Leu Ala Phe
        35                  40                  45

His Asn Ser Pro Pro Ala Phe Leu Glu Thr Thr His Ser Val Pro Lys
    50                  55                  60

Val Gly Pro Ile Ser Leu Gly Ile Asn Leu Val Lys Thr Glu Gly Ala
65                  70                  75                  80

Ala Ala Leu Phe Ser Gly Val Ser Ala Thr Leu Leu Arg Gln Thr Leu
                85                  90                  95

Tyr Ser Thr Thr Arg Met Gly Leu Tyr Glu Val Leu Lys Asn Lys Trp
            100                 105                 110

Thr Asp Pro Glu Ser Gly Lys Leu Ser Leu Thr Arg Lys Ile Ala Ala
        115                 120                 125

Gly Leu Val Gly Gly Gly Ile Gly Ala Ala Val Gly Asn Pro Ala Asp
    130                 135                 140

Val Ala Met Val Arg Met Gln Ala Asp Gly Arg Leu Pro Val Ala Glu
```

| | | | 145 | | | 150 | | | 155 | | | 160 | |
|---|---|---|---|---|---|---|---|---|---|---|---|---|---|
Arg Arg Asn Tyr Ala Gly Val Gly Asp Ala Ile Lys Arg Met Ala Lys
                   165                  170                175

Gln Glu Gly Val Val Ser Leu Trp Arg Gly Ser Ala Leu Thr Ile Asn
  180                     185                 190

Arg Ala Met Ile Val Thr Ala Ala Gln Leu Ala Ser Tyr Asp Gln Phe
         195                  200                205

Lys Glu Gly Met Val Glu Ser Gly Gly Met Lys Asp Gly Leu Gly Thr
 210                   215                 220

His Val Ala Ser Phe Ala Ala Gly Ile Val Ala Ala Val Ala Ser
225              230              235            240

Asn Pro Val Asp Val Ile Lys Thr Arg Val Met Asn Met Lys Val Asp
         245                  250              255

Ala Arg Gly Gly Glu Ala Gln Tyr Lys Gly Ala Trp Asp Cys Ala Val
             260                265              270

Lys Thr Val Arg Ala Glu Gly Pro Met Ala Leu Tyr Lys Gly Phe Val
     275                  280              285

Pro Thr Val Cys Arg Gln Gly Pro Phe Thr Val Val Leu Phe Val Thr
290              295              300

Leu Glu Gln Val Lys Lys Leu Leu Arg Asp Phe
305            310              315

```
<210> SEQ ID NO 39
<211> LENGTH: 1275
<212> TYPE: DNA
<213> ORGANISM: Brassica napus
<220> FEATURE:
<221> NAME/KEY: CDS
<222> LOCATION: (328)..(1194)
<223> OTHER INFORMATION: mitochondrial carrier protein (BN42986056)

<400> SEQUENCE: 39
tctaaaaaaa cttttttgtct gaacggcata tgtctcagag acctcaagtt cctcattctt      60
cttctatagc tttcggtctc cattctcatc tcctaatctc cagtgagatc agctccaatt     120
ccaactggtc tctctaagaa aaaataatc aaacctttc aaaattttct ctcggatttt     180
ctcggaataa aaatctaacc tttctgactt ttttgatttt cgatttgata aaaacaagaa     240
atgggtctta agggtttcgc tgaaggaggc atcgcatcga tcgtagcggg atgttcgacc     300
```
cacccgcttg atctaatcaa ggtctga atg cag ctc caa ggg gaa tca gcc tcg    354
                                          Met Gln Leu Gln Gly Glu Ser Ala Ser
                                             1            5 att cag aca aat ctc cga cca gct ctt gct ttc cag act tcc tcc gcc    402
Ile Gln Thr Asn Leu Arg Pro Ala Leu Ala Phe Gln Thr Ser Ser Ala
10               15                 20                 25 gtt cac gcg cct tcg cct cct ccg cgc gtg ggt ata atc acc atc gga    450
Val His Ala Pro Ser Pro Pro Pro Arg Val Gly Ile Ile Thr Ile Gly
               30                 35                 40 tct cgc atc atc aga caa gaa ggc acg tgc act ctc ttc tcc ggc atc    498
Ser Arg Ile Ile Arg Gln Glu Gly Thr Cys Thr Leu Phe Ser Gly Ile
                   45                 50                55 tcc gcc acc tcc gcc acc gtt ctc cgc cag act ctc tac tcg acg act    546
Ser Ala Thr Ser Ala Thr Val Leu Arg Gln Thr Leu Tyr Ser Thr Thr
         60                  65                70 cgc atg ggt cta tac gac atc ctg aaa acc aaa tgg acc gac ccg gaa    594
Arg Met Gly Leu Tyr Asp Ile Leu Lys Thr Lys Trp Thr Asp Pro Glu
75               80                85 acc aaa acc ata cct ttg acc cgc aaa ctc gcc gcc ggg ttc atc gcc    642
Thr Lys Thr Ile Pro Leu Thr Arg Lys Leu Ala Ala Gly Phe Ile Ala

```
                                                  90                      95                     100                      105
gga ggt atc ggc gcc gcc gtc ggg aac ccg gcg gat gtc gcc atg gtg            690
Gly Gly Ile Gly Ala Ala Val Gly Asn Pro Ala Asp Val Ala Met Val
                110                     115                     120 cgc atg caa gcc gac ggg agg ctc ccg gtg gtc gac cgg agg aac tac            738
Arg Met Gln Ala Asp Gly Arg Leu Pro Val Val Asp Arg Arg Asn Tyr
            125                     130                     135 aag agc gtt ttg gac gcg atc gcg cag atg gtt cgc ggc gaa ggc gtc            786
Lys Ser Val Leu Asp Ala Ile Ala Gln Met Val Arg Gly Glu Gly Val
        140                     145                     150 acg tcg ctg tgg aga ggt tcg tcg atg acg atc aac aga gcg atg ctc            834
Thr Ser Leu Trp Arg Gly Ser Ser Met Thr Ile Asn Arg Ala Met Leu
    155                     160                     165 gtg acg gcg tcg cag ctg gct acg tac gac tcg gtg aaa gag acg att            882
Val Thr Ala Ser Gln Leu Ala Thr Tyr Asp Ser Val Lys Glu Thr Ile
170                     175                     180                     185 ttg gag aaa ggg ttg atg agg gac ggg ctc ggg act cac gtg acg tcg            930
Leu Glu Lys Gly Leu Met Arg Asp Gly Leu Gly Thr His Val Thr Ser
                190                     195                     200 agc ttc gcg gcg ggg ttt gtg gct tcg gtc gcg tcg aac ccc gtg gat            978
Ser Phe Ala Ala Gly Phe Val Ala Ser Val Ala Ser Asn Pro Val Asp
            205                     210                     215 gtg atc aag acg aga gtg atg aat atg aaa gtg gag gcg ggg aaa acg           1026
Val Ile Lys Thr Arg Val Met Asn Met Lys Val Glu Ala Gly Lys Thr
        220                     225                     230 gcg ccg tat aag gga gcg gtt gat tgc gcg ttg aag acg gtg aga gcg           1074
Ala Pro Tyr Lys Gly Ala Val Asp Cys Ala Leu Lys Thr Val Arg Ala
    235                     240                     245 gaa ggg atc atg gct tta tac aaa ggg ttt ctg ccg acg gtg tcg aga           1122
Glu Gly Ile Met Ala Leu Tyr Lys Gly Phe Leu Pro Thr Val Ser Arg
250                     255                     260                     265 caa gca ccg ttc acg gtg att atg ttt gtg aca ctt gaa caa gtt aag           1170
Gln Ala Pro Phe Thr Val Ile Met Phe Val Thr Leu Glu Gln Val Lys
                270                     275                     280 aag gtg ttc aag gac ttt gac ttt tgagacaaga gttaaagatg atggtggcga          1224
Lys Val Phe Lys Asp Phe Asp Phe
            285 taatttgctt taaactaaat aaattttgtt tttttttatt gtattttctt t                  1275

<210> SEQ ID NO 40
<211> LENGTH: 289
<212> TYPE: PRT
<213> ORGANISM: Brassica napus

<400> SEQUENCE: 40

Met Gln Leu Gln Gly Glu Ser Ala Ser Ile Gln Thr Asn Leu Arg Pro
1               5                   10                  15

Ala Leu Ala Phe Gln Thr Ser Ser Ala Val His Ala Pro Ser Pro Pro
            20                  25                  30

Pro Arg Val Gly Ile Ile Thr Ile Gly Ser Arg Ile Ile Arg Gln Glu
        35                  40                  45

Gly Thr Cys Thr Leu Phe Ser Gly Ile Ser Ala Thr Ser Ala Thr Val
    50                  55                  60

Leu Arg Gln Thr Leu Tyr Ser Thr Thr Arg Met Gly Leu Tyr Asp Ile
65                  70                  75                  80

Leu Lys Thr Lys Trp Thr Asp Pro Glu Thr Lys Thr Ile Pro Leu Thr
                85                  90                  95

Arg Lys Leu Ala Ala Gly Phe Ile Ala Gly Gly Ile Gly Ala Ala Val
            100                 105                 110
```

```
Gly Asn Pro Ala Asp Val Ala Met Val Arg Met Gln Ala Asp Gly Arg
            115                 120                 125

Leu Pro Val Val Asp Arg Arg Asn Tyr Lys Ser Val Leu Asp Ala Ile
    130                 135                 140

Ala Gln Met Val Arg Gly Glu Gly Val Thr Ser Leu Trp Arg Gly Ser
145                 150                 155                 160

Ser Met Thr Ile Asn Arg Ala Met Leu Val Thr Ala Ser Gln Leu Ala
            165                 170                 175

Thr Tyr Asp Ser Val Lys Glu Thr Ile Leu Glu Lys Gly Leu Met Arg
            180                 185                 190

Asp Gly Leu Gly Thr His Val Thr Ser Ser Phe Ala Ala Gly Phe Val
        195                 200                 205

Ala Ser Val Ala Ser Asn Pro Val Asp Val Ile Lys Thr Arg Val Met
    210                 215                 220

Asn Met Lys Val Glu Ala Gly Lys Thr Ala Pro Tyr Lys Gly Ala Val
225                 230                 235                 240

Asp Cys Ala Leu Lys Thr Val Arg Ala Glu Gly Ile Met Ala Leu Tyr
                245                 250                 255

Lys Gly Phe Leu Pro Thr Val Ser Arg Gln Ala Pro Phe Thr Val Ile
                260                 265                 270

Met Phe Val Thr Leu Glu Gln Val Lys Lys Val Phe Lys Asp Phe Asp
            275                 280                 285

Phe

<210> SEQ ID NO 41
<211> LENGTH: 1100
<212> TYPE: DNA
<213> ORGANISM: Brassica napus
<220> FEATURE:
<221> NAME/KEY: CDS
<222> LOCATION: (128)..(1036)
<223> OTHER INFORMATION: mitochondrial carrier protein (BN49389066)

<400> SEQUENCE: 41
cgacgatttc gtttaatata aacatcacca agtgaatctc tccgcctctc tctctctttc      60
tctgcggaat ctcttcgtct cgttgcgttc gagagttccg tacgattccc aacaagaaag     120 ggaagag atg gcg gag gag aag aaa gta gct ccg att ggt atc tgg act      169
        Met Ala Glu Glu Lys Lys Val Ala Pro Ile Gly Ile Trp Thr
        1               5                   10 gcc gtg aag cct ttc gtc aat ggc ggt gcc tct ggt atg ctc gcc act      217
Ala Val Lys Pro Phe Val Asn Gly Gly Ala Ser Gly Met Leu Ala Thr
15                  20                  25                  30 tgc gtt atc cag cct att gac atg atc aag gtg agg att caa cta ggt      265
Cys Val Ile Gln Pro Ile Asp Met Ile Lys Val Arg Ile Gln Leu Gly
                35                  40                  45 cag gga tct gca gct agt gtg acc acc acc atg ttg aag aat gaa ggt      313
Gln Gly Ser Ala Ala Ser Val Thr Thr Thr Met Leu Lys Asn Glu Gly
            50                  55                  60 atc ggt gcc ttc tac aag gga tta tca gct ggt ttg ctg agg caa gca      361
Ile Gly Ala Phe Tyr Lys Gly Leu Ser Ala Gly Leu Leu Arg Gln Ala
        65                  70                  75 act tac acc aca gct cgt ctt gga tca ttc aag atg ctg act gcg aaa      409
Thr Tyr Thr Thr Ala Arg Leu Gly Ser Phe Lys Met Leu Thr Ala Lys
    80                  85                  90 gca agc gag gct aac gat ggg aag cca cta ccg ctg tat caa aaa gct      457
Ala Ser Glu Ala Asn Asp Gly Lys Pro Leu Pro Leu Tyr Gln Lys Ala
95                  100                 105                 110
```

```
cta tgt ggt ctg aca gct ggt gct atc ggt gcc tgc gtt ggt agt cca        505
Leu Cys Gly Leu Thr Ala Gly Ala Ile Gly Ala Cys Val Gly Ser Pro
            115                 120                 125 gcc gat tta gcg ctt atc aga atg caa gct gat aac act ttg ccg tta        553
Ala Asp Leu Ala Leu Ile Arg Met Gln Ala Asp Asn Thr Leu Pro Leu
            130                 135                 140 gct cag cgc agg aac tat acc aac gcc ttc cat gcg ctt tac cgt att        601
Ala Gln Arg Arg Asn Tyr Thr Asn Ala Phe His Ala Leu Tyr Arg Ile
        145                 150                 155 agc gct gat gaa gga gtt ttg gcg ctt tgg aaa ggt tgt ggg cca act        649
Ser Ala Asp Glu Gly Val Leu Ala Leu Trp Lys Gly Cys Gly Pro Thr
    160                 165                 170 gtg gtc aga gca atg gct ttg aac atg ggg atg ctt gcg tct tat gat        697
Val Val Arg Ala Met Ala Leu Asn Met Gly Met Leu Ala Ser Tyr Asp
175                 180                 185                 190 caa agt gct gag tat atg aga gat aat ctt ggt ctt ggg gag aca tcc        745
Gln Ser Ala Glu Tyr Met Arg Asp Asn Leu Gly Leu Gly Glu Thr Ser
                195                 200                 205 aca gtc gta gga gca agt gct gtt ttg gga ttc tgc gct gcg gct tgc        793
Thr Val Val Gly Ala Ser Ala Val Leu Gly Phe Cys Ala Ala Ala Cys
            210                 215                 220 agt ctt cca ttt gac ttt gtc aaa aca cag atc caa aaa atg caa ccc        841
Ser Leu Pro Phe Asp Phe Val Lys Thr Gln Ile Gln Lys Met Gln Pro
            225                 230                 235 gac gct cag ggt aaa tat cca tac act ggt tcg cag gac tgt gcg atg        889
Asp Ala Gln Gly Lys Tyr Pro Tyr Thr Gly Ser Gln Asp Cys Ala Met
        240                 245                 250 caa aac agg agg acc ttt gaa att cta cac agg ctt tcc ggt ata ctg        937
Gln Asn Arg Arg Thr Phe Glu Ile Leu His Arg Leu Ser Gly Ile Leu
255                 260                 265                 270 cgt cag gat cgc ccc tca cgt cat ggt gac atg gat ctt cct gaa cca        985
Arg Gln Asp Arg Pro Ser Arg His Gly Asp Met Asp Leu Pro Glu Pro
                275                 280                 285 gat tac aaa gtt cca aaa gaa cat tgg gat gtg atc ttc aag caa acc       1033
Asp Tyr Lys Val Pro Lys Glu His Trp Asp Val Ile Phe Lys Gln Thr
            290                 295                 300 tta tgaagtgcgc ggtgaaaata tgatgagaag aattcatttg ctttttaatc            1086
Leu atatacatga ttag                                                       1100
```

<210> SEQ ID NO 42
<211> LENGTH: 303
<212> TYPE: PRT
<213> ORGANISM: Brassica napus

<400> SEQUENCE: 42

```
Met Ala Glu Glu Lys Lys Val Ala Pro Ile Gly Ile Trp Thr Ala Val
1               5                   10                  15

Lys Pro Phe Val Asn Gly Gly Ala Ser Gly Met Leu Ala Thr Cys Val
            20                  25                  30

Ile Gln Pro Ile Asp Met Ile Lys Val Arg Ile Gln Leu Gly Gln Gly
        35                  40                  45

Ser Ala Ala Ser Val Thr Thr Thr Met Leu Lys Asn Glu Gly Ile Gly
    50                  55                  60

Ala Phe Tyr Lys Gly Leu Ser Ala Gly Leu Leu Arg Gln Ala Thr Tyr
65                  70                  75                  80

Thr Thr Ala Arg Leu Gly Ser Phe Lys Met Leu Thr Ala Lys Ala Ser
                85                  90                  95

Glu Ala Asn Asp Gly Lys Pro Leu Pro Leu Tyr Gln Lys Ala Leu Cys
```

```
                100                 105                 110
Gly Leu Thr Ala Gly Ala Ile Gly Ala Cys Val Gly Ser Pro Ala Asp
        115                 120                 125

Leu Ala Leu Ile Arg Met Gln Ala Asp Asn Thr Leu Pro Leu Ala Gln
    130                 135                 140

Arg Arg Asn Tyr Thr Asn Ala Phe His Ala Leu Tyr Arg Ile Ser Ala
145                 150                 155                 160

Asp Glu Gly Val Leu Ala Leu Trp Lys Gly Cys Gly Pro Thr Val Val
                165                 170                 175

Arg Ala Met Ala Leu Asn Met Gly Met Leu Ala Ser Tyr Asp Gln Ser
            180                 185                 190

Ala Glu Tyr Met Arg Asp Asn Leu Gly Leu Gly Glu Thr Ser Thr Val
        195                 200                 205

Val Gly Ala Ser Ala Val Leu Gly Phe Cys Ala Ala Ala Cys Ser Leu
    210                 215                 220

Pro Phe Asp Phe Val Lys Thr Gln Ile Gln Lys Met Gln Pro Asp Ala
225                 230                 235                 240

Gln Gly Lys Tyr Pro Tyr Thr Gly Ser Gln Asp Cys Ala Met Gln Asn
                245                 250                 255

Arg Arg Thr Phe Glu Ile Leu His Arg Leu Ser Gly Ile Leu Arg Gln
            260                 265                 270

Asp Arg Pro Ser Arg His Gly Asp Met Asp Leu Pro Glu Pro Asp Tyr
        275                 280                 285

Lys Val Pro Lys Glu His Trp Asp Val Ile Phe Lys Gln Thr Leu
    290                 295                 300

<210> SEQ ID NO 43
<211> LENGTH: 1115
<212> TYPE: DNA
<213> ORGANISM: Brassica napus
<220> FEATURE:
<221> NAME/KEY: CDS
<222> LOCATION: (81)..(977)
<223> OTHER INFORMATION: mitochondrial carrier protein (BN51339479)

<400> SEQUENCE: 43
ctttctccgc ctatctcttt ctctccgcgg attctcttct tctcgtttcg actccgtacg      60
atccccaaag aaaaaaagag atg gcg gaa gag aaa aaa gta gct ccg att ggt     113
                        Met Ala Glu Glu Lys Lys Val Ala Pro Ile Gly
                          1               5                  10 gtc tgg aat acc gtg aag ccc ttc gtc aat ggc ggt gcc tcc ggt atg     161
Val Trp Asn Thr Val Lys Pro Phe Val Asn Gly Gly Ala Ser Gly Met
            15                  20                  25 ctc gcc act tgc gtt atc cag ccg atc gac atg atc aag gtg agg att     209
Leu Ala Thr Cys Val Ile Gln Pro Ile Asp Met Ile Lys Val Arg Ile
        30                  35                  40 caa cta ggt cag gga tct gca gtc agt gtg acc aag aac atg ttg aag     257
Gln Leu Gly Gln Gly Ser Ala Val Ser Val Thr Lys Asn Met Leu Lys
    45                  50                  55 aat gat ggt att ggt gct ttc tac aag gga ttg tct gct ggt ttg cta     305
Asn Asp Gly Ile Gly Ala Phe Tyr Lys Gly Leu Ser Ala Gly Leu Leu
60                  65                  70                  75 agg caa gca act tac acc aca gcc cgt ctt gga tcc ttc aag atg ctg     353
Arg Gln Ala Thr Tyr Thr Thr Ala Arg Leu Gly Ser Phe Lys Met Leu
                80                  85                  90 act gca aaa gca att gag gct aac gat ggg aag ccg cta cct ctg tac     401
Thr Ala Lys Ala Ile Glu Ala Asn Asp Gly Lys Pro Leu Pro Leu Tyr
            95                 100                 105
```

| | | | | | | | | | | | | |
|---|---|---|---|---|---|---|---|---|---|---|---|---|
| cag | aag | gct | cta | tgt | ggt | ctg | aca | gct | ggt | gca | atc | ggt | gct | tgc | gtt | 449 |
| Gln | Lys | Ala | Leu | Cys | Gly | Leu | Thr | Ala | Gly | Ala | Ile | Gly | Ala | Cys | Val | |
| | | 110 | | | | | 115 | | | | | 120 | | | | |

| ggt | agt | cca | gct | gac | ttg | gcg | ctt | atc | aga | atg | caa | gct | gat | aac | acc | 497 |
| Gly | Ser | Pro | Ala | Asp | Leu | Ala | Leu | Ile | Arg | Met | Gln | Ala | Asp | Asn | Thr | |
| 125 | | | | | 130 | | | | | 135 | | | | | | |

| ttg | ccg | tta | gct | cag | cgc | agg | aac | tat | acc | aat | gcc | ttc | cat | gcg | ctt | 545 |
| Leu | Pro | Leu | Ala | Gln | Arg | Arg | Asn | Tyr | Thr | Asn | Ala | Phe | His | Ala | Leu | |
| 140 | | | | | 145 | | | | | 150 | | | | | 155 | |

| tac | cgt | att | agc | gct | gat | gaa | gga | gtt | ttg | gca | ctt | tgg | aaa | ggt | tgt | 593 |
| Tyr | Arg | Ile | Ser | Ala | Asp | Glu | Gly | Val | Leu | Ala | Leu | Trp | Lys | Gly | Cys | |
| | | | | 160 | | | | | 165 | | | | | 170 | | |

| ggt | cct | act | gtg | gtc | aga | gct | atg | gct | ttg | aac | atg | gga | atg | ctt | gct | 641 |
| Gly | Pro | Thr | Val | Val | Arg | Ala | Met | Ala | Leu | Asn | Met | Gly | Met | Leu | Ala | |
| | | | 175 | | | | | 180 | | | | | 185 | | | |

| tct | tat | gat | caa | agt | gct | gag | tac | atg | aga | gat | aat | ctc | ggt | ctt | ggg | 689 |
| Ser | Tyr | Asp | Gln | Ser | Ala | Glu | Tyr | Met | Arg | Asp | Asn | Leu | Gly | Leu | Gly | |
| | | | 190 | | | | | 195 | | | | | 200 | | | |

| gag | act | tct | acg | gtc | gta | gga | gca | agt | gct | gtt | tct | gga | ttc | tgc | gct | 737 |
| Glu | Thr | Ser | Thr | Val | Val | Gly | Ala | Ser | Ala | Val | Ser | Gly | Phe | Cys | Ala | |
| | 205 | | | | | 210 | | | | | 215 | | | | | |

| gcg | gct | tgc | agt | ctt | cca | ttt | gac | ttt | gtc | aaa | act | cag | atc | cag | aag | 785 |
| Ala | Ala | Cys | Ser | Leu | Pro | Phe | Asp | Phe | Val | Lys | Thr | Gln | Ile | Gln | Lys | |
| 220 | | | | | 225 | | | | | 230 | | | | | 235 | |

| atg | caa | cct | gac | gct | cag | ggg | aag | tat | cca | tac | acg | ggt | tcg | ctt | gac | 833 |
| Met | Gln | Pro | Asp | Ala | Gln | Gly | Lys | Tyr | Pro | Tyr | Thr | Gly | Ser | Leu | Asp | |
| | | | | 240 | | | | | 245 | | | | | 250 | | |

| tgt | gcc | atg | caa | acc | ttg | aag | tca | gga | gga | cct | ctt | aaa | ttc | tac | aca | 881 |
| Cys | Ala | Met | Gln | Thr | Leu | Lys | Ser | Gly | Gly | Pro | Leu | Lys | Phe | Tyr | Thr | |
| | | | 255 | | | | | 260 | | | | | 265 | | | |

| ggt | ttc | cct | gtt | tac | tgc | gtc | agg | atc | gcc | cct | cac | gtc | atg | atg | aca | 929 |
| Gly | Phe | Pro | Val | Tyr | Cys | Val | Arg | Ile | Ala | Pro | His | Val | Met | Met | Thr | |
| | | | 270 | | | | | 275 | | | | | 280 | | | |

| tgg | atc | ttc | ctg | aac | cag | att | aca | aag | ttt | caa | aag | acc | att | ggt | ctg | 977 |
| Trp | Ile | Phe | Leu | Asn | Gln | Ile | Thr | Lys | Phe | Gln | Lys | Thr | Ile | Gly | Leu | |
| | 285 | | | | | 290 | | | | | 295 | | | | | |

| tgagcttcaa gcattgtgaa gtgcgcgctg agaataagtt gaaaacgaaa acgcaattgg | 1037 |
| aattgtgtta gatttgcttt ttattcaata tacatgatcg catgccttaa cgcattattt | 1097 |
| gaagtgttgg agacttta | 1115 |

<210> SEQ ID NO 44
<211> LENGTH: 299
<212> TYPE: PRT
<213> ORGANISM: Brassica napus

<400> SEQUENCE: 44

Met Ala Glu Glu Lys Lys Val Ala Pro Ile Gly Val Trp Asn Thr Val
1               5                  10                  15

Lys Pro Phe Val Asn Gly Gly Ala Ser Gly Met Leu Ala Thr Cys Val
                20                  25                  30

Ile Gln Pro Ile Asp Met Ile Lys Val Arg Ile Gln Leu Gly Gln Gly
            35                  40                  45

Ser Ala Val Ser Val Thr Lys Asn Met Leu Asn Asp Gly Ile Gly
        50                  55                  60

Ala Phe Tyr Lys Gly Leu Ser Ala Gly Leu Leu Arg Gln Ala Thr Tyr
65                  70                  75                  80

Thr Thr Ala Arg Leu Gly Ser Phe Lys Met Leu Thr Ala Lys Ala Ile
                85                  90                  95

-continued

```
Glu Ala Asn Asp Gly Lys Pro Leu Pro Leu Tyr Gln Lys Ala Leu Cys
               100                 105                 110

Gly Leu Thr Ala Gly Ala Ile Gly Ala Cys Val Gly Ser Pro Ala Asp
           115                 120                 125

Leu Ala Leu Ile Arg Met Gln Ala Asp Asn Thr Leu Pro Leu Ala Gln
130                 135                 140

Arg Arg Asn Tyr Thr Asn Ala Phe His Ala Leu Tyr Arg Ile Ser Ala
145                 150                 155                 160

Asp Glu Gly Val Leu Ala Leu Trp Lys Gly Cys Gly Pro Thr Val Val
               165                 170                 175

Arg Ala Met Ala Leu Asn Met Gly Met Leu Ala Ser Tyr Asp Gln Ser
           180                 185                 190

Ala Glu Tyr Met Arg Asp Asn Leu Gly Leu Gly Glu Thr Ser Thr Val
       195                 200                 205

Val Gly Ala Ser Ala Val Ser Gly Phe Cys Ala Ala Ala Cys Ser Leu
   210                 215                 220

Pro Phe Asp Phe Val Lys Thr Gln Ile Gln Lys Met Gln Pro Asp Ala
225                 230                 235                 240

Gln Gly Lys Tyr Pro Tyr Thr Gly Ser Leu Asp Cys Ala Met Gln Thr
               245                 250                 255

Leu Lys Ser Gly Gly Pro Leu Lys Phe Tyr Thr Gly Phe Pro Val Tyr
           260                 265                 270

Cys Val Arg Ile Ala Pro His Val Met Met Thr Trp Ile Phe Leu Asn
       275                 280                 285

Gln Ile Thr Lys Phe Gln Lys Thr Ile Gly Leu
   290                 295
```

<210> SEQ ID NO 45
<211> LENGTH: 1436
<212> TYPE: DNA
<213> ORGANISM: Zea mays
<220> FEATURE:
<221> NAME/KEY: CDS
<222> LOCATION: (199)..(1092)
<223> OTHER INFORMATION: mitochondrial carrier protein (ZM57651070)

<400> SEQUENCE: 45

```
ctagcacgtg aaaattcctt cggctccagt tattacggag gattaggttg gtgaactggt      60
gactggagct ggaatcgcat ttcttgctct ttggtctctc cagaatcatc ctccggccag     120
ccgttcttgg aatcctcccg agattcgctt gcccgccctt ttcttttcaa gtggatctga     180
acttgggagg gaaccccg atg cag ccg cgg tac gga gaa gca cga caa ccg       231
                    Met Gln Pro Arg Tyr Gly Glu Ala Arg Gln Pro
                    1               5                   10 ctg ccg ggg cgg tac gcg ctg tac cac ttc ggc acc agc ggc gcc gcc       279
Leu Pro Gly Arg Tyr Ala Leu Tyr His Phe Gly Thr Ser Gly Ala Ala
            15                  20                  25 gtc gcc gcc gcc acc gcc gtg acc cat ccg ttc gat gtt atc aaa gtc       327
Val Ala Ala Ala Thr Ala Val Thr His Pro Phe Asp Val Ile Lys Val
        30                  35                  40 agg ctt caa atg cag ctt gct ggg caa aga gga aac tta gtt gga atg       375
Arg Leu Gln Met Gln Leu Ala Gly Gln Arg Gly Asn Leu Val Gly Met
 45                 50                  55 gga aca ata ttt aca caa atg gtt gaa agg gaa ggg act cgg tca ctc       423
Gly Thr Ile Phe Thr Gln Met Val Glu Arg Glu Gly Thr Arg Ser Leu
60                  65                  70                  75 tac ctg gga ctt gca cca gcg ttg gcg aga gct gtt gtc tat ggt ggc       471
Tyr Leu Gly Leu Ala Pro Ala Leu Ala Arg Ala Val Val Tyr Gly Gly
            80                  85                  90
```

```
ctt cgg ttt gga ctg tat gag ccc tgc aag cat gtc tgc agt tat gca      519
Leu Arg Phe Gly Leu Tyr Glu Pro Cys Lys His Val Cys Ser Tyr Ala
         95                 100                 105 ttt ggt tca aca aac ttt gct ttt aaa ttt gca tct gga gtc att gct      567
Phe Gly Ser Thr Asn Phe Ala Phe Lys Phe Ala Ser Gly Val Ile Ala
        110                 115                 120 ggg ggc ctt gca act gct tta aca aat ccc atg gaa gtt ttg aag gtg      615
Gly Gly Leu Ala Thr Ala Leu Thr Asn Pro Met Glu Val Leu Lys Val
125                 130                 135 agg ctg cag atg agt aaa agc agt acc agt aca ata aga gag atg aga      663
Arg Leu Gln Met Ser Lys Ser Ser Thr Ser Thr Ile Arg Glu Met Arg
140                 145                 150                 155 aaa gtt ata gcg cac gaa ggg ttt aaa gca ctt tgg aaa gga gtc ggc      711
Lys Val Ile Ala His Glu Gly Phe Lys Ala Leu Trp Lys Gly Val Gly
            160                 165                 170 cca gca atg aca aga gca ggt tgc ctt act gca tca caa atg gcg act      759
Pro Ala Met Thr Arg Ala Gly Cys Leu Thr Ala Ser Gln Met Ala Thr
            175                 180                 185 tac gat gag gcc aaa cag gcc tta atg aag tgg aca cca ctt gaa gaa      807
Tyr Asp Glu Ala Lys Gln Ala Leu Met Lys Trp Thr Pro Leu Glu Glu
            190                 195                 200 ggt ttt cag tta cat ctc atc tcg agt ttc ata gct gga aca gct ggt      855
Gly Phe Gln Leu His Leu Ile Ser Ser Phe Ile Ala Gly Thr Ala Gly
        205                 210                 215 act ctt gtg acc tca cct gta gac atg atc aaa aca cgg tta atg ctg      903
Thr Leu Val Thr Ser Pro Val Asp Met Ile Lys Thr Arg Leu Met Leu
220                 225                 230                 235 caa cag gag tcc aaa ggc gcc aga gta tac agg aac gga ttc cat tgt      951
Gln Gln Glu Ser Lys Gly Ala Arg Val Tyr Arg Asn Gly Phe His Cys
                240                 245                 250 gct tcc cag gtt gtg gtg aca gag ggt gtg aaa tca ctt tat aaa ggt      999
Ala Ser Gln Val Val Val Thr Glu Gly Val Lys Ser Leu Tyr Lys Gly
            255                 260                 265 gga ttt gcc aca ttc gcg aga gta ggc cct cag aca acg att acc ttt     1047
Gly Phe Ala Thr Phe Ala Arg Val Gly Pro Gln Thr Thr Ile Thr Phe
            270                 275                 280 atc gtg tgc gag aaa ctg cgc gaa ctt gca gga atg act gcc atc         1092
Ile Val Cys Glu Lys Leu Arg Glu Leu Ala Gly Met Thr Ala Ile
285                 290                 295 tagtgccacc ccaaattgca taatgtgtgg ggtccaacgg ttgaacagca tactctaccc   1152
gagttttcac accattcttt attcactatt catgatgaga agggagaaga taagcaccca   1212
ctgggatgtc taaggattgg gaagcccaga gctccttcag atttatcata cctcatttga   1272
aatttcgaaa tagcgtgatt gttcttatgt ttgctctaag acttactcat catatctcca   1332
atctcatctt gtatttcaaa ctacactcta caaacaatac agtctgtagt gtaaaaacat   1392
tattttgggt gaccatatgg gtaacctgct gtacaaaaaa aaaa                    1436
```

<210> SEQ ID NO 46
<211> LENGTH: 298
<212> TYPE: PRT
<213> ORGANISM: Zea mays

<400> SEQUENCE: 46

Met Gln Pro Arg Tyr Gly Glu Ala Arg Gln Pro Leu Pro Gly Arg Tyr
1               5                   10                  15

Ala Leu Tyr His Phe Gly Thr Ser Gly Ala Ala Val Ala Ala Ala Thr
            20                  25                  30

Ala Val Thr His Pro Phe Asp Val Ile Lys Val Arg Leu Gln Met Gln

```
                35                  40                  45
Leu Ala Gly Gln Arg Gly Asn Leu Val Gly Met Gly Thr Ile Phe Thr
 50                  55                  60

Gln Met Val Glu Arg Glu Gly Thr Arg Ser Leu Tyr Leu Gly Leu Ala
 65                  70                  75                  80

Pro Ala Leu Ala Arg Ala Val Val Tyr Gly Gly Leu Arg Phe Gly Leu
                 85                  90                  95

Tyr Glu Pro Cys Lys His Val Cys Ser Tyr Ala Phe Gly Ser Thr Asn
                100                 105                 110

Phe Ala Phe Lys Phe Ala Ser Gly Val Ile Ala Gly Gly Leu Ala Thr
                115                 120                 125

Ala Leu Thr Asn Pro Met Glu Val Leu Lys Val Arg Leu Gln Met Ser
    130                 135                 140

Lys Ser Ser Thr Ser Thr Ile Arg Glu Met Arg Lys Val Ile Ala His
145                 150                 155                 160

Glu Gly Phe Lys Ala Leu Trp Lys Gly Val Gly Pro Ala Met Thr Arg
                165                 170                 175

Ala Gly Cys Leu Thr Ala Ser Gln Met Ala Thr Tyr Asp Glu Ala Lys
                180                 185                 190

Gln Ala Leu Met Lys Trp Thr Pro Leu Glu Glu Gly Phe Gln Leu His
                195                 200                 205

Leu Ile Ser Ser Phe Ile Ala Gly Thr Ala Gly Thr Leu Val Thr Ser
    210                 215                 220

Pro Val Asp Met Ile Lys Thr Arg Leu Met Leu Gln Gln Glu Ser Lys
225                 230                 235                 240

Gly Ala Arg Val Tyr Arg Asn Gly Phe His Cys Ala Ser Gln Val Val
                245                 250                 255

Val Thr Glu Gly Val Lys Ser Leu Tyr Lys Gly Gly Phe Ala Thr Phe
                260                 265                 270

Ala Arg Val Gly Pro Gln Thr Thr Ile Thr Phe Ile Val Cys Glu Lys
                275                 280                 285

Leu Arg Glu Leu Ala Gly Met Thr Ala Ile
    290                 295

<210> SEQ ID NO 47
<211> LENGTH: 1359
<212> TYPE: DNA
<213> ORGANISM: Zea mays
<220> FEATURE:
<221> NAME/KEY: CDS
<222> LOCATION: (101)..(1033)
<223> OTHER INFORMATION: mitochondrial carrier protein (ZM62073276)

<400> SEQUENCE: 47
gccgcctctc ctactgcatc tccctcgctc tcgtcgcctc gttcgcttcg cctccgcccc      60
gccccgcccc gagcagagcg cagccctatc cggagctggg atg gcg gac gcg aag     115
                                                Met Ala Asp Ala Lys
                                                 1               5 cag cag cag cag cag cag cag cag cca cag cag gcg gca gcg gca gcc     163
Gln Gln Gln Gln Gln Gln Gln Gln Pro Gln Gln Ala Ala Ala Ala Ala
                 10                  15                  20 acc ggc gtg tgg aag acg gtc aag ccc ttc gtt aac ggc gag gcc tct     211
Thr Gly Val Trp Lys Thr Val Lys Pro Phe Val Asn Gly Glu Ala Ser
                 25                  30                  35 ggg atg ctc gcg acc tgc gtc atc cag cct atc gac atg gtc aag gtg     259
Gly Met Leu Ala Thr Cys Val Ile Gln Pro Ile Asp Met Val Lys Val
         40                  45                  50
```

```
agg atc cag ttg ggt gag ggc tct gct ggt cag gtc aca agg aac atg    307
Arg Ile Gln Leu Gly Glu Gly Ser Ala Gly Gln Val Thr Arg Asn Met
    55                  60                  65 ctt gca aat gag ggt gtc cgt tct ttc tac aag ggt ttg tcc gcc gga    355
Leu Ala Asn Glu Gly Val Arg Ser Phe Tyr Lys Gly Leu Ser Ala Gly
70                  75                  80                  85 ttg ctg agg caa gcg acg tac acg act gct cgt ctt gga tcc ttt agg    403
Leu Leu Arg Gln Ala Thr Tyr Thr Thr Ala Arg Leu Gly Ser Phe Arg
                90                  95                 100 gtt cta act aac aaa gca gtt gaa aag aat gaa ggg aag cca ttg cct    451
Val Leu Thr Asn Lys Ala Val Glu Lys Asn Glu Gly Lys Pro Leu Pro
            105                 110                 115 cta ttt cag aaa gct ttt att ggt ctg act gct ggt gca att ggt gct    499
Leu Phe Gln Lys Ala Phe Ile Gly Leu Thr Ala Gly Ala Ile Gly Ala
        120                 125                 130 tgt gtt ggt agt cct gct gat ctg gca ctc att aga atg caa gcc gat    547
Cys Val Gly Ser Pro Ala Asp Leu Ala Leu Ile Arg Met Gln Ala Asp
135                 140                 145 tcg acc ctg cca gtt gca caa cga cgc aac tat aag aat gct ttc cat    595
Ser Thr Leu Pro Val Ala Gln Arg Arg Asn Tyr Lys Asn Ala Phe His
150                 155                 160                 165 gca ctc tac cgt atc agt ggt gat gag gga gtc ctt gcg ctt tgg aag    643
Ala Leu Tyr Arg Ile Ser Gly Asp Glu Gly Val Leu Ala Leu Trp Lys
                170                 175                 180 ggt gca ggt cca act gtg gtg aga gct atg gca ctc aat atg ggt atg    691
Gly Ala Gly Pro Thr Val Val Arg Ala Met Ala Leu Asn Met Gly Met
            185                 190                 195 ctt gct tcc tat gac cag agt gtc gag cta ttt agg gac aaa ttt ggc    739
Leu Ala Ser Tyr Asp Gln Ser Val Glu Leu Phe Arg Asp Lys Phe Gly
        200                 205                 210 gca gga gaa att tct act gtt gtt gga gcc agc gct gtt tct gga ttc    787
Ala Gly Glu Ile Ser Thr Val Val Gly Ala Ser Ala Val Ser Gly Phe
215                 220                 225 ttt gcc tca gca tgc agt ttg ccc ttt gac tat gtg aag aca cag att    835
Phe Ala Ser Ala Cys Ser Leu Pro Phe Asp Tyr Val Lys Thr Gln Ile
230                 235                 240                 245 cag aag atg caa cct gat gcg aat ggc aag tac cca tac aca ggg tct    883
Gln Lys Met Gln Pro Asp Ala Asn Gly Lys Tyr Pro Tyr Thr Gly Ser
                250                 255                 260 ttg gac tgt gct gtg aag acc ttc aag agc ggt ggc cca ttc aag ttc    931
Leu Asp Cys Ala Val Lys Thr Phe Lys Ser Gly Gly Pro Phe Lys Phe
            265                 270                 275 tac act ggt ttc ccg gtg tac tgc gtc agg att gca ccc cat gtc atg    979
Tyr Thr Gly Phe Pro Val Tyr Cys Val Arg Ile Ala Pro His Val Met
        280                 285                 290 atg acc tgg ata ttc ttg aat cag atc cag aag ttt gag aag aag atc   1027
Met Thr Trp Ile Phe Leu Asn Gln Ile Gln Lys Phe Glu Lys Lys Ile
295                 300                 305 ggc ata taggattccc atcggacgga tacaggttg acagttctat gctattactg     1083
Gly Ile
310 cttgactctg taataacatt ccagctgctt tcgcaccatg gtagttggtt ttggtagaga  1143 caagtctgtt acaatttttt accttagctt tccaattatt gtgttgcaat aatcgaatta  1203 attgttgctg ggggattttt ttgggggggt gggagggtgg catgcttttg ttggctggga  1263 tgtagccata aggagagggg gatactgcct agttatgtca ttgaatggaa ttggaccata  1323 tttatacag attttttacct tcaaaaaaaa aaaaaa                            1359

<210> SEQ ID NO 48
```

```
<211> LENGTH: 311
<212> TYPE: PRT
<213> ORGANISM: Zea mays

<400> SEQUENCE: 48

Met Ala Asp Ala Lys Gln Gln Gln Gln Gln Gln Gln Pro Gln Gln
1               5                   10                  15

Ala Ala Ala Ala Thr Gly Val Trp Lys Thr Val Lys Pro Phe Val
            20                  25                  30

Asn Gly Glu Ala Ser Gly Met Leu Ala Thr Cys Val Ile Gln Pro Ile
        35                  40                  45

Asp Met Val Lys Val Arg Ile Gln Leu Gly Glu Gly Ser Ala Gly Gln
    50                  55                  60

Val Thr Arg Asn Met Leu Ala Asn Glu Gly Val Arg Ser Phe Tyr Lys
65                  70                  75                  80

Gly Leu Ser Ala Gly Leu Leu Arg Gln Ala Thr Tyr Thr Thr Ala Arg
                85                  90                  95

Leu Gly Ser Phe Arg Val Leu Thr Asn Lys Ala Val Glu Lys Asn Glu
            100                 105                 110

Gly Lys Pro Leu Pro Leu Phe Gln Lys Ala Phe Ile Gly Leu Thr Ala
        115                 120                 125

Gly Ala Ile Gly Ala Cys Val Gly Ser Pro Ala Asp Leu Ala Leu Ile
    130                 135                 140

Arg Met Gln Ala Asp Ser Thr Leu Pro Val Ala Gln Arg Arg Asn Tyr
145                 150                 155                 160

Lys Asn Ala Phe His Ala Leu Tyr Arg Ile Ser Gly Asp Glu Gly Val
                165                 170                 175

Leu Ala Leu Trp Lys Gly Ala Gly Pro Thr Val Val Arg Ala Met Ala
            180                 185                 190

Leu Asn Met Gly Met Leu Ala Ser Tyr Asp Gln Ser Val Glu Leu Phe
        195                 200                 205

Arg Asp Lys Phe Gly Ala Gly Glu Ile Ser Thr Val Val Gly Ala Ser
    210                 215                 220

Ala Val Ser Gly Phe Phe Ala Ser Ala Cys Ser Leu Pro Phe Asp Tyr
225                 230                 235                 240

Val Lys Thr Gln Ile Gln Lys Met Gln Pro Asp Ala Asn Gly Lys Tyr
                245                 250                 255

Pro Tyr Thr Gly Ser Leu Asp Cys Ala Val Lys Thr Phe Lys Ser Gly
            260                 265                 270

Gly Pro Phe Lys Phe Tyr Thr Gly Phe Pro Val Tyr Cys Val Arg Ile
        275                 280                 285

Ala Pro His Val Met Met Thr Trp Ile Phe Leu Asn Gln Ile Gln Lys
    290                 295                 300

Phe Glu Lys Lys Ile Gly Ile
305                 310

<210> SEQ ID NO 49
<211> LENGTH: 1287
<212> TYPE: DNA
<213> ORGANISM: Physcomitrella patens
<220> FEATURE:
<221> NAME/KEY: CDS
<222> LOCATION: (37)..(1104)
<223> OTHER INFORMATION: protein kinase (EST257)

<400> SEQUENCE: 49
cccggggatt cagcagtact tcacaagaag aatagc atg gtg cgt gca gat ctt      54
                                        Met Val Arg Ala Asp Leu
```

-continued

| | | | | | 1 | | | | | 5 | | | | |
|---|---|---|---|---|---|---|---|---|---|---|---|---|---|---|
| gtc | aac | ctt | gcg | gac | tta | gat | act | gct | cta | aac | aga | gtt | cat | aat | aag | 102 |
| Val | Asn | Leu | Ala | Asp | Leu | Asp | Thr | Ala | Leu | Asn | Arg | Val | His | Asn | Lys | |
| | | | 10 | | | | | 15 | | | | | 20 | | | |

| cta | cct | aat | tcc | ata | gaa | aca | gct | agt | gca | gag | cct | cct | gct | cct | cca | 150 |
| Leu | Pro | Asn | Ser | Ile | Glu | Thr | Ala | Ser | Ala | Glu | Pro | Pro | Ala | Pro | Pro | |
| | | 25 | | | | | 30 | | | | | 35 | | | | |

| gaa | gaa | tgg | gaa | ata | aat | cct | cga | gag | atc | act | ttg | aag | cat | atg | att | 198 |
| Glu | Glu | Trp | Glu | Ile | Asn | Pro | Arg | Glu | Ile | Thr | Leu | Lys | His | Met | Ile | |
| | 40 | | | | | 45 | | | | | 50 | | | | | |

| gcg | cgt | ggc | acc | ttt | ggg | act | gtc | cac | aaa | gga | gtg | tac | aaa | ggt | cag | 246 |
| Ala | Arg | Gly | Thr | Phe | Gly | Thr | Val | His | Lys | Gly | Val | Tyr | Lys | Gly | Gln | |
| 55 | | | | | 60 | | | | | 65 | | | | | 70 | |

| gat | gtc | gca | gtt | aag | cta | ctt | gag | tgg | ggc | gag | gag | aat | acc | atg | aag | 294 |
| Asp | Val | Ala | Val | Lys | Leu | Leu | Glu | Trp | Gly | Glu | Glu | Asn | Thr | Met | Lys | |
| | | | | 75 | | | | | 80 | | | | | 85 | | |

| aaa | aca | gag | gtt | caa | tac | tac | aga | aac | caa | ttc | aga | caa | gag | gtt | gct | 342 |
| Lys | Thr | Glu | Val | Gln | Tyr | Tyr | Arg | Asn | Gln | Phe | Arg | Gln | Glu | Val | Ala | |
| | | | 90 | | | | | 95 | | | | | 100 | | | |

| gtg | tgg | cat | aaa | ctc | gac | cac | cct | aat | gtc | acg | aag | ttc | atc | gga | gcc | 390 |
| Val | Trp | His | Lys | Leu | Asp | His | Pro | Asn | Val | Thr | Lys | Phe | Ile | Gly | Ala | |
| | | 105 | | | | | 110 | | | | | 115 | | | | |

| tcg | atg | ggg | aac | tca | gat | ttg | cgg | att | ccc | tca | gcc | gtg | gat | ggt | gat | 438 |
| Ser | Met | Gly | Asn | Ser | Asp | Leu | Arg | Ile | Pro | Ser | Ala | Val | Asp | Gly | Asp | |
| | 120 | | | | | 125 | | | | | 130 | | | | | |

| gat | gga | ttc | cat | cat | gtg | ccg | aac | aat | gct | tgt | tgt | gtt | gtc | gtt | gag | 486 |
| Asp | Gly | Phe | His | His | Val | Pro | Asn | Asn | Ala | Cys | Cys | Val | Val | Val | Glu | |
| 135 | | | | | 140 | | | | | 145 | | | | | 150 | |

| tac | ctt | gca | ggc | ggg | act | ctt | aaa | gat | cat | ctc | att | cgc | agc | cgg | cgg | 534 |
| Tyr | Leu | Ala | Gly | Gly | Thr | Leu | Lys | Asp | His | Leu | Ile | Arg | Ser | Arg | Arg | |
| | | | | 155 | | | | | 160 | | | | | 165 | | |

| aaa | aaa | ctc | tcg | tac | aag | gtg | gtc | gtg | caa | tta | gcc | ttg | gat | gtt | tct | 582 |
| Lys | Lys | Leu | Ser | Tyr | Lys | Val | Val | Val | Gln | Leu | Ala | Leu | Asp | Val | Ser | |
| | | | 170 | | | | | 175 | | | | | 180 | | | |

| aga | ggg | ctt | gca | tac | ctc | cat | tct | cag | aag | atc | gct | cat | cgt | gac | gtg | 630 |
| Arg | Gly | Leu | Ala | Tyr | Leu | His | Ser | Gln | Lys | Ile | Ala | His | Arg | Asp | Val | |
| | | | | 185 | | | | | 190 | | | | | 195 | | |

| aag | aca | gag | aac | atg | ttg | ctc | gat | aaa | cag | atg | agg | gtc | aaa | att | gca | 678 |
| Lys | Thr | Glu | Asn | Met | Leu | Leu | Asp | Lys | Gln | Met | Arg | Val | Lys | Ile | Ala | |
| | 200 | | | | | 205 | | | | | 210 | | | | | |

| gat | ttc | gga | gtt | gca | cga | gtg | gag | gca | tcc | aat | ccc | aag | gac | atg | act | 726 |
| Asp | Phe | Gly | Val | Ala | Arg | Val | Glu | Ala | Ser | Asn | Pro | Lys | Asp | Met | Thr | |
| 215 | | | | | 220 | | | | | 225 | | | | | 230 | |

| ggt | gat | act | ggt | acc | cca | gga | tac | atg | gct | ccg | gag | att | ctc | gac | ggc | 774 |
| Gly | Asp | Thr | Gly | Thr | Pro | Gly | Tyr | Met | Ala | Pro | Glu | Ile | Leu | Asp | Gly | |
| | | | | 235 | | | | | 240 | | | | | 245 | | |

| aag | ccc | tac | aac | aag | aag | tgc | gat | gtg | tac | agc | ttc | ggg | atc | tgt | ttg | 822 |
| Lys | Pro | Tyr | Asn | Lys | Lys | Cys | Asp | Val | Tyr | Ser | Phe | Gly | Ile | Cys | Leu | |
| | | | 250 | | | | | 255 | | | | | 260 | | | |

| tgg | gaa | gtt | tat | tgc | tgc | gac | atg | ccg | tac | ttg | gac | ctc | tcc | ttt | gcg | 870 |
| Trp | Glu | Val | Tyr | Cys | Cys | Asp | Met | Pro | Tyr | Leu | Asp | Leu | Ser | Phe | Ala | |
| | | | | 265 | | | | | 270 | | | | | 275 | | |

| gac | atg | aca | tcg | gca | gtt | gtg | cat | cag | aat | ttg | aga | ccc | gag | gtg | ccc | 918 |
| Asp | Met | Thr | Ser | Ala | Val | Val | His | Gln | Asn | Leu | Arg | Pro | Glu | Val | Pro | |
| | | 280 | | | | | 285 | | | | | 290 | | | | |

| aag | tgc | tgc | cct | cag | gga | ctc | gcg | gat | atc | atg | agg | cag | tgt | tgg | gat | 966 |
| Lys | Cys | Cys | Pro | Gln | Gly | Leu | Ala | Asp | Ile | Met | Arg | Gln | Cys | Trp | Asp | |
| 295 | | | | | 300 | | | | | 305 | | | | | 310 | |

| gca | aat | cct | gag | aaa | cgg | cct | gcc | atg | gct | gat | gtg | gtg | cag | atg | ctg | 1014 |
| Ala | Asn | Pro | Glu | Lys | Arg | Pro | Ala | Met | Ala | Asp | Val | Val | Gln | Met | Leu | |

```
                      315                 320                 325
gag gct cta gac acc tcc aaa ggt gga ggt atg ata cca aca gac gcc      1062
Glu Ala Leu Asp Thr Ser Lys Gly Gly Gly Met Ile Pro Thr Asp Ala
              330                 335                 340 cag ccg cat ggg tgt ctc tgt ttt ggg aga ttc aag ggc cca              1104
Gln Pro His Gly Cys Leu Cys Phe Gly Arg Phe Lys Gly Pro
              345                 350                 355 tagcacgttt ttggttttt ttttccttaa ttgtggtttt acattttatt tatattttc      1164 ccttttttaa tgtagggatg acatgataat aagtgtgcaa acattttgtt gtctcccctg    1224
gtttcgtttc aagcgtagct gcttgacttg caatttcagt aacctggtgc aggacccgtt    1284
aac                                                                  1287

<210> SEQ ID NO 50
<211> LENGTH: 356
<212> TYPE: PRT
<213> ORGANISM: Physcomitrella patens

<400> SEQUENCE: 50

Met Val Arg Ala Asp Leu Val Asn Leu Ala Asp Leu Asp Thr Ala Leu
1               5                   10                  15

Asn Arg Val His Asn Lys Leu Pro Asn Ser Ile Glu Thr Ala Ser Ala
                20                  25                  30

Glu Pro Pro Ala Pro Pro Glu Trp Glu Ile Asn Pro Arg Glu Ile
            35                  40                  45

Thr Leu Lys His Met Ile Ala Arg Gly Thr Phe Gly Thr Val His Lys
        50                  55                  60

Gly Val Tyr Lys Gly Gln Asp Val Ala Val Lys Leu Leu Glu Trp Gly
65                  70                  75                  80

Glu Glu Asn Thr Met Lys Lys Thr Glu Val Gln Tyr Tyr Arg Asn Gln
                85                  90                  95

Phe Arg Gln Glu Val Ala Val Trp His Lys Leu Asp His Pro Asn Val
            100                 105                 110

Thr Lys Phe Ile Gly Ala Ser Met Gly Asn Ser Asp Leu Arg Ile Pro
        115                 120                 125

Ser Ala Val Asp Gly Asp Gly Phe His His Val Pro Asn Asn Ala
    130                 135                 140

Cys Cys Val Val Val Glu Tyr Leu Ala Gly Gly Thr Leu Lys Asp His
145                 150                 155                 160

Leu Ile Arg Ser Arg Lys Lys Leu Ser Tyr Lys Val Val Gln
                165                 170                 175

Leu Ala Leu Asp Val Ser Arg Gly Leu Ala Tyr Leu His Ser Gln Lys
            180                 185                 190

Ile Ala His Arg Asp Val Lys Thr Glu Asn Met Leu Leu Asp Lys Gln
        195                 200                 205

Met Arg Val Lys Ile Ala Asp Phe Gly Val Ala Arg Val Glu Ala Ser
    210                 215                 220

Asn Pro Lys Asp Met Thr Gly Asp Thr Gly Thr Pro Gly Tyr Met Ala
225                 230                 235                 240

Pro Glu Ile Leu Asp Gly Lys Pro Tyr Asn Lys Lys Cys Asp Val Tyr
                245                 250                 255

Ser Phe Gly Ile Cys Leu Trp Glu Val Tyr Cys Cys Asp Met Pro Tyr
            260                 265                 270

Leu Asp Leu Ser Phe Ala Asp Met Thr Ser Ala Val Val His Gln Asn
        275                 280                 285
```

```
Leu Arg Pro Glu Val Pro Lys Cys Cys Pro Gln Gly Leu Ala Asp Ile
        290                 295                 300

Met Arg Gln Cys Trp Asp Ala Asn Pro Glu Lys Arg Pro Ala Met Ala
305                 310                 315                 320

Asp Val Val Gln Met Leu Glu Ala Leu Asp Thr Ser Lys Gly Gly Gly
                325                 330                 335

Met Ile Pro Thr Asp Ala Gln Pro His Gly Cys Leu Cys Phe Gly Arg
            340                 345                 350

Phe Lys Gly Pro
        355

<210> SEQ ID NO 51
<211> LENGTH: 1304
<212> TYPE: DNA
<213> ORGANISM: Linum usitatissimum
<220> FEATURE:
<221> NAME/KEY: CDS
<222> LOCATION: (21)..(1112)
<223> OTHER INFORMATION: protein kinase (LU61665952)

<400> SEQUENCE: 51
agggtgatca cgagggaggt atg aat tct aag gtg aag gga aat gga agt gtt       53
                     Met Asn Ser Lys Val Lys Gly Asn Gly Ser Val
                       1               5                  10 agt aga aaa gat atg att ttt cga gcg gat cga atc gat ttg aag atc      101
Ser Arg Lys Asp Met Ile Phe Arg Ala Asp Arg Ile Asp Leu Lys Ile
             15                  20                  25 ctg gat gta cag cta gag aag cac ctg agt agg gtg tgg tcg agg aac      149
Leu Asp Val Gln Leu Glu Lys His Leu Ser Arg Val Trp Ser Arg Asn
         30                  35                  40 acc aca gac aac gct aag cct aaa gaa gag tgg gag att gat ttg tct      197
Thr Thr Asp Asn Ala Lys Pro Lys Glu Glu Trp Glu Ile Asp Leu Ser
     45                  50                  55 aag ttg gac atc aaa acc cag ata gct cgt ggt act tat ggc act gtt      245
Lys Leu Asp Ile Lys Thr Gln Ile Ala Arg Gly Thr Tyr Gly Thr Val
 60                  65                  70                  75 tat aaa ggc act tat gat aat caa gat gtt gca gtg aaa gtg ttg gat      293
Tyr Lys Gly Thr Tyr Asp Asn Gln Asp Val Ala Val Lys Val Leu Asp
                 80                  85                  90 tgg ggg gaa gat ggt atg act aca gta tct gaa gct gct tct ctt cga      341
Trp Gly Glu Asp Gly Met Thr Thr Val Ser Glu Ala Ala Ser Leu Arg
             95                 100                 105 gca tca ttt cgt caa gag gtt gct gtt tgg cat aag ctt gac cat cct      389
Ala Ser Phe Arg Gln Glu Val Ala Val Trp His Lys Leu Asp His Pro
         110                 115                 120 aat gtt acc aaa ttc gtt gga gca tcg atg gga act tca aat ctc aag      437
Asn Val Thr Lys Phe Val Gly Ala Ser Met Gly Thr Ser Asn Leu Lys
     125                 130                 135 gtt tca aat aat aaa tct gat ggt cag cat act gct aga gca tgt tgt      485
Val Ser Asn Asn Lys Ser Asp Gly Gln His Thr Ala Arg Ala Cys Cys
140                 145                 150                 155 gtt gtg gtt gag tat caa cct ggt gga aca cta aag cag tac ttg ata      533
Val Val Val Glu Tyr Gln Pro Gly Gly Thr Leu Lys Gln Tyr Leu Ile
                 160                 165                 170 aga aat agg cga aag aaa ctt cct tat aaa gtt gta ata caa ctt gct      581
Arg Asn Arg Arg Lys Lys Leu Pro Tyr Lys Val Val Ile Gln Leu Ala
             175                 180                 185 ttg gat ctc tct agg ggt ttg agt tac cta cat tcg aag aaa att gtg      629
Leu Asp Leu Ser Arg Gly Leu Ser Tyr Leu His Ser Lys Lys Ile Val
         190                 195                 200 cac cgt gat gtg aag tcg gaa aac atg ttg ctt gat aat cat aga aat      677
```

```
                His Arg Asp Val Lys Ser Glu Asn Met Leu Leu Asp Asn His Arg Asn
                205                 210                 215 ctt agg att gcg gat ttt ggt gtt gct cga gtc gaa gct caa aat cca          725
Leu Arg Ile Ala Asp Phe Gly Val Ala Arg Val Glu Ala Gln Asn Pro
220                 225                 230                 235 agt gat atg act ggt gaa act ggt acc ctt gga tac atg gca cct gag          773
Ser Asp Met Thr Gly Glu Thr Gly Thr Leu Gly Tyr Met Ala Pro Glu
                240                 245                 250 gtc ctt gat ggc aag cca tat aac aga agg tgt gat gtt tat agc ttc          821
Val Leu Asp Gly Lys Pro Tyr Asn Arg Arg Cys Asp Val Tyr Ser Phe
                255                 260                 265 ggc ata tgt tta tgg gaa atc tat tgt tgt gat atg cca tat cca gat          869
Gly Ile Cys Leu Trp Glu Ile Tyr Cys Cys Asp Met Pro Tyr Pro Asp
                270                 275                 280 ctt agc ttt gct gat gtg acg tcc gcg gtt gtt cga caa aac ttg agg          917
Leu Ser Phe Ala Asp Val Thr Ser Ala Val Val Arg Gln Asn Leu Arg
285                 290                 295 ccg gag att ccg aga tgt tgt cca agt tca cta gga agc atc atg aag          965
Pro Glu Ile Pro Arg Cys Cys Pro Ser Ser Leu Gly Ser Ile Met Lys
300                 305                 310                 315 aaa tgt tgg gat gca caa tca gag aac cgt cca gaa atg gct gaa gtg         1013
Lys Cys Trp Asp Ala Gln Ser Glu Asn Arg Pro Glu Met Ala Glu Val
                320                 325                 330 gtg aag atg ttg gaa gcc att gat aca agt aaa gga gga gga atg atc         1061
Val Lys Met Leu Glu Ala Ile Asp Thr Ser Lys Gly Gly Gly Met Ile
                335                 340                 345 cct gaa gac cag aac cct ggt tgt ttc tgc ttc gcc cca acc cgt ggc         1109
Pro Glu Asp Gln Asn Pro Gly Cys Phe Cys Phe Ala Pro Thr Arg Gly
                350                 355                 360 cct taaaccccct tattaattta ctccccaaac agtcctcatc catctatgtg             1162
Pro tgcacaaatt tcaatttctt tatatttgag ttgttttctt tgtttatcat tttcttgtgt       1222
tcttcacttc tgcacatatt ttgatttga actacctaaa gggagtgaaa ggattaatgt        1282
tataagtaaa aaaaaaaaaa aa                                                1304

<210> SEQ ID NO 52
<211> LENGTH: 364
<212> TYPE: PRT
<213> ORGANISM: Linum usitatissimum

<400> SEQUENCE: 52

Met Asn Ser Lys Val Lys Gly Asn Gly Ser Val Ser Arg Lys Asp Met
1               5                   10                  15

Ile Phe Arg Ala Asp Arg Ile Asp Leu Lys Ile Leu Asp Val Gln Leu
                20                  25                  30

Glu Lys His Leu Ser Arg Val Trp Ser Arg Asn Thr Thr Asp Asn Ala
            35                  40                  45

Lys Pro Lys Glu Glu Trp Glu Ile Asp Leu Ser Lys Leu Asp Ile Lys
        50                  55                  60

Thr Gln Ile Ala Arg Gly Thr Tyr Gly Thr Val Tyr Lys Gly Thr Tyr
65                  70                  75                  80

Asp Asn Gln Asp Val Ala Val Lys Val Leu Trp Gly Glu Asp Gly
                85                  90                  95

Met Thr Thr Val Ser Glu Ala Ala Ser Leu Arg Ala Ser Phe Arg Gln
                100                 105                 110

Glu Val Ala Val Trp His Lys Leu Asp His Pro Asn Val Thr Lys Phe
            115                 120                 125
```

```
Val Gly Ala Ser Met Gly Thr Ser Asn Leu Lys Val Ser Asn Asn Lys
        130                 135                 140

Ser Asp Gly Gln His Thr Ala Arg Ala Cys Cys Val Val Glu Tyr
145                 150                 155                 160

Gln Pro Gly Gly Thr Leu Lys Gln Tyr Leu Ile Arg Asn Arg Lys
                165                 170                 175

Lys Leu Pro Tyr Lys Val Val Ile Gln Leu Ala Leu Asp Leu Ser Arg
                180                 185                 190

Gly Leu Ser Tyr Leu His Ser Lys Lys Ile Val His Arg Asp Val Lys
                195                 200                 205

Ser Glu Asn Met Leu Leu Asp Asn His Arg Asn Leu Arg Ile Ala Asp
        210                 215                 220

Phe Gly Val Ala Arg Val Glu Ala Gln Asn Pro Ser Asp Met Thr Gly
225                 230                 235                 240

Glu Thr Gly Thr Leu Gly Tyr Met Ala Pro Glu Val Leu Asp Gly Lys
                245                 250                 255

Pro Tyr Asn Arg Arg Cys Asp Val Tyr Ser Phe Gly Ile Cys Leu Trp
                260                 265                 270

Glu Ile Tyr Cys Cys Asp Met Pro Tyr Pro Asp Leu Ser Phe Ala Asp
                275                 280                 285

Val Thr Ser Ala Val Arg Gln Asn Leu Arg Pro Glu Ile Pro Arg
290                 295                 300

Cys Cys Pro Ser Ser Leu Gly Ser Ile Met Lys Lys Cys Trp Asp Ala
305                 310                 315                 320

Gln Ser Glu Asn Arg Pro Glu Met Ala Glu Val Val Lys Met Leu Glu
                325                 330                 335

Ala Ile Asp Thr Ser Lys Gly Gly Met Ile Pro Gly Asp Gln Asn
                340                 345                 350

Pro Gly Cys Phe Cys Phe Ala Pro Thr Arg Gly Pro
                355                 360

<210> SEQ ID NO 53
<211> LENGTH: 1405
<212> TYPE: DNA
<213> ORGANISM: Triticum aestivum
<220> FEATURE:
<221> NAME/KEY: CDS
<222> LOCATION: (40)..(1122)
<223> OTHER INFORMATION: protein kinase (TA56863186)

<400> SEQUENCE: 53
agcactgaca actacaacct cgctggtggc tccgttacc atg tca gtg gac aac      54
                                           Met Ser Val Asp Asn
                                           1               5 agc agc gtg ggc tcg aac gag tcc cgc acc gtc ata ctt aag cac ccg    102
Ser Ser Val Gly Ser Asn Glu Ser Arg Thr Val Ile Leu Lys His Pro
            10                  15                  20 ggc ctc cgt gat gct cca acc gca agc tac tcg gtt ggc aac agt gtc    150
Gly Leu Arg Asp Ala Pro Thr Ala Ser Tyr Ser Val Gly Asn Ser Val
        25                  30                  35 ttt cgt ccc aac cgt gtg gct gcg cac acc cta aat gaa gat gca ttg    198
Phe Arg Pro Asn Arg Val Ala Ala His Thr Leu Asn Glu Asp Ala Leu
    40                  45                  50 gcc agg gtt ctg atg gac cca aat cat cca aca gag ata ctt agc aag    246
Ala Arg Val Leu Met Asp Pro Asn His Pro Thr Glu Ile Leu Ser Lys
55                  60                  65 tac cag cag tgg gcc att gat ctg ggg agg ttg gat atg ggg gtt ccc    294
Tyr Gln Gln Trp Ala Ile Asp Leu Gly Arg Leu Asp Met Gly Val Pro
70                  75                  80                  85
```

| | |
|---|---|
| ttt gca cag gga gcc ttt ggg aag ctg tac cgg gga aca tat att gga<br>Phe Ala Gln Gly Ala Phe Gly Lys Leu Tyr Arg Gly Thr Tyr Ile Gly<br>             90                        95                       100 | 342 |
| gaa gat gtt gcc att aag ctg ctg gag aag cct gac aat gat atc gag<br>Glu Asp Val Ala Ile Lys Leu Leu Glu Lys Pro Asp Asn Asp Ile Glu<br>            105                      110                   115 | 390 |
| aga gca caa tcg ttg gaa cag cag ttt gtg caa gaa gtt atg atg tta<br>Arg Ala Gln Ser Leu Glu Gln Gln Phe Val Gln Glu Val Met Met Leu<br>            120                      125                   130 | 438 |
| tct acc cta agg cac cca aat ata gta aga ttt ata ggg gct tgc agg<br>Ser Thr Leu Arg His Pro Asn Ile Val Arg Phe Ile Gly Ala Cys Arg<br>135                      140                      145 | 486 |
| aag tca att gtg tgg tgc att att act gag tat gca aaa ggt ggc tca<br>Lys Ser Ile Val Trp Cys Ile Ile Thr Glu Tyr Ala Lys Gly Gly Ser<br>150                    155                      160                 165 | 534 |
| gtc agg cag ttc ctg gca aaa agg cag aac aag tcg gta cct ttg agg<br>Val Arg Gln Phe Leu Ala Lys Arg Gln Asn Lys Ser Val Pro Leu Arg<br>                 170                      175                 180 | 582 |
| ctg gct gtc aaa caa gca ttg gat gta gcg agg gga atg gcg tat gtg<br>Leu Ala Val Lys Gln Ala Leu Asp Val Ala Arg Gly Met Ala Tyr Val<br>            185                      190                   195 | 630 |
| cat gct ctg gga ttt atc cat agg gac ctg aag tcg gat aat ctt cta<br>His Ala Leu Gly Phe Ile His Arg Asp Leu Lys Ser Asp Asn Leu Leu<br>               200                      205                   210 | 678 |
| att gca gca gac aga tcc att aag att gct gac ttt gga gtt gct cga<br>Ile Ala Ala Asp Arg Ser Ile Lys Ile Ala Asp Phe Gly Val Ala Arg<br>            215                      220                   225 | 726 |
| att gaa gtg aaa aca gag ggg atg aca cca gag aca gga acc tac cgc<br>Ile Glu Val Lys Thr Glu Gly Met Thr Pro Glu Thr Gly Thr Tyr Arg<br>230                      235                      240                 245 | 774 |
| tgg atg gca ccg gaa atg atc cag cac agg cct tat gat cat aag gtt<br>Trp Met Ala Pro Glu Met Ile Gln His Arg Pro Tyr Asp His Lys Val<br>               250                      255                   260 | 822 |
| gat gtc tac agc ttt ggg att gtc ttg tgg gag ctt ata act ggc atg<br>Asp Val Tyr Ser Phe Gly Ile Val Leu Trp Glu Leu Ile Thr Gly Met<br>               265                      270                 275 | 870 |
| ctt cct ttc aca aac atg aca gct gtt cag gcg gct ttt gct gtt gta<br>Leu Pro Phe Thr Asn Met Thr Ala Val Gln Ala Ala Phe Ala Val Val<br>            280                      285                   290 | 918 |
| aat aag ggt gct cgt cca gcg atc cca cat gac tgc ctg cct tcc cta<br>Asn Lys Gly Ala Arg Pro Ala Ile Pro His Asp Cys Leu Pro Ser Leu<br>295                      300                      305 | 966 |
| acc cac atc atg acg cgc tgt tgg gat gca aac cct gaa gtt cgc cca<br>Thr His Ile Met Thr Arg Cys Trp Asp Ala Asn Pro Glu Val Arg Pro<br>310                      315                      320                 325 | 1014 |
| cca ttc acc gag atc gtc tgc atg ctt gag aac gcc gag atg gag gtc<br>Pro Phe Thr Glu Ile Val Cys Met Leu Glu Asn Ala Glu Met Glu Val<br>               330                      335                 340 | 1062 |
| gtg agc cat gtc cgt aaa gcg cgc ttc cgc tgc tgc gtt gct gaa ccc<br>Val Ser His Val Arg Lys Ala Arg Phe Arg Cys Cys Val Ala Glu Pro<br>            345                      350                   355 | 1110 |
| atg acc acc gac tgaaactaaa gcaggttaga ctatcgcagc gggcattagg<br>Met Thr Thr Asp<br>            360 | 1162 |
| gaagaaaaca ggtaaggatg aagaaaagag gcaatgccaa tgtgttcatc gttgtcagtg | 1222 |
| cgtgggtct gtgtgccttt accagtgcgc attctgtctt gtgtaagttg cacacctcaa | 1282 |
| gtaaaagtaa tttcgtatag atgttgcctt gtatgctaac aaagacctaa tggagctttt | 1342 |
| ccgtgttaat aatatccgct tgctcttgta ctcgtgcaag tttgtgccaa aaaaaaaaaa | 1402 | aaa 1405

<210> SEQ ID NO 54
<211> LENGTH: 361
<212> TYPE: PRT
<213> ORGANISM: Triticum aestivum

<400> SEQUENCE: 54

```
Met Ser Val Asp Asn Ser Ser Val Gly Ser Asn Glu Ser Arg Thr Val
1               5                   10                  15

Ile Leu Lys His Pro Gly Leu Arg Asp Ala Pro Thr Ala Ser Tyr Ser
            20                  25                  30

Val Gly Asn Ser Val Phe Arg Pro Asn Arg Val Ala Ala His Thr Leu
        35                  40                  45

Asn Glu Asp Ala Leu Ala Arg Val Leu Met Asp Pro Asn His Pro Thr
    50                  55                  60

Glu Ile Leu Ser Lys Tyr Gln Gln Trp Ala Ile Asp Leu Gly Arg Leu
65                  70                  75                  80

Asp Met Gly Val Pro Phe Ala Gln Gly Ala Phe Gly Lys Leu Tyr Arg
                85                  90                  95

Gly Thr Tyr Ile Gly Glu Asp Val Ala Ile Lys Leu Leu Glu Lys Pro
            100                 105                 110

Asp Asn Asp Ile Glu Arg Ala Gln Ser Leu Glu Gln Gln Phe Val Gln
        115                 120                 125

Glu Val Met Met Leu Ser Thr Leu Arg His Pro Asn Ile Val Arg Phe
130                 135                 140

Ile Gly Ala Cys Arg Lys Ser Ile Val Trp Cys Ile Thr Glu Tyr
145                 150                 155                 160

Ala Lys Gly Gly Ser Val Arg Gln Phe Leu Ala Lys Arg Gln Asn Lys
                165                 170                 175

Ser Val Pro Leu Arg Leu Ala Val Lys Gln Ala Leu Asp Val Ala Arg
            180                 185                 190

Gly Met Ala Tyr Val His Ala Leu Gly Phe Ile His Arg Asp Leu Lys
        195                 200                 205

Ser Asp Asn Leu Leu Ile Ala Ala Asp Arg Ser Ile Lys Ile Ala Asp
    210                 215                 220

Phe Gly Val Ala Arg Ile Glu Val Lys Thr Glu Gly Met Thr Pro Glu
225                 230                 235                 240

Thr Gly Thr Tyr Arg Trp Met Ala Pro Glu Met Ile Gln His Arg Pro
                245                 250                 255

Tyr Asp His Lys Val Asp Val Tyr Ser Phe Gly Ile Val Leu Trp Glu
            260                 265                 270

Leu Ile Thr Gly Met Leu Pro Phe Thr Asn Met Thr Ala Val Gln Ala
        275                 280                 285

Ala Phe Ala Val Val Asn Lys Gly Ala Arg Pro Ala Ile Pro His Asp
    290                 295                 300

Cys Leu Pro Ser Leu Thr His Ile Met Thr Arg Cys Trp Asp Ala Asn
305                 310                 315                 320

Pro Glu Val Arg Pro Pro Phe Thr Gly Ile Val Cys Met Leu Glu Asn
                325                 330                 335

Ala Glu Met Glu Val Val Ser His Val Arg Lys Ala Arg Phe Arg Cys
            340                 345                 350

Cys Val Ala Glu Pro Met Thr Thr Asp
        355                 360
```

<210> SEQ ID NO 55
<211> LENGTH: 1714
<212> TYPE: DNA
<213> ORGANISM: Zea mays
<220> FEATURE:
<221> NAME/KEY: CDS
<222> LOCATION: (400)..(1509)
<223> OTHER INFORMATION: protein kinase (ZM62026837)

<400> SEQUENCE: 55

```
cgcgcggcca aactcctgtt cttccacctg ctggctgctc ctgcctcccc tgcgccccaa      60
acccacccgc ctcgccgtcc ccgcaggccg cagcctgctc tcggctcccg ccgccgtcta     120
ccgcgtcctg cggctgcggt gttgcgtcac ctcgggttcg ccttaacttc acaatcctc     180 gccgtcctgg tgctccgccg cccctccctt tgtactcgcg ctggagctgc agatccaccg     240
cgacctggcg accaattcct cctcccgctg aagaattggc gaccttggcc tccgcccccg     300
cggcgcggag gagtcaactg tggtagcaac caccgcggag gctgcaagcc ttcggtaagg     360
gaggaaagtt gacttgttgg aagccggtcc agggccgcg atg acg tcg acc gcc        414
                                            Met Thr Ser Thr Ala
                                              1               5 gcc ggc gcg tcg tcg tcg gcg gcg aag agc gag tcc tac ctg cgg gcc       462
Ala Gly Ala Ser Ser Ser Ala Ala Lys Ser Glu Ser Tyr Leu Arg Ala
            10                  15                  20 gac aag atc gac ctc gag agc ctg gac atc cag ctg gag aag cag ctg       510
Asp Lys Ile Asp Leu Glu Ser Leu Asp Ile Gln Leu Glu Lys Gln Leu
        25                  30                  35 gcc aag acc tgg gag aag cac aag ggg tcg tac aac cag ggg ccc agg       558
Ala Lys Thr Trp Glu Lys His Lys Gly Ser Tyr Asn Gln Gly Pro Arg
    40                  45                  50 gag gac tgg gag atc gac ctc gcc aag ctc gag att cgc tac gtc ata       606
Glu Asp Trp Glu Ile Asp Leu Ala Lys Leu Glu Ile Arg Tyr Val Ile
55                  60                  65 gcg cag ggc acc tac ggc acg gtg tat cgc ggc acg tat gat ggg cag       654
Ala Gln Gly Thr Tyr Gly Thr Val Tyr Arg Gly Thr Tyr Asp Gly Gln
 70                  75                  80                  85 gac gtc gca gta aaa cta ttg gat tgg ggt gaa gat ggc ttt gcg tca       702
Asp Val Ala Val Lys Leu Leu Asp Trp Gly Glu Asp Gly Phe Ala Ser
                90                  95                 100 gaa act gaa act gcc aca ctg cga gca tca ttt aag cag gag gtt gct       750
Glu Thr Glu Thr Ala Thr Leu Arg Ala Ser Phe Lys Gln Glu Val Ala
            105                 110                 115 gtc tgg cat gag ctc aac cat ccg aat gtt aca aag ttt gtt ggt gca       798
Val Trp His Glu Leu Asn His Pro Asn Val Thr Lys Phe Val Gly Ala
        120                 125                 130 tca atg ggt act aca gac ctt aag att cca gcc aat agt tct aac agt       846
Ser Met Gly Thr Thr Asp Leu Lys Ile Pro Ala Asn Ser Ser Asn Ser
    135                 140                 145 ggt ggg cgc act gag ctg ccg cca aaa gca tgt tgt gtt gtg tc gaa        894
Gly Gly Arg Thr Glu Leu Pro Pro Lys Ala Cys Cys Val Val Val Glu
150                 155                 160                 165 tat ctc gct gga gga tca ctg aag cag tat tta ata aag aac agg cga       942
Tyr Leu Ala Gly Gly Ser Leu Lys Gln Tyr Leu Ile Lys Asn Arg Arg
                170                 175                 180 agg aag ctt gca tac aag gtt gtt gtt cag ata gca ctg gat ctt gcc       990
Arg Lys Leu Ala Tyr Lys Val Val Val Gln Ile Ala Leu Asp Leu Ala
            185                 190                 195 aga gga ttg aac tat cta cat tca aga aag ata gta cat cgg gat gta      1038
Arg Gly Leu Asn Tyr Leu His Ser Arg Lys Ile Val His Arg Asp Val
        200                 205                 210
```

```
aaa act gaa aat atg ctg ctc gat aca cag cga aac ctt aag att gct    1086
Lys Thr Glu Asn Met Leu Leu Asp Thr Gln Arg Asn Leu Lys Ile Ala
    215                 220                 225 gat ttt ggt gtt gct cgt gtt gag gct cag aat cca aag gac atg aca    1134
Asp Phe Gly Val Ala Arg Val Glu Ala Gln Asn Pro Lys Asp Met Thr
230                 235                 240                 245 ggc gcg act ggg aca ctt ggc tac atg gcc gag gtg ctt gaa ggc        1182
Gly Ala Thr Gly Thr Leu Gly Tyr Met Ala Pro Glu Val Leu Glu Gly
            250                 255                 260 aag cca tac aac aga aag tgt gat gtc tac agt ttt ggc ata tgc tta    1230
Lys Pro Tyr Asn Arg Lys Cys Asp Val Tyr Ser Phe Gly Ile Cys Leu
        265                 270                 275 tgg gaa ata tac tgc tgt gac atg cca tat cca gac ctc agt ttt gca    1278
Trp Glu Ile Tyr Cys Cys Asp Met Pro Tyr Pro Asp Leu Ser Phe Ala
    280                 285                 290 gac gtc tcg tcc gcc gtc gtt cac cag aac ctg cgg cct gac atc cct    1326
Asp Val Ser Ser Ala Val Val His Gln Asn Leu Arg Pro Asp Ile Pro
295                 300                 305 cgc tgc tgc cca agc cca atg gcg aac atc atg cgg aag tgc tgg gac    1374
Arg Cys Cys Pro Ser Pro Met Ala Asn Ile Met Arg Lys Cys Trp Asp
310                 315                 320                 325 gca aac ccg gat aag cgc cct gac atg gac gac gtg gtg cgg ttc ctg    1422
Ala Asn Pro Asp Lys Arg Pro Asp Met Asp Asp Val Val Arg Phe Leu
            330                 335                 340 gag gcc ctc gac acg agc aag ggc ggt ggc atg ata cca gaa ggc cag    1470
Glu Ala Leu Asp Thr Ser Lys Gly Gly Gly Met Ile Pro Glu Gly Gln
        345                 350                 355 gca ggc ggg tgc ttg tgt ttc ttc aga gcc cgt ggt cct tagaaccaac     1519
Ala Gly Gly Cys Leu Cys Phe Phe Arg Ala Arg Gly Pro
    360                 365                 370 caacccttc cagccatcct ctacttgtct ctgccatact acagtattgg agccagatgt   1579
aggcctttgt tgttcatcgg atagggggatt gcagataact tgatgacaat ctttgtgatt  1639
ggttgacact tgttatacgt tctatagtga tgtgaatacc agtgaggagt ccataataca   1699
gagtgaaaaa aaaaa                                                    1714

<210> SEQ ID NO 56
<211> LENGTH: 370
<212> TYPE: PRT
<213> ORGANISM: Zea mays

<400> SEQUENCE: 56

Met Thr Ser Thr Ala Ala Gly Ala Ser Ser Ala Ala Lys Ser Glu
1               5                   10                  15

Ser Tyr Leu Arg Ala Asp Lys Ile Asp Leu Glu Ser Leu Asp Ile Gln
            20                  25                  30

Leu Glu Lys Gln Leu Ala Lys Thr Trp Glu Lys His Lys Gly Ser Tyr
        35                  40                  45

Asn Gln Gly Pro Arg Glu Asp Trp Glu Ile Asp Leu Ala Lys Leu Glu
    50                  55                  60

Ile Arg Tyr Val Ile Ala Gln Gly Thr Tyr Gly Thr Val Tyr Arg Gly
65                  70                  75                  80

Thr Tyr Asp Gly Gln Asp Val Ala Val Lys Leu Leu Asp Trp Gly Glu
                85                  90                  95

Asp Gly Phe Ala Ser Glu Thr Glu Thr Ala Thr Leu Arg Ala Ser Phe
            100                 105                 110

Lys Gln Glu Val Ala Val Trp His Glu Leu Asn His Pro Asn Val Thr
        115                 120                 125
```

```
Lys Phe Val Gly Ala Ser Met Gly Thr Thr Asp Leu Lys Ile Pro Ala
    130                 135                 140

Asn Ser Ser Asn Ser Gly Gly Arg Thr Glu Leu Pro Pro Lys Ala Cys
145                 150                 155                 160

Cys Val Val Glu Tyr Leu Ala Gly Gly Ser Leu Lys Gln Tyr Leu
                165                 170                 175

Ile Lys Asn Arg Arg Arg Lys Leu Ala Tyr Lys Val Val Gln Ile
            180                 185                 190

Ala Leu Asp Leu Ala Arg Gly Leu Asn Tyr Leu His Ser Arg Lys Ile
        195                 200                 205

Val His Arg Asp Val Lys Thr Glu Asn Met Leu Leu Asp Thr Gln Arg
    210                 215                 220

Asn Leu Lys Ile Ala Asp Phe Gly Val Ala Arg Val Glu Ala Gln Asn
225                 230                 235                 240

Pro Lys Asp Met Thr Gly Ala Thr Gly Thr Leu Gly Tyr Met Ala Pro
                245                 250                 255

Glu Val Leu Glu Gly Lys Pro Tyr Asn Arg Lys Cys Asp Val Tyr Ser
            260                 265                 270

Phe Gly Ile Cys Leu Trp Glu Ile Tyr Cys Cys Asp Met Pro Tyr Pro
        275                 280                 285

Asp Leu Ser Phe Ala Asp Val Ser Ser Ala Val Val His Gln Asn Leu
    290                 295                 300

Arg Pro Asp Ile Pro Arg Cys Cys Pro Ser Pro Met Ala Asn Ile Met
305                 310                 315                 320

Arg Lys Cys Trp Asp Ala Asn Pro Asp Lys Arg Pro Asp Met Asp Asp
                325                 330                 335

Val Val Arg Phe Leu Glu Ala Leu Asp Thr Ser Lys Gly Gly Met
            340                 345                 350

Ile Pro Glu Gly Gln Ala Gly Gly Cys Leu Cys Phe Phe Arg Ala Arg
        355                 360                 365

Gly Pro
    370

<210> SEQ ID NO 57
<211> LENGTH: 1494
<212> TYPE: DNA
<213> ORGANISM: Zea mays
<220> FEATURE:
<221> NAME/KEY: CDS
<222> LOCATION: (159)..(1289)
<223> OTHER INFORMATION: protein kinase (ZM65457595)

<400> SEQUENCE: 57
acctcgccac cctcctgcct cctccgcatc cgcgccccct cgcttagcct aaaccgcggg      60
gcagctagtc tcgccaccgc aggccgcacc ggtcatcaca ccgaagcgca cgcggggagc    120
ccccgtagag ttccggggcg accaggccaa ctaacgcc atg aag gag gaa ggc ggc    176
                                          Met Lys Glu Glu Gly Gly
                                            1               5 ggc ggg gac gcg ggg ttc gtg cgg gcg gac cag atc gac ctc aag agc     224
Gly Gly Asp Ala Gly Phe Val Arg Ala Asp Gln Ile Asp Leu Lys Ser
        10                  15                  20 ctg gac gag cag ctg gag cgc cat ctc acc cgc gcc tgg acc atg gag     272
Leu Asp Glu Gln Leu Glu Arg His Leu Thr Arg Ala Trp Thr Met Glu
    25                  30                  35 aag cgc aag gag gag gcc tcc gcc ggc gct ggc gcc ggc gcc agg cag     320
Lys Arg Lys Glu Glu Ala Ser Ala Gly Ala Gly Ala Gly Ala Arg Gln
40                  45                  50
```

-continued

| | |
|---|---|
| cac cag cag tcc cgg cgc ccg cgg agg gag gac tgg gag atc gac ccc<br>His Gln Gln Ser Arg Arg Pro Arg Arg Glu Asp Trp Glu Ile Asp Pro<br>55                   60                   65                70 | 368 |
| gcc aag ctt gtc gtc aag ggc gtc atc gcc cgc ggc acc ttt ggc acc<br>Ala Lys Leu Val Val Lys Gly Val Ile Ala Arg Gly Thr Phe Gly Thr<br>                75                   80                   85 | 416 |
| gtc cac cgc ggc atc tac gac gct cac gac gtc gca gtg aaa cta ctt<br>Val His Arg Gly Ile Tyr Asp Ala His Asp Val Ala Val Lys Leu Leu<br>              90                   95                  100 | 464 |
| gat tgg gga gag gat ggg cat aga tca gaa caa gac att gca gca cta<br>Asp Trp Gly Glu Asp Gly His Arg Ser Glu Gln Asp Ile Ala Ala Leu<br>          105                   110                 115 | 512 |
| aga gca gct ttt tca caa gag gtc tct gtt tgg cat aag ctt gac cat<br>Arg Ala Ala Phe Ser Gln Glu Val Ser Val Trp His Lys Leu Asp His<br>120                   125                   130 | 560 |
| cca aat gta acc aag ttt att gga gct ata atg ggt gca agg gat ctg<br>Pro Asn Val Thr Lys Phe Ile Gly Ala Ile Met Gly Ala Arg Asp Leu<br>135                   140                   145                 150 | 608 |
| aat att caa acg gaa aac ggc cac att ggc atg cca act aat atc tgc<br>Asn Ile Gln Thr Glu Asn Gly His Ile Gly Met Pro Thr Asn Ile Cys<br>                 155                   160                 165 | 656 |
| tgt gtc gtt gtg gag tac ctt cct ggt ggt gca cta aaa tca ttt ctg<br>Cys Val Val Val Glu Tyr Leu Pro Gly Gly Ala Leu Lys Ser Phe Leu<br>                 170                   175                 180 | 704 |
| ata aag aac agg aga aag aag cta gct ttt aag gtc gtt gtt caa atc<br>Ile Lys Asn Arg Arg Lys Lys Leu Ala Phe Lys Val Val Val Gln Ile<br>          185                   190                 195 | 752 |
| gct ctt gac ctt gcc agg gga tta agc tat ctc cat tcc aag aag att<br>Ala Leu Asp Leu Ala Arg Gly Leu Ser Tyr Leu His Ser Lys Lys Ile<br>200                   205                   210 | 800 |
| gtg cac cgt gat gtg aag act gaa aat atg ctt ctt gac aaa acg aga<br>Val His Arg Asp Val Lys Thr Glu Asn Met Leu Leu Asp Lys Thr Arg<br>215                   220                   225                 230 | 848 |
| acc gtg aag atc gct gat ttt ggt gtt gct cgc ctt gaa gct tca aat<br>Thr Val Lys Ile Ala Asp Phe Gly Val Ala Arg Leu Glu Ala Ser Asn<br>                 235                   240                 245 | 896 |
| ccc agt gac atg acg ggc gaa act gga acg ctt ggt tac atg aca cct<br>Pro Ser Asp Met Thr Gly Glu Thr Gly Thr Leu Gly Tyr Met Thr Pro<br>               250                   255                 260 | 944 |
| gag gtt ctc aat gga aat ccc tac aac agg aaa tgc gat gtt tac agc<br>Glu Val Leu Asn Gly Asn Pro Tyr Asn Arg Lys Cys Asp Val Tyr Ser<br>          265                   270                 275 | 992 |
| ttc ggg atc tgt ttg tgg gag ata tac tgc tgt gat atg cca tat cct<br>Phe Gly Ile Cys Leu Trp Glu Ile Tyr Cys Cys Asp Met Pro Tyr Pro<br>280                   285                   290 | 1040 |
| gac ttg agc ttt tct gag gtc acg tct gcg gtt gtc cgt cag aac ctg<br>Asp Leu Ser Phe Ser Glu Val Thr Ser Ala Val Val Arg Gln Asn Leu<br>295                   300                   305                 310 | 1088 |
| agg ccg gag ata cca cgc tgc tgc ccg agc tct cta tcg aac gtg atg<br>Arg Pro Glu Ile Pro Arg Cys Cys Pro Ser Ser Leu Ser Asn Val Met<br>                 315                   320                 325 | 1136 |
| aag cgc tgc tgg gac gcc aac ccc gac aag cga cct gag atg gcc gag<br>Lys Arg Cys Trp Asp Ala Asn Pro Asp Lys Arg Pro Glu Met Ala Glu<br>               330                   335                 340 | 1184 |
| gcg gtg tcc atg ctg gag gcg atc gac acg tcg aag ggt gga ggc atg<br>Ala Val Ser Met Leu Glu Ala Ile Asp Thr Ser Lys Gly Gly Gly Met<br>          345                   350                 355 | 1232 |
| atc cct gtg gac cag cgg cca gga tgc ctt gcg tgc ttc cgg cag tac<br>Ile Pro Val Asp Gln Arg Pro Gly Cys Leu Ala Cys Phe Arg Gln Tyr<br>360                   365                   370 | 1280 |

```
                                                             -continued aga ggt cca tgacagatag gtggaaacct gttggagctg cggcctctag        1329
Arg Gly Pro
375 atctcgtgga tgccgatcga tcgcgtgttg ttttctgggg aagcaaactg gttaatggag  1389 ctagcccgcc ttaccggctc gtgtaaatcc tctgtccatc aattctgtaa ctctgtttta  1449 tcgattaatg aaagaaccg ggcttgctcg aaaaaaaaaa aaaaa              1494

<210> SEQ ID NO 58
<211> LENGTH: 377
<212> TYPE: PRT
<213> ORGANISM: Zea mays

<400> SEQUENCE: 58

Met Lys Glu Glu Gly Gly Gly Asp Ala Gly Phe Val Arg Ala Asp
1               5                   10                  15

Gln Ile Asp Leu Lys Ser Leu Asp Glu Gln Leu Glu Arg His Leu Thr
            20                  25                  30

Arg Ala Trp Thr Met Glu Lys Arg Lys Glu Ala Ser Ala Gly Ala
        35                  40                  45

Gly Ala Gly Ala Arg Gln His Gln Gln Ser Arg Arg Pro Arg Arg Glu
    50                  55                  60

Asp Trp Glu Ile Asp Pro Ala Lys Leu Val Val Lys Gly Val Ile Ala
65                  70                  75                  80

Arg Gly Thr Phe Gly Thr Val His Arg Gly Ile Tyr Asp Ala His Asp
                85                  90                  95

Val Ala Val Lys Leu Leu Asp Trp Gly Glu Asp Gly His Arg Ser Glu
            100                 105                 110

Gln Asp Ile Ala Ala Leu Arg Ala Ala Phe Ser Gln Glu Val Ser Val
        115                 120                 125

Trp His Lys Leu Asp His Pro Asn Val Thr Lys Phe Ile Gly Ala Ile
    130                 135                 140

Met Gly Ala Arg Asp Leu Asn Ile Gln Thr Glu Asn Gly His Ile Gly
145                 150                 155                 160

Met Pro Thr Asn Ile Cys Cys Val Val Glu Tyr Leu Pro Gly Gly
                165                 170                 175

Ala Leu Lys Ser Phe Leu Ile Lys Asn Arg Arg Lys Lys Leu Ala Phe
            180                 185                 190

Lys Val Val Gln Ile Ala Leu Asp Leu Ala Arg Gly Leu Ser Tyr
        195                 200                 205

Leu His Ser Lys Lys Ile Val His Arg Asp Val Lys Thr Glu Asn Met
    210                 215                 220

Leu Leu Asp Lys Thr Arg Thr Val Lys Ile Ala Asp Phe Gly Val Ala
225                 230                 235                 240

Arg Leu Glu Ala Ser Asn Pro Ser Asp Met Thr Gly Glu Thr Gly Thr
                245                 250                 255

Leu Gly Tyr Met Thr Pro Glu Val Leu Asn Gly Asn Pro Tyr Asn Arg
            260                 265                 270

Lys Cys Asp Val Tyr Ser Phe Gly Ile Cys Leu Trp Glu Ile Tyr Cys
        275                 280                 285

Cys Asp Met Pro Tyr Pro Asp Leu Ser Phe Ser Glu Val Thr Ser Ala
    290                 295                 300

Val Val Arg Gln Asn Leu Arg Pro Glu Ile Pro Arg Cys Cys Pro Ser
305                 310                 315                 320

Ser Leu Ser Asn Val Met Lys Arg Cys Trp Asp Ala Asn Pro Asp Lys
                325                 330                 335
```

```
Arg Pro Glu Met Ala Glu Ala Val Ser Met Leu Glu Ala Ile Asp Thr
            340                 345                 350
Ser Lys Gly Gly Gly Met Ile Pro Val Asp Gln Arg Pro Gly Cys Leu
        355                 360                 365
Ala Cys Phe Arg Gln Tyr Arg Gly Pro
        370                 375

<210> SEQ ID NO 59
<211> LENGTH: 1584
<212> TYPE: DNA
<213> ORGANISM: Zea mays
<220> FEATURE:
<221> NAME/KEY: CDS
<222> LOCATION: (215)..(1360)
<223> OTHER INFORMATION: protein kinase (ZM67230154)

<400> SEQUENCE: 59
cggcaaccca ctatctcatg cgctcacatg gagactcccg cacgaactgg aatcatctcc      60
gcctcgccac ctcttcatct tcttccccag tagccgccgc caccaccact gcagcagcca     120
aaccacgtga cacctcccgc gccgctcaac cccacagcat ccgttgccac cgccgctcac     180
ctccccggcg ctcccggcta caaccactgc aagc atg agg cag cca acc agc gcg    235
                                    Met Arg Gln Pro Thr Ser Ala
                                      1               5 ggc ggc gac gct ggg ttc ttg cgc gcg gac cag atc gac ctc aag agc      283
Gly Gly Asp Ala Gly Phe Leu Arg Ala Asp Gln Ile Asp Leu Lys Ser
         10                  15                  20 ctg gac gag cag ctc gag cgc cac ctc gga cat ccc gcg gag cgg gta      331
Leu Asp Glu Gln Leu Glu Arg His Leu Gly His Pro Ala Glu Arg Val
 25                  30                  35 gtt ggc cca gtc tct ggg aca ggg agc cgc cgc ggc gaa acg gcc aag      379
Val Gly Pro Val Ser Gly Thr Gly Ser Arg Arg Gly Glu Thr Ala Lys
 40                  45                  50                  55 ctg ggt ccg gag gag ctg acg cca ctg cag cgg tgc cgt gag gac tgg      427
Leu Gly Pro Glu Glu Leu Thr Pro Leu Gln Arg Cys Arg Glu Asp Trp
             60                  65                  70 gag atc gac cct acc aag ctc atc atc aag ggc gtc atc gcg cgc ggc      475
Glu Ile Asp Pro Thr Lys Leu Ile Ile Lys Gly Val Ile Ala Arg Gly
         75                  80                  85 acc ttt ggc acc gtc cac cgc ggc gtc tac gac ggc cag gac gtc gct      523
Thr Phe Gly Thr Val His Arg Gly Val Tyr Asp Gly Gln Asp Val Ala
         90                  95                 100 gta aaa ttg ctt gac tgg ggc gaa gat ggc cat aga tca gaa caa gaa      571
Val Lys Leu Leu Asp Trp Gly Glu Asp Gly His Arg Ser Glu Gln Glu
105                 110                 115 att ggt gca cta aga gca gcg ttt gca caa gag gtc gct gtc tgg cat      619
Ile Gly Ala Leu Arg Ala Ala Phe Ala Gln Glu Val Ala Val Trp His
120                 125                 130                 135 aag ctt gag cat cca aac gtt act aag ttt att ggg gct ata atg ggc      667
Lys Leu Glu His Pro Asn Val Thr Lys Phe Ile Gly Ala Ile Met Gly
             140                 145                 150 gca aga gat tta aat ata caa acg gaa cat gga cag ctt ggc atg cca      715
Ala Arg Asp Leu Asn Ile Gln Thr Glu His Gly Gln Leu Gly Met Pro
         155                 160                 165 agc aat att tgc tgt gtt gtt gtt gag tac ctt gct gga ggt gcg ctg      763
Ser Asn Ile Cys Cys Val Val Val Glu Tyr Leu Ala Gly Gly Ala Leu
         170                 175                 180 aaa aat ttt ctg ata aag aac agg aga agg aaa ctt gcc ttt aaa gtt      811
Lys Asn Phe Leu Ile Lys Asn Arg Arg Arg Lys Leu Ala Phe Lys Val
185                 190                 195
```

```
gtg gtc caa ata gct ctt gac ctt gcc agg gga tta tgc tac ctc cac    859
Val Val Gln Ile Ala Leu Asp Leu Ala Arg Gly Leu Cys Tyr Leu His
200                 205                 210                 215 tca aag aaa ata gtg cac cgt gat gtc aag act gaa aac atg ctt ctg    907
Ser Lys Lys Ile Val His Arg Asp Val Lys Thr Glu Asn Met Leu Leu
                220                 225                 230 gac aag acg aga acg gta aag atc gct gat ttt ggt gtt gct cga gtc    955
Asp Lys Thr Arg Thr Val Lys Ile Ala Asp Phe Gly Val Ala Arg Val
            235                 240                 245 gag gct tca aat cct agc gat atg acg gga gaa aca ggg acg ctt ggt   1003
Glu Ala Ser Asn Pro Ser Asp Met Thr Gly Glu Thr Gly Thr Leu Gly
        250                 255                 260 tac atg gct cct gag gtt ctc aat ggc cat gct tac aac agg aag tgt   1051
Tyr Met Ala Pro Glu Val Leu Asn Gly His Ala Tyr Asn Arg Lys Cys
    265                 270                 275 gac gtg tac agc ttt ggg atc tgc ctg tgg gag ata tac tgc tgt gac   1099
Asp Val Tyr Ser Phe Gly Ile Cys Leu Trp Glu Ile Tyr Cys Cys Asp
280                 285                 290                 295 atg ccg tac cct gat ctc agt ttt tct gag gtc acc tct gcc gtc gtt   1147
Met Pro Tyr Pro Asp Leu Ser Phe Ser Glu Val Thr Ser Ala Val Val
                300                 305                 310 cgc cag aat ctg agg cct gag ata ccg cgc tgc tgc ccg agc tcg cta   1195
Arg Gln Asn Leu Arg Pro Glu Ile Pro Arg Cys Cys Pro Ser Ser Leu
            315                 320                 325 gcg aat gtg atg aag cga tgc tgg gac gcg aac ccg gac aag cgt ccc   1243
Ala Asn Val Met Lys Arg Cys Trp Asp Ala Asn Pro Asp Lys Arg Pro
        330                 335                 340 gag atg gcg gag gtg gtg tcc atg ctg gag gcg atc gac acg tcc aag   1291
Glu Met Ala Glu Val Val Ser Met Leu Glu Ala Ile Asp Thr Ser Lys
    345                 350                 355 ggt ggc ggc atg atc cct aag gac cag acg cag ggc tgc ctc tcg tgc   1339
Gly Gly Gly Met Ile Pro Lys Asp Gln Thr Gln Gly Cys Leu Ser Cys
360                 365                 370                 375 ttc cgc cag tac cga ggt ccc taacgcaggg ttgtttattt atacccggtg      1390
Phe Arg Gln Tyr Arg Gly Pro
                380 aaatgatgat attggtctct acactacaac tcagtgtaat ctaatcgcag aagtggctat  1450 ataatggaga agcttatcat tgcttgccat gggtgtaaat ggatggggcg gggtggttga  1510 cgattggtgt gcttgtatgc tcgcttcgag ttataatgct tgctgtaagt taaggtgtgg  1570 aaaaaaaaaa aaaa                                                    1584

<210> SEQ ID NO 60
<211> LENGTH: 382
<212> TYPE: PRT
<213> ORGANISM: Zea mays

<400> SEQUENCE: 60

Met Arg Gln Pro Thr Ser Ala Gly Gly Asp Ala Gly Phe Leu Arg Ala
1               5                   10                  15

Asp Gln Ile Asp Leu Lys Ser Leu Asp Glu Gln Leu Glu Arg His Leu
            20                  25                  30

Gly His Pro Ala Glu Arg Val Val Gly Pro Val Ser Gly Thr Gly Ser
        35                  40                  45

Arg Arg Gly Glu Thr Ala Lys Leu Gly Pro Glu Glu Leu Thr Pro Leu
    50                  55                  60

Gln Arg Cys Arg Glu Asp Trp Glu Ile Asp Pro Thr Lys Leu Ile Ile
65                  70                  75                  80

Lys Gly Val Ile Ala Arg Gly Thr Phe Gly Thr Val His Arg Gly Val
```

```
                85                  90                  95
Tyr Asp Gly Gln Asp Val Ala Val Lys Leu Leu Asp Trp Gly Glu Asp
            100                 105                 110

Gly His Arg Ser Glu Gln Glu Ile Gly Ala Leu Arg Ala Ala Phe Ala
            115                 120                 125

Gln Glu Val Ala Val Trp His Lys Leu Glu His Pro Asn Val Thr Lys
            130                 135                 140

Phe Ile Gly Ala Ile Met Gly Ala Arg Asp Leu Asn Ile Gln Thr Glu
145                 150                 155                 160

His Gly Gln Leu Gly Met Pro Ser Asn Ile Cys Cys Val Val Glu
            165                 170                 175

Tyr Leu Ala Gly Gly Ala Leu Lys Asn Phe Leu Ile Lys Asn Arg Arg
            180                 185                 190

Arg Lys Leu Ala Phe Lys Val Val Gln Ile Ala Leu Asp Leu Ala
            195                 200                 205

Arg Gly Leu Cys Tyr Leu His Ser Lys Lys Ile Val His Arg Asp Val
            210                 215                 220

Lys Thr Glu Asn Met Leu Leu Asp Lys Thr Arg Thr Val Lys Ile Ala
225                 230                 235                 240

Asp Phe Gly Val Ala Arg Val Glu Ala Ser Asn Pro Ser Asp Met Thr
            245                 250                 255

Gly Glu Thr Gly Thr Leu Gly Tyr Met Ala Pro Glu Val Leu Asn Gly
            260                 265                 270

His Ala Tyr Asn Arg Lys Cys Asp Val Tyr Ser Phe Gly Ile Cys Leu
            275                 280                 285

Trp Glu Ile Tyr Cys Cys Asp Met Pro Tyr Pro Asp Leu Ser Phe Ser
            290                 295                 300

Glu Val Thr Ser Ala Val Val Arg Gln Asn Leu Arg Pro Glu Ile Pro
305                 310                 315                 320

Arg Cys Cys Pro Ser Ser Leu Ala Asn Val Met Lys Arg Cys Trp Asp
            325                 330                 335

Ala Asn Pro Asp Lys Arg Pro Glu Met Ala Glu Val Val Ser Met Leu
            340                 345                 350

Glu Ala Ile Asp Thr Ser Lys Gly Gly Gly Met Ile Pro Lys Asp Gln
            355                 360                 365

Thr Gln Gly Cys Leu Ser Cys Phe Arg Gln Tyr Arg Gly Pro
            370                 375                 380

<210> SEQ ID NO 61
<211> LENGTH: 2085
<212> TYPE: DNA
<213> ORGANISM: Physcomitrella patens
<220> FEATURE:
<221> NAME/KEY: CDS
<222> LOCATION: (34)..(1911)
<223> OTHER INFORMATION: peptidyl prolyl isomerase (EST465)

<400> SEQUENCE: 61
gggcctcctt cctagccttc atctgctgcg acg atg gag gag ctc gcc tca tct      54
                                    Met Glu Glu Leu Ala Ser Ser
                                    1               5 gat gtt ccg aac aag ttg aag aag aag gaa tct aag atg aag aag agg     102
Asp Val Pro Asn Lys Leu Lys Lys Lys Glu Ser Lys Met Lys Lys Arg
        10                  15                  20 gtt ata act cca ggg gcc ttg ctg aag gca gta gta agg tct gga gag     150
Val Ile Thr Pro Gly Ala Leu Leu Lys Ala Val Val Arg Ser Gly Glu
    25                  30                  35
```

```
ggg act aaa cgt cct gta gaa ggt gat cag att atc ttc cat tat gtc     198
Gly Thr Lys Arg Pro Val Glu Gly Asp Gln Ile Ile Phe His Tyr Val
 40              45                  50                  55 aca cga aca aat cag gga gtg gtg gtt gag aca tcg cga tct gac ttt     246
Thr Arg Thr Asn Gln Gly Val Val Val Glu Thr Ser Arg Ser Asp Phe
                 60                  65                  70 gga gga aag gga gtt cct ctt aga ctt gtt ctg gga aaa agc aaa atg     294
Gly Gly Lys Gly Val Pro Leu Arg Leu Val Leu Gly Lys Ser Lys Met
             75                  80                  85 att gct gga tgg gag gaa ggc atc acc acc atg gcc aaa ggt gaa ata     342
Ile Ala Gly Trp Glu Glu Gly Ile Thr Thr Met Ala Lys Gly Glu Ile
         90                  95                 100 gct atg ctg aaa gtg caa cct gaa tta cat tat ggt gac ccg gag tgt     390
Ala Met Leu Lys Val Gln Pro Glu Leu His Tyr Gly Asp Pro Glu Cys
        105                 110                 115 cct gta cca gtg ccc gag aac ttt cca gtt tct gat gag ctc ctt tac     438
Pro Val Pro Val Pro Glu Asn Phe Pro Val Ser Asp Glu Leu Leu Tyr
120             125                 130                 135 gaa gtg gag ttg ttc aac ttc tgt aag gcg aag att atc aca gag gat     486
Glu Val Glu Leu Phe Asn Phe Cys Lys Ala Lys Ile Ile Thr Glu Asp
                140                 145                 150 ctt ggt gtg aca aaa gtg gtc tta gaa gag ggt gag ggc tgg gaa act     534
Leu Gly Val Thr Lys Val Val Leu Glu Glu Gly Glu Gly Trp Glu Thr
            155                 160                 165 gca agg cct ccg tac gag gtg aag ctt tgg att aca ggc cgg atc tta     582
Ala Arg Pro Pro Tyr Glu Val Lys Leu Trp Ile Thr Gly Arg Ile Leu
        170                 175                 180 ggt ggg tcc aca ttt ttt act cat aaa gag tgc gat ccc att cat gtt     630
Gly Gly Ser Thr Phe Phe Thr His Lys Glu Cys Asp Pro Ile His Val
185                 190                 195 gaa ttc ggc aag gaa cag ttg cca gaa gga ctt gag aag gca gtc ggc     678
Glu Phe Gly Lys Glu Gln Leu Pro Glu Gly Leu Glu Lys Ala Val Gly
200                 205                 210                 215 act atg acg agg aaa gaa aag tca att atc tac att tca agt tca tac     726
Thr Met Thr Arg Lys Glu Lys Ser Ile Ile Tyr Ile Ser Ser Ser Tyr
                220                 225                 230 tgt acg aat tct tca aat gca tac aaa ttg aat ata tct cct caa gcg     774
Cys Thr Asn Ser Ser Asn Ala Tyr Lys Leu Asn Ile Ser Pro Gln Ala
            235                 240                 245 caa gaa cta gaa ttt gaa gtg cag ttg gtg cag ctc att cag gta aga     822
Gln Glu Leu Glu Phe Glu Val Gln Leu Val Gln Leu Ile Gln Val Arg
        250                 255                 260 gac atg ttt gga gat gga gga ttg att aag aga cgc ctg cga gac gga     870
Asp Met Phe Gly Asp Gly Gly Leu Ile Lys Arg Arg Leu Arg Asp Gly
265                 270                 275 cta ggt gaa ttt cct gtg gac tgt cct ctg caa gat agt gtg ctt aga     918
Leu Gly Glu Phe Pro Val Asp Cys Pro Leu Gln Asp Ser Val Leu Arg
280                 285                 290                 295 gtc cac tat aag gct atg cta cct gat gat ggc ggc aga ata ttt att     966
Val His Tyr Lys Ala Met Leu Pro Asp Asp Gly Gly Arg Ile Phe Ile
                300                 305                 310 gac acc aga agt aat gga ggg gag cct gtt gag ttt gct tct ggt gag    1014
Asp Thr Arg Ser Asn Gly Gly Glu Pro Val Glu Phe Ala Ser Gly Glu
            315                 320                 325 ggt gtg gta cca gag gga ctt gag gca agt ttg agg ttg atg ctt ccg    1062
Gly Val Val Pro Glu Gly Leu Glu Ala Ser Leu Arg Leu Met Leu Pro
        330                 335                 340 ggg gag ctc gca ctg atc aac agc gtc tct aag tac gca tat gac aaa    1110
Gly Glu Leu Ala Leu Ile Asn Ser Val Ser Lys Tyr Ala Tyr Asp Lys
345                 350                 355
```

| | | | | | | | | | | | | | | | |
|---|---|---|---|---|---|---|---|---|---|---|---|---|---|---|---|
| ttt | caa | agg | cca | gag | agt | gtt | cca | gag | gga | gct | tca | gtc | caa | tgg | gaa |
| Phe | Gln | Arg | Pro | Glu | Ser | Val | Pro | Glu | Gly | Ala | Ser | Val | Gln | Trp | Glu |
| 360 | | | | 365 | | | | | 370 | | | | | 375 | |

1158 gtg gaa tta ctg gaa ttt gag agt gca aag gat tgg acg ggc ctt aat  1206
Val Glu Leu Leu Glu Phe Glu Ser Ala Lys Asp Trp Thr Gly Leu Asn
        380                 385                 390 ttt caa gag atc atg gct gaa gct gat tcc ata aag acc aca ggt aac  1254
Phe Gln Glu Ile Met Ala Glu Ala Asp Ser Ile Lys Thr Thr Gly Asn
            395                 400                 405 cgg tta ttt aag gag ggc aag cac gag ctg gct aaa gct aag tac gaa  1302
Arg Leu Phe Lys Glu Gly Lys His Glu Leu Ala Lys Ala Lys Tyr Glu
                410                 415                 420 aag gtg ttg agg gat ttc aga cat gta aac cct ggc agt gat gaa gaa  1350
Lys Val Leu Arg Asp Phe Arg His Val Asn Pro Gly Ser Asp Glu Glu
    425                 430                 435 gca aag gaa cta caa gac acc aat aac gca ctg cgg ctt aat gta gca  1398
Ala Lys Glu Leu Gln Asp Thr Asn Asn Ala Leu Arg Leu Asn Val Ala
440                 445                 450                 455 gct tgt tat cat aaa ctc cat gag tac atc aaa tgc ata gaa aca tgc  1446
Ala Cys Tyr His Lys Leu His Glu Tyr Ile Lys Cys Ile Glu Thr Cys
                460                 465                 470 aac aag gtg cta gaa ggt aac ccg cat cat gtc aaa ggg tta ttt cgc  1494
Asn Lys Val Leu Glu Gly Asn Pro His His Val Lys Gly Leu Phe Arg
        475                 480                 485 cga gga act gct tac atg gaa acg ggg gac ttt gat gaa gct aga gct  1542
Arg Gly Thr Ala Tyr Met Glu Thr Gly Asp Phe Asp Glu Ala Arg Ala
            490                 495                 500 gat ttc aag cag atg ata aca gtt gac aag gct gtc aca gtt gat gca  1590
Asp Phe Lys Gln Met Ile Thr Val Asp Lys Ala Val Thr Val Asp Ala
    505                 510                 515 act gct gct tta cag aag ctc aag caa aaa gaa cgg gaa gct gag ctg  1638
Thr Ala Ala Leu Gln Lys Leu Lys Gln Lys Glu Arg Glu Ala Glu Leu
520                 525                 530                 535 aaa gct aag aaa cag ttc aaa ggg cta ttt gac tta aaa cct gga gaa  1686
Lys Ala Lys Lys Gln Phe Lys Gly Leu Phe Asp Leu Lys Pro Gly Glu
                540                 545                 550 ctc tct gag ggg cta gaa gag gta aag ccc gta agc gaa atc cat gag  1734
Leu Ser Glu Gly Leu Glu Glu Val Lys Pro Val Ser Glu Ile His Glu
        555                 560                 565 aag act gtt gtc aac gag gaa ctt ccg ata gca tct atg gat caa cat  1782
Lys Thr Val Val Asn Glu Glu Leu Pro Ile Ala Ser Met Asp Gln His
            570                 575                 580 caa cac tca aag cac gaa aca gag gaa ggg agc cat gaa tcg ccc agg  1830
Gln His Ser Lys His Glu Thr Glu Glu Gly Ser His Glu Ser Pro Arg
    585                 590                 595 gca agc agc cga ttg tta aga ctt ctg aaa ggt gga gag cac ctg ata  1878
Ala Ser Ser Arg Leu Leu Arg Leu Leu Lys Gly Gly Glu His Leu Ile
600                 605                 610                 615 agg aca gtc act ttt ggg aag tgt acg att ctt taatttttca tattgctact  1931
Arg Thr Val Thr Phe Gly Lys Cys Thr Ile Leu
                620                 625 gctaggatct cccctttta ctgtactggt gactaccta tgctcattta catttctaag  1991
ccgttatagc tgttattaac cattcgataa tgtactatga acaatattcc actagcgttt  2051
tatggctatt tttcattaag tcctcgtgcc gtta  2085

<210> SEQ ID NO 62
<211> LENGTH: 626
<212> TYPE: PRT
<213> ORGANISM: Physcomitrella patens

<400> SEQUENCE: 62

```
Met Glu Glu Leu Ala Ser Ser Asp Val Pro Asn Lys Leu Lys Lys Lys
1               5                   10                  15

Glu Ser Lys Met Lys Lys Arg Val Ile Thr Pro Gly Ala Leu Leu Lys
                20                  25                  30

Ala Val Val Arg Ser Gly Glu Gly Thr Lys Arg Pro Val Glu Gly Asp
            35                  40                  45

Gln Ile Ile Phe His Tyr Val Thr Arg Thr Asn Gln Gly Val Val Val
        50                  55                  60

Glu Thr Ser Arg Ser Asp Phe Gly Gly Lys Gly Val Pro Leu Arg Leu
65                  70                  75                  80

Val Leu Gly Lys Ser Lys Met Ile Ala Gly Trp Glu Gly Ile Thr
                85                  90                  95

Thr Met Ala Lys Gly Glu Ile Ala Met Leu Lys Val Gln Pro Glu Leu
                100                 105                 110

His Tyr Gly Asp Pro Glu Cys Pro Val Pro Val Pro Glu Asn Phe Pro
            115                 120                 125

Val Ser Asp Glu Leu Leu Tyr Glu Val Glu Leu Phe Asn Phe Cys Lys
130                 135                 140

Ala Lys Ile Ile Thr Glu Asp Leu Gly Val Thr Lys Val Val Leu Glu
145                 150                 155                 160

Glu Gly Glu Gly Trp Glu Thr Ala Arg Pro Pro Tyr Glu Val Lys Leu
                165                 170                 175

Trp Ile Thr Gly Arg Ile Leu Gly Gly Ser Thr Phe Phe Thr His Lys
                180                 185                 190

Glu Cys Asp Pro Ile His Val Glu Phe Gly Lys Glu Gln Leu Pro Glu
            195                 200                 205

Gly Leu Glu Lys Ala Val Gly Thr Met Thr Arg Lys Glu Lys Ser Ile
210                 215                 220

Ile Tyr Ile Ser Ser Tyr Cys Thr Asn Ser Ser Asn Ala Tyr Lys
225                 230                 235                 240

Leu Asn Ile Ser Pro Gln Ala Gln Glu Leu Glu Phe Glu Val Gln Leu
                245                 250                 255

Val Gln Leu Ile Gln Val Arg Asp Met Phe Asp Gly Gly Leu Ile
                260                 265                 270

Lys Arg Arg Leu Arg Asp Gly Leu Gly Glu Phe Pro Val Asp Cys Pro
                275                 280                 285

Leu Gln Asp Ser Val Leu Arg Val His Tyr Lys Ala Met Leu Pro Asp
                290                 295                 300

Asp Gly Gly Arg Ile Phe Ile Asp Thr Arg Ser Asn Gly Gly Glu Pro
305                 310                 315                 320

Val Glu Phe Ala Ser Gly Gly Val Val Pro Gly Leu Glu Ala
                325                 330                 335

Ser Leu Arg Leu Met Leu Pro Gly Glu Leu Ala Leu Ile Asn Ser Val
                340                 345                 350

Ser Lys Tyr Ala Tyr Asp Lys Phe Gln Arg Pro Glu Ser Val Pro Glu
                355                 360                 365

Gly Ala Ser Val Gln Trp Glu Val Glu Leu Leu Glu Phe Glu Ser Ala
            370                 375                 380

Lys Asp Trp Thr Gly Leu Asn Phe Gln Glu Ile Met Ala Glu Ala Asp
385                 390                 395                 400

Ser Ile Lys Thr Thr Gly Asn Arg Leu Phe Lys Glu Gly Lys His Glu
                405                 410                 415
```

```
Leu Ala Lys Ala Lys Tyr Glu Lys Val Leu Arg Asp Phe Arg His Val
            420                 425                 430

Asn Pro Gly Ser Asp Glu Glu Ala Lys Glu Leu Gln Asp Thr Asn Asn
            435                 440                 445

Ala Leu Arg Leu Asn Val Ala Ala Cys Tyr His Lys Leu His Glu Tyr
            450                 455                 460

Ile Lys Cys Ile Glu Thr Cys Asn Lys Val Leu Glu Gly Asn Pro His
465                 470                 475                 480

His Val Lys Gly Leu Phe Arg Arg Gly Thr Ala Tyr Met Glu Thr Gly
                485                 490                 495

Asp Phe Asp Glu Ala Arg Ala Asp Phe Lys Gln Met Ile Thr Val Asp
            500                 505                 510

Lys Ala Val Thr Val Asp Ala Thr Ala Ala Leu Gln Lys Leu Lys Gln
            515                 520                 525

Lys Glu Arg Glu Ala Glu Leu Lys Ala Lys Gln Phe Lys Gly Leu
            530                 535                 540

Phe Asp Leu Lys Pro Gly Glu Leu Ser Glu Gly Leu Glu Glu Val Lys
545                 550                 555                 560

Pro Val Ser Glu Ile His Glu Lys Thr Val Val Asn Glu Glu Leu Pro
                565                 570                 575

Ile Ala Ser Met Asp Gln His Gln His Ser Lys His Glu Thr Glu Glu
            580                 585                 590

Gly Ser His Glu Ser Pro Arg Ala Ser Ser Arg Leu Leu Arg Leu Leu
                595                 600                 605

Lys Gly Gly Glu His Leu Ile Arg Thr Val Thr Phe Gly Lys Cys Thr
610                 615                 620

Ile Leu
625

<210> SEQ ID NO 63
<211> LENGTH: 336
<212> TYPE: DNA
<213> ORGANISM: Saccharomyces cerevisiae
<220> FEATURE:
<221> NAME/KEY: CDS
<222> LOCATION: (1)..(336)
<223> OTHER INFORMATION: unknown protein 1 (YBL109w)

<400> SEQUENCE: 63 atg tcc cta cgg cct tgt cta aca cca tcc agc atg caa tac agt gac      48
Met Ser Leu Arg Pro Cys Leu Thr Pro Ser Ser Met Gln Tyr Ser Asp
1               5                   10                  15 ata tat ata tac cct aac act acc cta acc cta ccc tat ttc aac cct      96
Ile Tyr Ile Tyr Pro Asn Thr Thr Leu Thr Leu Pro Tyr Phe Asn Pro
            20                  25                  30 tcc aac ctg tct ctc aac tta ccc tca cat tac cct acc tct cca ctt     144
Ser Asn Leu Ser Leu Asn Leu Pro Ser His Tyr Pro Thr Ser Pro Leu
        35                  40                  45 gtt acc ctg tcc cat tca acc ata cca ctc cca acc acc atc cat ccc     192
Val Thr Leu Ser His Ser Thr Ile Pro Leu Pro Thr Thr Ile His Pro
    50                  55                  60 tct act tac tac cac caa tca acc gtc cac cat aac cgt tac cct cca     240
Ser Thr Tyr Tyr His Gln Ser Thr Val His His Asn Arg Tyr Pro Pro
65                  70                  75                  80 att agc cat att caa ctt cac tac cac tta ccc tgc cat tac tct acc     288
Ile Ser His Ile Gln Leu His Tyr His Leu Pro Cys His Tyr Ser Thr
                85                  90                  95 atc cac cat ctg cta ctc acc ata ctg ttg ttc tac cct cca tat taa     336
Ile His His Leu Leu Leu Thr Ile Leu Leu Phe Tyr Pro Pro Tyr
```

<210> SEQ ID NO 64
<211> LENGTH: 111
<212> TYPE: PRT
<213> ORGANISM: Saccharomyces cerevisiae

<400> SEQUENCE: 64

```
Met Ser Leu Arg Pro Cys Leu Thr Pro Ser Ser Met Gln Tyr Ser Asp
1               5                   10                  15

Ile Tyr Ile Tyr Pro Asn Thr Thr Leu Thr Leu Pro Tyr Phe Asn Pro
            20                  25                  30

Ser Asn Leu Ser Leu Asn Leu Pro Ser His Tyr Pro Thr Ser Pro Leu
        35                  40                  45

Val Thr Leu Ser His Ser Thr Ile Pro Leu Pro Thr Thr Ile His Pro
    50                  55                  60

Ser Thr Tyr Tyr His Gln Ser Thr Val His His Asn Arg Tyr Pro Pro
65                  70                  75                  80

Ile Ser His Ile Gln Leu His Tyr Leu Pro Cys His Tyr Ser Thr
                85                  90                  95

Ile His His Leu Leu Leu Thr Ile Leu Leu Phe Tyr Pro Pro Tyr
                100                 105                 110
```

<210> SEQ ID NO 65
<211> LENGTH: 315
<212> TYPE: DNA
<213> ORGANISM: Saccharomyces cerevisiae
<220> FEATURE:
<221> NAME/KEY: CDS
<222> LOCATION: (1)..(315)
<223> OTHER INFORMATION: unknown protein 2 (YBL100c)

<400> SEQUENCE: 65

```
atg ttg ttc aaa cca aaa aca cga gca ata cca tca ccg act gca aga      48
Met Leu Phe Lys Pro Lys Thr Arg Ala Ile Pro Ser Pro Thr Ala Arg
1               5                   10                  15 act cta cca gtt tcg ttc aaa ttg gcc tcg tcg gac aca ccc tta att      96
Thr Leu Pro Val Ser Phe Lys Leu Ala Ser Ser Asp Thr Pro Leu Ile
            20                  25                  30 ctt tcc tct aag atg gag gaa act tct gtg ggt tgt gcc ttg gtg gaa     144
Leu Ser Ser Lys Met Glu Glu Thr Ser Val Gly Cys Ala Leu Val Glu
        35                  40                  45 gcc aat ctt ctg gtg gaa gcc aaa gca gca gcg gca ggt ctt gcg gcc     192
Ala Asn Leu Leu Val Glu Ala Lys Ala Ala Ala Gly Leu Ala Ala
    50                  55                  60 ttg gta gag tta att aga gtt ctc gat aga gaa cga ata gca gca gta     240
Leu Val Glu Leu Ile Arg Val Leu Asp Arg Glu Arg Ile Ala Ala Val
65                  70                  75                  80 cga gcc aac att att ata tgt gcg tgt ttt ttt tat tta ttt tgt tac     288
Arg Ala Asn Ile Ile Ile Cys Ala Cys Phe Phe Tyr Leu Phe Cys Tyr
                85                  90                  95 tgt tct tgc gat agt tat gag agc taa                                 315
Cys Ser Cys Asp Ser Tyr Glu Ser
                100
```

<210> SEQ ID NO 66
<211> LENGTH: 104
<212> TYPE: PRT
<213> ORGANISM: Saccharomyces cerevisiae

<400> SEQUENCE: 66

Met Leu Phe Lys Pro Lys Thr Arg Ala Ile Pro Ser Pro Thr Ala Arg

```
                  1               5                  10                  15
Thr Leu Pro Val Ser Phe Lys Leu Ala Ser Ser Asp Thr Pro Leu Ile
                          20                  25                  30

Leu Ser Ser Lys Met Glu Glu Thr Ser Val Gly Cys Ala Leu Val Glu
             35                  40                  45

Ala Asn Leu Leu Val Glu Ala Lys Ala Ala Ala Gly Leu Ala Ala
    50                  55                  60

Leu Val Glu Leu Ile Arg Val Leu Asp Arg Glu Arg Ile Ala Ala Val
65                  70                  75                  80

Arg Ala Asn Ile Ile Ile Cys Ala Cys Phe Phe Tyr Leu Phe Cys Tyr
                85                  90                  95

Cys Ser Cys Asp Ser Tyr Glu Ser
            100
```

```
<210> SEQ ID NO 67
<211> LENGTH: 1401
<212> TYPE: DNA
<213> ORGANISM: Saccharomyces cerevisiae
<220> FEATURE:
<221> NAME/KEY: CDS
<222> LOCATION: (1)..(1401)
<223> OTHER INFORMATION: ornithine decarboxylase (YKL184w)

<400> SEQUENCE: 67
```

```
atg tct agt act caa gta gga aat gct cta tct agt tcc act act act       48
Met Ser Ser Thr Gln Val Gly Asn Ala Leu Ser Ser Thr Thr Thr
1               5                  10                  15 tta gtg gac ttg tct aat tct acg gtt acc caa aag aag caa tat tat       96
Leu Val Asp Leu Ser Asn Ser Thr Val Thr Gln Lys Lys Gln Tyr Tyr
             20                  25                  30 aaa gat ggc gag acg ctg cac aat ctt ttg ctt gaa cta aag aat aac      144
Lys Asp Gly Glu Thr Leu His Asn Leu Leu Leu Glu Leu Lys Asn Asn
         35                  40                  45 caa gat ttg gaa ctt tta ccg cat gaa caa gcg cat cct aaa ata ttt      192
Gln Asp Leu Glu Leu Leu Pro His Glu Gln Ala His Pro Lys Ile Phe
     50                  55                  60 caa gcg ctc aag gct cgt att ggt aga att aat aat gaa acg tgc gac      240
Gln Ala Leu Lys Ala Arg Ile Gly Arg Ile Asn Asn Glu Thr Cys Asp
65                  70                  75                  80 ccc ggt gag gag aac tcg ttt ttc ata tgc gat ttg gga gaa gtc aag      288
Pro Gly Glu Glu Asn Ser Phe Phe Ile Cys Asp Leu Gly Glu Val Lys
                85                  90                  95 aga tta ttc aac aac tgg gtg aag gag ctt cct aga att aag cca ttt      336
Arg Leu Phe Asn Asn Trp Val Lys Glu Leu Pro Arg Ile Lys Pro Phe
            100                 105                 110 tat gcc gtc aaa tgt aat cct gat acc aag gtt ttg tca tta tta gca      384
Tyr Ala Val Lys Cys Asn Pro Asp Thr Lys Val Leu Ser Leu Leu Ala
        115                 120                 125 gag ttg ggc gtt aat ttc gat tgc gct tcc aaa gtg gaa att gac aga      432
Glu Leu Gly Val Asn Phe Asp Cys Ala Ser Lys Val Glu Ile Asp Arg
    130                 135                 140 gta tta tcg atg aac atc tcg ccg gat aga att gtt tac gct aat cct      480
Val Leu Ser Met Asn Ile Ser Pro Asp Arg Ile Val Tyr Ala Asn Pro
145                 150                 155                 160 tgt aaa gta gca tct ttc att aga tat gca gct tca aaa aat gta atg      528
Cys Lys Val Ala Ser Phe Ile Arg Tyr Ala Ala Ser Lys Asn Val Met
                165                 170                 175 aag tct act ttt gac aat gta gaa gaa ttg cat aaa atc aaa aag ttt      576
Lys Ser Thr Phe Asp Asn Val Glu Glu Leu His Lys Ile Lys Lys Phe
            180                 185                 190
```

| | | |
|---|---|---|
| cat cct gag tct cag ttg tta tta aga atc gct acc gat gac tct acc<br>His Pro Glu Ser Gln Leu Leu Leu Arg Ile Ala Thr Asp Asp Ser Thr<br>    195                            200                           205 | 624 |
| gct caa tgt cga ctt tcc acc aaa tat ggc tgt gaa atg gaa aac gta<br>Ala Gln Cys Arg Leu Ser Thr Lys Tyr Gly Cys Glu Met Glu Asn Val<br>210                         215                       220 | 672 |
| gac gtt tta tta aag gct ata aag gaa cta ggt tta aac ctg gct ggt<br>Asp Val Leu Leu Lys Ala Ile Lys Glu Leu Gly Leu Asn Leu Ala Gly<br>225                     230                     235                 240 | 720 |
| gtt tct ttc cac gtc ggt tca ggc gct tct gat ttt aca agc tta tac<br>Val Ser Phe His Val Gly Ser Gly Ala Ser Asp Phe Thr Ser Leu Tyr<br>                  245                     250                   255 | 768 |
| aaa gcc gtt aga gat gca aga acg gta ttt gac aaa gct gct aac gaa<br>Lys Ala Val Arg Asp Ala Arg Thr Val Phe Asp Lys Ala Ala Asn Glu<br>            260                     265                   270 | 816 |
| tac ggg ttg ccc cct ttg aag att ttg gat gta ggt ggt gga ttt caa<br>Tyr Gly Leu Pro Pro Leu Lys Ile Leu Asp Val Gly Gly Gly Phe Gln<br>       275                   280                     285 | 864 |
| ttt gaa tcc ttc aaa gaa tca act gct gtt ttg cgt cta gcg cta gag<br>Phe Glu Ser Phe Lys Glu Ser Thr Ala Val Leu Arg Leu Ala Leu Glu<br>    290                     295                     300 | 912 |
| gaa ttt ttc cct gta ggt tgt ggt gtt gat ata att gca gag cct ggc<br>Glu Phe Phe Pro Val Gly Cys Gly Val Asp Ile Ile Ala Glu Pro Gly<br>305                     310                     315                 320 | 960 |
| aga tac ttt gta gct aca gcg ttc act ttg gca tct cat gtg att gcg<br>Arg Tyr Phe Val Ala Thr Ala Phe Thr Leu Ala Ser His Val Ile Ala<br>                  325                     330                   335 | 1008 |
| aag aga aaa ctg tct gag aat gaa gca atg att tac act aac gat ggt<br>Lys Arg Lys Leu Ser Glu Asn Glu Ala Met Ile Tyr Thr Asn Asp Gly<br>            340                     345                   350 | 1056 |
| gta tac ggg aac atg aat tgt att tta ttc gat cat caa gag ccc cat<br>Val Tyr Gly Asn Met Asn Cys Ile Leu Phe Asp His Gln Glu Pro His<br>       355                   360                     365 | 1104 |
| cca aga acc ctt tat cat aat ttg gaa ttt cat tac gac gat ttt gaa<br>Pro Arg Thr Leu Tyr His Asn Leu Glu Phe His Tyr Asp Asp Phe Glu<br>    370                     375                     380 | 1152 |
| tcc act act gcg gtc ctc gac tct atc aac aaa aca aga tct gag tat<br>Ser Thr Thr Ala Val Leu Asp Ser Ile Asn Lys Thr Arg Ser Glu Tyr<br>385                     390                     395                 400 | 1200 |
| cca tat aaa gtt tcc atc tgg gga ccc aca tgt gat ggt ttg gat tgt<br>Pro Tyr Lys Val Ser Ile Trp Gly Pro Thr Cys Asp Gly Leu Asp Cys<br>                  405                     410                   415 | 1248 |
| att gcc aaa gag tat tac atg aag cat gat gtt ata gtc ggt gat tgg<br>Ile Ala Lys Glu Tyr Tyr Met Lys His Asp Val Ile Val Gly Asp Trp<br>            420                     425                   430 | 1296 |
| ttt tat ttt cct gcc ctg ggt gcc tac aca tca tcg gcg gct act caa<br>Phe Tyr Phe Pro Ala Leu Gly Ala Tyr Thr Ser Ser Ala Ala Thr Gln<br>       435                   440                     445 | 1344 |
| ttc aac ggc ttt gag cag act gcg gat ata gta tac ata gac tct gaa<br>Phe Asn Gly Phe Glu Gln Thr Ala Asp Ile Val Tyr Ile Asp Ser Glu<br>    450                     455                     460 | 1392 |
| ctc gat taa<br>Leu Asp<br>465 | 1401 |

<210> SEQ ID NO 68
<211> LENGTH: 466
<212> TYPE: PRT
<213> ORGANISM: Saccharomyces cerevisiae

<400> SEQUENCE: 68

```
Met Ser Ser Thr Gln Val Gly Asn Ala Leu Ser Ser Thr Thr Thr
1               5                   10                  15

Leu Val Asp Leu Ser Asn Ser Thr Val Thr Gln Lys Lys Gln Tyr Tyr
            20                  25                  30

Lys Asp Gly Glu Thr Leu His Asn Leu Leu Glu Leu Lys Asn Asn
            35                  40                  45

Gln Asp Leu Glu Leu Leu Pro His Glu Gln Ala His Pro Lys Ile Phe
50                      55                  60

Gln Ala Leu Lys Ala Arg Ile Gly Arg Ile Asn Asn Glu Thr Cys Asp
65                  70                  75                  80

Pro Gly Glu Glu Asn Ser Phe Phe Ile Cys Asp Leu Gly Glu Val Lys
                85                  90                  95

Arg Leu Phe Asn Asn Trp Val Lys Glu Leu Pro Arg Ile Lys Pro Phe
                100                 105                 110

Tyr Ala Val Lys Cys Asn Pro Asp Thr Lys Val Leu Ser Leu Leu Ala
            115                 120                 125

Glu Leu Gly Val Asn Phe Asp Cys Ala Ser Lys Val Glu Ile Asp Arg
        130                 135                 140

Val Leu Ser Met Asn Ile Ser Pro Asp Arg Ile Val Tyr Ala Asn Pro
145                 150                 155                 160

Cys Lys Val Ala Ser Phe Ile Arg Tyr Ala Ala Ser Lys Asn Val Met
                165                 170                 175

Lys Ser Thr Phe Asp Asn Val Glu Glu Leu His Lys Ile Lys Lys Phe
            180                 185                 190

His Pro Glu Ser Gln Leu Leu Leu Arg Ile Ala Thr Asp Asp Ser Thr
        195                 200                 205

Ala Gln Cys Arg Leu Ser Thr Lys Tyr Gly Cys Glu Met Glu Asn Val
    210                 215                 220

Asp Val Leu Leu Lys Ala Ile Lys Glu Leu Gly Leu Asn Leu Ala Gly
225                 230                 235                 240

Val Ser Phe His Val Gly Ser Gly Ala Ser Asp Phe Thr Ser Leu Tyr
                245                 250                 255

Lys Ala Val Arg Asp Ala Arg Thr Val Phe Asp Lys Ala Ala Asn Glu
            260                 265                 270

Tyr Gly Leu Pro Pro Leu Lys Ile Leu Asp Val Gly Gly Gly Phe Gln
        275                 280                 285

Phe Glu Ser Phe Lys Glu Ser Thr Ala Val Leu Arg Leu Ala Leu Glu
290                 295                 300

Glu Phe Phe Pro Val Gly Cys Gly Val Asp Ile Ile Ala Glu Pro Gly
305                 310                 315                 320

Arg Tyr Phe Val Ala Thr Ala Phe Thr Leu Ala Ser His Val Ile Ala
                325                 330                 335

Lys Arg Lys Leu Ser Glu Asn Glu Ala Met Ile Tyr Thr Asn Asp Gly
            340                 345                 350

Val Tyr Gly Asn Met Asn Cys Ile Leu Phe Asp His Gln Glu Pro His
        355                 360                 365

Pro Arg Thr Leu Tyr His Asn Leu Glu Phe His Tyr Asp Asp Phe Glu
    370                 375                 380

Ser Thr Thr Ala Val Leu Asp Ser Ile Asn Lys Thr Arg Ser Glu Tyr
385                 390                 395                 400

Pro Tyr Lys Val Ser Ile Trp Gly Pro Thr Cys Asp Gly Leu Asp Cys
                405                 410                 415

Ile Ala Lys Glu Tyr Tyr Met Lys His Asp Val Ile Val Gly Asp Trp
            420                 425                 430
```

```
Phe Tyr Phe Pro Ala Leu Gly Ala Tyr Thr Ser Ser Ala Ala Thr Gln
        435                 440                 445

Phe Asn Gly Phe Glu Gln Thr Ala Asp Ile Val Tyr Ile Asp Ser Glu
        450                 455                 460

Leu Asp
465

<210> SEQ ID NO 69
<211> LENGTH: 1452
<212> TYPE: DNA
<213> ORGANISM: Saccharomyces cerevisiae
<220> FEATURE:
<221> NAME/KEY: CDS
<222> LOCATION: (1)..(1452)
<223> OTHER INFORMATION: glutathione reductase (YPL091w)

<400> SEQUENCE: 69 atg ctt tct gca acc aaa caa aca ttt aga agt cta cag ata aga act    48
Met Leu Ser Ala Thr Lys Gln Thr Phe Arg Ser Leu Gln Ile Arg Thr
1               5                   10                  15 atg tcc acg aac acc aag cat tac gat tac ctc gtc atc ggg ggt ggc    96
Met Ser Thr Asn Thr Lys His Tyr Asp Tyr Leu Val Ile Gly Gly Gly
            20                  25                  30 tca ggg ggt gtt gct tcc gca aga aga gct gca tct tat ggt gcg aag   144
Ser Gly Gly Val Ala Ser Ala Arg Arg Ala Ala Ser Tyr Gly Ala Lys
        35                  40                  45 aca tta cta gtt gaa gct aag gct ctt ggt ggt acc tgt gtt aac gtg   192
Thr Leu Leu Val Glu Ala Lys Ala Leu Gly Gly Thr Cys Val Asn Val
    50                  55                  60 ggt tgt gtt ccg aag aaa gtc atg tgg tat gct tct gac ctc gct act   240
Gly Cys Val Pro Lys Lys Val Met Trp Tyr Ala Ser Asp Leu Ala Thr
65                  70                  75                  80 aga gta tcc cat gca aat gaa tat gga tta tat cag aat ctt cca tta   288
Arg Val Ser His Ala Asn Glu Tyr Gly Leu Tyr Gln Asn Leu Pro Leu
                85                  90                  95 gat aaa gag cat ttg act ttt aat tgg cca gaa ttt aag cag aaa agg   336
Asp Lys Glu His Leu Thr Phe Asn Trp Pro Glu Phe Lys Gln Lys Arg
            100                 105                 110 gat gct tat gtc cat agg ttg aac ggt ata tac cag aag aat tta gaa   384
Asp Ala Tyr Val His Arg Leu Asn Gly Ile Tyr Gln Lys Asn Leu Glu
        115                 120                 125 aaa gaa aaa gtg gat gtt gta ttt gga tgg gct aga ttc aat aag gac   432
Lys Glu Lys Val Asp Val Val Phe Gly Trp Ala Arg Phe Asn Lys Asp
    130                 135                 140 ggt aat gtt gaa gtt cag aaa agg gat aat act act gaa gtt tac tcc   480
Gly Asn Val Glu Val Gln Lys Arg Asp Asn Thr Thr Glu Val Tyr Ser
145                 150                 155                 160 gct aac cat att tta gtt gcg acc ggt gga aag gct att ttc ccc gaa   528
Ala Asn His Ile Leu Val Ala Thr Gly Gly Lys Ala Ile Phe Pro Glu
                165                 170                 175 aac att cca ggt ttc gaa tta ggt act gat tct gat ggg ttc ttt aga   576
Asn Ile Pro Gly Phe Glu Leu Gly Thr Asp Ser Asp Gly Phe Phe Arg
            180                 185                 190 ttg gaa gaa caa cct aag aaa gtt gtt gtt gtt ggc gct ggt tat att   624
Leu Glu Glu Gln Pro Lys Lys Val Val Val Val Gly Ala Gly Tyr Ile
        195                 200                 205 ggt att gag cta gca ggt gtg ttc cat ggg ctg gga tcc gaa acg cac   672
Gly Ile Glu Leu Ala Gly Val Phe His Gly Leu Gly Ser Glu Thr His
    210                 215                 220 ttg gta att aga ggt gaa act gtc ttg aga aaa ttt gat gaa tgc atc   720
Leu Val Ile Arg Gly Glu Thr Val Leu Arg Lys Phe Asp Glu Cys Ile
```

```
                    225                 230                 235                 240 cag aac act att act gac cat tac gta aag gaa ggc atc aac gtt cat      768
Gln Asn Thr Ile Thr Asp His Tyr Val Lys Glu Gly Ile Asn Val His
                    245                 250                 255 aaa cta tcc aaa att gtt aag gtg gag aaa aat gta gaa act gac aaa      816
Lys Leu Ser Lys Ile Val Lys Val Glu Lys Asn Val Glu Thr Asp Lys
                    260                 265                 270 ctg aaa ata cat atg aat gac tca aag tcc atc gat gac gtt gac gaa      864
Leu Lys Ile His Met Asn Asp Ser Lys Ser Ile Asp Asp Val Asp Glu
                275                 280                 285 tta att tgg aca att gga cgt aaa tcc cat cta ggt atg ggt tca gaa      912
Leu Ile Trp Thr Ile Gly Arg Lys Ser His Leu Gly Met Gly Ser Glu
            290                 295                 300 aat gta ggt ata aag ctg aac tct cat gac caa ata att gct gat gaa      960
Asn Val Gly Ile Lys Leu Asn Ser His Asp Gln Ile Ile Ala Asp Glu
305                 310                 315                 320 tat cag aac acc aat gtt cca aac att tat tct cta ggt gac gtt gtt     1008
Tyr Gln Asn Thr Asn Val Pro Asn Ile Tyr Ser Leu Gly Asp Val Val
                325                 330                 335 gga aaa gtt gaa ttg aca cct gtc gct att gca gcg ggc aga aag ctg     1056
Gly Lys Val Glu Leu Thr Pro Val Ala Ile Ala Ala Gly Arg Lys Leu
                340                 345                 350 tct aat aga ctt ttt ggt cca gag aaa ttc cgt aat gac aaa cta gat     1104
Ser Asn Arg Leu Phe Gly Pro Glu Lys Phe Arg Asn Asp Lys Leu Asp
            355                 360                 365 tac gag aac gtc ccc agc gta att ttc tca cat cct gaa gcc ggt tcc     1152
Tyr Glu Asn Val Pro Ser Val Ile Phe Ser His Pro Glu Ala Gly Ser
        370                 375                 380 att ggt att tct gag aag gaa gcc att gaa aag tac ggt aag gag aat     1200
Ile Gly Ile Ser Glu Lys Glu Ala Ile Glu Lys Tyr Gly Lys Glu Asn
385                 390                 395                 400 ata aag gtc tac aat tcc aaa ttt acc gcc atg tac tat gct atg ttg     1248
Ile Lys Val Tyr Asn Ser Lys Phe Thr Ala Met Tyr Tyr Ala Met Leu
                405                 410                 415 agt gag aaa tca ccc aca aga tat aaa att gtt tgt gcg gga cca aat     1296
Ser Glu Lys Ser Pro Thr Arg Tyr Lys Ile Val Cys Ala Gly Pro Asn
                420                 425                 430 gaa aag gtt gtc ggt ctg cac att gtt ggt gat tcc tct gca gaa atc     1344
Glu Lys Val Val Gly Leu His Ile Val Gly Asp Ser Ser Ala Glu Ile
            435                 440                 445 ttg caa ggg ttc ggt gtt gct ata aag atg ggt gcc act aag gct gat     1392
Leu Gln Gly Phe Gly Val Ala Ile Lys Met Gly Ala Thr Lys Ala Asp
        450                 455                 460 ttc gat aat tgt gtt gct att cat ccg act agc gca gaa gaa ttg gtt     1440
Phe Asp Asn Cys Val Ala Ile His Pro Thr Ser Ala Glu Glu Leu Val
465                 470                 475                 480 act atg aga taa                                                      1452
Thr Met Arg <210> SEQ ID NO 70
<211> LENGTH: 483
<212> TYPE: PRT
<213> ORGANISM: Saccharomyces cerevisiae

<400> SEQUENCE: 70

Met Leu Ser Ala Thr Lys Gln Thr Phe Arg Ser Leu Gln Ile Arg Thr
1               5                   10                  15

Met Ser Thr Asn Thr Lys His Tyr Asp Tyr Leu Val Ile Gly Gly Gly
            20                  25                  30

Ser Gly Gly Val Ala Ser Ala Arg Arg Ala Ala Ser Tyr Gly Ala Lys
```

-continued

```
            35                  40                  45
Thr Leu Leu Val Glu Ala Lys Ala Leu Gly Thr Cys Val Asn Val
 50                  55                  60
Gly Cys Val Pro Lys Lys Val Met Trp Tyr Ala Ser Asp Leu Ala Thr
 65                  70                  75                  80
Arg Val Ser His Ala Asn Glu Tyr Gly Leu Tyr Gln Asn Leu Pro Leu
                 85                  90                  95
Asp Lys Glu His Leu Thr Phe Asn Trp Pro Glu Phe Lys Gln Lys Arg
                100                 105                 110
Asp Ala Tyr Val His Arg Leu Asn Gly Ile Tyr Gln Lys Asn Leu Glu
                115                 120                 125
Lys Glu Lys Val Asp Val Val Phe Gly Trp Ala Arg Phe Asn Lys Asp
                130                 135                 140
Gly Asn Val Glu Val Gln Lys Arg Asp Asn Thr Thr Glu Val Tyr Ser
145                 150                 155                 160
Ala Asn His Ile Leu Val Ala Thr Gly Gly Lys Ala Ile Phe Pro Glu
                    165                 170                 175
Asn Ile Pro Gly Phe Glu Leu Gly Thr Asp Ser Asp Gly Phe Phe Arg
                180                 185                 190
Leu Glu Glu Gln Pro Lys Lys Val Val Val Gly Ala Gly Tyr Ile
                195                 200                 205
Gly Ile Glu Leu Ala Gly Val Phe His Gly Leu Gly Ser Glu Thr His
                210                 215                 220
Leu Val Ile Arg Gly Glu Thr Val Leu Arg Lys Phe Asp Glu Cys Ile
225                 230                 235                 240
Gln Asn Thr Ile Thr Asp His Tyr Val Lys Glu Gly Ile Asn Val His
                    245                 250                 255
Lys Leu Ser Lys Ile Val Lys Val Glu Lys Asn Val Glu Thr Asp Lys
                260                 265                 270
Leu Lys Ile His Met Asn Asp Ser Lys Ser Ile Asp Asp Val Asp Glu
                275                 280                 285
Leu Ile Trp Thr Ile Gly Arg Lys Ser His Leu Gly Met Gly Ser Glu
                290                 295                 300
Asn Val Gly Ile Lys Leu Asn Ser His Asp Gln Ile Ile Ala Asp Glu
305                 310                 315                 320
Tyr Gln Asn Thr Asn Val Pro Asn Ile Tyr Ser Leu Gly Asp Val Val
                    325                 330                 335
Gly Lys Val Glu Leu Thr Pro Val Ala Ile Ala Ala Gly Arg Lys Leu
                340                 345                 350
Ser Asn Arg Leu Phe Gly Pro Glu Lys Phe Arg Asn Asp Lys Leu Asp
                355                 360                 365
Tyr Glu Asn Val Pro Ser Val Ile Phe Ser His Pro Glu Ala Gly Ser
                370                 375                 380
Ile Gly Ile Ser Glu Lys Glu Ala Ile Glu Lys Tyr Gly Lys Glu Asn
385                 390                 395                 400
Ile Lys Val Tyr Asn Ser Lys Phe Thr Ala Met Tyr Tyr Ala Met Leu
                    405                 410                 415
Ser Glu Lys Ser Pro Thr Arg Tyr Lys Ile Val Cys Ala Gly Pro Asn
                420                 425                 430
Glu Lys Val Val Gly Leu His Ile Val Gly Asp Ser Ala Glu Ile
                435                 440                 445
Leu Gln Gly Phe Gly Val Ala Ile Lys Met Gly Ala Thr Lys Ala Asp
                450                 455                 460
```

Phe Asp Asn Cys Val Ala Ile His Pro Thr Ser Ala Glu Glu Leu Val
465                 470                 475                 480

Thr Met Arg

<210> SEQ ID NO 71
<211> LENGTH: 390
<212> TYPE: DNA
<213> ORGANISM: Triticum aestivum
<220> FEATURE:
<221> NAME/KEY: CDS
<222> LOCATION: (1)..(390)
<223> OTHER INFORMATION: unknown protein 3 (TA54587433)

<400> SEQUENCE: 71

```
atg gcg gtc atg tca cgg ttg aag agg ctg gcg gcg ccc gcg ctg ctg      48
Met Ala Val Met Ser Arg Leu Lys Arg Leu Ala Ala Pro Ala Leu Leu
1               5                   10                  15 gtg ctg ctt gcg ctg gcg gcc tcc gcg gcc gtg gcg gcg aag acg acc      96
Val Leu Leu Ala Leu Ala Ala Ser Ala Ala Val Ala Ala Lys Thr Thr
            20                  25                  30 cag gac ggc gcg gag gcg gcg ccg ggc aag gat gaa gag tcg tgg acg     144
Gln Asp Gly Ala Glu Ala Ala Pro Gly Lys Asp Glu Glu Ser Trp Thr
        35                  40                  45 ggg tgg gcc aag gac aag atc tcc gag ggg ctg ggg ctc aag cac gac     192
Gly Trp Ala Lys Asp Lys Ile Ser Glu Gly Leu Gly Leu Lys His Asp
    50                  55                  60 gct gac gag gag gcc gcg cgc gag acc gtc cag cac acc gcc tcc gag     240
Ala Asp Glu Glu Ala Ala Arg Glu Thr Val Gln His Thr Ala Ser Glu
65                  70                  75                  80 acg ggg agt cag gtg agc ggc aag gca gcg gac gcc aag gag gcg gcc     288
Thr Gly Ser Gln Val Ser Gly Lys Ala Ala Asp Ala Lys Glu Ala Ala
                85                  90                  95 aag gga acg gtc ggg gag aag ctc ggg gag gtg aag gac aag gtc acc     336
Lys Gly Thr Val Gly Glu Lys Leu Gly Glu Val Lys Asp Lys Val Thr
            100                 105                 110 ggc gca gca gcc gac ggc aag gac aag acg cac cgc aag gat gac ttg     384
Gly Ala Ala Ala Asp Gly Lys Asp Lys Thr His Arg Lys Asp Asp Leu
        115                 120                 125 ctg tga                                                              390
Leu
```

<210> SEQ ID NO 72
<211> LENGTH: 129
<212> TYPE: PRT
<213> ORGANISM: Triticum aestivum

<400> SEQUENCE: 72

Met Ala Val Met Ser Arg Leu Lys Arg Leu Ala Ala Pro Ala Leu Leu
1               5                   10                  15

Val Leu Leu Ala Leu Ala Ala Ser Ala Ala Val Ala Ala Lys Thr Thr
            20                  25                  30

Gln Asp Gly Ala Glu Ala Ala Pro Gly Lys Asp Glu Glu Ser Trp Thr
        35                  40                  45

Gly Trp Ala Lys Asp Lys Ile Ser Glu Gly Leu Gly Leu Lys His Asp
    50                  55                  60

Ala Asp Glu Glu Ala Ala Arg Glu Thr Val Gln His Thr Ala Ser Glu
65                  70                  75                  80

Thr Gly Ser Gln Val Ser Gly Lys Ala Ala Asp Ala Lys Glu Ala Ala
                85                  90                  95

Lys Gly Thr Val Gly Glu Lys Leu Gly Glu Val Lys Asp Lys Val Thr
            100                 105                 110

Gly Ala Ala Ala Asp Gly Lys Asp Lys Thr His Arg Lys Asp Asp Leu
            115                 120                 125

Leu

<210> SEQ ID NO 73
<211> LENGTH: 921
<212> TYPE: DNA
<213> ORGANISM: Zea mays
<220> FEATURE:
<221> NAME/KEY: CDS
<222> LOCATION: (1)..(921)
<223> OTHER INFORMATION: protein phosphatase 2A (ZM68532504)

<400> SEQUENCE: 73

```
atg ccg tcg cac ggg gat ctg gac cgg cag atc gcg cag ctg cgc gac      48
Met Pro Ser His Gly Asp Leu Asp Arg Gln Ile Ala Gln Leu Arg Asp
1               5                   10                  15 tgc aag tac ctg ccc gag gcg gag gtc aag gcg ctc tgc gag cag gcc      96
Cys Lys Tyr Leu Pro Glu Ala Glu Val Lys Ala Leu Cys Glu Gln Ala
                20                  25                  30 aag gcc atc ctt atg gag gag tgg aac gtg cag ccc gtg cgc tgt cct     144
Lys Ala Ile Leu Met Glu Glu Trp Asn Val Gln Pro Val Arg Cys Pro
            35                  40                  45 gtc acc gtc tgt ggc gac atc cac ggc cag ttc tat gac ctc atc gag     192
Val Thr Val Cys Gly Asp Ile His Gly Gln Phe Tyr Asp Leu Ile Glu
        50                  55                  60 ctc ttc cgc atc ggc ggc gac gct ccc gac acc aac tac ctc ttc atg     240
Leu Phe Arg Ile Gly Gly Asp Ala Pro Asp Thr Asn Tyr Leu Phe Met
65                  70                  75                  80 ggc gac tac gtc gat cgt ggg tac tat tca gtt gaa aca gtt tct ctg     288
Gly Asp Tyr Val Asp Arg Gly Tyr Tyr Ser Val Glu Thr Val Ser Leu
                85                  90                  95 tta gtg gct ttg aaa gtc cgt tac aga gat aga att aca ata ctt aga     336
Leu Val Ala Leu Lys Val Arg Tyr Arg Asp Arg Ile Thr Ile Leu Arg
                100                 105                 110 gga aat cat gag agc aga caa atc act caa gta tat ggc ttc tat gat     384
Gly Asn His Glu Ser Arg Gln Ile Thr Gln Val Tyr Gly Phe Tyr Asp
            115                 120                 125 gaa tgc tta aga aag tat gga aat gca aat gtc tgg aag tat ttt aca     432
Glu Cys Leu Arg Lys Tyr Gly Asn Ala Asn Val Trp Lys Tyr Phe Thr
        130                 135                 140 gac ttg ttt gat ttt ttg cct ctc aca gct ctt ata gaa aat cag gtc     480
Asp Leu Phe Asp Phe Leu Pro Leu Thr Ala Leu Ile Glu Asn Gln Val
145                 150                 155                 160 ttc tgt ctt cac ggt ggc ctc tct ccg tca ttg gac acg ttg gat aat     528
Phe Cys Leu His Gly Gly Leu Ser Pro Ser Leu Asp Thr Leu Asp Asn
                165                 170                 175 att cgt tct ctt gat cgc gta cag gag gtt cct cat gaa gga ccc atg     576
Ile Arg Ser Leu Asp Arg Val Gln Glu Val Pro His Glu Gly Pro Met
            180                 185                 190 tgt gat ctt ttg tgg tct gac cca gat gac cga tgt gga tgg gga att     624
Cys Asp Leu Leu Trp Ser Asp Pro Asp Asp Arg Cys Gly Trp Gly Ile
        195                 200                 205 tca cca aga gga gca ggt tac aca ttt ggg caa gac att gcg cag cag     672
Ser Pro Arg Gly Ala Gly Tyr Thr Phe Gly Gln Asp Ile Ala Gln Gln
    210                 215                 220 ttc aac cat aca aat ggt ctt tct ctc att tca agg gcc cat caa ctt     720
Phe Asn His Thr Asn Gly Leu Ser Leu Ile Ser Arg Ala His Gln Leu
225                 230                 235                 240 gta atg gaa gga ttt aat tgg tgc cag gat aag aat gta gtc aca gtc     768
Val Met Glu Gly Phe Asn Trp Cys Gln Asp Lys Asn Val Val Thr Val
```

```
                    245                 250                 255
ttc agc gcg cct aat tat tgt tac cgc tgt ggt aac atg gct gct att      816
Phe Ser Ala Pro Asn Tyr Cys Tyr Arg Cys Gly Asn Met Ala Ala Ile
        260                 265                 270 ctt gaa atc ggg gaa aac atg gac cag aac ttc ctt caa ttc gac ccg      864
Leu Glu Ile Gly Glu Asn Met Asp Gln Asn Phe Leu Gln Phe Asp Pro
            275                 280                 285 gca cct cgg caa att gag cca gac aca act cgg aaa acc cca gac tac      912
Ala Pro Arg Gln Ile Glu Pro Asp Thr Thr Arg Lys Thr Pro Asp Tyr
290                 295                 300 ttt ttg taa                                                          921
Phe Leu
305

<210> SEQ ID NO 74
<211> LENGTH: 306
<212> TYPE: PRT
<213> ORGANISM: Zea mays

<400> SEQUENCE: 74

Met Pro Ser His Gly Asp Leu Asp Arg Gln Ile Ala Gln Leu Arg Asp
1               5                   10                  15

Cys Lys Tyr Leu Pro Glu Ala Glu Val Lys Ala Leu Cys Glu Gln Ala
            20                  25                  30

Lys Ala Ile Leu Met Glu Glu Trp Asn Val Gln Pro Val Arg Cys Pro
        35                  40                  45

Val Thr Val Cys Gly Asp Ile His Gly Gln Phe Tyr Asp Leu Ile Glu
    50                  55                  60

Leu Phe Arg Ile Gly Gly Asp Ala Pro Asp Thr Asn Tyr Leu Phe Met
65                  70                  75                  80

Gly Asp Tyr Val Asp Arg Gly Tyr Tyr Ser Val Glu Thr Val Ser Leu
                85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys Tyr Phe Thr
    130                 135                 140

Asp Leu Phe Asp Phe Leu Pro Leu Thr Ala Leu Ile Glu Asn Gln Val
145                 150                 155                 160

Phe Cys Leu His Gly Gly Leu Ser Pro Ser Leu Asp Thr Leu Asp Asn
                165                 170                 175

Ile Arg Ser Leu Asp Arg Val Gln Glu Val Pro His Glu Gly Pro Met
            180                 185                 190

Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Gln Gln
    210                 215                 220

Phe Asn His Thr Asn Gly Leu Ser Leu Ile Ser Arg Ala His Gln Leu
225                 230                 235                 240

Val Met Glu Gly Phe Asn Trp Cys Gln Asp Lys Asn Val Val Thr Val
                245                 250                 255

Phe Ser Ala Pro Asn Tyr Cys Tyr Arg Cys Gly Asn Met Ala Ala Ile
            260                 265                 270

Leu Glu Ile Gly Glu Asn Met Asp Gln Asn Phe Leu Gln Phe Asp Pro
        275                 280                 285
```

```
Ala Pro Arg Gln Ile Glu Pro Asp Thr Thr Arg Lys Thr Pro Asp Tyr
290                 295                 300

Phe Leu
305

<210> SEQ ID NO 75
<211> LENGTH: 1162
<212> TYPE: DNA
<213> ORGANISM: Brassica napus
<220> FEATURE:
<221> NAME/KEY: CDS
<222> LOCATION: (131)..(1048)
<223> OTHER INFORMATION: protein phosphatase 2A (BN42856089)

<400> SEQUENCE: 75
aaaactccaa aaacaaacca ttttccatct ctcaggccaa aaaaaccaga gatttgatct      60
ctctggcgat tcatcatcct cttcatccac cacacgccgt ataagttaaa ggatcggtgg     120
tggtctctcg atg ccg ccg aac gga gat cta gac cgt cag atc tcc cag       169
            Met Pro Pro Asn Gly Asp Leu Asp Arg Gln Ile Ser Gln
              1               5                  10 ctg atg gag tgt aaa ccg cta tct gag gcc gat gtg aag acg ctc tgc       217
Leu Met Glu Cys Lys Pro Leu Ser Glu Ala Asp Val Lys Thr Leu Cys
         15                  20                  25 gat caa gcg agg gcc atc ctc gtc gag gag tgg aac gtt cag ccc gtg       265
Asp Gln Ala Arg Ala Ile Leu Val Glu Glu Trp Asn Val Gln Pro Val
 30                  35                  40                  45 aag tgt cct gtc acc gtc tgc ggc gat atc cac gga cag ttc tat gac       313
Lys Cys Pro Val Thr Val Cys Gly Asp Ile His Gly Gln Phe Tyr Asp
                 50                  55                  60 ctt atc gag ctc ttt cga atc ggt ggg aat cct ccg gat act aac tac       361
Leu Ile Glu Leu Phe Arg Ile Gly Gly Asn Pro Pro Asp Thr Asn Tyr
             65                  70                  75 ctc ttc atg gga gac tat gta gac cgt ggc tac tat tca gta gaa aca       409
Leu Phe Met Gly Asp Tyr Val Asp Arg Gly Tyr Tyr Ser Val Glu Thr
         80                  85                  90 gtt tct cta ttg gtg gca ctg aaa gtg cga tac agg gat agg att aca       457
Val Ser Leu Leu Val Ala Leu Lys Val Arg Tyr Arg Asp Arg Ile Thr
 95                 100                 105 atc ttg cga ggg aat cac gag agt cgg cag att act caa gtc tat ggg       505
Ile Leu Arg Gly Asn His Glu Ser Arg Gln Ile Thr Gln Val Tyr Gly
110                 115                 120                 125 ttt tat gat gaa tgt ttg agg aag tat gga aat gca aat gtc tgg aag       553
Phe Tyr Asp Glu Cys Leu Arg Lys Tyr Gly Asn Ala Asn Val Trp Lys
                130                 135                 140 ttt ttc acg gac ctt ttc gat tat ctt cct ctt act gct ctc ata gag       601
Phe Phe Thr Asp Leu Phe Asp Tyr Leu Pro Leu Thr Ala Leu Ile Glu
            145                 150                 155 agt cag gtt ttc tgc ttg cat gga ggg ctt tca cct tct ctg gac acc       649
Ser Gln Val Phe Cys Leu His Gly Gly Leu Ser Pro Ser Leu Asp Thr
        160                 165                 170 ctt gat aat atc cga agc ttg gat cgt ata caa gag gtt cca cat gaa       697
Leu Asp Asn Ile Arg Ser Leu Asp Arg Ile Gln Glu Val Pro His Glu
    175                 180                 185 gga cca atg tgt gat tta tta tgg tct gat ccc gat gat cga tgt ggg       745
Gly Pro Met Cys Asp Leu Leu Trp Ser Asp Pro Asp Asp Arg Cys Gly
190                 195                 200                 205 tgg gga ata tct cca cga ggt gct ggt tat aca ttt gga caa gac atc       793
Trp Gly Ile Ser Pro Arg Gly Ala Gly Tyr Thr Phe Gly Gln Asp Ile
                210                 215                 220 gca act cag ttt aat cac aac aat gga ctc agt ctc ata tca aga gca       841
Ala Thr Gln Phe Asn His Asn Asn Gly Leu Ser Leu Ile Ser Arg Ala
```

```
                        225                 230                 235
cat caa ctt gtc atg gaa ggc ttt aac tgg tgt cag gac aaa aat gtt      889
His Gln Leu Val Met Glu Gly Phe Asn Trp Cys Gln Asp Lys Asn Val
                240                 245                 250 gtg acg gtg ttt agt gca cca aac tat tgc tac cgg tgt gga aac atg      937
Val Thr Val Phe Ser Ala Pro Asn Tyr Cys Tyr Arg Cys Gly Asn Met
        255                 260                 265 gca gct att cta gag ata gga gag aac atg gac cag aac ttc ctc cag      985
Ala Ala Ile Leu Glu Ile Gly Glu Asn Met Asp Gln Asn Phe Leu Gln
270                 275                 280                 285 ttc gat cca gct cct cgt caa gtc gaa cca gat act acc cgc aag acc     1033
Phe Asp Pro Ala Pro Arg Gln Val Glu Pro Asp Thr Thr Arg Lys Thr
                290                 295                 300 cct gat tat ttt ttg tgatttattt gcattttttt ttcttttgtt cccaaccatt     1088
Pro Asp Tyr Phe Leu
                305 tataatttt aaaaaatctg ttttatcttg cttatgaata atcattctag tgtctcttca    1148
aaaaaaaaaa aaaa                                                     1162

<210> SEQ ID NO 76
<211> LENGTH: 306
<212> TYPE: PRT
<213> ORGANISM: Brassica napus

<400> SEQUENCE: 76

Met Pro Pro Asn Gly Asp Leu Asp Arg Gln Ile Ser Gln Leu Met Glu
1               5                   10                  15

Cys Lys Pro Leu Ser Glu Ala Asp Val Lys Thr Leu Cys Asp Gln Ala
                20                  25                  30

Arg Ala Ile Leu Val Glu Glu Trp Asn Val Gln Pro Val Lys Cys Pro
            35                  40                  45

Val Thr Val Cys Gly Asp Ile His Gly Gln Phe Tyr Asp Leu Ile Glu
        50                  55                  60

Leu Phe Arg Ile Gly Gly Asn Pro Pro Asp Thr Asn Tyr Leu Phe Met
65                  70                  75                  80

Gly Asp Tyr Val Asp Arg Gly Tyr Tyr Ser Val Glu Thr Val Ser Leu
                85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys Phe Phe Thr
    130                 135                 140

Asp Leu Phe Asp Tyr Leu Pro Leu Thr Ala Leu Ile Glu Ser Gln Val
145                 150                 155                 160

Phe Cys Leu His Gly Gly Leu Ser Pro Ser Leu Asp Thr Leu Asp Asn
                165                 170                 175

Ile Arg Ser Leu Asp Arg Ile Gln Glu Val Pro His Glu Gly Pro Met
            180                 185                 190

Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Thr Gln
    210                 215                 220

Phe Asn His Asn Asn Gly Leu Ser Leu Ile Ser Arg Ala His Gln Leu
225                 230                 235                 240

Val Met Glu Gly Phe Asn Trp Cys Gln Asp Lys Asn Val Val Thr Val
```

```
                            245                 250                 255
Phe Ser Ala Pro Asn Tyr Cys Tyr Arg Cys Gly Asn Met Ala Ala Ile
                260                 265                 270

Leu Glu Ile Gly Glu Asn Met Asp Gln Asn Phe Leu Gln Phe Asp Pro
            275                 280                 285

Ala Pro Arg Gln Val Glu Pro Asp Thr Thr Arg Lys Thr Pro Asp Tyr
        290                 295                 300

Phe Leu
305

<210> SEQ ID NO 77
<211> LENGTH: 1221
<212> TYPE: DNA
<213> ORGANISM: Brassica napus
<220> FEATURE:
<221> NAME/KEY: CDS
<222> LOCATION: (40)..(957)
<223> OTHER INFORMATION: protein phosphatase 2A (BN43206527)

<400> SEQUENCE: 77
ccaaagacca tttgatctct ggcgatttca tcttccgat atg ccg ccg aac gga        54
                                            Met Pro Pro Asn Gly
                                            1               5 gat cta gac cgt cag atc gag cat ctg atg gag tgc aaa cct tta tcg      102
Asp Leu Asp Arg Gln Ile Glu His Leu Met Glu Cys Lys Pro Leu Ser
            10                  15                  20 gag gag gat gtg agg acg ctc tgc gat caa gct aag gcc atc ctc gtc      150
Glu Glu Asp Val Arg Thr Leu Cys Asp Gln Ala Lys Ala Ile Leu Val
        25                  30                  35 gag gaa tgg aac gtc cag ccc gtg aaa tgc ccc gtc acc gtc tgc ggc      198
Glu Glu Trp Asn Val Gln Pro Val Lys Cys Pro Val Thr Val Cys Gly
    40                  45                  50 gat atc cac ggc cag ttc tat gac ctt atc gag ctt ttc cga atc ggt      246
Asp Ile His Gly Gln Phe Tyr Asp Leu Ile Glu Leu Phe Arg Ile Gly
55                  60                  65 ggt aac gcc ccc gat acg aat tac ctc ttc atg ggt gac tat gta gac      294
Gly Asn Ala Pro Asp Thr Asn Tyr Leu Phe Met Gly Asp Tyr Val Asp
70                  75                  80                  85 cgt ggc tac tat tca gtg gaa acg gtt tct tta ttg gtg gca ttg aaa      342
Arg Gly Tyr Tyr Ser Val Glu Thr Val Ser Leu Leu Val Ala Leu Lys
                90                  95                  100 gtc aga tac agg gat agg att aca atc ttg cga ggg aac cac gag agt      390
Val Arg Tyr Arg Asp Arg Ile Thr Ile Leu Arg Gly Asn His Glu Ser
            105                 110                 115 cgt cag atc acc caa gta tat ggt ttt tat gac gag tgc ttg agg aag      438
Arg Gln Ile Thr Gln Val Tyr Gly Phe Tyr Asp Glu Cys Leu Arg Lys
        120                 125                 130 tac gga aac gca aat gtg tgg aag tat ttc aca gac ctt ttc gat tat      486
Tyr Gly Asn Ala Asn Val Trp Lys Tyr Phe Thr Asp Leu Phe Asp Tyr
    135                 140                 145 ctt cct ctt act gct ctt atc gag agt cag gtt ttc tgt ttg cat gga      534
Leu Pro Leu Thr Ala Leu Ile Glu Ser Gln Val Phe Cys Leu His Gly
150                 155                 160                 165 ggg cta tca cct tct ctg gat aca ctt gat aat atc cga agc ttg gat      582
Gly Leu Ser Pro Ser Leu Asp Thr Leu Asp Asn Ile Arg Ser Leu Asp
                170                 175                 180 cgt ata caa gag gtt cca cac gaa gga cca atg tgt gat tta cta tgg      630
Arg Ile Gln Glu Val Pro His Glu Gly Pro Met Cys Asp Leu Leu Trp
            185                 190                 195 tct gat cca gat gat cga tgc ggg tgg gga ata tct cca aga ggt gct      678
Ser Asp Pro Asp Asp Arg Cys Gly Trp Gly Ile Ser Pro Arg Gly Ala
```

```
                      200                 205                 210
ggt tat aca ttt gga cag gat ata gca act cag ttt aat cac aac aat       726
Gly Tyr Thr Phe Gly Gln Asp Ile Ala Thr Gln Phe Asn His Asn Asn
    215                 220                 225 gga ctc agt ctc ata tca aga gcg cat cag ctt gtc atg gaa ggt ttt       774
Gly Leu Ser Leu Ile Ser Arg Ala His Gln Leu Val Met Glu Gly Phe
230                 235                 240                 245 aac tgg tgt cag gat aag aat gtg gtg acg gtg ttt agt gca cca aac       822
Asn Trp Cys Gln Asp Lys Asn Val Val Thr Val Phe Ser Ala Pro Asn
                250                 255                 260 tat tgc tac cgg tgt gga aac atg gca gcg att cta gag ata agt gag       870
Tyr Cys Tyr Arg Cys Gly Asn Met Ala Ala Ile Leu Glu Ile Ser Glu
            265                 270                 275 aac atg gag cag aac ttc ctt cag ttt gat cca gct cca aga caa gtc       918
Asn Met Glu Gln Asn Phe Leu Gln Phe Asp Pro Ala Pro Arg Gln Val
280                 285                 290 gaa cct gat act acc cgt aag acc cct gat tat ttt ttg tgatttatt         967
Glu Pro Asp Thr Thr Arg Lys Thr Pro Asp Tyr Phe Leu
        295                 300                 305 tgtatttttt tttcttctaa gcggagttcg agtttccctc aaaacgaaag aaagaaacaa    1027
acatcatttt gttgttgttg atgtgattgc tgagaacaaa gtttgtagta aagcgtcta     1087 tatatagaat agtgtcttct cattgtcatt tcacttgtta ctgcatagag gaatgaggtt    1147
tcgaaccctg cccgccactt tcatttcagt ttcatttata aaatatgagt ttgataccga    1207
aaaaaaaaaa aaaa                                                       1221

<210> SEQ ID NO 78
<211> LENGTH: 306
<212> TYPE: PRT
<213> ORGANISM: Brassica napus

<400> SEQUENCE: 78

Met Pro Pro Asn Gly Asp Leu Asp Arg Gln Ile Glu His Leu Met Glu
1               5                   10                  15

Cys Lys Pro Leu Ser Glu Glu Asp Val Arg Thr Leu Cys Asp Gln Ala
            20                  25                  30

Lys Ala Ile Leu Val Glu Glu Trp Asn Val Gln Pro Val Lys Cys Pro
        35                  40                  45

Val Thr Val Cys Gly Asp Ile His Gly Gln Phe Tyr Asp Leu Ile Glu
    50                  55                  60

Leu Phe Arg Ile Gly Gly Asn Ala Pro Asp Thr Asn Tyr Leu Phe Met
65                  70                  75                  80

Gly Asp Tyr Val Asp Arg Gly Tyr Tyr Ser Val Glu Thr Val Ser Leu
                85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys Tyr Phe Thr
    130                 135                 140

Asp Leu Phe Asp Tyr Leu Pro Leu Thr Ala Leu Ile Glu Ser Gln Val
145                 150                 155                 160

Phe Cys Leu His Gly Gly Leu Ser Pro Ser Leu Asp Thr Leu Asp Asn
                165                 170                 175

Ile Arg Ser Leu Asp Arg Ile Gln Glu Val Pro His Glu Gly Pro Met
            180                 185                 190
```

```
Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Thr Gln
    210                 215                 220

Phe Asn His Asn Asn Gly Leu Ser Leu Ile Ser Arg Ala His Gln Leu
225                 230                 235                 240

Val Met Glu Gly Phe Asn Trp Cys Gln Asp Lys Asn Val Val Thr Val
                245                 250                 255

Phe Ser Ala Pro Asn Tyr Cys Tyr Arg Cys Gly Asn Met Ala Ala Ile
                260                 265                 270

Leu Glu Ile Ser Glu Asn Met Glu Gln Asn Phe Leu Gln Phe Asp Pro
            275                 280                 285

Ala Pro Arg Gln Val Glu Pro Asp Thr Thr Arg Lys Thr Pro Asp Tyr
        290                 295                 300

Phe Leu
305

<210> SEQ ID NO 79
<211> LENGTH: 1222
<212> TYPE: DNA
<213> ORGANISM: Helianthus annuus
<220> FEATURE:
<221> NAME/KEY: CDS
<222> LOCATION: (138)..(1055)
<223> OTHER INFORMATION: protein phosphatase 2A (HA66872964)

<400> SEQUENCE: 79
ctaaaaatat ctttaaccgc cggctgccat gacggaaccc taagcaactt ctccggcgac        60
tccggcggag ctccgttcaa cctaaatgcg aatcattctt ccagatcttc aaatccgaac       120
acacaaatca cgtaaca atg ccg tcg caa tcg gat ctg gac cgt cag atc        170
                Met Pro Ser Gln Ser Asp Leu Asp Arg Gln Ile
                  1               5                  10 gag cac ttg atg gac tgt aaa ccg ctg ccg gag gcg gag gtg cgg acg       218
Glu His Leu Met Asp Cys Lys Pro Leu Pro Glu Ala Glu Val Arg Thr
                15                  20                  25 ttg tgt gat cag gcg agg acg att ttg gtc gag gag tgg aat gtg cag       266
Leu Cys Asp Gln Ala Arg Thr Ile Leu Val Glu Glu Trp Asn Val Gln
         30                  35                  40 ccg gtg aag tgt ccg gtg act gtt tgc ggt gat att cat ggg cag ttt       314
Pro Val Lys Cys Pro Val Thr Val Cys Gly Asp Ile His Gly Gln Phe
     45                  50                  55 cat gat ttg ctt gag ctg ttt cgg atc gga gga agt gct ccg gac acg       362
His Asp Leu Leu Glu Leu Phe Arg Ile Gly Gly Ser Ala Pro Asp Thr
60                  65                  70                  75 aat tac ttg ttt atg gga gat tat gtt gat cga ggc tat tac tcg gtg       410
Asn Tyr Leu Phe Met Gly Asp Tyr Val Asp Arg Gly Tyr Tyr Ser Val
                80                  85                  90 gag act gtt acg ctt ctt gtg gca ttg aaa gtt cgt tac aga gat agg       458
Glu Thr Val Thr Leu Leu Val Ala Leu Lys Val Arg Tyr Arg Asp Arg
             95                 100                 105 att act att ctc aga gga aac cat gag agc agg cag ata act caa gtg       506
Ile Thr Ile Leu Arg Gly Asn His Glu Ser Arg Gln Ile Thr Gln Val
        110                 115                 120 tat gga ttt tac gat gaa tgc ttg agg aag tac gga aac gca aat gta       554
Tyr Gly Phe Tyr Asp Glu Cys Leu Arg Lys Tyr Gly Asn Ala Asn Val
    125                 130                 135 tgg aaa cat ttc act gac ctt ttt gat tat cta cct ctc act gcc ctt       602
Trp Lys His Phe Thr Asp Leu Phe Asp Tyr Leu Pro Leu Thr Ala Leu
140                 145                 150                 155
```

```
atc gag agt cag ata ttc tgt ctc cat ggt ggc ttg tct cca tct ttg    650
Ile Glu Ser Gln Ile Phe Cys Leu His Gly Gly Leu Ser Pro Ser Leu
            160                 165                 170 gat aca cta gat aac ata cgt gct tta gat cgc ata caa gag gtt cct    698
Asp Thr Leu Asp Asn Ile Arg Ala Leu Asp Arg Ile Gln Glu Val Pro
                175                 180                 185 cat gag ggg cca atg tgt gac ctt ttg tgg tct gat cct gat gac cgg    746
His Glu Gly Pro Met Cys Asp Leu Leu Trp Ser Asp Pro Asp Asp Arg
            190                 195                 200 tgt ggt tgg gga ata tct cct cgt gga gcc ggt tac act ttc ggg cag    794
Cys Gly Trp Gly Ile Ser Pro Arg Gly Ala Gly Tyr Thr Phe Gly Gln
        205                 210                 215 gat ata gcc gca cag ttt aac cat aca aac ggg ctc tcg ctt att tct    842
Asp Ile Ala Ala Gln Phe Asn His Thr Asn Gly Leu Ser Leu Ile Ser
220                 225                 230                 235 cgg gct cac cag ctt gtc atg gaa ggt tac aat tgg tct cag gag aac    890
Arg Ala His Gln Leu Val Met Glu Gly Tyr Asn Trp Ser Gln Glu Asn
                240                 245                 250 aac gtt gta acc ata ttt agt gca cca aac tac tgc tat aga tgc ggg    938
Asn Val Val Thr Ile Phe Ser Ala Pro Asn Tyr Cys Tyr Arg Cys Gly
                255                 260                 265 aat atg gct gcg ata ctt gag gtt gga gag aat atg gac cag aat ttc    986
Asn Met Ala Ala Ile Leu Glu Val Gly Glu Asn Met Asp Gln Asn Phe
            270                 275                 280 tta caa ttt gac cca gcc cct cgt cag gtt gag ccc gat gtt gca cga   1034
Leu Gln Phe Asp Pro Ala Pro Arg Gln Val Glu Pro Asp Val Ala Arg
        285                 290                 295 aga act ccg gat tac ttc ctg taaattttgtg ttggataata tgacctttgc     1085
Arg Thr Pro Asp Tyr Phe Leu
300                 305 atgcatccta tttatgttgt tatagttttc gctttcccct gctagagagt ccccctattc 1145 ttgagaatta aagacaatat gtatgattgt ttgtcccttg ttctatttga gattatttgt 1205 ttaaaaaaaa aaaaaaa                                                1222

<210> SEQ ID NO 80
<211> LENGTH: 306
<212> TYPE: PRT
<213> ORGANISM: Helianthus annuus

<400> SEQUENCE: 80

Met Pro Ser Gln Ser Asp Leu Asp Arg Gln Ile Glu His Leu Met Asp
1               5                   10                  15

Cys Lys Pro Leu Pro Glu Ala Glu Val Arg Thr Leu Cys Asp Gln Ala
            20                  25                  30

Arg Thr Ile Leu Val Glu Glu Trp Asn Val Gln Pro Val Lys Cys Pro
        35                  40                  45

Val Thr Val Cys Gly Asp Ile His Gly Gln Phe His Asp Leu Leu Glu
    50                  55                  60

Leu Phe Arg Ile Gly Gly Ser Ala Pro Asp Thr Asn Tyr Leu Phe Met
65                  70                  75                  80

Gly Asp Tyr Val Asp Arg Gly Tyr Tyr Ser Val Glu Thr Val Thr Leu
                85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys His Phe Thr
    130                 135                 140
```

```
Asp Leu Phe Asp Tyr Leu Pro Leu Thr Ala Leu Ile Glu Ser Gln Ile
145                 150                 155                 160

Phe Cys Leu His Gly Gly Leu Ser Pro Ser Leu Asp Thr Leu Asp Asn
            165                 170                 175

Ile Arg Ala Leu Asp Arg Ile Gln Glu Val Pro His Glu Gly Pro Met
        180                 185                 190

Cys Asp Leu Leu Trp Ser Asp Pro Asp Arg Cys Gly Trp Gly Ile
        195                 200                 205

Ser Pro Arg Gly Ala Gly Tyr Thr Phe Gly Gln Asp Ile Ala Ala Gln
        210                 215                 220

Phe Asn His Thr Asn Gly Leu Ser Leu Ile Ser Arg Ala His Gln Leu
225                 230                 235                 240

Val Met Glu Gly Tyr Asn Trp Ser Gln Glu Asn Asn Val Val Thr Ile
                245                 250                 255

Phe Ser Ala Pro Asn Tyr Cys Tyr Arg Cys Gly Asn Met Ala Ala Ile
                260                 265                 270

Leu Glu Val Gly Glu Asn Met Asp Gln Asn Phe Leu Gln Phe Asp Pro
        275                 280                 285

Ala Pro Arg Gln Val Glu Pro Asp Val Ala Arg Arg Thr Pro Asp Tyr
        290                 295                 300

Phe Leu
305

<210> SEQ ID NO 81
<211> LENGTH: 1495
<212> TYPE: DNA
<213> ORGANISM: Linum usitatissimum
<220> FEATURE:
<221> NAME/KEY: CDS
<222> LOCATION: (196)..(1113)
<223> OTHER INFORMATION: protein phosphatase 2A (LU61662612)

<400> SEQUENCE: 81
catctctctt tctctctctt ccattttcgt tcttttgaat ctccgttagc cctacaaatc      60
catggtcatg gcctgagaga gatagaggga tagagctctc agttcctaat caccttacct    120
gacctaaccc cacggacata ttatcgaagg tctgcgagca ggagagcgca ggaggaagag    180
tggggccagg gtacg atg ccg tcc cac gcc gat ctg gac cgt cag atc gag    231
                Met Pro Ser His Ala Asp Leu Asp Arg Gln Ile Glu
                1               5                   10 cac ttg atg cag tgc aag cca ctt tct gag gcc gaa gtg aag gct ctc    279
His Leu Met Gln Cys Lys Pro Leu Ser Glu Ala Glu Val Lys Ala Leu
        15                  20                  25 tgc gag cag gcc agg gcc gtc ctc gtc gag gaa tgg aac gtc cag ccg    327
Cys Glu Gln Ala Arg Ala Val Leu Val Glu Glu Trp Asn Val Gln Pro
30                  35                  40 gtc aag tgt ccg gtg act gtc tgc ggc gac atc cac ggc cag ttt cac    375
Val Lys Cys Pro Val Thr Val Cys Gly Asp Ile His Gly Gln Phe His
45                  50                  55                  60 gat ctt gtc gag ctc ttt cga atc gga gga aac gcc cct gac acg aac    423
Asp Leu Val Glu Leu Phe Arg Ile Gly Gly Asn Ala Pro Asp Thr Asn
                65                  70                  75 tac ctc ttc atg ggc gac tat gta gat cga ggg tat tat tcg gtg gag    471
Tyr Leu Phe Met Gly Asp Tyr Val Asp Arg Gly Tyr Tyr Ser Val Glu
            80                  85                  90 act gtc acc ctt cta gtc gcc ttg aaa gta aga tat aga gat agg atc    519
Thr Val Thr Leu Leu Val Ala Leu Lys Val Arg Tyr Arg Asp Arg Ile
        95                  100                 105
```

| | | |
|---|---|---|
| aca att ctg aga gga aat cat gaa agt cgt caa ata act caa gtg tat<br>Thr Ile Leu Arg Gly Asn His Glu Ser Arg Gln Ile Thr Gln Val Tyr<br>110                                    115                               120 | 567 | |
| gga ttc tat gat gag tgc ttg aga aaa tat gga aat gcc aat gtg tgg<br>Gly Phe Tyr Asp Glu Cys Leu Arg Lys Tyr Gly Asn Ala Asn Val Trp<br>125                                  130                               135                         140 | 615 | |
| aaa cat ttt acc gat ctc ttt gat tat cta cca ctt aca gct ctg att<br>Lys His Phe Thr Asp Leu Phe Asp Tyr Leu Pro Leu Thr Ala Leu Ile<br>                                145                               150                           155 | 663 | |
| gag agt cag gtc ttc tgc tta cat ggt gga ctt tcc cct tca cta gac<br>Glu Ser Gln Val Phe Cys Leu His Gly Gly Leu Ser Pro Ser Leu Asp<br>160                                  165                             170 | 711 | |
| acg cta gac aac att cgc tcc ctt gat cgt atc caa gag gtt ccg cac<br>Thr Leu Asp Asn Ile Arg Ser Leu Asp Arg Ile Gln Glu Val Pro His<br>                 175                         180                           185 | 759 | |
| gag ggt cct atg tgc gac ctc cta tgg tcg gac ccg gat gac cgt tgc<br>Glu Gly Pro Met Cys Asp Leu Leu Trp Ser Asp Pro Asp Asp Arg Cys<br>            190                         195                         200 | 807 | |
| ggg tgg ggg atc tct cct cgt gga gct ggc tac acc ttt gga cag gac<br>Gly Trp Gly Ile Ser Pro Arg Gly Ala Gly Tyr Thr Phe Gly Gln Asp<br>205                                  210                             215                     220 | 855 | |
| ata tct caa cag ttc aac cac acg aac ggc ctt tct ctc ata tcc aga<br>Ile Ser Gln Gln Phe Asn His Thr Asn Gly Leu Ser Leu Ile Ser Arg<br>                             225                             230                         235 | 903 | |
| gct cac cag ctg gtc atg gaa ggt tac aat tgg gcc cag gac aag aat<br>Ala His Gln Leu Val Met Glu Gly Tyr Asn Trp Ala Gln Asp Lys Asn<br>          240                         245                         250 | 951 | |
| gtg gtg acg gtg ttc agc gcc ccg aac tac tgc tac cgg tgt ggg aac<br>Val Val Thr Val Phe Ser Ala Pro Asn Tyr Cys Tyr Arg Cys Gly Asn<br>               255                         260                        265 | 999 | |
| atg gcg gcc att ctc gag atc gga gag aac atg gag cag aac ttc ctg<br>Met Ala Ala Ile Leu Glu Ile Gly Glu Asn Met Glu Gln Asn Phe Leu<br>270                                  275                             280 | 1047 | |
| cag ttc gac cca gct cct cga cag atc gaa ccg gag acg act cgc aga<br>Gln Phe Asp Pro Ala Pro Arg Gln Ile Glu Pro Glu Thr Thr Arg Arg<br>285                                  290                             295                     300 | 1095 | |
| aca ccc gat tat ttt ttg tgaaatgcat agcttcttct tcctccctcc<br>Thr Pro Asp Tyr Phe Leu<br>                       305 | 1143 | |
| ttcttgcttg gaaatgggat ccgtgtccat ttttctaat cgcctgccct gctatgtgct | 1203 | |
| tatgtttttt gtagatgcat tcatcatcat catatccaga atagagaaga aattttggtg | 1263 | |
| tttgctttga ttgagaaaag gcggggaggg aaaaatcggc ctctagagat gctgggtgtt | 1323 | |
| gtcatttttc ttcttcttct tcctcctttt gggatggttt cgttttact ttttcttttg | 1383 | |
| ggtttctatt gttatcctg cattcatttg agtttaacaa agtttattat ttacagtctg | 1443 | |
| ggtgtgttat taatattatt cactgtggtc ttgtaccaaa aaaaaaaaaa aa | 1495 | |

<210> SEQ ID NO 82
<211> LENGTH: 306
<212> TYPE: PRT
<213> ORGANISM: Linum usitatissimum

<400> SEQUENCE: 82

Met Pro Ser His Ala Asp Leu Asp Arg Gln Ile Glu His Leu Met Gln
1               5                    10                    15

Cys Lys Pro Leu Ser Glu Ala Glu Val Lys Ala Leu Cys Glu Gln Ala
                   20                    25                    30

Arg Ala Val Leu Val Glu Glu Trp Asn Val Gln Pro Val Lys Cys Pro
               35                      40                    45

```
Val Thr Val Cys Gly Asp Ile His Gly Gln Phe His Asp Leu Val Glu
 50                  55                  60

Leu Phe Arg Ile Gly Gly Asn Ala Pro Asp Thr Asn Tyr Leu Phe Met
 65                  70                  75                  80

Gly Asp Tyr Val Asp Arg Gly Tyr Tyr Ser Val Glu Val Thr Leu
                 85                  90                  95

Leu Val Ala Leu Lys Val Arg Tyr Arg Asp Arg Ile Thr Ile Leu Arg
                100                 105                 110

Gly Asn His Glu Ser Arg Gln Ile Thr Gln Val Tyr Gly Phe Tyr Asp
                115                 120                 125

Glu Cys Leu Arg Lys Tyr Gly Asn Ala Asn Val Trp Lys His Phe Thr
                130                 135                 140

Asp Leu Phe Asp Tyr Leu Pro Leu Thr Ala Leu Ile Glu Ser Gln Val
145                 150                 155                 160

Phe Cys Leu His Gly Gly Leu Ser Pro Ser Leu Asp Thr Leu Asp Asn
                165                 170                 175

Ile Arg Ser Leu Asp Arg Ile Gln Glu Val Pro His Glu Gly Pro Met
                180                 185                 190

Cys Asp Leu Leu Trp Ser Asp Pro Asp Arg Cys Gly Trp Gly Ile
                195                 200                 205

Ser Pro Arg Gly Ala Gly Tyr Thr Phe Gly Gln Asp Ile Ser Gln Gln
                210                 215                 220

Phe Asn His Thr Asn Gly Leu Ser Leu Ile Ser Arg Ala His Gln Leu
225                 230                 235                 240

Val Met Glu Gly Tyr Asn Trp Ala Gln Asp Lys Asn Val Val Thr Val
                245                 250                 255

Phe Ser Ala Pro Asn Tyr Cys Tyr Arg Cys Gly Asn Met Ala Ala Ile
                260                 265                 270

Leu Glu Ile Gly Glu Asn Met Glu Gln Asn Phe Leu Gln Phe Asp Pro
                275                 280                 285

Ala Pro Arg Gln Ile Glu Pro Glu Thr Thr Arg Thr Pro Asp Tyr
                290                 295                 300

Phe Leu
305

<210> SEQ ID NO 83
<211> LENGTH: 1345
<212> TYPE: DNA
<213> ORGANISM: Oryza sativa
<220> FEATURE:
<221> NAME/KEY: CDS
<222> LOCATION: (173)..(1093)
<223> OTHER INFORMATION: protein phosphatase 2A (OS32806943)

<400> SEQUENCE: 83
gaggcttgag ctccacctcc acctcctcca cctccaaccc ccgatccccc gcaaaccta    60 gccctctccc ccaccctcct cgccggcggc gagcggcggc ggcgcgcggc gggacccgga   120 gccccccagta gcgcctcctc cgtcctcccc tccctgaggt gcggggggaga gg atg ccg  178
                                                          Met Pro
                                                            1 tcg tcg cac ggg gat ctg gac cgg cag atc gcg cag ctg cgg gag tgc    226
Ser Ser His Gly Asp Leu Asp Arg Gln Ile Ala Gln Leu Arg Glu Cys
        5                  10                  15 aag cac ctg gcg gag ggg gag gtg agg gcg ctg tgc gag cag gcg aag   274
Lys His Leu Ala Glu Gly Glu Val Arg Ala Leu Cys Glu Gln Ala Lys
     20                  25                  30
```

| | | | | | | | | | | | | | | |
|---|---|---|---|---|---|---|---|---|---|---|---|---|---|---|
| gcc | atc | ctc | atg | gag | gag | tgg | aac | gtg | cag | ccg | gtg | cgg | tgc | ccc gtc | 322
| Ala | Ile | Leu | Met | Glu | Glu | Trp | Asn | Val | Gln | Pro | Val | Arg | Cys | Pro Val |
| 35 | | | | 40 | | | | | 45 | | | | | 50 |

```
gcc atc ctc atg gag gag tgg aac gtg cag ccg gtg cgg tgc ccc gtc      322
Ala Ile Leu Met Glu Glu Trp Asn Val Gln Pro Val Arg Cys Pro Val
 35          40              45              50 acg gtc tgc ggc gac atc cac ggc cag ttc tac gac ctc atc gag ctc      370
Thr Val Cys Gly Asp Ile His Gly Gln Phe Tyr Asp Leu Ile Glu Leu
             55              60              65 ttc cgc atc ggc ggc gag gcg ccc gac acc aac tac ctc ttc atg ggc      418
Phe Arg Ile Gly Gly Glu Ala Pro Asp Thr Asn Tyr Leu Phe Met Gly
         70              75              80 gac tac gtc gac cgt ggc tac tac tca gtg gag act gtt tcg ttg ttg      466
Asp Tyr Val Asp Arg Gly Tyr Tyr Ser Val Glu Thr Val Ser Leu Leu
             85              90              95 gtg gct ttg aaa gta cgc tac aga gat cga att aca ata ttg aga gga      514
Val Ala Leu Lys Val Arg Tyr Arg Asp Arg Ile Thr Ile Leu Arg Gly
    100             105             110 aat cat gag agc aga caa atc act caa gtg tac ggc ttc tac gat gaa      562
Asn His Glu Ser Arg Gln Ile Thr Gln Val Tyr Gly Phe Tyr Asp Glu
115             120             125             130 tgc ttg aga aag tat gga aat gca aat gta tgg aaa tac ttt aca gac      610
Cys Leu Arg Lys Tyr Gly Asn Ala Asn Val Trp Lys Tyr Phe Thr Asp
            135             140             145 ttg ttt gat tat ttg cct ctc aca gct ctt ata gaa aac cag gtg ttc      658
Leu Phe Asp Tyr Leu Pro Leu Thr Ala Leu Ile Glu Asn Gln Val Phe
            150             155             160 tgc ctt cac ggt ggt ctc tct cca tca ttg gat act tta gat aac atc      706
Cys Leu His Gly Gly Leu Ser Pro Ser Leu Asp Thr Leu Asp Asn Ile
        165             170             175 cgt gct ctt gat cgt ata caa gag gtt cct cat gaa gga ccc atg tgt      754
Arg Ala Leu Asp Arg Ile Gln Glu Val Pro His Glu Gly Pro Met Cys
        180             185             190 gat ctt ttg tgg tct gac cca gat gac aga tgc ggg tgg gga att tca      802
Asp Leu Leu Trp Ser Asp Pro Asp Asp Arg Cys Gly Trp Gly Ile Ser
195             200             205             210 ccg aga gga gca ggt tat aca ttt ggg caa gat atc gct caa cag ttt      850
Pro Arg Gly Ala Gly Tyr Thr Phe Gly Gln Asp Ile Ala Gln Gln Phe
            215             220             225 aac cat aca aat ggt cta tct ctc atc tca agg gca cat caa ctt gta      898
Asn His Thr Asn Gly Leu Ser Leu Ile Ser Arg Ala His Gln Leu Val
        230             235             240 atg gaa gga ttt aat tgg tgt cag gac aag aat gtt gtg acg gtc ttc      946
Met Glu Gly Phe Asn Trp Cys Gln Asp Lys Asn Val Val Thr Val Phe
    245             250             255 agt gca cca aac tac tgt tat cgc tgt ggt aac atg gct gca att ctt      994
Ser Ala Pro Asn Tyr Cys Tyr Arg Cys Gly Asn Met Ala Ala Ile Leu
260             265             270 gag att ggc gaa aac atg gat cag aac ttc ctc caa ttt gat cca gct     1042
Glu Ile Gly Glu Asn Met Asp Gln Asn Phe Leu Gln Phe Asp Pro Ala
275             280             285             290 cct cgg caa att gaa cca gac aca aca cgc aag act ccc gac tac ttt     1090
Pro Arg Gln Ile Glu Pro Asp Thr Thr Arg Lys Thr Pro Asp Tyr Phe
            295             300             305 ttg taatttgtgg tgttgacaat tttaactcac ctgtgttgat gctcctctcc          1143
Leu tccgcggtgt cggggtctgt agatcttctg tccttagata cgggttccac gagcccggct   1203
gtatgtctct caattctttt gtttggagat tttgttgctg cttctcaacc tttatacaag   1263
acgttaaaag ttacatgcac tggatttttt tctcaaaaaa aaaaaaaaaa aaaaaaaaaa   1323
aaaaaagaaa aaaaaaaaaa aa                                           1345
```

<210> SEQ ID NO 84
<211> LENGTH: 307
<212> TYPE: PRT
<213> ORGANISM: Oryza sativa

<400> SEQUENCE: 84

```
Met Pro Ser Ser His Gly Asp Leu Asp Arg Gln Ile Ala Gln Leu Arg
1               5                   10                  15

Glu Cys Lys His Leu Ala Glu Gly Glu Val Arg Ala Leu Cys Glu Gln
            20                  25                  30

Ala Lys Ala Ile Leu Met Glu Glu Trp Asn Val Gln Pro Val Arg Cys
        35                  40                  45

Pro Val Thr Val Cys Gly Asp Ile His Gly Gln Phe Tyr Asp Leu Ile
    50                  55                  60

Glu Leu Phe Arg Ile Gly Gly Glu Ala Pro Asp Thr Asn Tyr Leu Phe
65                  70                  75                  80

Met Gly Asp Tyr Val Asp Arg Gly Tyr Tyr Ser Val Glu Thr Val Ser
                85                  90                  95

Leu Leu Val Ala Leu Lys Val Arg Tyr Arg Asp Arg Ile Thr Ile Leu
            100                 105                 110

Arg Gly Asn His Glu Ser Arg Gln Ile Thr Gln Val Tyr Gly Phe Tyr
        115                 120                 125

Asp Glu Cys Leu Arg Lys Tyr Gly Asn Ala Asn Val Trp Lys Tyr Phe
    130                 135                 140

Thr Asp Leu Phe Asp Tyr Leu Pro Leu Thr Ala Leu Ile Glu Asn Gln
145                 150                 155                 160

Val Phe Cys Leu His Gly Gly Leu Ser Pro Ser Leu Asp Thr Leu Asp
                165                 170                 175

Asn Ile Arg Ala Leu Asp Arg Ile Gln Glu Val Pro His Glu Gly Pro
            180                 185                 190

Met Cys Asp Leu Leu Trp Ser Asp Pro Asp Asp Arg Cys Gly Trp Gly
        195                 200                 205

Ile Ser Pro Arg Gly Ala Gly Tyr Thr Phe Gly Gln Asp Ile Ala Gln
    210                 215                 220

Gln Phe Asn His Thr Asn Gly Leu Ser Leu Ile Ser Arg Ala His Gln
225                 230                 235                 240

Leu Val Met Glu Gly Phe Asn Trp Cys Gln Asp Lys Asn Val Val Thr
                245                 250                 255

Val Phe Ser Ala Pro Asn Tyr Cys Tyr Arg Cys Gly Asn Met Ala Ala
            260                 265                 270

Ile Leu Glu Ile Gly Glu Asn Met Asp Gln Asn Phe Leu Gln Phe Asp
        275                 280                 285

Pro Ala Pro Arg Gln Ile Glu Pro Asp Thr Thr Arg Lys Thr Pro Asp
    290                 295                 300

Tyr Phe Leu
305
```

<210> SEQ ID NO 85
<211> LENGTH: 1332
<212> TYPE: DNA
<213> ORGANISM: Oryza sativa
<220> FEATURE:
<221> NAME/KEY: CDS
<222> LOCATION: (111)..(1028)
<223> OTHER INFORMATION: protein phosphatase 2A (OS34738749)

<400> SEQUENCE: 85
ggtcgacgcc gtcaccgtcg cgccaactgc cgcaaaccga ataaaccgaa tcgatctgag    60

```
                                                                         116
agaagaagaa gaagaagacg cgatctcgga ggtgggagcg aaacgaaacg atg ccg
                                                     Met Pro
                                                     1 tct cac gcg gat ctg gaa cga cag atc gag cag ctg atg gag tgc aag    164
Ser His Ala Asp Leu Glu Arg Gln Ile Glu Gln Leu Met Glu Cys Lys
    5                   10                  15 cct ctg tcg gag tcg gag gtg aag gcg ctg tgt gat caa gcg agg gcg    212
Pro Leu Ser Glu Ser Glu Val Lys Ala Leu Cys Asp Gln Ala Arg Ala
20                  25                  30 att ctc gtg gag gaa tgg aac gtg caa ccg gtg aag tgc ccc gtc acc    260
Ile Leu Val Glu Glu Trp Asn Val Gln Pro Val Lys Cys Pro Val Thr
35                  40                  45                  50 gtc tgc ggc gat att cac ggc cag ttt tac gat ctc atc gag ctg ttt    308
Val Cys Gly Asp Ile His Gly Gln Phe Tyr Asp Leu Ile Glu Leu Phe
                55                  60                  65 cgg att gga ggg aac gca ccc gat acc aat tat ctc ttc atg ggt gat    356
Arg Ile Gly Gly Asn Ala Pro Asp Thr Asn Tyr Leu Phe Met Gly Asp
            70                  75                  80 tat gta gat cgt gga tac tat tca gtg gag act gtt aca ctt ttg gtg    404
Tyr Val Asp Arg Gly Tyr Tyr Ser Val Glu Thr Val Thr Leu Leu Val
        85                  90                  95 gct ttg aaa gtc cgt tac aga gat aga atc aca att ctc agg gga aat    452
Ala Leu Lys Val Arg Tyr Arg Asp Arg Ile Thr Ile Leu Arg Gly Asn
    100                 105                 110 cat gaa agt cgt caa att act caa gtg tat ggc ttc tat gat gaa tgc    500
His Glu Ser Arg Gln Ile Thr Gln Val Tyr Gly Phe Tyr Asp Glu Cys
115                 120                 125                 130 ttg aga aaa tat gga aat gcc aat gtc tgg aaa tac ttt aca gac ttg    548
Leu Arg Lys Tyr Gly Asn Ala Asn Val Trp Lys Tyr Phe Thr Asp Leu
                135                 140                 145 ttt gat tat tta cct ctg act gcc ctc att gag agt cag att ttc tgc    596
Phe Asp Tyr Leu Pro Leu Thr Ala Leu Ile Glu Ser Gln Ile Phe Cys
            150                 155                 160 ttg cat gga ggt ctc tca cct tct ttg gat aca ctg gat aac atc aga    644
Leu His Gly Gly Leu Ser Pro Ser Leu Asp Thr Leu Asp Asn Ile Arg
        165                 170                 175 gca ttg gat cgt ata caa gag gtt cca cat gaa gga cca atg tgt gat    692
Ala Leu Asp Arg Ile Gln Glu Val Pro His Glu Gly Pro Met Cys Asp
    180                 185                 190 ctc ttg tgg tct gac cct gat gat cgc tgt gga tgg gga ata tct cca    740
Leu Leu Trp Ser Asp Pro Asp Asp Arg Cys Gly Trp Gly Ile Ser Pro
195                 200                 205                 210 cgt ggt gca gga tac aca ttt gga cag gat ata gct gct cag ttt aat    788
Arg Gly Ala Gly Tyr Thr Phe Gly Gln Asp Ile Ala Ala Gln Phe Asn
                215                 220                 225 cat acc aat ggt ctc tcc ctg ata tcg aga gct cat cag ctt gtt atg    836
His Thr Asn Gly Leu Ser Leu Ile Ser Arg Ala His Gln Leu Val Met
            230                 235                 240 gaa gga ttc aat tgg tgc cag gac aaa aat gtg gtg act gta ttt agt    884
Glu Gly Phe Asn Trp Cys Gln Asp Lys Asn Val Val Thr Val Phe Ser
        245                 250                 255 gca cca aat tac tgt tac cga tgt ggg aat atg gct gct ata cta gaa    932
Ala Pro Asn Tyr Cys Tyr Arg Cys Gly Asn Met Ala Ala Ile Leu Glu
    260                 265                 270 ata gga gag aat atg gat cag aat ttc ctt cag ttt gat cca gcg ccc    980
Ile Gly Glu Asn Met Asp Gln Asn Phe Leu Gln Phe Asp Pro Ala Pro
275                 280                 285                 290 agg caa att gag cct gac acc aca cgc aag act cca gat tat ttt tta    1028
Arg Gln Ile Glu Pro Asp Thr Thr Arg Lys Thr Pro Asp Tyr Phe Leu
                295                 300                 305
```

```
taatttcatt tatctgcctg tttgtagtta ctgctctctg ccattactgt agatgtgtct   1088
ttaaggaaag gagttttgct gtttaagtgg agggtggtca tcaacataat tctttctttt   1148
ggagtttacc tcctgctgct gccgctgccg ctgccttatt tgtacaagaa accaatagaa   1208
ctgacacaag ccaccaattg gggttgtata tttttgggag gaagcggtaa taacatggta   1268
tatcttgttc tgtaatcctt tttctttaaa ttgaatctca agttagagag caaaaaaaaa   1328
aaaa                                                                1332
```

<210> SEQ ID NO 86
<211> LENGTH: 306
<212> TYPE: PRT
<213> ORGANISM: Oryza sativa

<400> SEQUENCE: 86

```
Met Pro Ser His Ala Asp Leu Glu Arg Gln Ile Glu Gln Leu Met Glu
1               5                   10                  15

Cys Lys Pro Leu Ser Glu Ser Glu Val Lys Ala Leu Cys Asp Gln Ala
            20                  25                  30

Arg Ala Ile Leu Val Glu Glu Trp Asn Val Gln Pro Val Lys Cys Pro
        35                  40                  45

Val Thr Val Cys Gly Asp Ile His Gly Gln Phe Tyr Asp Leu Ile Glu
    50                  55                  60

Leu Phe Arg Ile Gly Gly Asn Ala Pro Asp Thr Asn Tyr Leu Phe Met
65                  70                  75                  80

Gly Asp Tyr Val Asp Arg Gly Tyr Tyr Ser Val Glu Thr Val Thr Leu
                85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys Tyr Phe Thr
    130                 135                 140

Asp Leu Phe Asp Tyr Leu Pro Leu Thr Ala Leu Ile Glu Ser Gln Ile
145                 150                 155                 160

Phe Cys Leu His Gly Gly Leu Ser Pro Ser Leu Asp Thr Leu Asp Asn
                165                 170                 175

Ile Arg Ala Leu Asp Arg Ile Gln Glu Val Pro His Glu Gly Pro Met
            180                 185                 190

Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Ala Gln
    210                 215                 220

Phe Asn His Thr Asn Gly Leu Ser Leu Ile Ser Arg Ala His Gln Leu
225                 230                 235                 240

Val Met Glu Gly Phe Asn Trp Cys Gln Asp Lys Asn Val Val Thr Val
                245                 250                 255

Phe Ser Ala Pro Asn Tyr Cys Tyr Arg Cys Gly Asn Met Ala Ala Ile
            260                 265                 270

Leu Glu Ile Gly Glu Asn Met Asp Gln Asn Phe Leu Gln Phe Asp Pro
        275                 280                 285

Ala Pro Arg Gln Ile Glu Pro Asp Thr Thr Arg Lys Thr Pro Asp Tyr
    290                 295                 300

Phe Leu
305
```

<210> SEQ ID NO 87
<211> LENGTH: 1222
<212> TYPE: DNA
<213> ORGANISM: Zea mays
<220> FEATURE:
<221> NAME/KEY: CDS
<222> LOCATION: (95)..(1012)
<223> OTHER INFORMATION: protein phosphatase 2A (ZM59400933)

<400> SEQUENCE: 87

```
ctgaccgcca gcgggcccgc aggccggaga aggagtcgga gtcgccccca cccacccacc      60
ctctgccgcg gcgggagc gggcggcgga cgag atg ccg tcg cac ggg gat ctg        115
                                 Met Pro Ser His Gly Asp Leu
                                  1               5 gac cgg cag atc gcg cag ctg cgc gac tgc aag tac ctg ccc gag gcg        163
Asp Arg Gln Ile Ala Gln Leu Arg Asp Cys Lys Tyr Leu Pro Glu Ala
         10                  15                  20 gag gtc aag gtg ctc tgc gag cag gcc aag gcc atc ctc atg gag gaa        211
Glu Val Lys Val Leu Cys Glu Gln Ala Lys Ala Ile Leu Met Glu Glu
 25                  30                  35 tgg aac gtg cag ccc gtg cgc tgc ccc gtc acc gtc tgc ggc gac atc        259
Trp Asn Val Gln Pro Val Arg Cys Pro Val Thr Val Cys Gly Asp Ile
 40                  45                  50                  55 cac ggc cag ttc tat gac ctc atc gag ctc ttc cgc atc ggc ggc gac        307
His Gly Gln Phe Tyr Asp Leu Ile Glu Leu Phe Arg Ile Gly Gly Asp
             60                  65                  70 tct ccc gac acc aac tac ctc ttc atg ggc gac tac gtc gat cgt ggc        355
Ser Pro Asp Thr Asn Tyr Leu Phe Met Gly Asp Tyr Val Asp Arg Gly
         75                  80                  85 tat tat tca gtt gaa acg gtt tct ctg tta gtg gct ttg aaa gtc cgt        403
Tyr Tyr Ser Val Glu Thr Val Ser Leu Leu Val Ala Leu Lys Val Arg
     90                  95                 100 tac aga gat aga att aca ata ctt cga gga aat cat gag agc aga caa        451
Tyr Arg Asp Arg Ile Thr Ile Leu Arg Gly Asn His Glu Ser Arg Gln
105                 110                 115 atc act caa gtg tac ggc ttc tat gat gaa tgc tta aga aaa tat gga        499
Ile Thr Gln Val Tyr Gly Phe Tyr Asp Glu Cys Leu Arg Lys Tyr Gly
120                 125                 130                 135 aat gca aat gta tgg aag tat ttt aca gac ttg ttt gat tat ttg cct        547
Asn Ala Asn Val Trp Lys Tyr Phe Thr Asp Leu Phe Asp Tyr Leu Pro
            140                 145                 150 ctc aca gct ctt ata gaa aat cag gtc ttc tgt ctt cat gga ggc ctc        595
Leu Thr Ala Leu Ile Glu Asn Gln Val Phe Cys Leu His Gly Gly Leu
        155                 160                 165 tct ccg tca ttg gac aca ttg gat aac att cgt tct ctt gat cgc ata        643
Ser Pro Ser Leu Asp Thr Leu Asp Asn Ile Arg Ser Leu Asp Arg Ile
    170                 175                 180 cag gag gta cct cat gaa gga ccc atg tgt gat ctt ttg tgg tct gac        691
Gln Glu Val Pro His Glu Gly Pro Met Cys Asp Leu Leu Trp Ser Asp
185                 190                 195 cca gat gac cga tgt ggg tgg gga att tca ccc aga gga gca ggt tac        739
Pro Asp Asp Arg Cys Gly Trp Gly Ile Ser Pro Arg Gly Ala Gly Tyr
200                 205                 210                 215 aca ttt ggg caa gac att gca cag cag ttc aac cat aca aat ggt ctc        787
Thr Phe Gly Gln Asp Ile Ala Gln Gln Phe Asn His Thr Asn Gly Leu
            220                 225                 230 tct ctc att tca agg gcc cat caa ctt gta atg gaa gga ttt aat tgg        835
Ser Leu Ile Ser Arg Ala His Gln Leu Val Met Glu Gly Phe Asn Trp
        235                 240                 245 tgc cag gat aag aat gta gtc aca gtc ttc agt gcg cct aat tac tgt        883
Cys Gln Asp Lys Asn Val Val Thr Val Phe Ser Ala Pro Asn Tyr Cys
```

```
Cys Gln Asp Lys Asn Val Val Thr Val Phe Ser Ala Pro Asn Tyr Cys
            250                 255                 260 tac cgc tgt ggt aac atg gct gct att ctt gaa atc ggg gaa aac atg       931
Tyr Arg Cys Gly Asn Met Ala Ala Ile Leu Glu Ile Gly Glu Asn Met
        265                 270                 275 gac cag aac ttc ctt caa ttc aac ccc gca cct cgg caa att gag cca       979
Asp Gln Asn Phe Leu Gln Phe Asn Pro Ala Pro Arg Gln Ile Glu Pro
280                 285                 290                 295 gac aca act cgc aaa acc cca gac tac ttt ctg taattgtggt ggtgaccta     1032
Asp Thr Thr Arg Lys Thr Pro Asp Tyr Phe Leu
                300                 305 actttctggt gtttgatgct cctctcttcc gcagcatcag ggtatgtaga tcttgtcctt    1092
agatatgggt cccatgtgcc cggccttaac gtctccctat tcttttgttt ggagattttg    1152
tttctgcttc tcgatcttga tacaagatgt tagaagttga atgccagtgt atttttttca    1212
aaaaaaaaaa                                                           1222

<210> SEQ ID NO 88
<211> LENGTH: 306
<212> TYPE: PRT
<213> ORGANISM: Zea mays

<400> SEQUENCE: 88

Met Pro Ser His Gly Asp Leu Asp Arg Gln Ile Ala Gln Leu Arg Asp
1               5                   10                  15

Cys Lys Tyr Leu Pro Glu Ala Glu Val Lys Val Leu Cys Glu Gln Ala
            20                  25                  30

Lys Ala Ile Leu Met Glu Glu Trp Asn Val Gln Pro Val Arg Cys Pro
        35                  40                  45

Val Thr Val Cys Gly Asp Ile His Gly Gln Phe Tyr Asp Leu Ile Glu
    50                  55                  60

Leu Phe Arg Ile Gly Gly Asp Ser Pro Asp Thr Asn Tyr Leu Phe Met
65                  70                  75                  80

Gly Asp Tyr Val Asp Arg Gly Tyr Tyr Ser Val Glu Thr Val Ser Leu
                85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys Tyr Phe Thr
    130                 135                 140

Asp Leu Phe Asp Tyr Leu Pro Leu Thr Ala Leu Ile Glu Asn Gln Val
145                 150                 155                 160

Phe Cys Leu His Gly Gly Leu Ser Pro Ser Leu Asp Thr Leu Asp Asn
                165                 170                 175

Ile Arg Ser Leu Asp Arg Ile Gln Glu Val Pro His Glu Gly Pro Met
            180                 185                 190

Cys Asp Leu Leu Trp Ser Asp Pro Asp Asp Arg Cys Gly Trp Gly Ile
        195                 200                 205

Ser Pro Arg Gly Ala Gly Tyr Thr Phe Gly Gln Asp Ile Ala Gln Gln
    210                 215                 220

Phe Asn His Thr Asn Gly Leu Ser Leu Ile Ser Arg Ala His Gln Leu
225                 230                 235                 240

Val Met Glu Gly Phe Asn Trp Cys Gln Asp Lys Asn Val Val Thr Val
                245                 250                 255

Phe Ser Ala Pro Asn Tyr Cys Tyr Arg Cys Gly Asn Met Ala Ala Ile
```

-continued

```
                   260                 265                 270
Leu Glu Ile Gly Glu Asn Met Asp Gln Asn Phe Leu Gln Phe Asn Pro
            275                 280                 285

Ala Pro Arg Gln Ile Glu Pro Asp Thr Thr Arg Lys Thr Pro Asp Tyr
            290                 295                 300

Phe Leu
305

<210> SEQ ID NO 89
<211> LENGTH: 1278
<212> TYPE: DNA
<213> ORGANISM: Zea mays
<220> FEATURE:
<221> NAME/KEY: CDS
<222> LOCATION: (148)..(1065)
<223> OTHER INFORMATION: protein phosphatase 2A (ZM62132060)

<400> SEQUENCE: 89
aatcgtcgct ccacctcctc ctcgtctatc gccgatctcc cccaaaccct agccccgacc      60
tgaccgccgg cgggcccgcc ggccggagaa ggagtcgctc ccacccatcc aacttctgcg     120
gcggaagggg agcgggcggc ggacgag atg ccg tcg cac ggg gat ctg gac cgg    174
                              Met Pro Ser His Gly Asp Leu Asp Arg
                                1               5 cag atc gcg cag ctg cgc gac tgc aag tac ctg ccc gag gcg gag gtc      222
Gln Ile Ala Gln Leu Arg Asp Cys Lys Tyr Leu Pro Glu Ala Glu Val
 10                  15                  20                  25 aag gcg ctc tgc gag cag gcc aag gcc atc ctt atg gag gag tgg aac      270
Lys Ala Leu Cys Glu Gln Ala Lys Ala Ile Leu Met Glu Glu Trp Asn
                 30                  35                  40 gtg cag ccc gtg cgc tgt cct gtc acc gtc tgt ggc gac atc cac ggc      318
Val Gln Pro Val Arg Cys Pro Val Thr Val Cys Gly Asp Ile His Gly
             45                  50                  55 cag ttc tat gac ctc atc gag ctc ttc cgc atc ggc ggc gac gct ccc      366
Gln Phe Tyr Asp Leu Ile Glu Leu Phe Arg Ile Gly Gly Asp Ala Pro
         60                  65                  70 gac acc aac tac ctc ttc atg ggc gac tac gtc gat cgt ggg tac tat      414
Asp Thr Asn Tyr Leu Phe Met Gly Asp Tyr Val Asp Arg Gly Tyr Tyr
     75                  80                  85 tca gtt gaa aca gtt tct ctg tta gtg gct ttg aaa gtc cgt tac aga      462
Ser Val Glu Thr Val Ser Leu Leu Val Ala Leu Lys Val Arg Tyr Arg
 90                  95                 100                 105 gat aga att aca ata ctt aga gga aat cat gag agc aga caa atc act      510
Asp Arg Ile Thr Ile Leu Arg Gly Asn His Glu Ser Arg Gln Ile Thr
                110                 115                 120 caa gta tat ggc ttc tat gat gaa tgc tta aga aag tat gga aat gca      558
Gln Val Tyr Gly Phe Tyr Asp Glu Cys Leu Arg Lys Tyr Gly Asn Ala
            125                 130                 135 aat gtc tgg aag tat ttt aca gac ttg ttt gat ttt ttg cct ctc aca      606
Asn Val Trp Lys Tyr Phe Thr Asp Leu Phe Asp Phe Leu Pro Leu Thr
        140                 145                 150 gct ctt ata gaa aat cag gtc ttc tgt ctt cac ggt ggc ctc tct ccg      654
Ala Leu Ile Glu Asn Gln Val Phe Cys Leu His Gly Gly Leu Ser Pro
    155                 160                 165 tca ttg gac acg ttg gat aat att cgt tct ctt gat cgc gta cag gag      702
Ser Leu Asp Thr Leu Asp Asn Ile Arg Ser Leu Asp Arg Val Gln Glu
170                 175                 180                 185 gtt cct cat gaa gga ccc atg tgt gat ctt ttg tgg tct gac cca gat      750
Val Pro His Glu Gly Pro Met Cys Asp Leu Leu Trp Ser Asp Pro Asp
                190                 195                 200 gac cga tgt gga tgg gga att tca cca aga gga gca ggt tac aca ttt      798
```

```
Asp Arg Cys Gly Trp Gly Ile Ser Pro Arg Gly Ala Gly Tyr Thr Phe
            205                 210                 215 ggg caa gac att gcg cag cag ttc aac cat aca aat ggt ctt tct ctc    846
Gly Gln Asp Ile Ala Gln Gln Phe Asn His Thr Asn Gly Leu Ser Leu
            220                 225                 230 att tca agg gcc cat caa ctt gta atg gaa gga ttt aat tgg tgc cag    894
Ile Ser Arg Ala His Gln Leu Val Met Glu Gly Phe Asn Trp Cys Gln
            235                 240                 245 gat aag aat gta gtc aca gtc ttc agc gcg cct aat tat tgt tac cgc    942
Asp Lys Asn Val Val Thr Val Phe Ser Ala Pro Asn Tyr Cys Tyr Arg
250                 255                 260                 265 tgt ggt aac atg gct gct att ctt gaa atc ggg aaa aac atg gac cag    990
Cys Gly Asn Met Ala Ala Ile Leu Glu Ile Gly Lys Asn Met Asp Gln
                270                 275                 280 aac ttc ctt caa ttc gac ccg gca cct cgg caa att gag cca gac aca   1038
Asn Phe Leu Gln Phe Asp Pro Ala Pro Arg Gln Ile Glu Pro Asp Thr
            285                 290                 295 act cgg aaa acc cca gac tac ttt ttg taattgtggt ggtgacatta         1085
Thr Arg Lys Thr Pro Asp Tyr Phe Leu
            300                 305 acttactggt gttgatgctc ctcttttccg cagcatcagg gtctgtagat catctgtcct 1145 tagatatggg ttccatgagc ccgacctgta cgtctcccaa ttctttttgtt tggagatttt 1205 gttgccgctt aacgatcttt atacaatatg ttaaaaagtt aaatgccatt ggattttcct 1265 ccaaaaaaaa aaa                                                    1278

<210> SEQ ID NO 90
<211> LENGTH: 306
<212> TYPE: PRT
<213> ORGANISM: Zea mays

<400> SEQUENCE: 90

Met Pro Ser His Gly Asp Leu Asp Arg Gln Ile Ala Gln Leu Arg Asp
1               5                   10                  15

Cys Lys Tyr Leu Pro Glu Ala Glu Val Lys Ala Leu Cys Glu Gln Ala
            20                  25                  30

Lys Ala Ile Leu Met Glu Glu Trp Asn Val Gln Pro Val Arg Cys Pro
        35                  40                  45

Val Thr Val Cys Gly Asp Ile His Gly Gln Phe Tyr Asp Leu Ile Glu
    50                  55                  60

Leu Phe Arg Ile Gly Gly Asp Ala Pro Asp Thr Asn Tyr Leu Phe Met
65                  70                  75                  80

Gly Asp Tyr Val Asp Arg Gly Tyr Tyr Ser Val Glu Thr Val Ser Leu
                85                  90                  95

Leu Val Ala Leu Lys Val Arg Tyr Arg Asp Arg Ile Thr Ile Leu Arg
            100                 105                 110

Gly Asn His Glu Ser Arg Gln Ile Thr Gln Val Tyr Gly Phe Tyr Asp
        115                 120                 125

Glu Cys Leu Arg Lys Tyr Gly Asn Ala Asn Val Trp Lys Tyr Phe Thr
    130                 135                 140

Asp Leu Phe Asp Phe Leu Pro Leu Thr Ala Leu Ile Glu Asn Gln Val
145                 150                 155                 160

Phe Cys Leu His Gly Gly Leu Ser Pro Ser Leu Asp Thr Leu Asp Asn
                165                 170                 175

Ile Arg Ser Leu Asp Arg Val Gln Glu Val Pro His Glu Gly Pro Met
            180                 185                 190

Cys Asp Leu Leu Trp Ser Asp Pro Asp Asp Arg Cys Gly Trp Gly Ile
```

```
                        195                 200                 205
Ser Pro Arg Gly Ala Gly Tyr Thr Phe Gly Gln Asp Ile Ala Gln Gln
    210                 215                 220

Phe Asn His Thr Asn Gly Leu Ser Leu Ile Ser Arg Ala His Gln Leu
225                 230                 235                 240

Val Met Glu Gly Phe Asn Trp Cys Gln Asp Lys Asn Val Val Thr Val
                245                 250                 255

Phe Ser Ala Pro Asn Tyr Cys Tyr Arg Cys Gly Asn Met Ala Ala Ile
            260                 265                 270

Leu Glu Ile Gly Lys Asn Met Asp Gln Asn Phe Leu Gln Phe Asp Pro
        275                 280                 285

Ala Pro Arg Gln Ile Glu Pro Asp Thr Thr Arg Lys Thr Pro Asp Tyr
    290                 295                 300

Phe Leu
305

<210> SEQ ID NO 91
<211> LENGTH: 1068
<212> TYPE: DNA
<213> ORGANISM: Zea mays
<220> FEATURE:
<221> NAME/KEY: CDS
<222> LOCATION: (1)..(1068)
<223> OTHER INFORMATION: MEK1 protein kinase (ZM59202533)

<400> SEQUENCE: 91 atg aag ggg aag aag ccg gtc aag gag ctc aag ctc acc gtg ccg gcg      48
Met Lys Gly Lys Lys Pro Val Lys Glu Leu Lys Leu Thr Val Pro Ala
1               5                   10                  15 cag gag acc ccg gta gac aag ttc ctg acg gca agt ggc acg ttc aag      96
Gln Glu Thr Pro Val Asp Lys Phe Leu Thr Ala Ser Gly Thr Phe Lys
            20                  25                  30 gat ggt gag ctg agg ctc aat cag agc ggc ttg cgg ctt atc tct gag     144
Asp Gly Glu Leu Arg Leu Asn Gln Ser Gly Leu Arg Leu Ile Ser Glu
        35                  40                  45 gaa aac ggg gat gaa gat gaa tct aca aag ctg aag gtg gaa gat gtg     192
Glu Asn Gly Asp Glu Asp Glu Ser Thr Lys Leu Lys Val Glu Asp Val
    50                  55                  60 cag tta tca atg gat gat ctt gag atg att caa gtc att ggc aaa gga     240
Gln Leu Ser Met Asp Asp Leu Glu Met Ile Gln Val Ile Gly Lys Gly
65                  70                  75                  80 agc ggt ggt gtt gtc cag cta gtg agg cac aaa tgg gtg ggc aca ttg     288
Ser Gly Gly Val Val Gln Leu Val Arg His Lys Trp Val Gly Thr Leu
                85                  90                  95 ttt gcc tta aag ggt att caa atg aac att cag gag tca gtt cgt aaa     336
Phe Ala Leu Lys Gly Ile Gln Met Asn Ile Gln Glu Ser Val Arg Lys
            100                 105                 110 caa ata gta cag gag ctc aaa ata aac caa gca aca cag agc cct cat     384
Gln Ile Val Gln Glu Leu Lys Ile Asn Gln Ala Thr Gln Ser Pro His
        115                 120                 125 ata gtt atg tgc cat caa tct ttt tac cac aat ggt gta ata tat ctt     432
Ile Val Met Cys His Gln Ser Phe Tyr His Asn Gly Val Ile Tyr Leu
    130                 135                 140 gtt ctt gag tac atg gac cgt gga tcg ctt gca gac att gtt aag caa     480
Val Leu Glu Tyr Met Asp Arg Gly Ser Leu Ala Asp Ile Val Lys Gln
145                 150                 155                 160 gtg aag act att ctg gag cca tac ctt gca gta ctt tgt aag cag gtc     528
Val Lys Thr Ile Leu Glu Pro Tyr Leu Ala Val Leu Cys Lys Gln Val
                165                 170                 175 ttg gag ggt tta ttg tat ctt cat cat caa agg cac gtg att cac agg     576
```

```
Leu Glu Gly Leu Leu Tyr Leu His His Gln Arg His Val Ile His Arg
            180                 185                 190 gac ata aaa cca tct aac ttg ttg gtc aac cgt aaa ggt gaa gtc aag     624
Asp Ile Lys Pro Ser Asn Leu Leu Val Asn Arg Lys Gly Glu Val Lys
            195                 200                 205 att acc gac ttc gga gtg agt gct gtg cta gca agc tca ata ggt cag     672
Ile Thr Asp Phe Gly Val Ser Ala Val Leu Ala Ser Ser Ile Gly Gln
    210                 215                 220 cga gat aca ttt gtt gga acc tac aac tat atg gcg cct gag cgg att     720
Arg Asp Thr Phe Val Gly Thr Tyr Asn Tyr Met Ala Pro Glu Arg Ile
225                 230                 235                 240 agt ggt agc act tat gac tac aaa agt gac ata tgg agt ttg ggc tta     768
Ser Gly Ser Thr Tyr Asp Tyr Lys Ser Asp Ile Trp Ser Leu Gly Leu
                    245                 250                 255 gtt ata ctt gag tgt gcc att ggc cgg ttc cct tat ata cct tcg gaa     816
Val Ile Leu Glu Cys Ala Ile Gly Arg Phe Pro Tyr Ile Pro Ser Glu
                260                 265                 270 ggt gaa ggt tgg tta agc ttt tat gaa ctt ctg gag gcc att gtc gat     864
Gly Glu Gly Trp Leu Ser Phe Tyr Glu Leu Leu Glu Ala Ile Val Asp
            275                 280                 285 cag cca cca cct tct gca cct gca gat cag ttc tct cca gaa ttc tgc     912
Gln Pro Pro Pro Ser Ala Pro Ala Asp Gln Phe Ser Pro Glu Phe Cys
        290                 295                 300 tca ttt atc tcc tct tgc ata cag aaa gat ccg gct cag agg atg tct     960
Ser Phe Ile Ser Ser Cys Ile Gln Lys Asp Pro Ala Gln Arg Met Ser
305                 310                 315                 320 gct tca gaa ctc ttg aat cac cct ttt ttg aag aag ttc gag gat aag    1008
Ala Ser Glu Leu Leu Asn His Pro Phe Leu Lys Lys Phe Glu Asp Lys
                    325                 330                 335 gac tta aac ctg ggg att ctt gtg gag aac ctg gaa cct cca atg aat    1056
Asp Leu Asn Leu Gly Ile Leu Val Glu Asn Leu Glu Pro Pro Met Asn
                340                 345                 350 ata ccc gaa tag                                                    1068
Ile Pro Glu
        355

<210> SEQ ID NO 92
<211> LENGTH: 355
<212> TYPE: PRT
<213> ORGANISM: Zea mays

<400> SEQUENCE: 92

Met Lys Gly Lys Lys Pro Val Lys Glu Leu Lys Leu Thr Val Pro Ala
1               5                   10                  15

Gln Glu Thr Pro Val Asp Lys Phe Leu Thr Ala Ser Gly Thr Phe Lys
            20                  25                  30

Asp Gly Glu Leu Arg Leu Asn Gln Ser Gly Leu Arg Leu Ile Ser Glu
        35                  40                  45

Glu Asn Gly Asp Glu Asp Glu Ser Thr Lys Leu Lys Val Glu Asp Val
    50                  55                  60

Gln Leu Ser Met Asp Asp Leu Glu Met Ile Gln Val Ile Gly Lys Gly
65                  70                  75                  80

Ser Gly Gly Val Val Gln Leu Val Arg His Lys Trp Val Gly Thr Leu
                85                  90                  95

Phe Ala Leu Lys Gly Ile Gln Met Asn Ile Gln Glu Ser Val Arg Lys
            100                 105                 110

Gln Ile Val Gln Glu Leu Lys Ile Asn Gln Ala Thr Gln Ser Pro His
        115                 120                 125

Ile Val Met Cys His Gln Ser Phe Tyr His Asn Gly Val Ile Tyr Leu
```

```
              130                 135                 140
Val Leu Glu Tyr Met Asp Arg Gly Ser Leu Ala Asp Ile Val Lys Gln
145                 150                 155                 160

Val Lys Thr Ile Leu Glu Pro Tyr Leu Ala Val Leu Cys Lys Gln Val
                165                 170                 175

Leu Glu Gly Leu Leu Tyr Leu His His Gln Arg His Val Ile His Arg
                180                 185                 190

Asp Ile Lys Pro Ser Asn Leu Val Asn Arg Lys Gly Glu Val Lys
                195                 200                 205

Ile Thr Asp Phe Gly Val Ser Ala Val Leu Ala Ser Ser Ile Gly Gln
        210                 215                 220

Arg Asp Thr Phe Val Gly Thr Tyr Asn Tyr Met Ala Pro Glu Arg Ile
225                 230                 235                 240

Ser Gly Ser Thr Tyr Asp Tyr Lys Ser Asp Ile Trp Ser Leu Gly Leu
                245                 250                 255

Val Ile Leu Glu Cys Ala Ile Gly Arg Phe Pro Tyr Ile Pro Ser Glu
                260                 265                 270

Gly Glu Gly Trp Leu Ser Phe Tyr Glu Leu Leu Glu Ala Ile Val Asp
                275                 280                 285

Gln Pro Pro Pro Ser Ala Pro Ala Asp Gln Phe Ser Pro Glu Phe Cys
290                 295                 300

Ser Phe Ile Ser Ser Cys Ile Gln Lys Asp Pro Ala Gln Arg Met Ser
305                 310                 315                 320

Ala Ser Glu Leu Leu Asn His Pro Phe Leu Lys Lys Phe Glu Asp Lys
                325                 330                 335

Asp Leu Asn Leu Gly Ile Leu Val Glu Asn Leu Glu Pro Pro Met Asn
                340                 345                 350

Ile Pro Glu
        355

<210> SEQ ID NO 93
<211> LENGTH: 1303
<212> TYPE: DNA
<213> ORGANISM: Brassica napus
<220> FEATURE:
<221> NAME/KEY: CDS
<222> LOCATION: (73)..(1137)
<223> OTHER INFORMATION: MEK1 protein kinase (BN41901422)

<400> SEQUENCE: 93
gtcattcttc taatttctct gacctctgct actgtctatc cgttcgtgtt gctttgatct    60
ctctaatcag ac atg aag aga ggc agc ttg agt ctt aat ccc atc tct ctc   111
              Met Lys Arg Gly Ser Leu Ser Leu Asn Pro Ile Ser Leu
                1               5                   10 cct cct cct gag caa tcc atc tcc aaa ttc tta aca cag agc gga acg      159
Pro Pro Pro Glu Gln Ser Ile Ser Lys Phe Leu Thr Gln Ser Gly Thr
         15                  20                  25 ttc aag gat gga gac ctt caa gtg aac aaa gat gga atc cag aca gta      207
Phe Lys Asp Gly Asp Leu Gln Val Asn Lys Asp Gly Ile Gln Thr Val
 30                  35                  40                  45 tct cat tct gag cct gga gct cca cca cct att gat cca ttg gac aac      255
Ser His Ser Glu Pro Gly Ala Pro Pro Pro Ile Asp Pro Leu Asp Asn
                 50                  55                  60 cag ttg agt ttg gct gac ctt gaa gtg atc aaa gtc att ggc aaa gga      303
Gln Leu Ser Leu Ala Asp Leu Glu Val Ile Lys Val Ile Gly Lys Gly
             65                  70                  75 agc agt ggt agt gtt cag ctg gtt aaa cac aaa cta act caa cag ttt      351
Ser Ser Gly Ser Val Gln Leu Val Lys His Lys Leu Thr Gln Gln Phe
```

```
                80                  85                  90
ttc gct act aag gtt att cag tta aac aca gaa gag tcc aca tgt cga    399
Phe Ala Thr Lys Val Ile Gln Leu Asn Thr Glu Glu Ser Thr Cys Arg
 95                 100                 105 gcc att tct cag gag ctg agg ata aac ttg gca tct caa tgt cca tat    447
Ala Ile Ser Gln Glu Leu Arg Ile Asn Leu Ala Ser Gln Cys Pro Tyr
110                 115                 120                 125 ctc gtc tca tgt tat cag tct ttc tac cat aac ggt ctc gtc tca atc    495
Leu Val Ser Cys Tyr Gln Ser Phe Tyr His Asn Gly Leu Val Ser Ile
                130                 135                 140 gta atg gag ttc atg gac ggt gga tct ctt ttg gat ttg ttg aag aaa    543
Val Met Glu Phe Met Asp Gly Gly Ser Leu Leu Asp Leu Leu Lys Lys
            145                 150                 155 gtc cag aga gtt cct gaa aac atg ctc gct gcc atc tcc aag cga gtg    591
Val Gln Arg Val Pro Glu Asn Met Leu Ala Ala Ile Ser Lys Arg Val
        160                 165                 170 ctc cga ggc ttg tgc tat att cac gat gag agg cga atc att cac cgg    639
Leu Arg Gly Leu Cys Tyr Ile His Asp Glu Arg Arg Ile Ile His Arg
    175                 180                 185 gac ttg aag cct tcc aac ttg cta atc aat cac aga ggt gaa gtc aag    687
Asp Leu Lys Pro Ser Asn Leu Leu Ile Asn His Arg Gly Glu Val Lys
190                 195                 200                 205 atc gca gac ttt ggt gtc agc aag atc ttg tct agc aca agc agt cta    735
Ile Ala Asp Phe Gly Val Ser Lys Ile Leu Ser Ser Thr Ser Ser Leu
                210                 215                 220 gcg cat acc ttc gtg ggc aca gac ttc tat atg tcg cca gag aga atc    783
Ala His Thr Phe Val Gly Thr Asp Phe Tyr Met Ser Pro Glu Arg Ile
            225                 230                 235 agt ggg aaa gcg tat ggg aac aag tgt gat att tgg agt ttg gga gtg    831
Ser Gly Lys Ala Tyr Gly Asn Lys Cys Asp Ile Trp Ser Leu Gly Val
        240                 245                 250 gtt ctc ctc gaa tgt gca acg ggt aag ttt ccg tat act cct cct gaa    879
Val Leu Leu Glu Cys Ala Thr Gly Lys Phe Pro Tyr Thr Pro Pro Glu
    255                 260                 265 aac atg aag gga tgg act agc atg tat gag cta gtt gac gcc att gtt    927
Asn Met Lys Gly Trp Thr Ser Met Tyr Glu Leu Val Asp Ala Ile Val
270                 275                 280                 285 gaa aac ccg cct cct cgt gca cct tcc cac ctg ttc tct cca gag ttt    975
Glu Asn Pro Pro Pro Arg Ala Pro Ser His Leu Phe Ser Pro Glu Phe
                290                 295                 300 tgc tcc ttc atc tcg caa tgt gta caa aaa gat cca agg gac cgg aaa   1023
Cys Ser Phe Ile Ser Gln Cys Val Gln Lys Asp Pro Arg Asp Arg Lys
            305                 310                 315 tca gca atg gag ctt ctg gac cat agg ttc gta aac atg ttt gaa gat   1071
Ser Ala Met Glu Leu Leu Asp His Arg Phe Val Asn Met Phe Glu Asp
        320                 325                 330 gtg gat gtg gat ctc tcg tct tac ttc acc gcc gca gga tct ttg att   1119
Val Asp Val Asp Leu Ser Ser Tyr Phe Thr Ala Ala Gly Ser Leu Ile
    335                 340                 345 ccc cca cta gcc aac agc tagaaccgag tttgaacaat cctttttaaca         1167
Pro Pro Leu Ala Asn Ser
350             355 ccaagttata tatatgtatt ttatatccac tggaagagac gatatttacg agatgttgcg   1227
acttatgaga gaattctctt gatagacatt tatattttca agtattgaaa tttatttggg   1287
taaaaaaaaa aaaaaa                                                   1303

<210> SEQ ID NO 94
<211> LENGTH: 355
<212> TYPE: PRT
```

<213> ORGANISM: Brassica napus

<400> SEQUENCE: 94

Met Lys Arg Gly Ser Leu Ser Leu Asn Pro Ile Ser Leu Pro Pro Pro
1               5                   10                  15

Glu Gln Ser Ile Ser Lys Phe Leu Thr Gln Ser Gly Thr Phe Lys Asp
            20                  25                  30

Gly Asp Leu Gln Val Asn Lys Asp Gly Ile Gln Thr Val Ser His Ser
        35                  40                  45

Glu Pro Gly Ala Pro Pro Ile Asp Pro Leu Asp Asn Gln Leu Ser
    50                  55                  60

Leu Ala Asp Leu Glu Val Ile Lys Val Ile Gly Lys Gly Ser Ser Gly
65                  70                  75                  80

Ser Val Gln Leu Val Lys His Lys Leu Thr Gln Phe Phe Ala Thr
                85                  90                  95

Lys Val Ile Gln Leu Asn Thr Glu Gly Ser Thr Cys Arg Ala Ile Ser
            100                 105                 110

Gln Glu Leu Arg Ile Asn Leu Ala Ser Gln Cys Pro Tyr Leu Val Ser
        115                 120                 125

Cys Tyr Gln Ser Phe Tyr His Asn Gly Leu Val Ser Ile Val Met Glu
130                 135                 140

Phe Met Asp Gly Gly Ser Leu Leu Asp Leu Leu Lys Lys Val Gln Arg
145                 150                 155                 160

Val Pro Glu Asn Met Leu Ala Ala Ile Ser Lys Arg Val Leu Arg Gly
                165                 170                 175

Leu Cys Tyr Ile His Asp Glu Arg Arg Ile Ile His Arg Asp Leu Lys
            180                 185                 190

Pro Ser Asn Leu Leu Ile Asn His Arg Gly Glu Val Lys Ile Ala Asp
        195                 200                 205

Phe Gly Val Ser Lys Ile Leu Ser Ser Thr Ser Ser Leu Ala His Thr
210                 215                 220

Phe Val Gly Thr Asp Phe Tyr Met Ser Pro Glu Arg Ile Ser Gly Lys
225                 230                 235                 240

Ala Tyr Gly Asn Lys Cys Asp Ile Trp Ser Leu Gly Val Val Leu Leu
                245                 250                 255

Glu Cys Ala Thr Gly Lys Phe Pro Tyr Thr Pro Pro Gly Asn Met Lys
            260                 265                 270

Gly Trp Thr Ser Met Tyr Glu Leu Val Asp Ala Ile Val Glu Asn Pro
        275                 280                 285

Pro Pro Arg Ala Pro Ser His Leu Phe Ser Pro Glu Phe Cys Ser Phe
290                 295                 300

Ile Ser Gln Cys Val Gln Lys Asp Pro Arg Asp Arg Lys Ser Ala Met
305                 310                 315                 320

Glu Leu Leu Asp His Arg Phe Val Asn Met Phe Glu Asp Val Asp Val
                325                 330                 335

Asp Leu Ser Ser Tyr Phe Thr Ala Ala Gly Ser Leu Ile Pro Pro Leu
            340                 345                 350

Ala Asn Ser
        355

<210> SEQ ID NO 95
<211> LENGTH: 1268
<212> TYPE: DNA
<213> ORGANISM: Brassica napus
<220> FEATURE:
<221> NAME/KEY: CDS
<222> LOCATION: (60)..(1073)
<223> OTHER INFORMATION: MEK1 protein kinase (BN47868329)

<400> SEQUENCE: 95

```
ccagatcgtt aaaccataat ccaaaccaag cttgcaaaaa cttttgatcc taaaccgag        59 atg aaa cca atc caa ccg cca cca gga gta atc ggt ccg gtt aag aac       107
Met Lys Pro Ile Gln Pro Pro Pro Gly Val Ile Gly Pro Val Lys Asn
 1               5                  10                  15 cgc cct cgc cgg cgt cca gac ctc tcc tta cca ctt cct cac cgc gac       155
Arg Pro Arg Arg Arg Pro Asp Leu Ser Leu Pro Leu Pro His Arg Asp
             20                  25                  30 gtt tcc ctc gcc gta cct ctc ccc ctc cca cca act tcc ggc ggc ggt       203
Val Ser Leu Ala Val Pro Leu Pro Leu Pro Pro Thr Ser Gly Gly Gly
         35                  40                  45 tcc acc acc tca gag cct aaa agc tac tca gac tta gta cgt ggc aac       251
Ser Thr Thr Ser Glu Pro Lys Ser Tyr Ser Asp Leu Val Arg Gly Asn
     50                  55                  60 cgg atc gga agc gga gcc ggt gga acg gtt tac aga gta gtc cac cgt       299
Arg Ile Gly Ser Gly Ala Gly Gly Thr Val Tyr Arg Val Val His Arg
 65                  70                  75                  80 cca acc tcc cgc gta tac gca ctc aag ata atc aac ggt aac cac gat       347
Pro Thr Ser Arg Val Tyr Ala Leu Lys Ile Ile Asn Gly Asn His Asp
                 85                  90                  95 gac act gtt cgt ggc cag atc tgc aga gag atc aag att ctc cga gac       395
Asp Thr Val Arg Gly Gln Ile Cys Arg Glu Ile Lys Ile Leu Arg Asp
            100                 105                 110 gtg aat cac ccc aac gtg gtg aaa tgc cac gag atg ttc gat caa aac       443
Val Asn His Pro Asn Val Val Lys Cys His Glu Met Phe Asp Gln Asn
        115                 120                 125 gga gag atc cag gtc ttg ctc gag ctc atg gac caa gga tct tta gaa       491
Gly Glu Ile Gln Val Leu Leu Glu Leu Met Asp Gln Gly Ser Leu Glu
    130                 135                 140 ggt gct cat atc tcg aac gag caa cag tta tct gac cta tct cgt cag       539
Gly Ala His Ile Ser Asn Glu Gln Gln Leu Ser Asp Leu Ser Arg Gln
145                 150                 155                 160 ata cta aac ggt ttg gct tat ctt cac ggc cgt cat ata gtc cat aga       587
Ile Leu Asn Gly Leu Ala Tyr Leu His Gly Arg His Ile Val His Arg
                165                 170                 175 gac ata aag cca tcg aat cta ctt ata aac tcg gac aat aac gtc aag       635
Asp Ile Lys Pro Ser Asn Leu Leu Ile Asn Ser Asp Asn Asn Val Lys
            180                 185                 190 att gct gat ttt gga gtg agc agg gtc ttg gct cag acc ctg tct ccg       683
Ile Ala Asp Phe Gly Val Ser Arg Val Leu Ala Gln Thr Leu Ser Pro
        195                 200                 205 tgt aag tcc tct gtt ggg act att gct tac atg agt cct gag agg atc       731
Cys Lys Ser Ser Val Gly Thr Ile Ala Tyr Met Ser Pro Glu Arg Ile
    210                 215                 220 aac acg gat ttg aat cag ggg atg tat gat ggt tgc gct ggg gat att       779
Asn Thr Asp Leu Asn Gln Gly Met Tyr Asp Gly Cys Ala Gly Asp Ile
225                 230                 235                 240 tgg agc ttc ggt gtt agt gtt ctt gag ttt ttc ttg ggg agg ttt cct       827
Trp Ser Phe Gly Val Ser Val Leu Glu Phe Phe Leu Gly Arg Phe Pro
                245                 250                 255 ttt aat gtg aat agg cta ggt gat tgg gct agt ctt atg tgt gct att       875
Phe Asn Val Asn Arg Leu Gly Asp Trp Ala Ser Leu Met Cys Ala Ile
            260                 265                 270 tgt atg tct aag ccg cct gaa gct cct gcc acg gcg tct ccg gag ttt       923
Cys Met Ser Lys Pro Pro Glu Ala Pro Ala Thr Ala Ser Pro Glu Phe
        275                 280                 285 aga cac ttt gtt tcg tgt tgt ttg cag aga gaa ccg ggg agg agg caa       971
```

```
Arg His Phe Val Ser Cys Cys Leu Gln Arg Glu Pro Gly Arg Arg Gln
        290                 295                 300 act gct gtt cag ctt ttg caa cat cct ttt gtg cgt aga ggg gcg att     1019
Thr Ala Val Gln Leu Leu Gln His Pro Phe Val Arg Arg Gly Ala Ile
305                 310                 315                 320 cag agt cag aat agg tct cct cag aat cta cat caa ctc ttg cct cct     1067
Gln Ser Gln Asn Arg Ser Pro Gln Asn Leu His Gln Leu Leu Pro Pro
            325                 330                 335 cca cac taaaggttta gttttgtctg ataatgtttc tacactaaag gttgatcatg      1123
Pro His tcttgctgtt tagacaaact atatcattgt cttgtactta gctgaaagca aagcgtatat   1183
agtttgaatc actttgcacc tcatgatggt taatttcact aagtaattca gtagtagagt   1243
cattaaatgt aaaaaaaaaa aaaaa                                         1268

<210> SEQ ID NO 96
<211> LENGTH: 338
<212> TYPE: PRT
<213> ORGANISM: Brassica napus

<400> SEQUENCE: 96

Met Lys Pro Ile Gln Pro Pro Gly Val Ile Gly Pro Val Lys Asn
1               5                   10                  15

Arg Pro Arg Arg Pro Asp Leu Ser Leu Pro Leu Pro His Arg Asp
                20                  25                  30

Val Ser Leu Ala Val Pro Leu Pro Leu Pro Thr Ser Gly Gly Gly
            35                  40                  45

Ser Thr Thr Ser Glu Pro Lys Ser Tyr Ser Asp Leu Val Arg Gly Asn
50                  55                  60

Arg Ile Gly Ser Gly Ala Gly Thr Val Tyr Arg Val His Arg
65                  70                  75                  80

Pro Thr Ser Arg Val Tyr Ala Leu Lys Ile Ile Asn Gly Asn His Asp
                85                  90                  95

Asp Thr Val Arg Gly Gln Ile Cys Arg Glu Ile Lys Ile Leu Arg Asp
            100                 105                 110

Val Asn His Pro Asn Val Val Lys Cys His Glu Met Phe Asp Gln Asn
        115                 120                 125

Gly Glu Ile Gln Val Leu Leu Glu Leu Met Asp Gln Gly Ser Leu Glu
    130                 135                 140

Gly Ala His Ile Ser Asn Glu Gln Gln Leu Ser Asp Leu Ser Arg Gln
145                 150                 155                 160

Ile Leu Asn Gly Leu Ala Tyr Leu His Gly Arg His Ile Val His Arg
                165                 170                 175

Asp Ile Lys Pro Ser Asn Leu Leu Ile Asn Ser Asp Asn Val Lys
            180                 185                 190

Ile Ala Asp Phe Gly Val Ser Arg Val Leu Ala Gln Thr Leu Ser Pro
        195                 200                 205

Cys Lys Ser Ser Val Gly Thr Ile Ala Tyr Met Ser Pro Glu Arg Ile
    210                 215                 220

Asn Thr Asp Leu Asn Gln Gly Met Tyr Asp Gly Cys Ala Gly Asp Ile
225                 230                 235                 240

Trp Ser Phe Gly Val Ser Val Leu Glu Phe Phe Leu Gly Arg Phe Pro
                245                 250                 255

Phe Asn Val Asn Arg Leu Gly Asp Trp Ala Ser Leu Met Cys Ala Ile
            260                 265                 270

Cys Met Ser Lys Pro Pro Glu Ala Pro Ala Thr Ala Ser Pro Glu Phe
```

```
                275                 280                 285
Arg His Phe Val Ser Cys Cys Leu Gln Arg Glu Pro Gly Arg Arg Gln
            290                 295                 300

Thr Ala Val Gln Leu Leu Gln His Pro Phe Val Arg Arg Gly Ala Ile
305                 310                 315                 320

Gln Ser Gln Asn Arg Ser Pro Gln Asn Leu His Gln Leu Leu Pro Pro
                325                 330                 335

Pro His

<210> SEQ ID NO 97
<211> LENGTH: 872
<212> TYPE: DNA
<213> ORGANISM: Brassica napus
<220> FEATURE:
<221> NAME/KEY: CDS
<222> LOCATION: (80)..(670)
<223> OTHER INFORMATION: AP2 domain-containing transcription factor
      (BN42671700)

<400> SEQUENCE: 97
ctgcaaacta aaatctagaa ccggaacaga tctaaaccaa accaaaccga accgggtgtc       60
tttgtttgta actctccaa atg gtg aag aaa gcg atg aag gag gaa gaa gaa      112
                    Met Val Lys Lys Ala Met Lys Glu Glu Glu Glu
                      1               5                  10 gca gag atg aga aac tcg tcg atg cag tca aag tac aaa ggc gtg agg      160
Ala Glu Met Arg Asn Ser Ser Met Gln Ser Lys Tyr Lys Gly Val Arg
             15                  20                  25 aag agg aag tgg ggc aaa tgg gtt tcg gag atc aga ctt ccc aac agc      208
Lys Arg Lys Trp Gly Lys Trp Val Ser Glu Ile Arg Leu Pro Asn Ser
         30                  35                  40 aga gag cga atc tgg cta ggc tct ttc gac act ccc gag aag gcg gcg      256
Arg Glu Arg Ile Trp Leu Gly Ser Phe Asp Thr Pro Glu Lys Ala Ala
     45                  50                  55 cgt gcc ttc gac gcc gcc cag ttt tgt ctc cgc ggc tgc caa tcc ggt      304
Arg Ala Phe Asp Ala Ala Gln Phe Cys Leu Arg Gly Cys Gln Ser Gly
60                  65                  70                  75 ttc aat ttc ccc gat aat ccg ccg tcg atc tcc ggc gga agg tcg ctg      352
Phe Asn Phe Pro Asp Asn Pro Pro Ser Ile Ser Gly Gly Arg Ser Leu
                 80                  85                  90 acg cct ccg gag atc cgg gaa gcg gct gct cga tac gca aac gct cag      400
Thr Pro Pro Glu Ile Arg Glu Ala Ala Ala Arg Tyr Ala Asn Ala Gln
             95                 100                 105 gac gac gat att atc atc acc acc gga gaa gaa gaa tcg gtt ttg tcc      448
Asp Asp Asp Ile Ile Ile Thr Thr Gly Glu Glu Glu Ser Val Leu Ser
        110                 115                 120 gaa acc cga ccg gag tct cct tca aca acc tcc gtg tct gaa gca gat      496
Glu Thr Arg Pro Glu Ser Pro Ser Thr Thr Ser Val Ser Glu Ala Asp
    125                 130                 135 acg tcg ctg gat tgc gat cta tcg ttc tta gac acg ctt cct aat gat      544
Thr Ser Leu Asp Cys Asp Leu Ser Phe Leu Asp Thr Leu Pro Asn Asp
140                 145                 150                 155 ttc ggg atg ttt tct gtg ttt gat gac ttc tcc gac ggc ttc tcc ggc      592
Phe Gly Met Phe Ser Val Phe Asp Asp Phe Ser Asp Gly Phe Ser Gly
                160                 165                 170 gat cag ttt aca gag gtt tta ccc gtt gaa gat tac gga gat gtg att      640
Asp Gln Phe Thr Glu Val Leu Pro Val Glu Asp Tyr Gly Asp Val Ile
            175                 180                 185 ttt gat gag tct ctg ttt ctt tgg gat ttt taaatgtgta aagagttttg      690
Phe Asp Glu Ser Leu Phe Leu Trp Asp Phe
        190                 195
```

-continued

```
aattgttgtt tattcgggtc atggagagta atctggatat ttttgtaagt cggagctcca    750
gcgacccggg aacttgatca ttcttgcttt ggttgatgat atctatcatt ccttcatttt    810
ttgttgttat taatgaaaat atttggataa aatagcaatt acagaaaaaa aaaaaaaaaa    870
aa                                                                   872
```

```
<210> SEQ ID NO 98
<211> LENGTH: 197
<212> TYPE: PRT
<213> ORGANISM: Brassica napus

<400> SEQUENCE: 98

Met Val Lys Lys Ala Met Lys Glu Glu Glu Ala Glu Met Arg Asn
1               5                   10                  15

Ser Ser Met Gln Ser Lys Tyr Lys Gly Val Arg Lys Arg Lys Trp Gly
            20                  25                  30

Lys Trp Val Ser Glu Ile Arg Leu Pro Asn Ser Arg Glu Arg Ile Trp
        35                  40                  45

Leu Gly Ser Phe Asp Thr Pro Glu Lys Ala Ala Arg Ala Phe Asp Ala
    50                  55                  60

Ala Gln Phe Cys Leu Arg Gly Cys Gln Ser Gly Phe Asn Phe Pro Asp
65                  70                  75                  80

Asn Pro Pro Ser Ile Ser Gly Gly Arg Ser Leu Thr Pro Pro Glu Ile
                85                  90                  95

Arg Glu Ala Ala Ala Arg Tyr Ala Asn Ala Gln Asp Asp Asp Ile Ile
            100                 105                 110

Ile Thr Thr Gly Glu Glu Glu Ser Val Leu Ser Glu Thr Arg Pro Glu
        115                 120                 125

Ser Pro Ser Thr Thr Ser Val Ser Glu Ala Asp Thr Ser Leu Asp Cys
    130                 135                 140

Asp Leu Ser Phe Leu Asp Thr Leu Pro Asn Asp Phe Gly Met Phe Ser
145                 150                 155                 160

Val Phe Asp Asp Phe Ser Asp Gly Phe Ser Gly Asp Gln Phe Thr Glu
                165                 170                 175

Val Leu Pro Val Glu Asp Tyr Gly Asp Val Ile Phe Asp Glu Ser Leu
            180                 185                 190

Phe Leu Trp Asp Phe
        195
```

```
<210> SEQ ID NO 99
<211> LENGTH: 1405
<212> TYPE: DNA
<213> ORGANISM: Zea mays
<220> FEATURE:
<221> NAME/KEY: CDS
<222> LOCATION: (72)..(1121)
<223> OTHER INFORMATION: MEK1 protein kinase (ZM68416988)

<400> SEQUENCE: 99
ctcgcctcgc cttcctccga gccccggcga ggaagaggaa cccgccgccg ccgccgccgg     60
acgcacttcc g atg gcg acg cca cgg aag ccg atc aag ctc acg ctg ccg    110
              Met Ala Thr Pro Arg Lys Pro Ile Lys Leu Thr Leu Pro
              1               5                   10 tcc cac gag acc acc atc ggc aag ttc ctg acg cac agc ggg acg ttc    158
Ser His Glu Thr Thr Ile Gly Lys Phe Leu Thr His Ser Gly Thr Phe
        15                  20                  25 acg gac ggg gat ctg cgc gtg aac aag gac ggc ctc cgc atc gtc tcg    206
Thr Asp Gly Asp Leu Arg Val Asn Lys Asp Gly Leu Arg Ile Val Ser
30                  35                  40                  45
```

| | |
|---|---|
| cgg agg gag gga ggc gag gct cct cct ata gag ccg ttg gat agt caa<br>Arg Arg Glu Gly Gly Glu Ala Pro Pro Ile Glu Pro Leu Asp Ser Gln<br>                   50               55               60 | 254 |
| ctg agc tta gat gat cta gac gtt ata aaa gtg atc ggg aaa ggt agc<br>Leu Ser Leu Asp Asp Leu Asp Val Ile Lys Val Ile Gly Lys Gly Ser<br>          65               70               75 | 302 |
| agc gga aat gtg caa ttg gtc cgc cac aaa ttt act ggc cag ttt ttt<br>Ser Gly Asn Val Gln Leu Val Arg His Lys Phe Thr Gly Gln Phe Phe<br>        80                  85               90 | 350 |
| gct ctg aag gtt att caa cta aat att gat gag agt ata cgc aaa cag<br>Ala Leu Lys Val Ile Gln Leu Asn Ile Asp Glu Ser Ile Arg Lys Gln<br>95                  100              105 | 398 |
| att gcc aag gag ttg aag ata aac tta tca aca cag tgc caa tat gtt<br>Ile Ala Lys Glu Leu Lys Ile Asn Leu Ser Thr Gln Cys Gln Tyr Val<br>110               115             120            125 | 446 |
| gtt gtg ttc tat cag tgt ttc tat ttc aat ggt gcc att tct att gtt<br>Val Val Phe Tyr Gln Cys Phe Tyr Phe Asn Gly Ala Ile Ser Ile Val<br>                   130             135            140 | 494 |
| ttg gaa tac atg gat ggt ggc tcc ctt gca gat ttc ctg aag act gtt<br>Leu Glu Tyr Met Asp Gly Gly Ser Leu Ala Asp Phe Leu Lys Thr Val<br>               145                150           155 | 542 |
| aaa acc att cca gag gcc tac ctc gct gct atc tgt acg cag atg cta<br>Lys Thr Ile Pro Glu Ala Tyr Leu Ala Ala Ile Cys Thr Gln Met Leu<br>160               165             170 | 590 |
| aaa gga ctg atc tat ttg cat aac gag aag cgc gtt ata cac cga gat<br>Lys Gly Leu Ile Tyr Leu His Asn Glu Lys Arg Val Ile His Arg Asp<br>             175               180            185 | 638 |
| ctg aaa cca tca aat ata ttg ata aat cat agg ggt gaa gta aaa ata<br>Leu Lys Pro Ser Asn Ile Leu Ile Asn His Arg Gly Glu Val Lys Ile<br>190               195             200            205 | 686 |
| tca gat ttt ggt gtg agt gcc att ata tct agt tcc tct tcg caa cga<br>Ser Asp Phe Gly Val Ser Ala Ile Ile Ser Ser Ser Ser Gln Arg<br>                   210             215           220 | 734 |
| gat aca ttt att ggc aca cgc aac tac atg gcg cca gaa aga atc gat<br>Asp Thr Phe Ile Gly Thr Arg Asn Tyr Met Ala Pro Glu Arg Ile Asp<br>             225                230           235 | 782 |
| gga aag aaa cat ggt tct atg agt gat atc tgg agt ttg gga cta gtg<br>Gly Lys Lys His Gly Ser Met Ser Asp Ile Trp Ser Leu Gly Leu Val<br>        240                245               250 | 830 |
| ata ctg gaa tgt gca acc ggc atc ttt cca ttt cct cct tgt gaa agc<br>Ile Leu Glu Cys Ala Thr Gly Ile Phe Pro Phe Pro Pro Cys Glu Ser<br>255               260             265 | 878 |
| ttc tac gaa ctt ctc gtg gct gtt gtt gat caa ccg cca cct tct gcg<br>Phe Tyr Glu Leu Leu Val Ala Val Val Asp Gln Pro Pro Pro Ser Ala<br>270               275             280            285 | 926 |
| ccg ccg gat cag ttt tca cca gaa ttc tgt ggg ttc att tct gca tgt<br>Pro Pro Asp Gln Phe Ser Pro Glu Phe Cys Gly Phe Ile Ser Ala Cys<br>             290                295           300 | 974 |
| ctc cag aag gat gct aat gac agg tca tca gcc caa gcc tta ttg gac<br>Leu Gln Lys Asp Ala Asn Asp Arg Ser Ser Ala Gln Ala Leu Leu Asp<br>         305                310              315 | 1022 |
| cat ccg ttc ctg agc atg tat gat gac ctg cat gta gat ctt gct tcg<br>His Pro Phe Leu Ser Met Tyr Asp Asp Leu His Val Asp Leu Ala Ser<br>        320              325              330 | 1070 |
| tac ttc acg aca gca gga tct cct ctc gcc acc ttc aat tcc agg caa<br>Tyr Phe Thr Thr Ala Gly Ser Pro Leu Ala Thr Phe Asn Ser Arg Gln<br>        335              340              345 | 1118 |
| ctc taattttttt gtcctcctta ttacgcgaac ggtgtggcga caaatttctc<br>Leu<br>350 | 1171 |

```
tttttggaca aggcttggat tgtgtactga gctgtaatga tcttgtgtgt gtcaggtcgg    1231
tgattggctc catcacttta catatatgac atacatgtac agccttttag gataaaaatg    1291
agcactgaag ttttgcctat ctgtatatcg gcagcaaacg tttggtcatg tttgtttcac    1351
cttgtaatgt attgactcag atatgggatt ggtcattgtc tctaaaaaaa aaaa          1405
```

<210> SEQ ID NO 100
<211> LENGTH: 350
<212> TYPE: PRT
<213> ORGANISM: Zea mays

<400> SEQUENCE: 100

```
Met Ala Thr Pro Arg Lys Pro Ile Lys Leu Thr Leu Pro Ser His Glu
1               5                   10                  15

Thr Thr Ile Gly Lys Phe Leu Thr His Ser Gly Thr Phe Thr Asp Gly
            20                  25                  30

Asp Leu Arg Val Asn Lys Asp Gly Leu Arg Ile Val Ser Arg Arg Glu
        35                  40                  45

Gly Gly Glu Ala Pro Pro Ile Glu Pro Leu Asp Ser Gln Leu Ser Leu
    50                  55                  60

Asp Asp Leu Asp Val Ile Lys Val Ile Gly Lys Gly Ser Ser Gly Asn
65                  70                  75                  80

Val Gln Leu Val Arg His Lys Phe Thr Gly Gln Phe Phe Ala Leu Lys
                85                  90                  95

Val Ile Gln Leu Asn Ile Asp Glu Ser Ile Arg Lys Gln Ile Ala Lys
            100                 105                 110

Glu Leu Lys Ile Asn Leu Ser Thr Gln Cys Gln Tyr Val Val Val Phe
        115                 120                 125

Tyr Gln Cys Phe Tyr Phe Asn Gly Ala Ile Ser Ile Val Leu Glu Tyr
    130                 135                 140

Met Asp Gly Gly Ser Leu Ala Asp Phe Leu Lys Thr Val Lys Thr Ile
145                 150                 155                 160

Pro Glu Ala Tyr Leu Ala Ala Ile Cys Thr Gln Met Leu Lys Gly Leu
                165                 170                 175

Ile Tyr Leu His Asn Glu Lys Arg Val Ile His Arg Asp Leu Lys Pro
            180                 185                 190

Ser Asn Ile Leu Ile Asn His Arg Gly Glu Val Lys Ile Ser Asp Phe
        195                 200                 205

Gly Val Ser Ala Ile Ile Ser Ser Ser Ser Gln Arg Asp Thr Phe
    210                 215                 220

Ile Gly Thr Arg Asn Tyr Met Ala Pro Glu Arg Ile Asp Gly Lys Lys
225                 230                 235                 240

His Gly Ser Met Ser Asp Ile Trp Ser Leu Gly Leu Val Ile Leu Glu
                245                 250                 255

Cys Ala Thr Gly Ile Phe Pro Phe Pro Pro Cys Glu Ser Phe Tyr Glu
            260                 265                 270

Leu Leu Val Ala Val Asp Gln Pro Pro Ser Ala Pro Pro Asp
        275                 280                 285

Gln Phe Ser Pro Glu Phe Cys Gly Phe Ile Ser Ala Cys Leu Gln Lys
    290                 295                 300

Asp Ala Asn Asp Arg Ser Ser Ala Gln Ala Leu Leu Asp His Pro Phe
305                 310                 315                 320
```

-continued

```
Leu Ser Met Tyr Asp Asp Leu His Val Asp Leu Ala Ser Tyr Phe Thr
            325                 330                 335

Thr Ala Gly Ser Pro Leu Ala Thr Phe Asn Ser Arg Gln Leu
            340                 345             350
```